United States Patent
Nikolovska-Coleska et al.

(10) Patent No.: US 9,914,723 B2
(45) Date of Patent: Mar. 13, 2018

(54) SMALL MOLECULE INHIBITORS OF MCL-1 AND USES THEREOF

(71) Applicant: THE REGENTS OF THE UNIVERSITY OF MICHIGAN, Ann Arbor, MI (US)

(72) Inventors: Zaneta Nikolovska-Coleska, Ann Arbor, MI (US); Naval Bajwa, Lafayette, IN (US); Chenzhong Liao, Anhui (CN); Lei Miao, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/386,230

(22) PCT Filed: Mar. 29, 2013

(86) PCT No.: PCT/US2013/034565
§ 371 (c)(1),
(2) Date: Sep. 18, 2014

(87) PCT Pub. No.: WO2013/149124
PCT Pub. Date: Oct. 3, 2013

(65) Prior Publication Data
US 2015/0045357 A1 Feb. 12, 2015

Related U.S. Application Data

(60) Provisional application No. 61/617,473, filed on Mar. 29, 2012.

(51) Int. Cl.

| C07D 405/06 | (2006.01) |
| C07D 409/14 | (2006.01) |
| C07D 405/14 | (2006.01) |
| A61K 31/496 | (2006.01) |
| A61K 31/5377 | (2006.01) |
| C07D 307/92 | (2006.01) |
| A61K 45/06 | (2006.01) |

(52) U.S. Cl.
CPC .......... *C07D 405/06* (2013.01); *A61K 31/496* (2013.01); *A61K 31/5377* (2013.01); *A61K 45/06* (2013.01); *C07D 307/92* (2013.01); *C07D 405/14* (2013.01); *C07D 409/14* (2013.01)

(58) Field of Classification Search
CPC ... C07D 405/06; C07D 409/14; C07D 405/14
See application file for complete search history.

(56) References Cited

U.S. PATENT DOCUMENTS 5,244,917 A 9/1993 Petraitis
2009/0054402 A1 2/2009 Wang et al.

FOREIGN PATENT DOCUMENTS

WO 2010/024783 3/2010
WO 2011/094708 8/2011

OTHER PUBLICATIONS

CAS Registry No. 438484-78-7, which entered STN on Jul. 12, 2002.*
National Center for Biotechnology Information. PubChem BioAssay Database; AID=648, https://pubchem.ncbi.nlm.nih.gov/bioassay/648 (deposited Apr. 5, 2007; accessed Oct. 18, 2015).*
Emmett et al. Am. J. Cancer Res. 2011,1, 852-868.*
Glaser et al. Genes Dec. 2012, 26, 120-125.*
Skin Cancer Foundation, Melanoma Prevention Guidelines, obtained from http://www.skincancer.org/skin-cancer-information/melanoma/melanoma-prevention-guidelines on Oct. 18, 2015.*
Akgul et al. Cell. Mol. Life Sci. 2009, 66, 1326-1336.*
Luo et al. Cell 2009, 136, 823-837.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
National Center for Biotechnology Information. PubChem BioAssay Database; AID=1418, https://pubchem.ncbi.nlm.nih.gov/bioassay/1418 (deposit dated Oct. 29, 2008, accessed Oct. 18, 2015).*
National Center for Biotechnology Information. PubChem Compound Database; CID=3313092, https://pubchem.ncbi.nlm.nih.gov/compound/3313092 (created Sep. 7, 2005, accessed Oct. 18, 2015).*
CAS Registry No. 438484-89-0, which entered STN on Jul. 12, 2002.*
National Center for Biotechnology Information. PubChem BioAssay Database; AID=1021, https://pubchem.ncbi.nlm.nih.gov/bioassay/1021 (accessed May 14, 2016).*
National Center for Biotechnology Information. PubChem Compound Database; CID=3000201, https://pubchem.ncbi.nlm.nih.gov/compound/3000201 (accessed May 14, 2016).*
National Center for Biotechnology Information. PubChem BioAssay Database; AID=1418, https://pubchem.ncbi.nlm.nih.gov/bioassay/1418 (accessed May 14, 2016).*
National Center for Biotechnology Information. PubChem BioAssay Database; AID=1021, https://pubchem.ncbi.nlm.nih.gov/bioassay/1021 (deposited Jan. 8, 2008; accessed Sep. 18, 2016).*

(Continued)

*Primary Examiner* — Matthew P Coughlin
(74) *Attorney, Agent, or Firm* — Casimir Jones, SC

(57) ABSTRACT

This invention is in the field of medicinal chemistry. In particular, the invention relates to a new class of small-molecules having a [(1-Piperazinyl)-4-pyridinylmethyl]-Naphtho[1,2-b]furan structure which function as inhibitors of Mcl-1 protein, and their use as therapeutics for the treatment of cancer and other diseases.

11 Claims, 13 Drawing Sheets

(56) References Cited

OTHER PUBLICATIONS

National Center for Biotechnology Information. PubChem Compound Database; CID=3313095, https://pubchem.ncbi.nlm.nih.gov/compound/3313095 (created Sep. 7, 2005; accessed Sep. 18, 2016).*
National Center for Biotechnology Information. PubChem Compound Database; CID=3483973, https://pubchem.ncbi.nlm.nih.gov/compound/3483973 (created Sep. 8, 2005; accessed Sep. 18, 2016).*
CAS Registry Entry for Registry No. 132474-46-5, which entered STN on Mar. 8, 1991.*
CAS Registry Entry for Registry No. 371136-76-4, which entered STN on Nov. 20, 2001.*
CAS Registry Entry for Registry No. 438484-78-7, which entered STN on Jul. 12, 2002.*
CAS Registry Entry for Registry No. 438485-05-3, which entered STN on Jul. 12, 2002.*
CAS Registry Entry for Registry No. 438485-17-7, which entered STN on Jul. 12, 2002.*
CAS Registry Entry for Registry No. 438485-20-2, which entered STN on Jul. 12, 2002.*
CAS Registry Entry for Registry No. 438485-31-5, which entered STN on Jul. 12, 2002.*
CAS Registry Entry for Registry No. 438485-33-7, which entered STN on Jul. 12, 2002.*
CAS Registry Entry for Registry No. 438485-48-4, which entered STN on Jul. 12, 2002.*
CAS Registry Entry for Registry No. 438485-51-9, which entered STN on Jul. 12, 2002.*
CAS Registry No. 438488-44-9, which entered STN on Jul. 12, 2002.*
Backus HH, et al., "Rb, mcl-1 and p53 expression correlate with clinical outcome in patients with liver metastases from colorectal cancer." Ann Oncol. 2001; 12(6):779-85.
Boisvert-Adamo K., et al., "Mcl-1 is required for melanoma cell resistance to anoikis." Mol Cancer Res. 2009; 7:549-56.
Cavarretta IT, et al., "The antiapoptotic effect of IL-6 autocrine loop in a cellular model of advanced prostate cancer is mediated by Mcl-1." Oncogene 2007; 26: 2822-32.
Chen S, et al., "Mcl-1 down-regulation potentiates ABT-737 lethality by cooperatively inducing Bak activation and Bax translocation." Cancer Res. 2007; 67:782-91.
Cho-Vega JH, et al., "Mcl-1 expression in B-cell non-Hodgkin's lymphomas." Hum Pathol. 2004; 35(9)1095-100.
Chung TK, et al., "Expression of apoptotic regulators and their significance in cervical cancer." Cancer Lett. 2002; 180:63-8.
Day CL, et al., "Solution structure of prosurvival Mcl-1 and characterization of its binding by proapoptotic BH3-only ligands." J Biol Chem. 2005; 280(6):4738-44.
Day CL, et al., "Structure of the BH3 domains from the p53-inducible BH3-only proteins Noxa and Puma in complex with Mcl-1." J Mol Biol. 2008; 380(5):958-71.
Glaser SP, et al., "Anti-apoptotic Mcl-1 is essential for the development and sustained growth of acute myeloid leukemia." Genes Dev 2012; 26(2): 120-125.
Gomez-Bougie P, et al., "Noxa up-regulation and Mcl-1 cleavage are associated to apoptosis induction by bortezomib in multiple myeloma." Cancer Res. 2007; 67(11):5418-24.
Gomez-Bougie P, et al., "The imbalance between Bim and Mcl-1 expression controls the survival of human myeloma cells." Eur J Immunol. 2004; 34(11):3156-64.
Hanahan D, et al., "The hallmarks of cancer." Cell. 2000; 100(1):57-70.
Huang S, et al., "BH3 mimetic ABT-737 potentiates Trail-mediated apoptotic signaling by unsequestering Bim and Bak in human pancreatic cancer cells." Cancer Res. 2008; 68(8):2944-51.
Hussain SR, et al., "Mcl-1 is a relevant therapeutic target in acute and chronic lymphoid malignancies: down-regulation enhances rituximab-mediated apoptosis and complement-dependent cytotoxicity." Clin Cancer Res. 2007; 13(7):2144-50.
Jiang CC, et al., "Up-regulation of Mcl-1 is critical for survival of human melanoma cells upon endoplasmic reticulum stress." Cancer Res. 2008; 68:6708-17.
Kaufmann SH, et al., "Elevated Expression of the Apoptotic Regulator Mcl-1 at the Time of Leukemic Relapse." Blood 1998; 91(3):991-1000.
Khoury JD, et al., "Expression of Mcl-1 in mantle cell lymphoma is associated with high-grade morphology, a high proliferative state, and p53 overexpression." J Pathol. 2003; 199(1):90-7.
Kitada S, et al., "Expression of apoptosis-regulating proteins in chronic lymphocytic leukemia: correlations with In vitro and In vivo chemoresponses." Blood 1998; 91(9):3379-89.
MacCallum DE, et al., "Seliciclib (CYC202, R-Roscovitine) induces cell death in multiple myeloma cells by inhibition of RNA polymerase II-dependent transcription and down-regulation of Mcl-1." Cancer Res. 2005; 65(12):5399-407.
Marsden VS, et al., "Control of apoptosis in the immune system: Bcl-2, BH3-only proteins and more." Annu Rev Immunol. 2003; 21: 71-105.
Michels J, et al., "Mcl-1 is required for Akata6 B-lymphoma cell survival and is converted to a cell death molecule by efficient caspase-mediated cleavage." Oncogene 2004; 23(28):4818-27.
Miyamoto Y, et al., "Immunohistochemical analysis of Bcl-2, Bax, Bcl-X, and Mcl-1 expression in pancreatic cancers." Oncology 1999; 56(1)73-82.
Moulding DA, et al., "Apoptosis is rapidly triggered by antisense depletion of MCL-1 in differentiating U937 cells." Blood 2000; 96(5):1756-63.
Nguyen M, et al., "Small molecule obatoclax (GX15-070) antagonizes MCL-1 and overcomes MCL-1-mediated resistance to apoptosis." Proc Natl Acad Sci U S A. 2007; 104(49): 19512-19517.
Nijhawan D, et al., "Elimination of Mcl-1 is required for the initiation of apoptosis following ultraviolet irradiation." Genes Dev. 2003; 17(12):1475-86.
Oltersdorf T, et al., "An inhibitor of Bcl-2 family proteins induces regression of solid tumours." Nature. 2005;435:677-81.
Qin JZ, et al., "Enhanced Killing of Melanoma Cells by Simultaneously Targeting Mcl-1 and NOXA." Cancer Res. 2006; 66(19):9636-45.
Reynolds JE, et al., "BCL-2 and MCL-1 expression in Chinese hamster ovary cells inhibits intracellular acidification and apoptosis induced by staurosporine." Exp Cell Res. 1996; 225(2):430-6.
Reynolds JE, et al., "Mcl-1, a member of the Bcl-2 family, delays apoptosis induced by c-Myc overexpression in Chinese hamster ovary cells." Cancer Res. 1994; 54(24):6348-52.
Saxena A, et al., "Mc1-1 and Bcl-2/Bax Ratio Are Associated With Treatment Response but Not with Rai Stage in B-Cell Chronic Lymphocytic Leukemia." Am J Hematol. 2004; 7: 522-33.
Skvara H. et al., "Mcl-1 blocks radiation-induced apoptosis and inhibits clonogenic cell death." Anticancer Res. 2005, 25(4):2697-703.
Song L, et al., "Mcl-1 regulates survival and sensitivity to diverse apoptotic stimuli in human non-small cell lung cancer cells." Cancer Biol Ther. 2005; 4(3):267-76.
Thallinger C, et al., "Mcl-1 antisense therapy chemosensitizes human melanoma in a SCID mouse xenotransplantation model." J Invest Dermatol. 2003; 120(6)1081-6.
Tse C, et al., "ABT-263: a potent and orally bioavailable Bcl-2 family inhibitor." Cancer Res. 2008; 68(9):3421-8.
Van Delft MF, et al., "The BH3 mimetic ABT-737 targets selective Bcl-2 proteins and efficiently induces apoptosis via Bak/Bax if Mcl-1 is neutralized." Cancer Cell. 2006; 10(5): 389-399.
Wuilleme-Toumi S, et al., "Mcl-1 is overexpressed in multiple myeloma and associated with relapse and shorter survival." Leukemia 2005; 19(7):1248-52.
Zhang B, et al., "Myeloid cell factor-1 is a critical survival factor for multiple myeloma." Blood 2002; 99: 1885-93.
Zhou P, et al., "Mcl-1, a Bcl-2 family member, delays the death of hematopoietic cells under a variety of apoptosis-inducing conditions." Blood. 1997; 89(2):630-43.

(56) References Cited

OTHER PUBLICATIONS

Sieghart W., et al., "Mcl-1 overexpression in hepatocellular carcinoma: a potential target for antisense therapy." J Hepatol. 2006; 44:151-7.
International Search Report and Written Opinion, dated Sep. 2, 2013, PCT/US2013/034565.
PubChemCompound, datasheet [online compound summary] Retrieved from the Internet: <URL: http://pubchem.ncbi.nlm.nih.gov/summary/summary.dgi> See CID 3313094 (Sep. 7, 2005), CID 3316360 (Sep. 7, 2005), CID 2999047 (Jul. 30, 2005) etc.
Mukhanova et al. "Synthesis of Aminomethyl Derivatives of Naphto(1,2-b) Furan" Pharmaceutical Chemistry Journal, 1990, vol. 24, No. 11, pp. 802-805.
Supplementary European Search Report, EP Patent Application No. 13767518.7, dated Oct. 23, 2015.

\* cited by examiner

| | $R_1$ | $R_2$ | $IC_{50} \pm SD$ (µM) |
|---|---|---|---|
| UMI-1033 | 4-pyridyl | N-methylpiperazine | 0.075 ± 0.01 |
| UMI-1007 | 4-pyridyl | morpholine | 0.070 ± 0.02 |
| UMI-1014 | 4-pyridyl | -O-CH3 | 9.35 ± 0.64 |
| UMI-119 | -H | tetrahydroisoquinoline | 2.10 ± 0.10 |
| UMI-1011 | 4-pyridyl | tetrahydroisoquinoline | 0.19 ± 0.05 |

| | $R_2$ | $IC_{50} \pm SD$ (µM) |
|---|---|---|
| UMI-1033 | ⸺N⌒N─ | 0.075 ± 0.01 |
| UMI-1008 | ⸺N⌒N⁄ | 0.056 ± 0.01 |
| UMI-1009 | ⸺N⌒N⟨ | 0.053 ± 0.02 |
| UMI-1011 | ⸺N(tetrahydroisoquinoline) | 0.19 ± 0.05 |

| | $R_1$ | $IC_{50} \pm SD$ (µM) |
|---|---|---|
| UMI-1033 | (4-pyridyl) | 0.075 ± 0.01 |
| UMI-68 | (3-pyridyl) | 0.220 ± 0.08 |
| UMI-1001 | (phenyl) | 0.150 ± 0.05 |
| UMI-118 | (4-F-phenyl) | 0.190 ± 0.02 |
| UMI-117 | (4-Cl-phenyl) | 0.370 ± 0.09 |
| UMI-69 | (4-methyl-phenyl) | 0.410 ± 0.15 |
| UMI-1003 | (3-F-phenyl) | 0.200 ± 0.06 |
| UMI-1004 | (2-F,5-Cl-phenyl) | 2.600 ± 0.14 |
| UMI-1026 | (2-Cl-pyridyl) | 0.100 ± 0.04 |

|  | $R_3$ | $R_4$ | $IC_{50} \pm SD\ (\mu M)$ |
|---|---|---|---|
| UMI-1033 | –H | –CH=CH₂ | 0.075 ± 0.01 |
| UMI-1033-1 | –CH₂– | –CH=CH₂ | 0.210 ± 0.02 |
| UMI-1033-3 | –C(CH₃)₃ | –CH=CH₂ | 0.47 ± 0.08 |
| UMI-1033-2 | –Ph | –CH=CH₂ | 1.21 ± 0.41 |
| UMI-1035 | –H | –H | 0.051 ± 0.05 |

- ■ UMI-1033  $IC_{50} = 0.075\ \mu M$
- ▽ UMI-1014  $IC_{50} = 9.35\ \mu M$
- ▲ UMI-1031  $IC_{50} = 25.75\ \mu M$
- ○ UMI-1037  $IC_{50} = 116.9\ \mu M$

FIGURE 9

|  | SK-mel-147 IC50 [μM] | C8161 IC50 [μM] | SK-mel-103 IC50 [μM] | Malme-3M IC50 [μM] | G-361 IC50 [μM] | UACC-62 IC50 [μM] | WM-1366 IC50 [μM] | SK-mel-94 IC50 [μM] |
|---|---|---|---|---|---|---|---|---|
| UMI-1009 | 2.26 | 2.63 | 4.67 | 4.58 | 3.13 | 1.66 | 3.32 | 2.73 |
| UMI-1008 | 5.16 | 4.65 | 7.92 | 8.41 | 7.13 | 5.84 | 9.37 | 6.93 |
| UMI-1004 | 5.60 | 6.76 | 6.70 | 7.02 | 6.90 | 6.55 | 7.23 | 13.07 |
| UMI-1033 | 9.13 | 9.81 | 11.42 | 13.67 | 21.34 | 12.94 | 14.52 | 22.44 |
| UMI-1007 | 9.47 | 8.85 | 14.07 | 14.08 | 14.39 | 11.61 | 14.33 | 14.63 |
| UMI-1001 | 11.78 | 7.30 | 13.61 | 12.19 | 11.72 | 19.30 | 11.10 | 15.34 |
| UMI-1003 | 13.77 | 9.14 | 12.83 | 14.11 | 13.15 | 15.69 | 15.68 | 19.89 |

SMALL MOLECULE INHIBITORS OF MCL-1 AND USES THEREOF

CROSS-REFERENCE TO RELATED APPLICATIONS

This application is a national stage of International (PCT) Patent Application Serial No. PCT/US2013/034565, filed Mar. 29, 2013, which claims the benefit of and priority to U.S. Provisional Patent Application No. 61/617,473, filed Mar. 29, 2012, the contents of each of which are hereby incorporated by reference for all purposes.

STATEMENT REGARDING FEDERALLY SPONSORED RESEARCH OR DEVELOPMENT

This invention was made with government support under Grant Nos. CA149442 and CA158976 awarded by the National Institutes of Health. The government has certain rights in the invention.

FIELD OF THE INVENTION

This invention is in the field of medicinal chemistry. In particular, the invention relates to a new class of small-molecules having a [(1-piperazinyl)-4-pyridinylmethyl]-Naphtho[1,2-b]furan structure which function as inhibitors of Mcl-1 protein, and their use as therapeutics for the treatment of cancer and other diseases.

INTRODUCTION

Mcl-1 plays profound roles in response to a variety of death stimuli. Functional studies have confirmed that Mcl-1 is capable of blocking apoptosis induced by various apoptotic stimuli, including chemotherapy and radiation (see, e.g., Reynolds J E, at al, Cancer Res. 1994; 54:6348-52; Reynolds J E, at al, Exp Cell Res. 1996; 225:430-6, Zhou P, at al, Blood 1997; 89: 630-43). Antisense or siRNA strategies have shown that the anti-apoptotic function of Mcl-1 is essential for maintenance of cell viability (Moulding D A, et al., Blood 2000; 96: 1756-63, Marsden V S, et al., Annu Rev Immunol. 2003; 21: 71-105, Nijhawan D, et al., Genes Dev. 2003; 17:1475-86). The biological significance of Mcl-1 protein expression in support of cell survival has been well documented in a number of cell systems, including human myeloblastic leukemia (Moulding D A, et al., Blood 2000; 96: 1756-63), myeloma (Marsden V S, et al., Annu Rev Immunol. 2003; 21: 71-105, MacCallum D E, et al., Cancer Res. 2005; 65:5399-407, Zhang B, et al., Blood 2002; 99: 1885-93), B-lymphoma (Michels J, et al., Oncogene 2005; 23: 4818-27), non-small cell lung cancer cells (Song L, et al., Cancer Biol Ther. 2005; 4: 267-76), melanoma (Qin J Z, et al., Cancer Res. 2006; 66: 9636-45) and prostate cancer (Cavarretta I T, et al., Oncogene 2007; 26: 2822-32). Furthermore, Mcl-1 is overexpressed in many human tumor specimens (Miyamoto Y, et al., Oncology 1999; 56:73-82, Chung T K, et al., Cancer Lett. 2002; 180:63-8, Sieghart W, et al., J. Hepatol. 2006; 44:151-7, Cho-Vega J H, et al., Hum Pathol. 2004; 35: 1095-100, Khoury J D, et al., J. Pathol. 2003; 199:90-7) and metastatic tissue (Backus H H, et al., Ann Oncol. 2001; 12: 779-85) and its overexpression contributes to chemoresistance and disease relapse (Wuilleme-Toumi S, et al., Leukemia 2005; 19:1248-52, Kaufmann S H, et al., Blood 1998; 91:991-1000, Kitada S, et al., Blood 1998; 91:3379-89, Saxena A, et al., Am J. Hematol. 2004; 7: 522-33). It was shown that Mcl-1 down-regulation is important to make multiple myeloma cells susceptible to BH3-only proteins and therefore to mitochondrial disruption (Gomez-Bougie P, et al., Eur J Immunol. 2004; 34:3156-64, Gomez-Bougie P, et al., Cancer Res. 2007; 67:5418-24). Down-regulation of Mcl-1 is increasing the sensitivity to rituximab-mediated killing of chronic and acute lymphoid leukemia (CLL and ALL) (Hussain S R, et al., Clin Cancer Res. 2007; 13:2144-50). Antisense strategies targeting Mcl-1 in vitro and in vivo have given promising results in sensitizing human melanoma to drugs (Thallinger C, et al., J Invest Dermatol. 2003; 120:1081-6). These data suggest that therapies which specifically target Mcl-1 could be effective in the treatment of hematological and other malignanices as a single agent and in combination with other therapy.

SUMMARY OF THE INVENTION

A hallmark of cancer cells is defects in the apoptotic cell death program (see, e.g., Hanahan D, et al., Cell. 2000; 100:57-70; herein incorporated by reference in its entirety). The broad resistance of pancreatic cancer (PC), for example, to existing chemotherapeutic agents and radiation therapy is due, in large part, to defects in apoptotic signaling pathways. Mcl-1 is a potent anti-apoptotic protein and an important survival factor for many cancers, including PC. Its overexpression has been associated with tumor initiation, progression and resistance to current anticancer therapies. Recent independent studies using a genetic approach to down-regulation of Mcl-1 provided a significant proof-of-concept that selective, small-molecule Mcl-1 inhibitors may have potential as a new treatment for PC by overcoming the apoptosis resistance of cancer cells to current therapeutic agents. Mcl-1 is a homologous protein related to other anti-apoptotic proteins such as Bcl-2 and Bcl-$x_L$, but it has a distinctly different structure and exhibits selective binding to the pro-apoptotic BH3-only proteins. This suggests that specific targeting of the Mcl-1 protein is possible and that drugs specific to Mcl-1 can be developed.

Using high throughput screening, experiments conducted during the course of developing embodiments for the present invention identified a new class of small-molecules having a [(1-piperazinyl)-4-pyridinylmethyl]-Naphtho[1,2-b]furan structure which function as inhibitors of Mcl-1 protein.

Accordingly, the present invention contemplates that exposure of animals (e.g., humans) suffering from cancer (e.g., and/or cancer related disorders) to therapeutically effective amounts of drug(s) (e.g., small molecules) that inhibit the activity of Mcl-1 will inhibit the growth of cancer cells or supporting cells outright and/or render such cells as a population more susceptible to the cell death-inducing activity of cancer therapeutic drugs or radiation therapies. In some embodiments, the inhibition of Mcl-1 activity occurs through, for example, inhibiting the interaction between Mcl-1 and Bak and/or Bax. In some embodiments, the inhibition of Mcl-1 activity occurs through, for example, binding the BH3 binding groove of Mcl-1. The present invention contemplates that inhibitors of Mcl-1 activity satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain [(1-piperazinyl)-4-pyridinylmethyl]-Naphtho[1,2-b]furan compounds function as inhibitors of Mcl-1 protein, and serve as therapeutics for the treatment of cancer and other diseases. Thus, the present invention relates to [(1-piperazinyl)-4-pyridinylmethyl]-Naphtho[1,2-b]furan compounds useful for inhibiting Mcl-1 activity (e.g., thereby facilitating cell apoptosis), and increasing the sensitivity of cells to inducers of apoptosis and/or cell cycle arrest. Certain [(1-piperazinyl)-4-pyridinylmethyl]-Naphtho[1,2-b]furan compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, [(1-piperazinyl)-4-pyridinylmethyl]-Naphtho[1,2-b]furan compounds having the following Formula I:

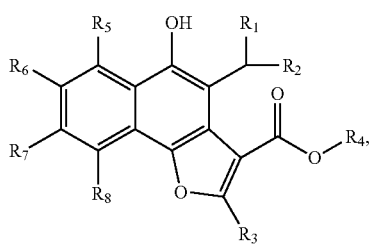

including pharmaceutically acceptable salts, solvates, and/or prodrugs thereof.

Formula I is not limited to a particular chemical moieties for R1, R2, R3 and/or R4. In some embodiments, R1, R2, R3, R4, R5, R6, R7 and/or R8 include any chemical moieties that permit the resulting compound to bind with an Mcl-1 protein. In some embodiments, R1, R2, R3, R4, R5, R6, R7 and/or R8 include any chemical moieties that permits the resulting compound to inhibit the activity of Mcl-1 protein.

In some embodiments, R1 may be, for example, hydrogen, a phenyl group (substituted or unsubstituted) or a pyridine (substituted or unsubstituted). In some embodiments, R1 may be, for example, any of the following chemical moieties: hydrogen,

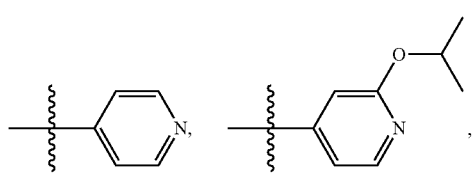

-continued

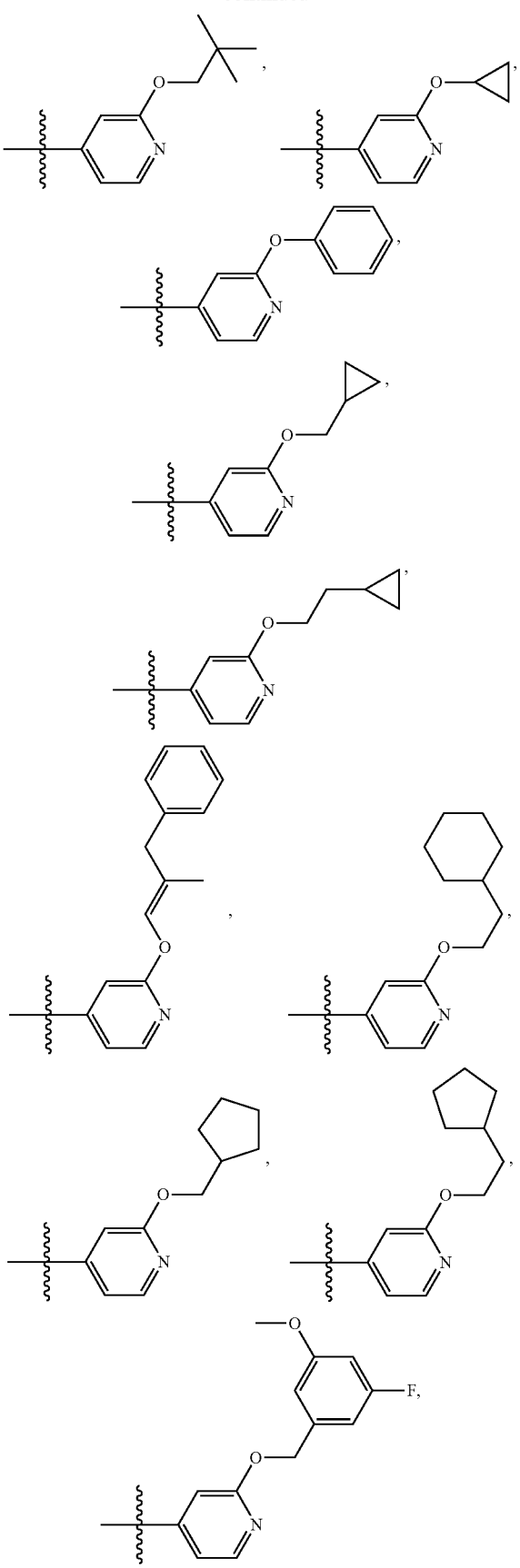

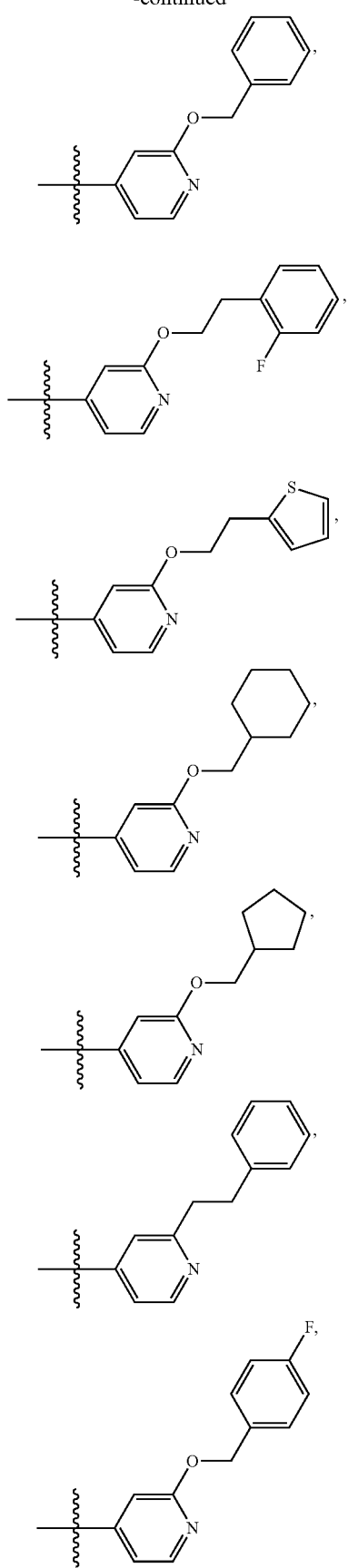
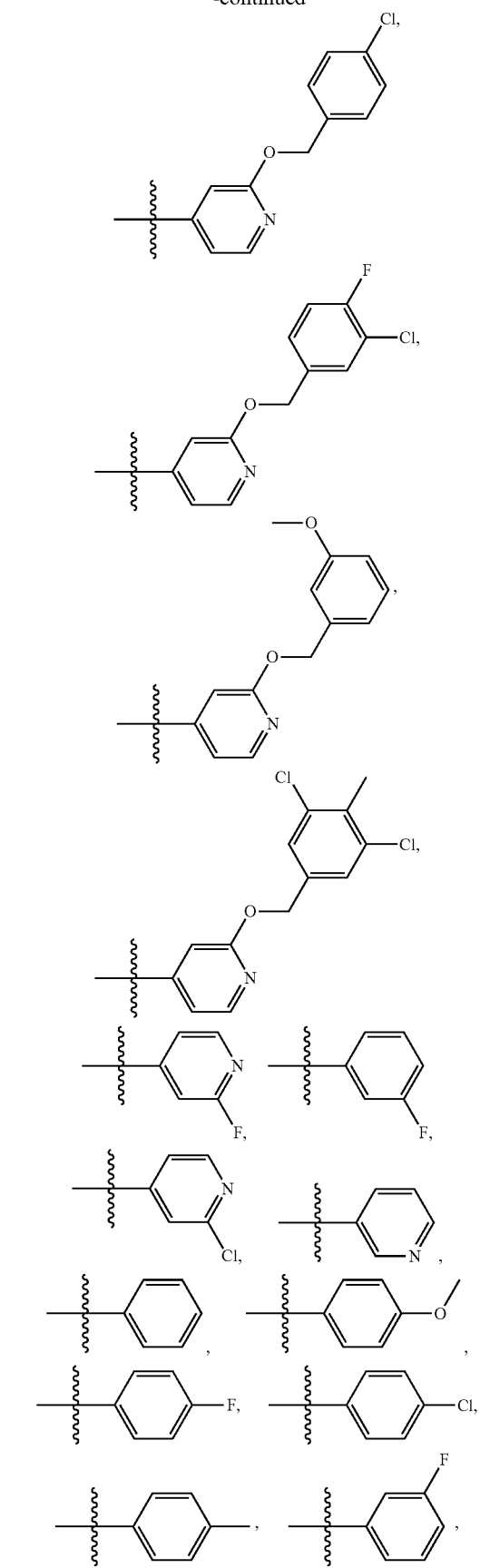

-continued

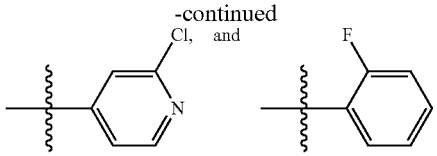

In some embodiments, R2 may be, for example, hydrogen, a piperazine group (substituted or unsubstituted), or a morpholino group (substituted or unsubstituted). In some embodiments, R2 may be, for example, any of the following chemical moieties:

hydrogen,

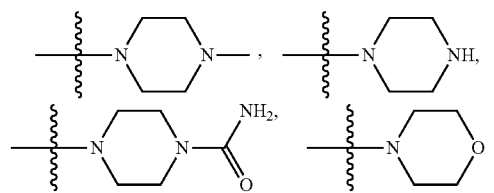

In some embodiments, R3 may be, for example, hydrogen, an alkyl moiety (substituted or unsubstituted) or aromatic (substituted or unsubstituted). In some embodiments, R3 may be, for example, hydrogen, methyl, ethyl, phenyl, or tert-butyl.

In some embodiments, R4 may be, for example, hydrogen or an alkyl moiety (substituted or unsubstituted). In some embodiments, R4 may be, for example,

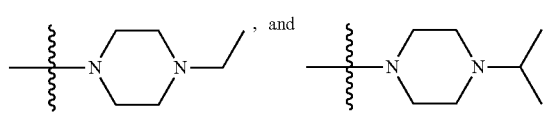

hydrogen, methyl or ethyl. FIG. 7 shows a synthetic scheme for developing compounds of Formula I where R4 is ethyl.

In some embodiments, R5, R6, R7, and R8 may independently be, for example, hydrogen,

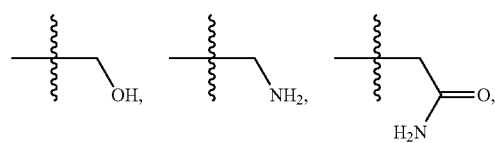

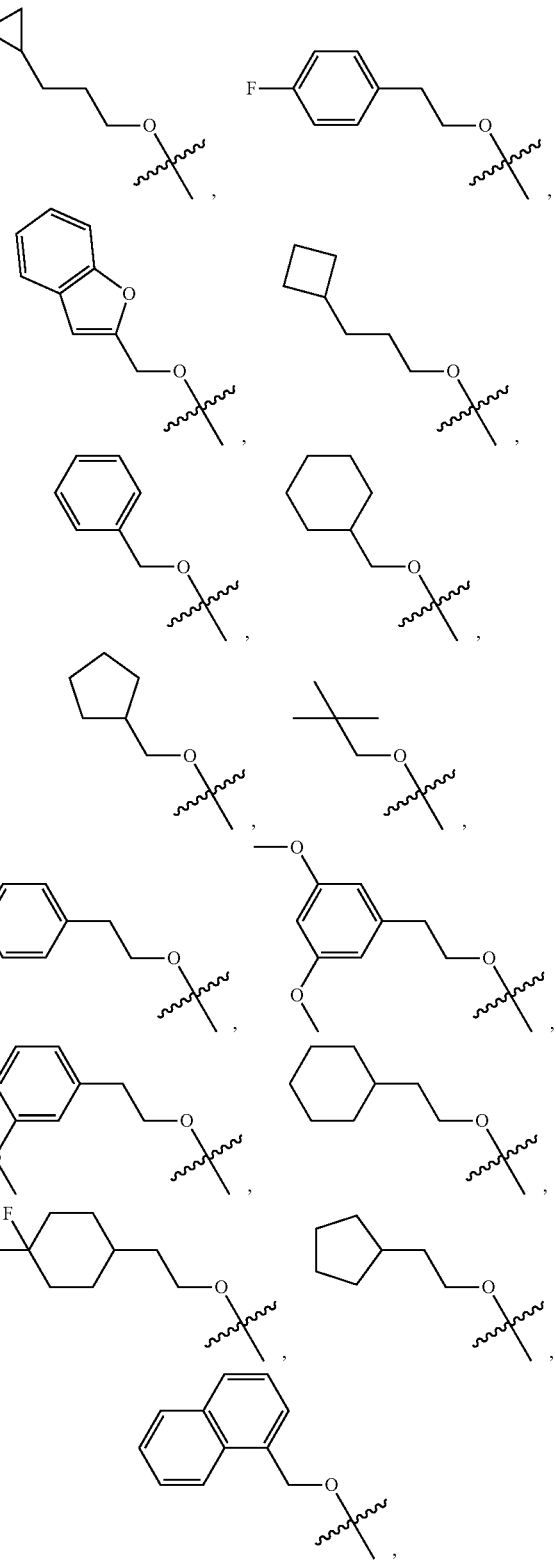

-continued

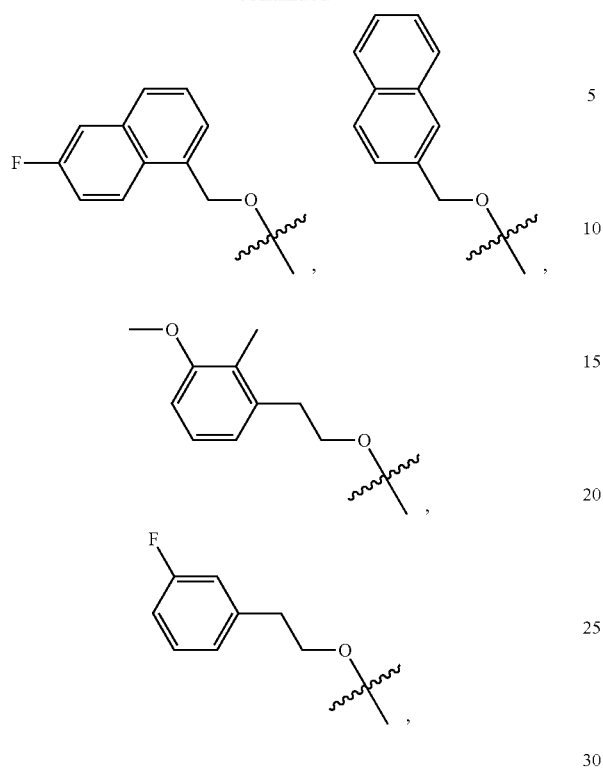

alkyl (e.g., substituted, unsubstituted) (e.g., methyl), or a halogen (e.g., chlorine, fluorine).

FIGS. 1, 2, 3, and 4 show various compounds for Formula I having various R1, R2, R3, R4, R5, R6, R7 and R8 groups, and related structure activity relationship (SAR) for each respective compound ($IC_{50}$ values were determined with fluorescence polarizing binding assay).

In some embodiments, the following compounds are encompassed within Formula I:

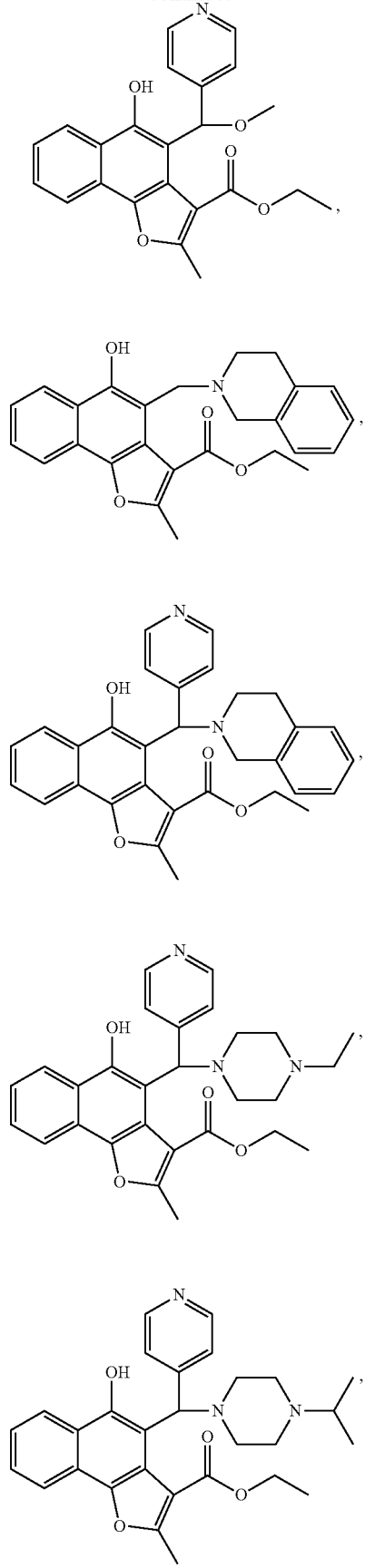

-continued

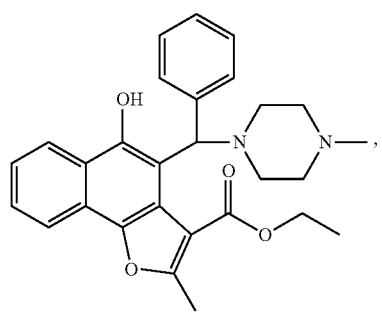
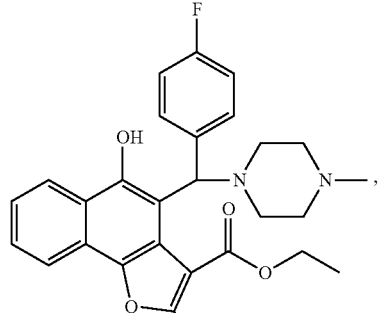
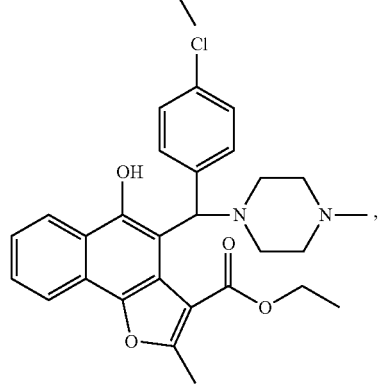
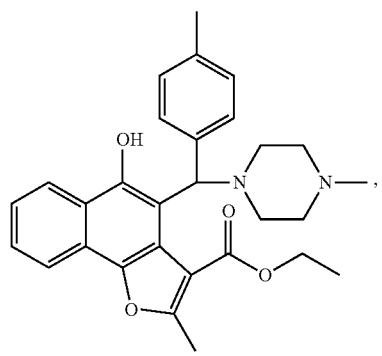
-continued
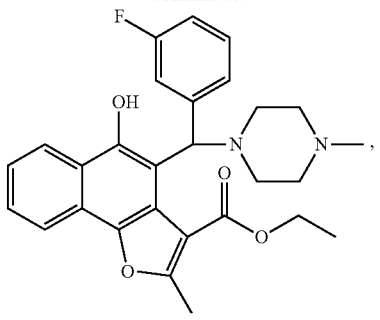
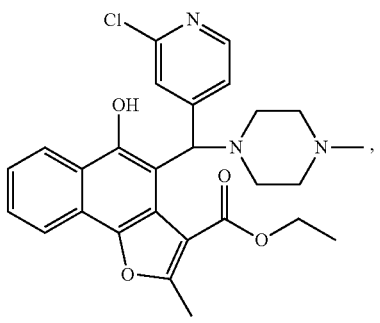
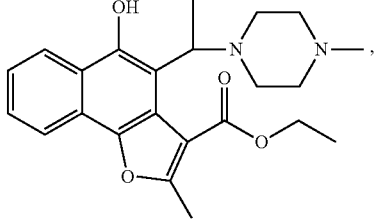
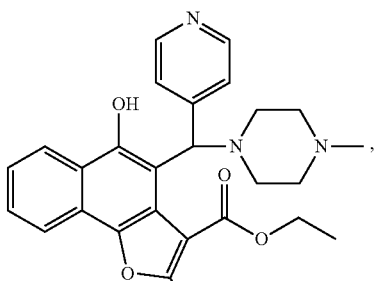
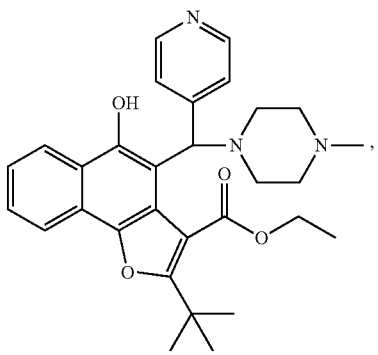

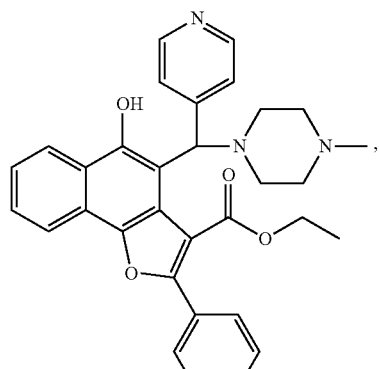
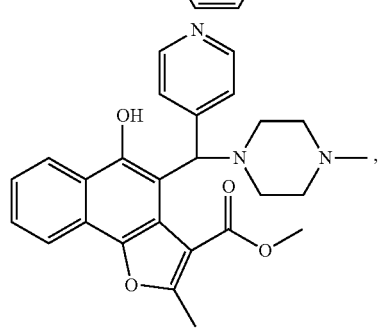
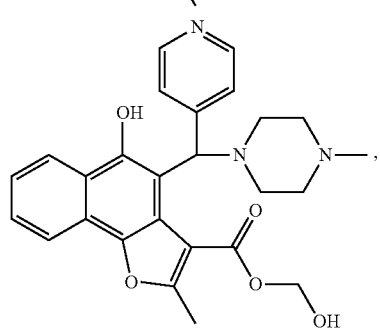
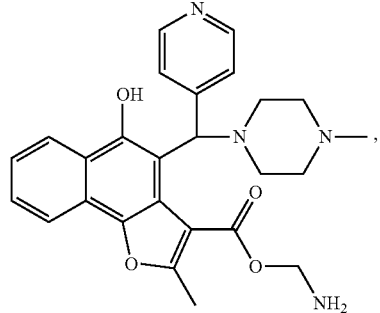
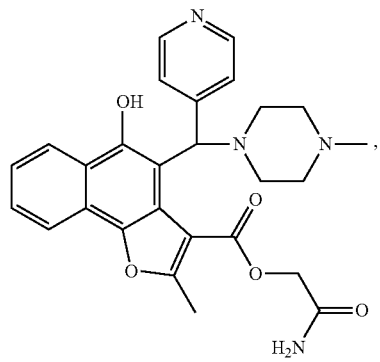
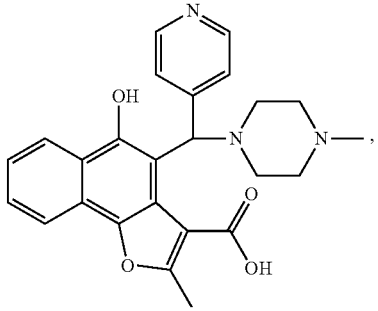
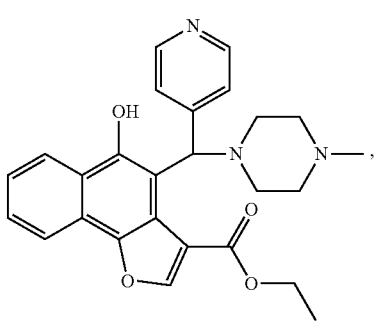
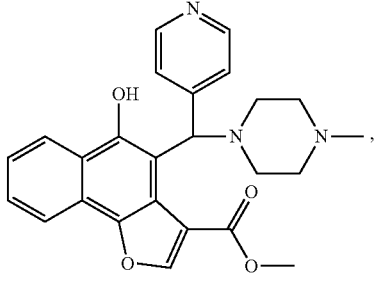
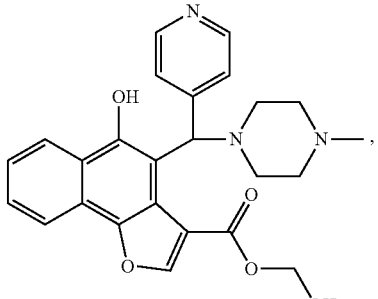
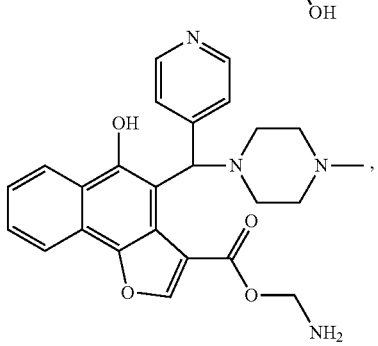

-continued
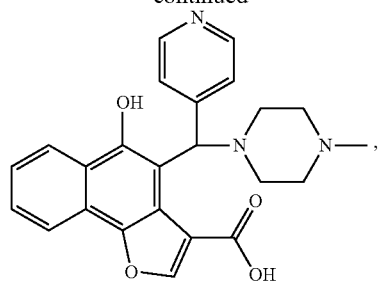
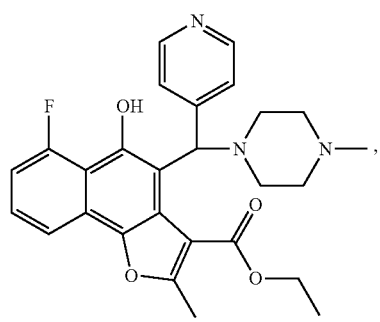
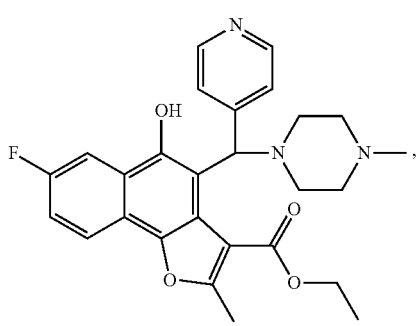
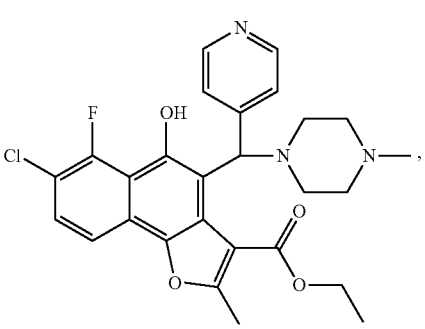
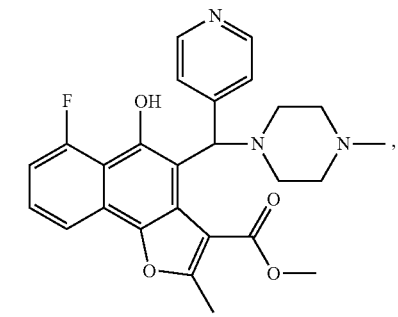
-continued
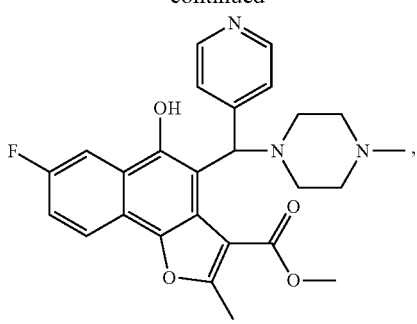
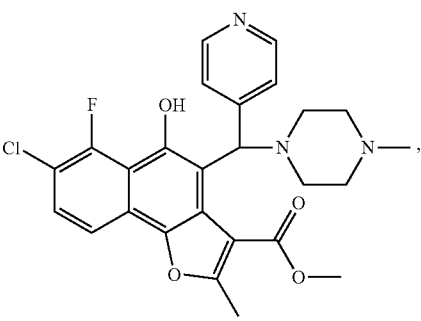
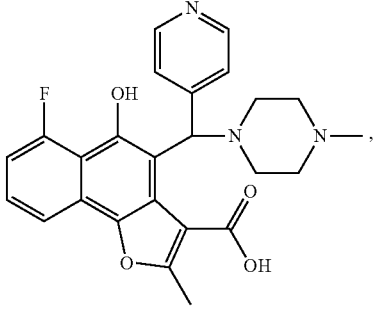
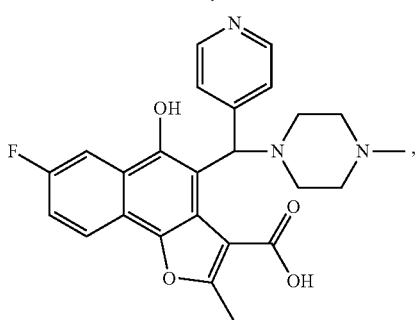
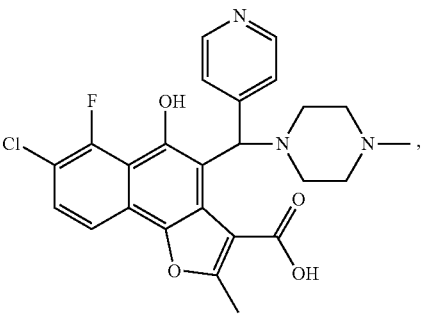

-continued
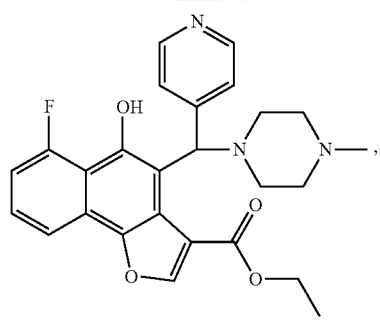
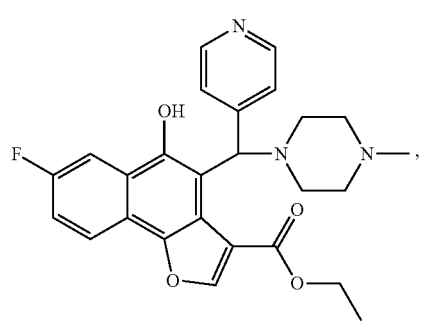
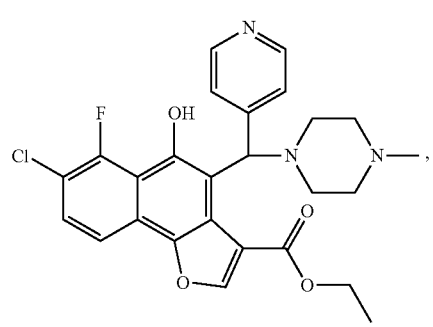
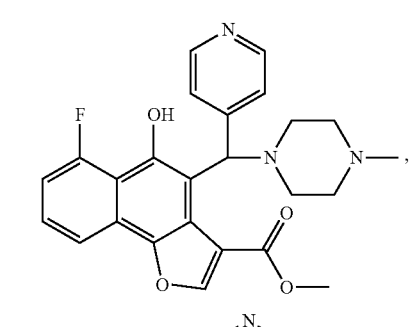
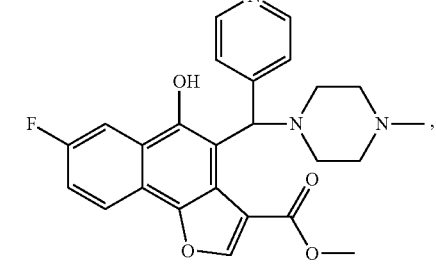
-continued
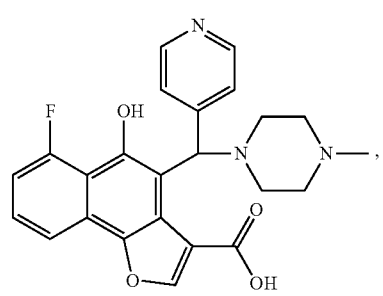
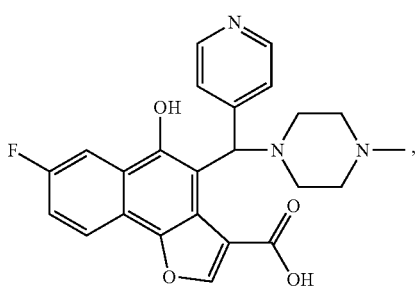
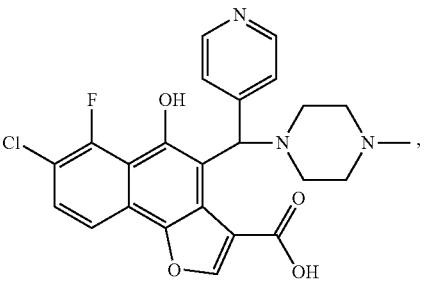
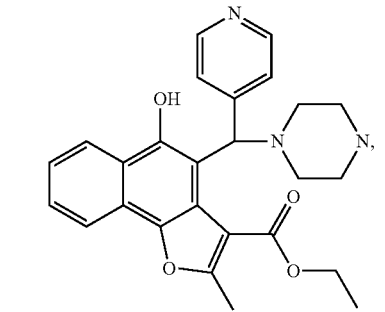

19
-continued
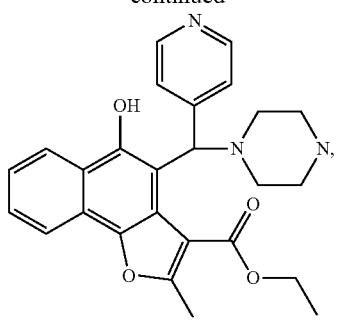
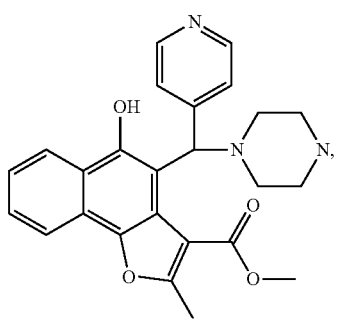
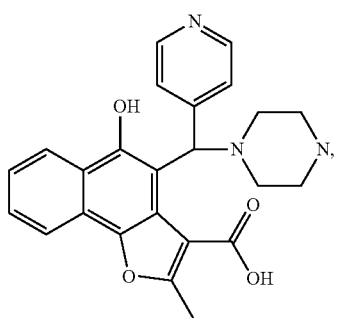
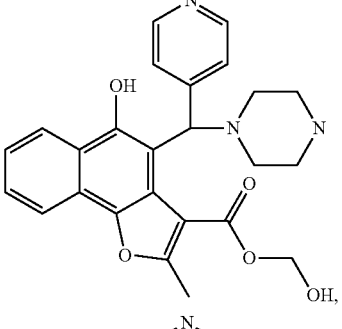
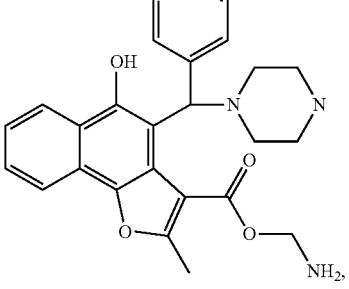
20
-continued
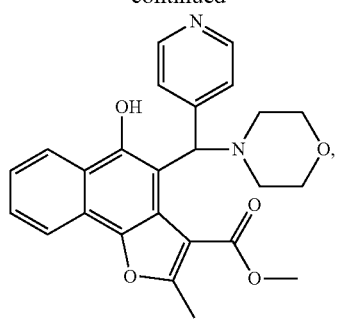
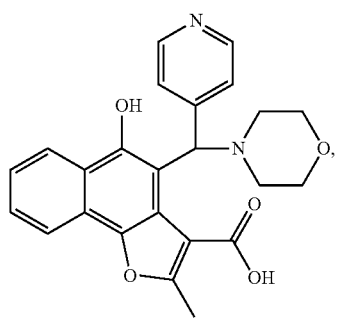
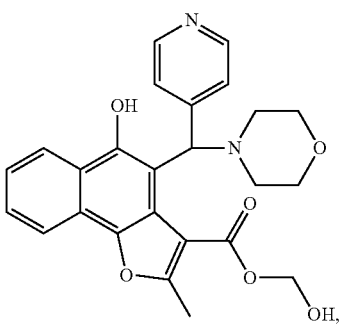
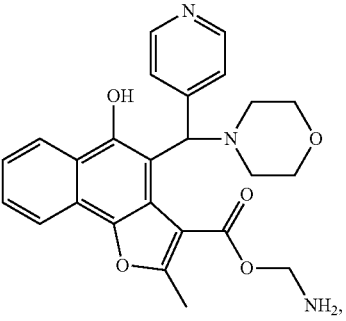
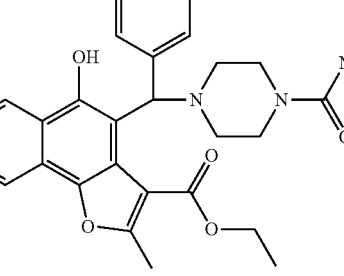

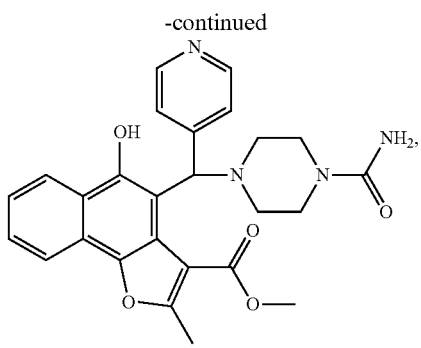
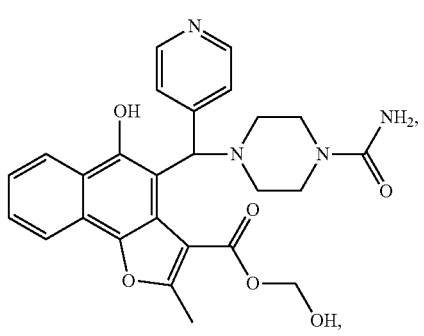
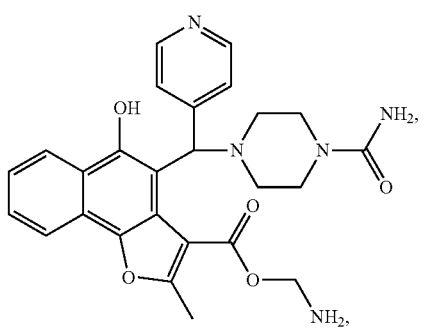
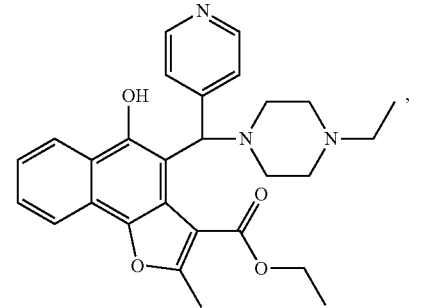
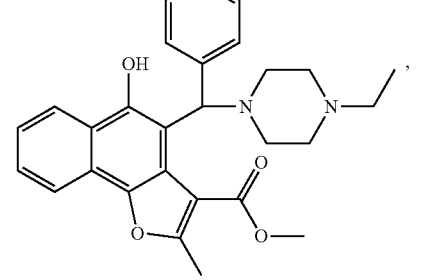
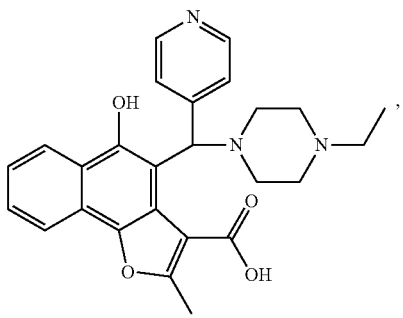
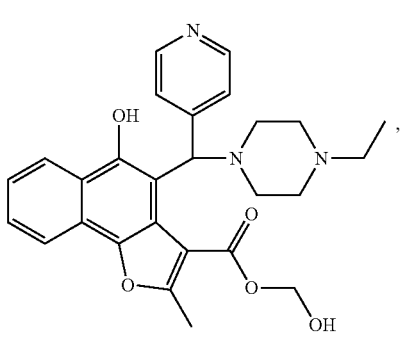
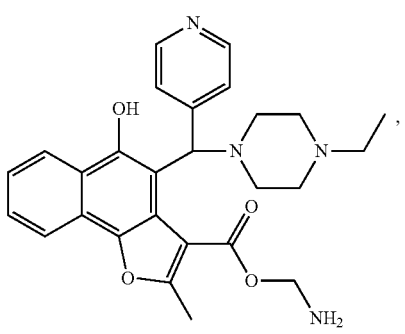
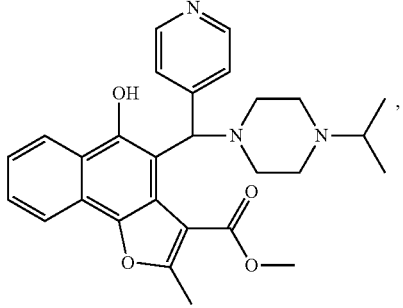
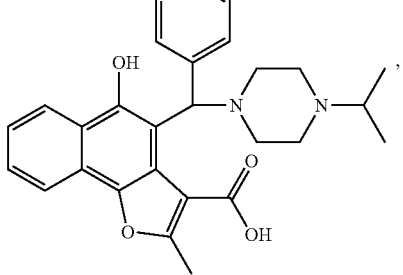

23
-continued
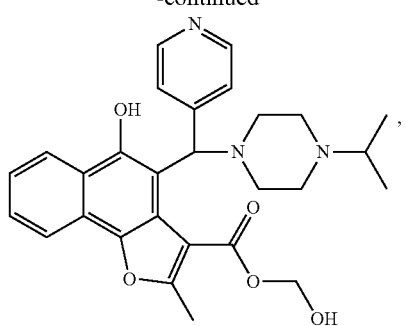
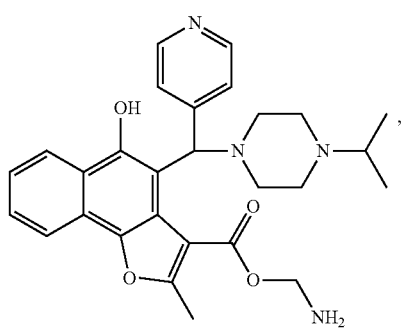
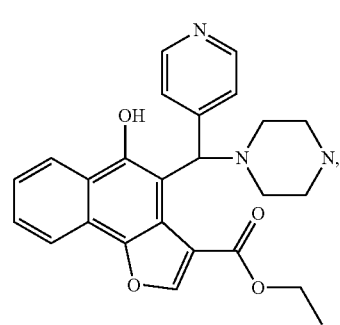
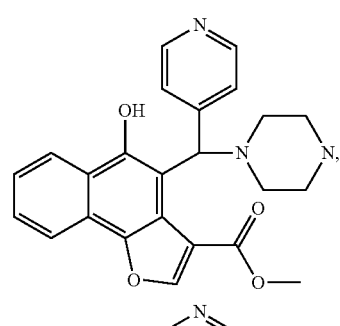
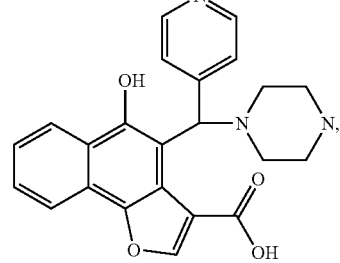
24
-continued
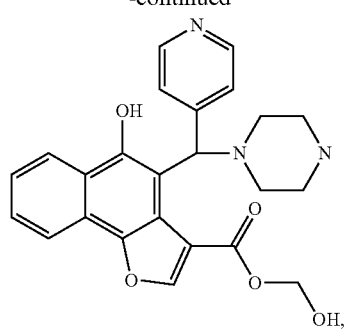
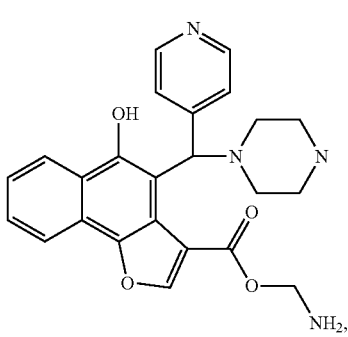
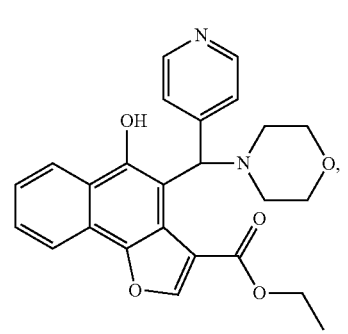
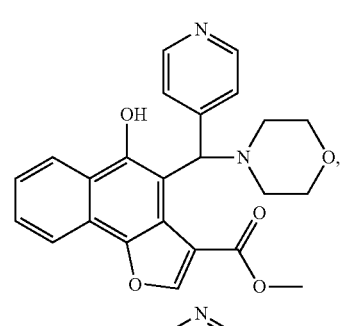
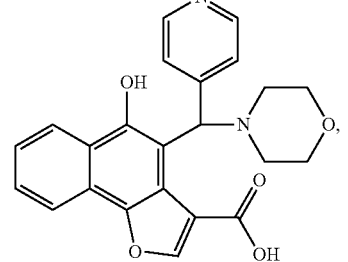

25
-continued
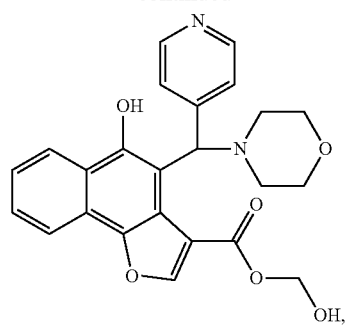
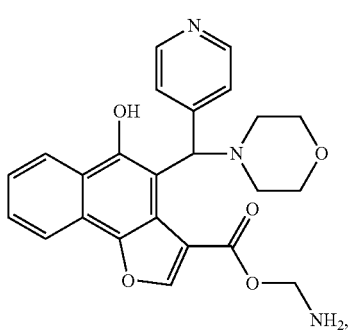
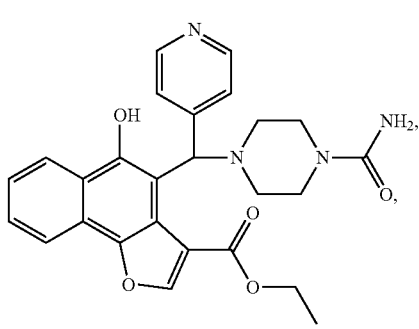
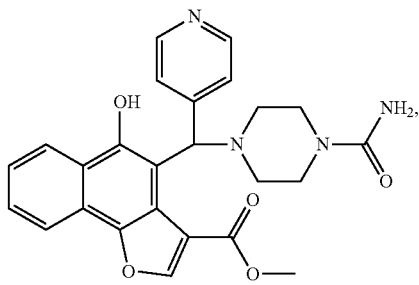
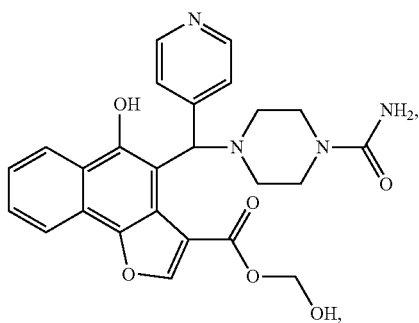
26
-continued
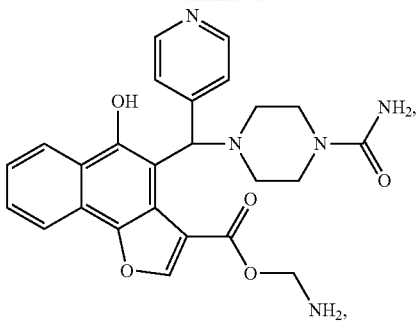
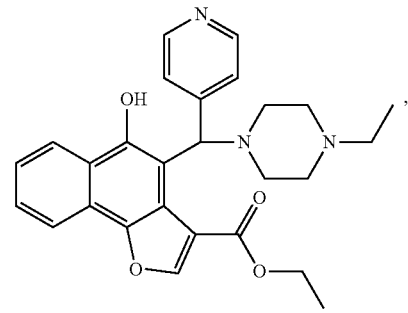
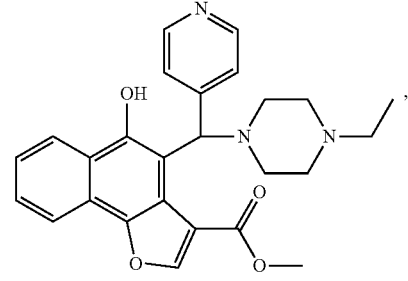
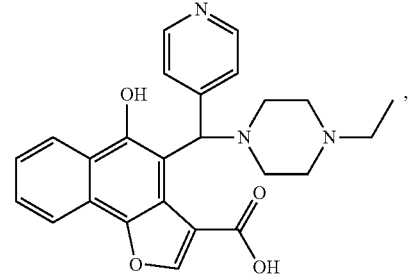
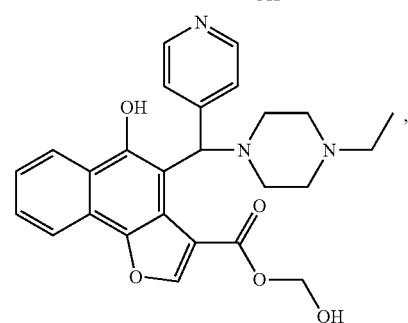

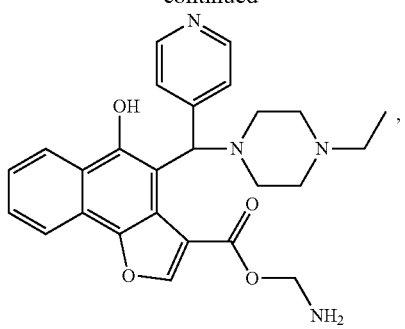
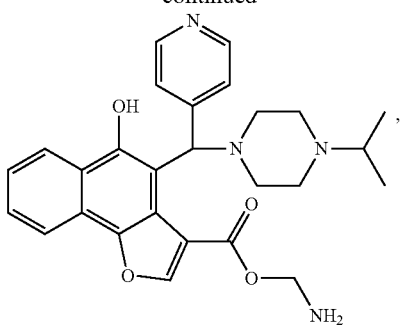

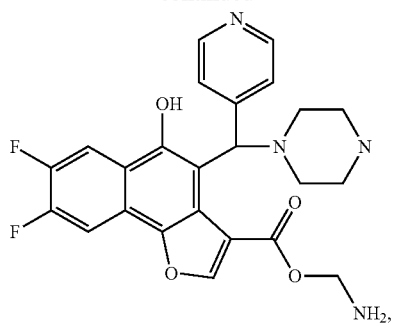
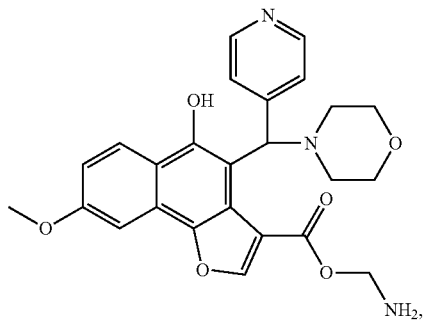
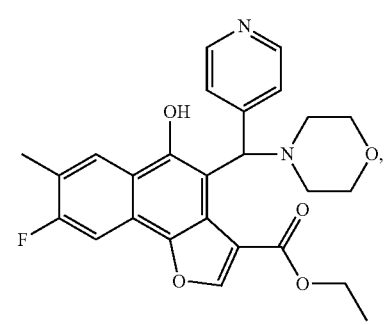
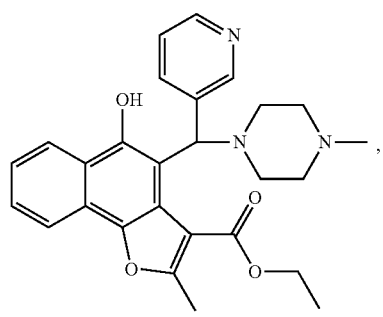
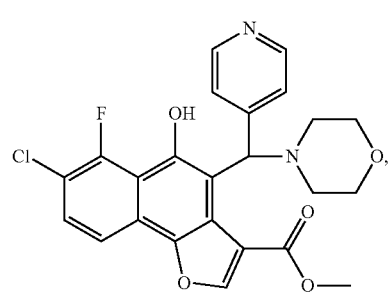
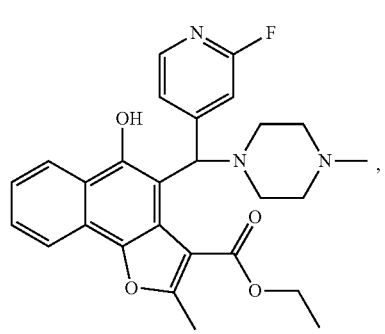
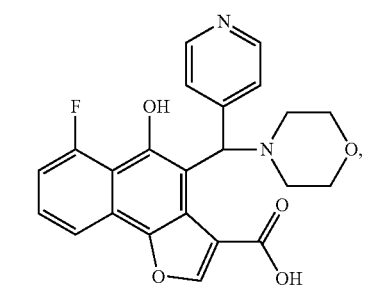
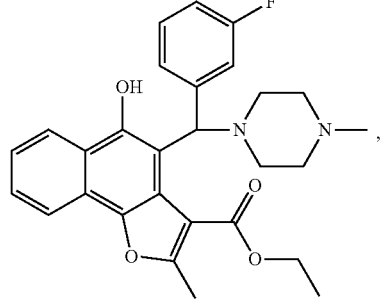
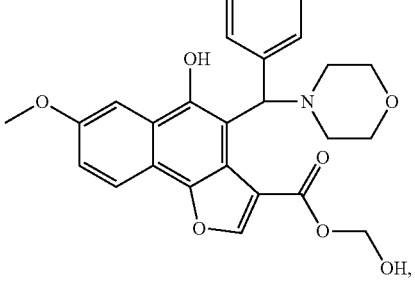
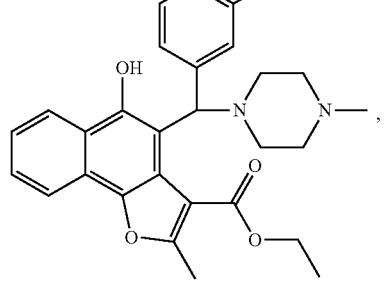

31
-continued
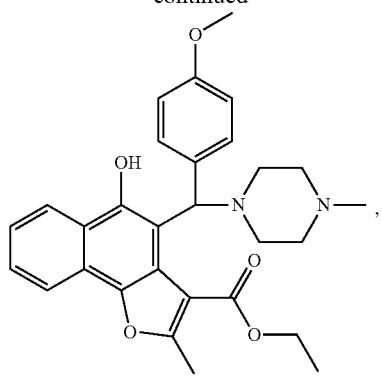
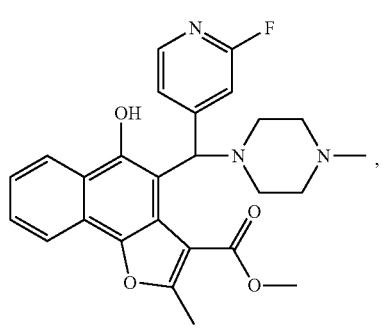
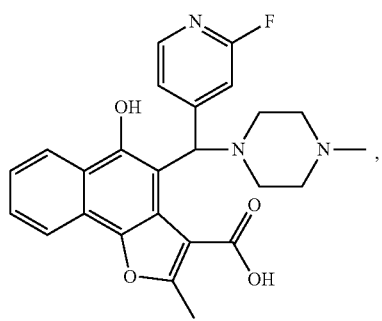
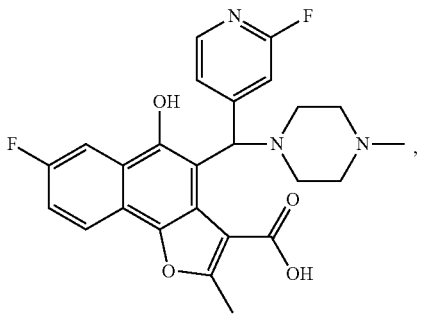
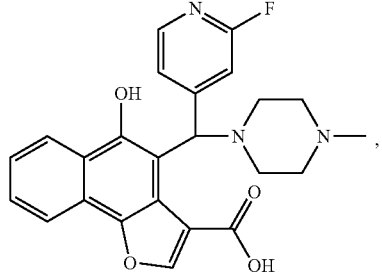
32
-continued
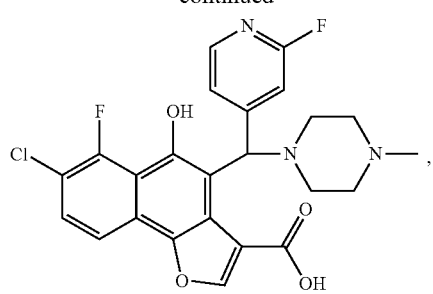
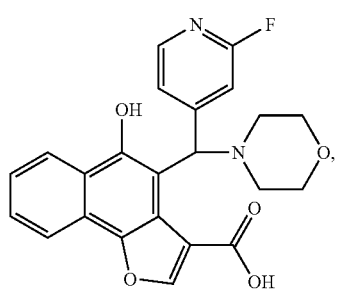
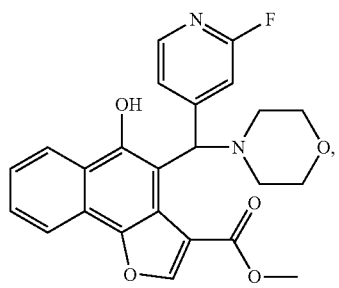
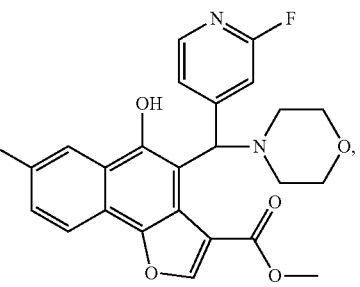
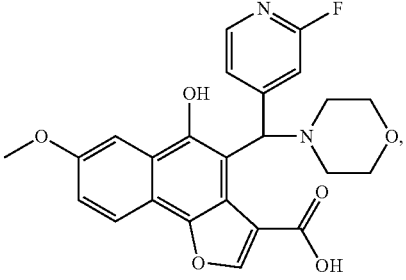

33
-continued
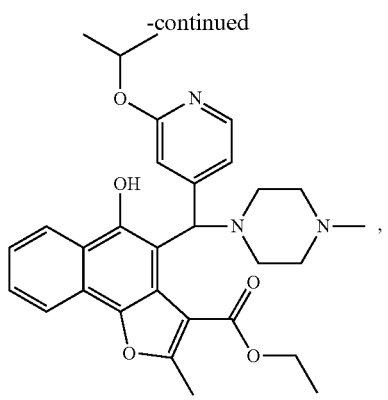
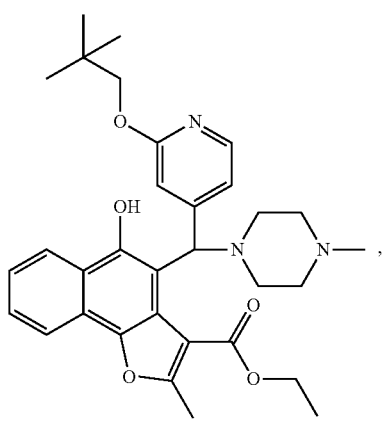
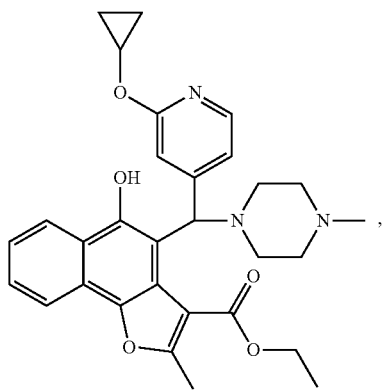
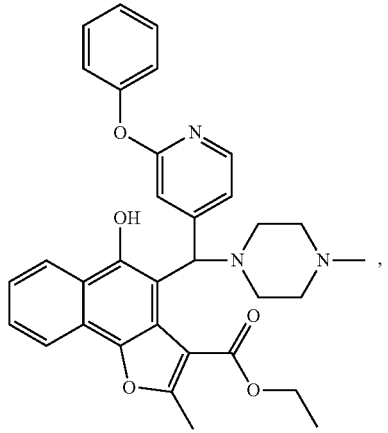
34
-continued
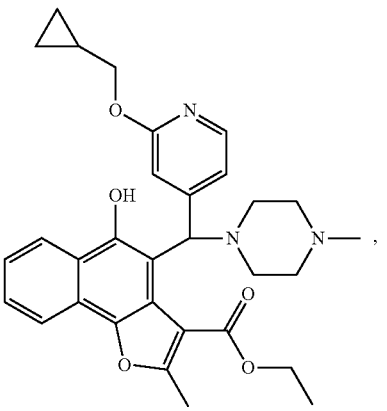
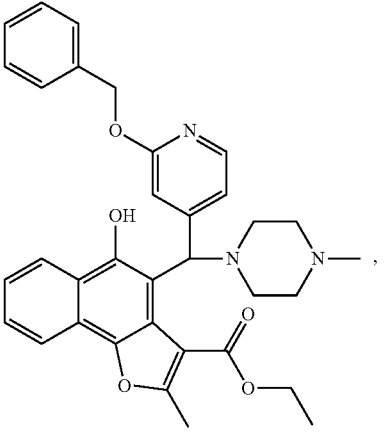
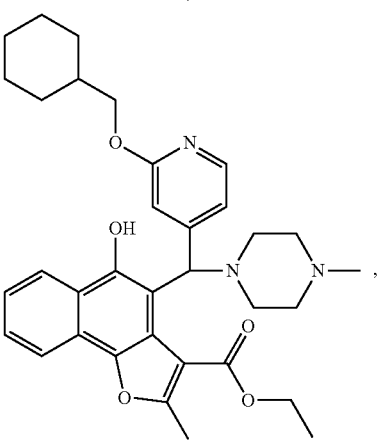
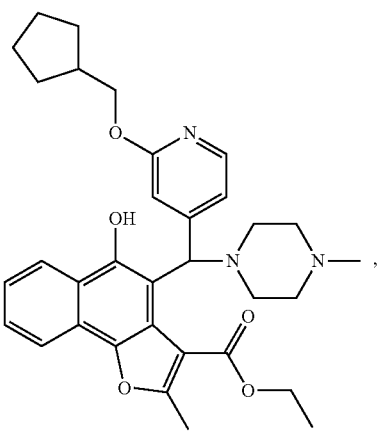

35
-continued
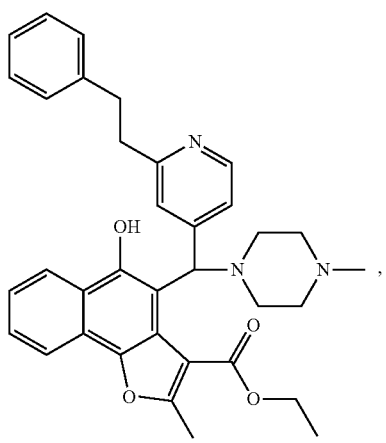
36
-continued
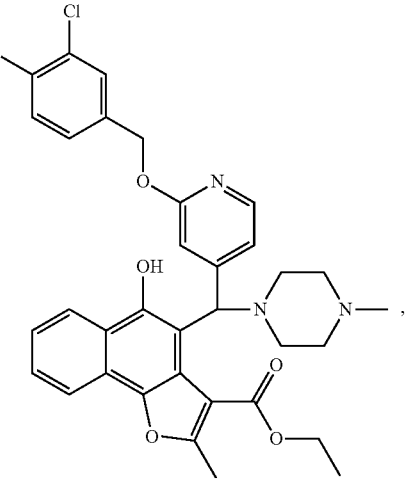
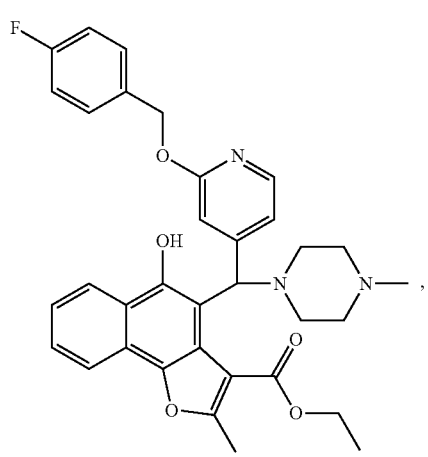
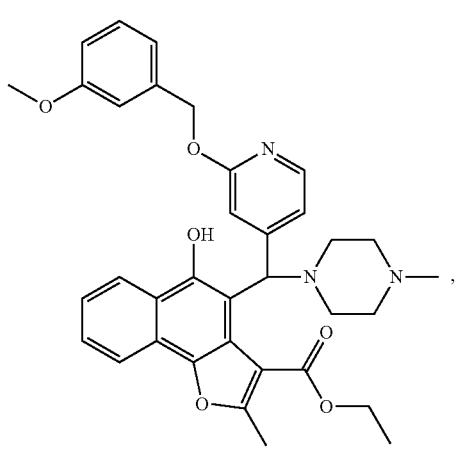
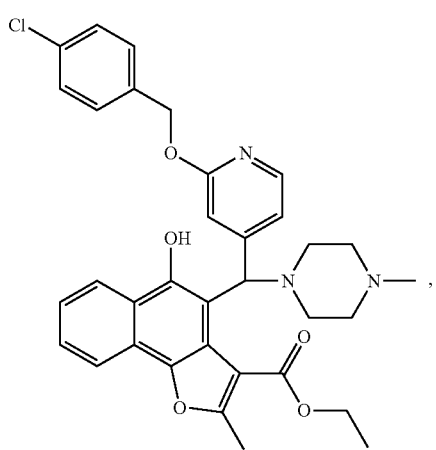
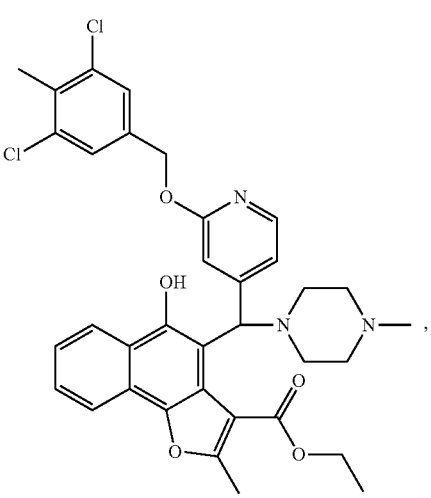

37
-continued
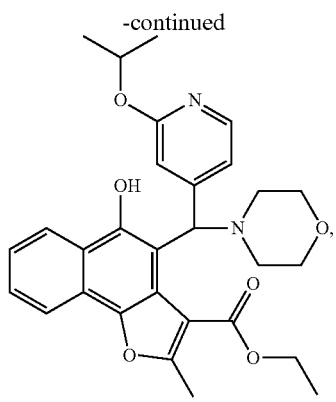
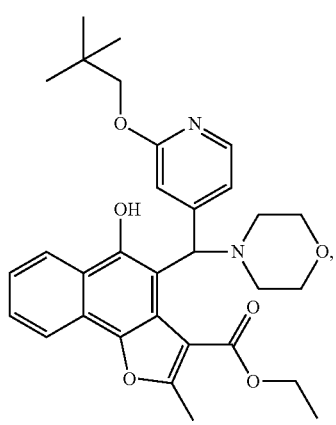
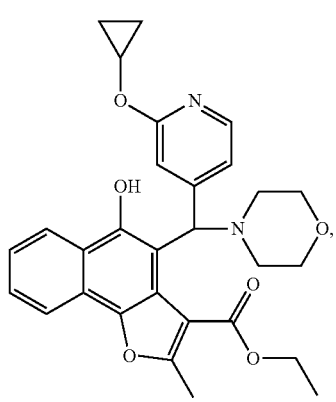
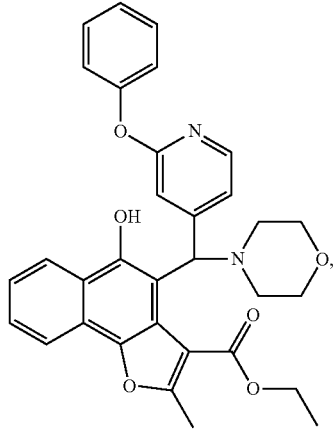
38
-continued
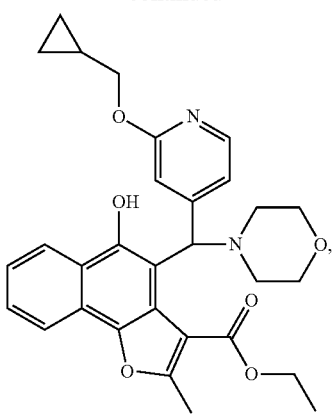
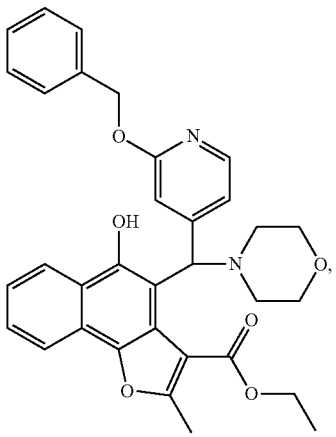
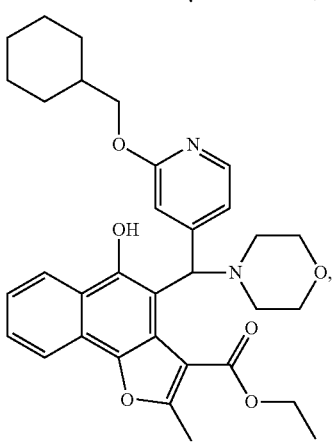
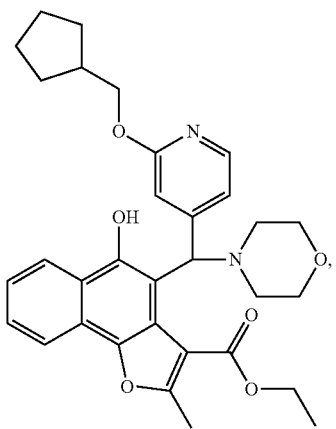

39
-continued
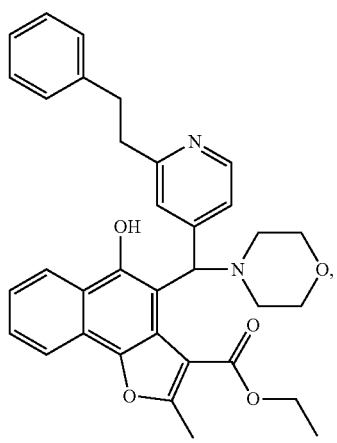
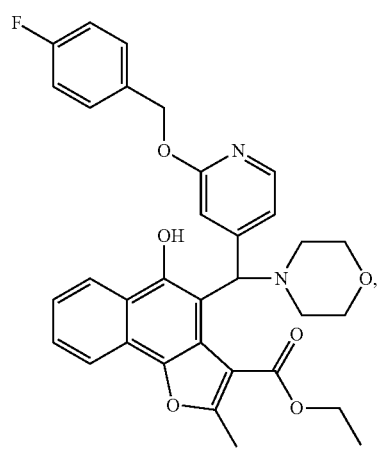
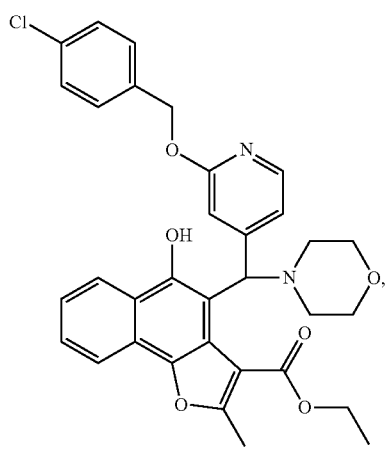
40
-continued
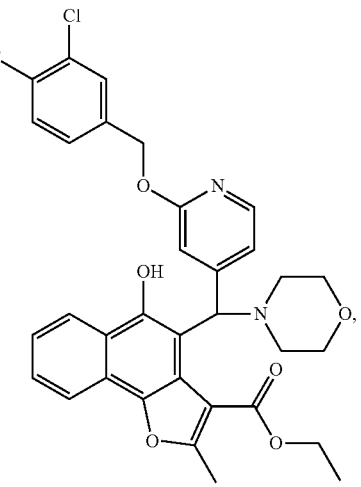
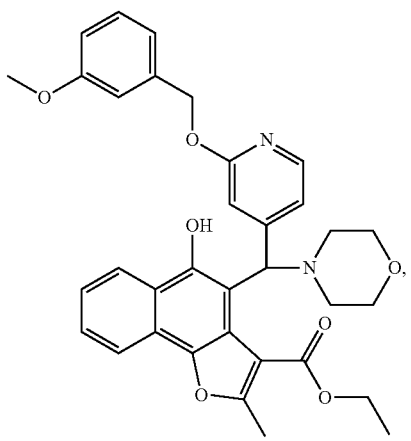
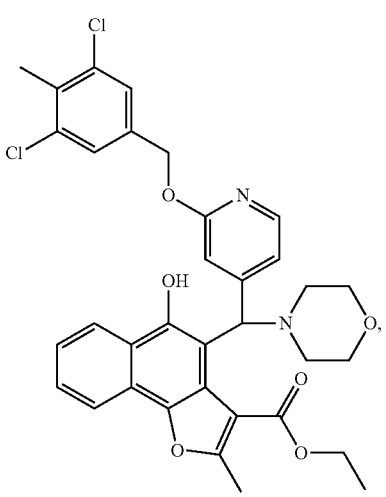

-continued
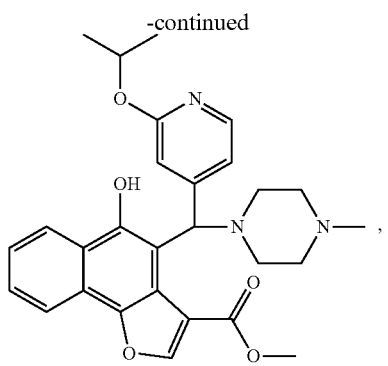
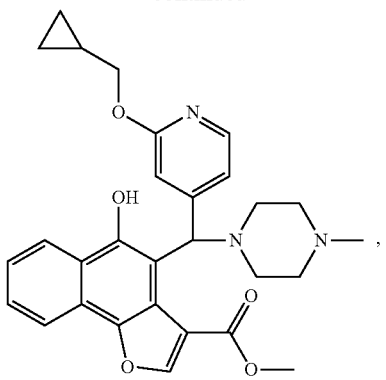
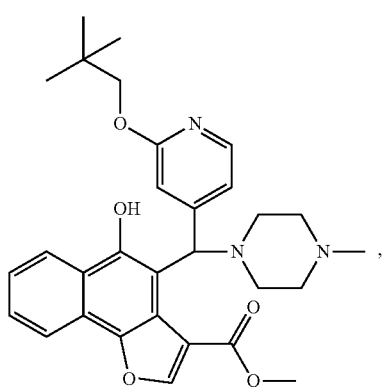
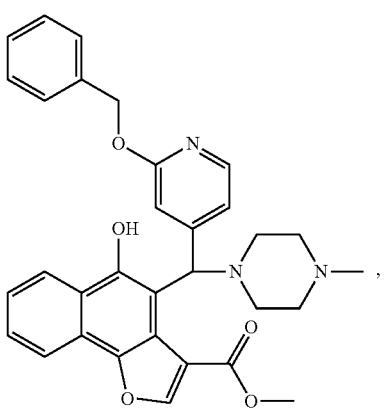
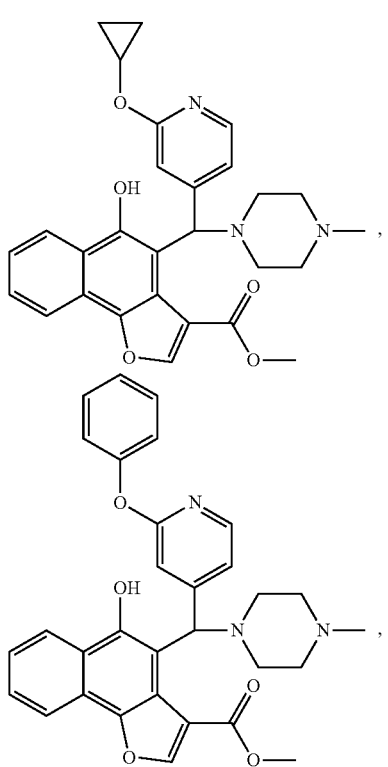
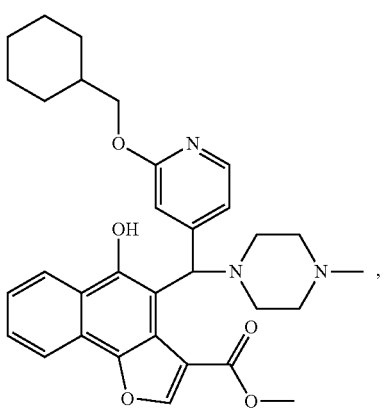
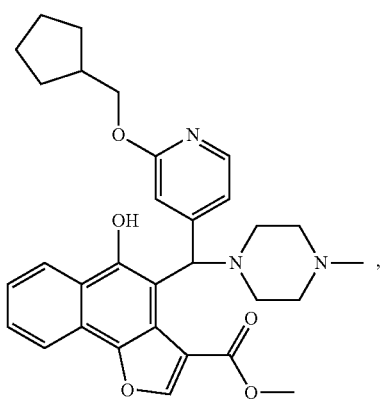

43
-continued
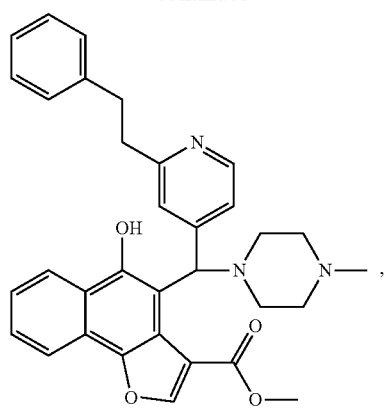
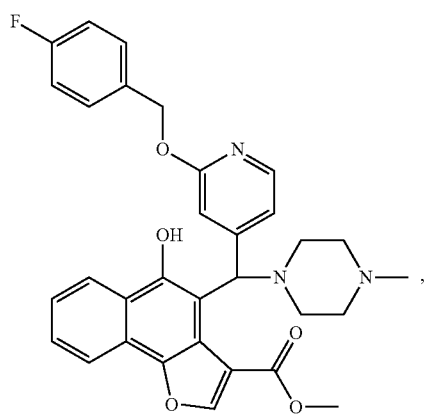
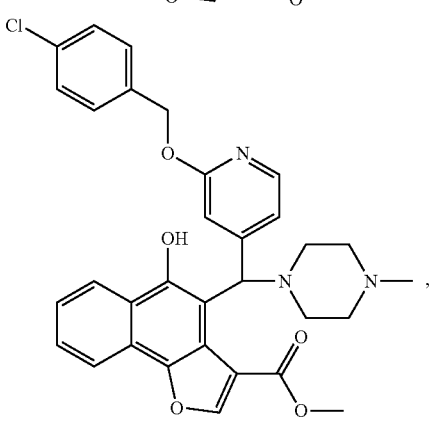
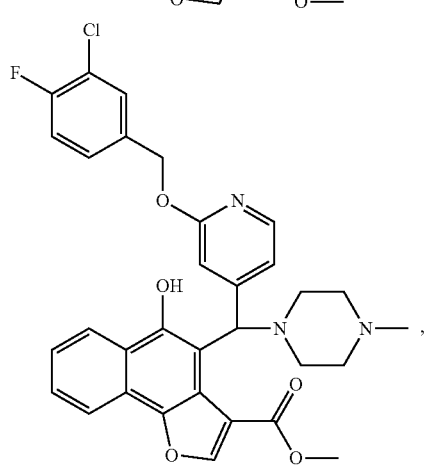
44
-continued
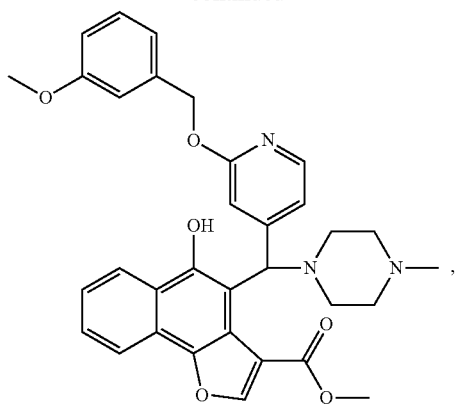
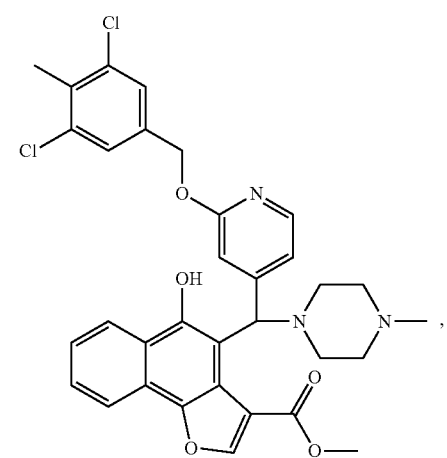
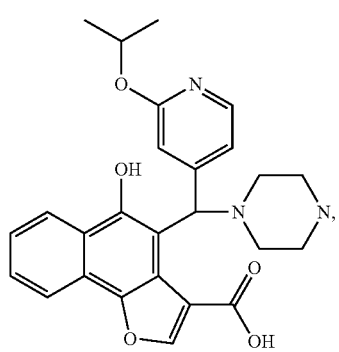
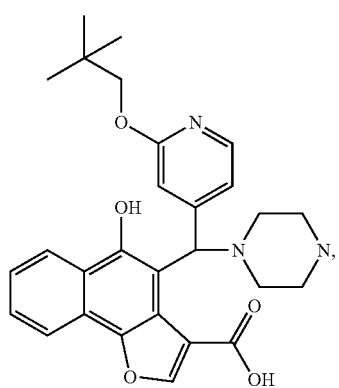

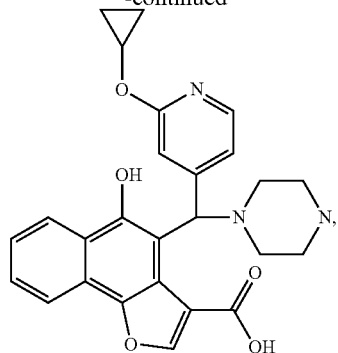
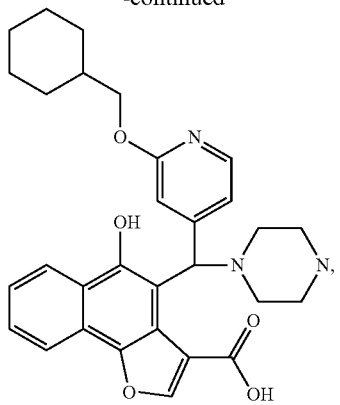

47
-continued
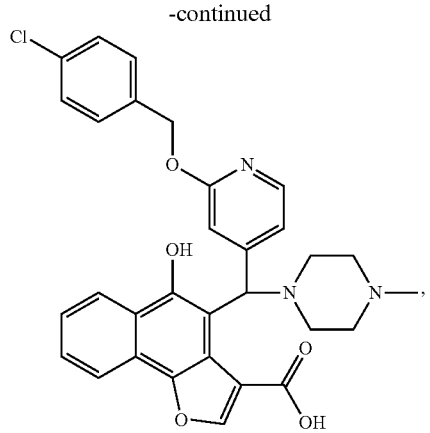
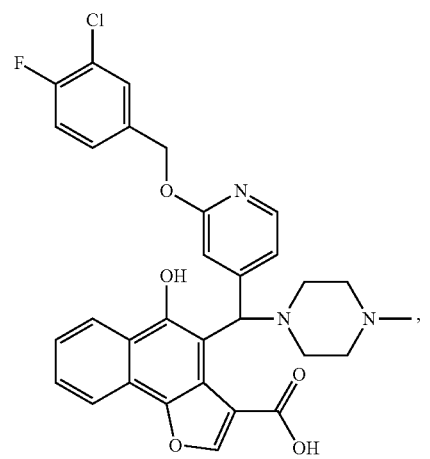
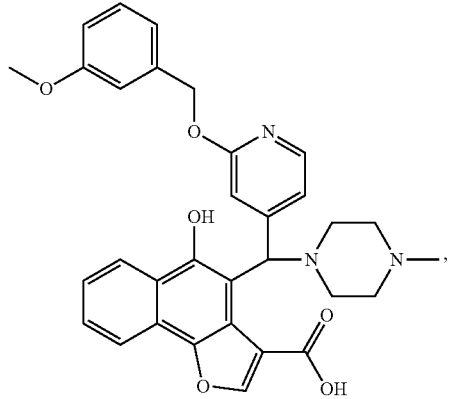
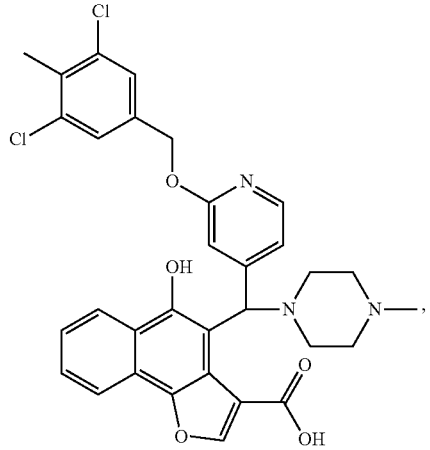
48
-continued
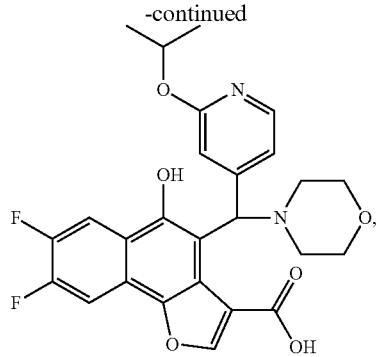
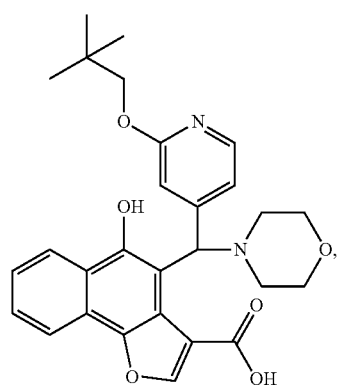
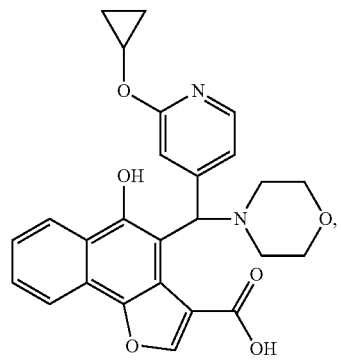
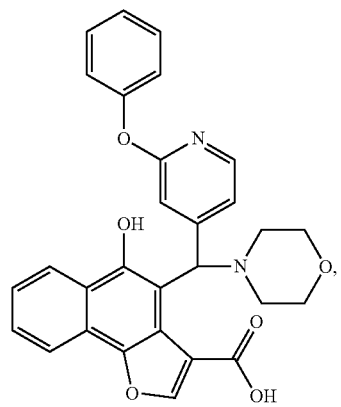

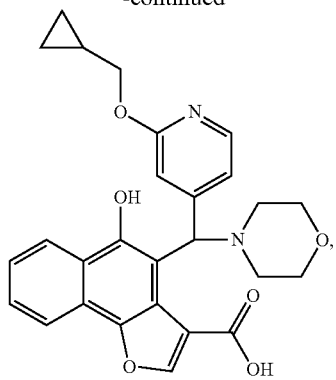
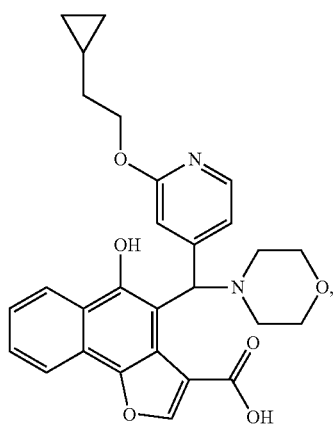
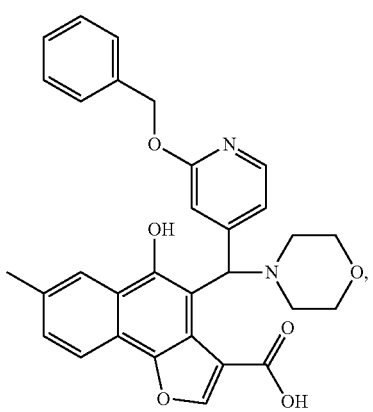
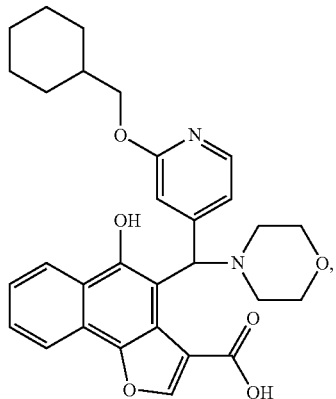
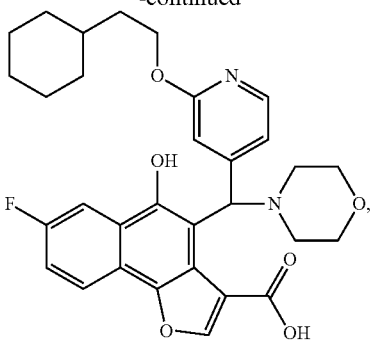
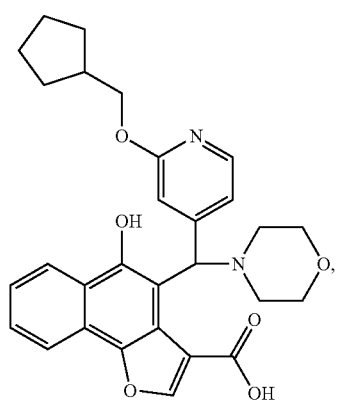
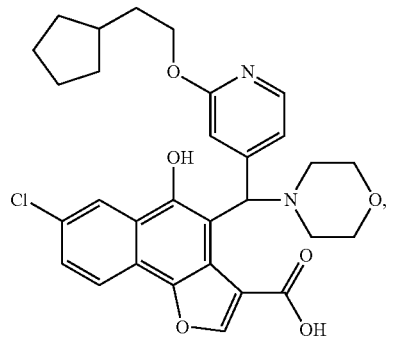
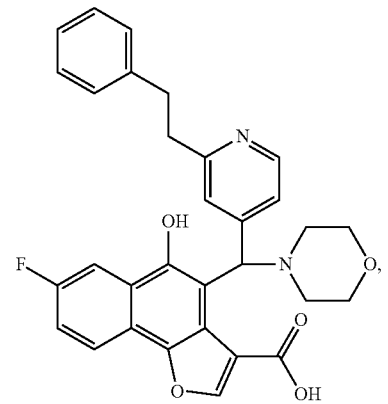

51
-continued
52
-continued
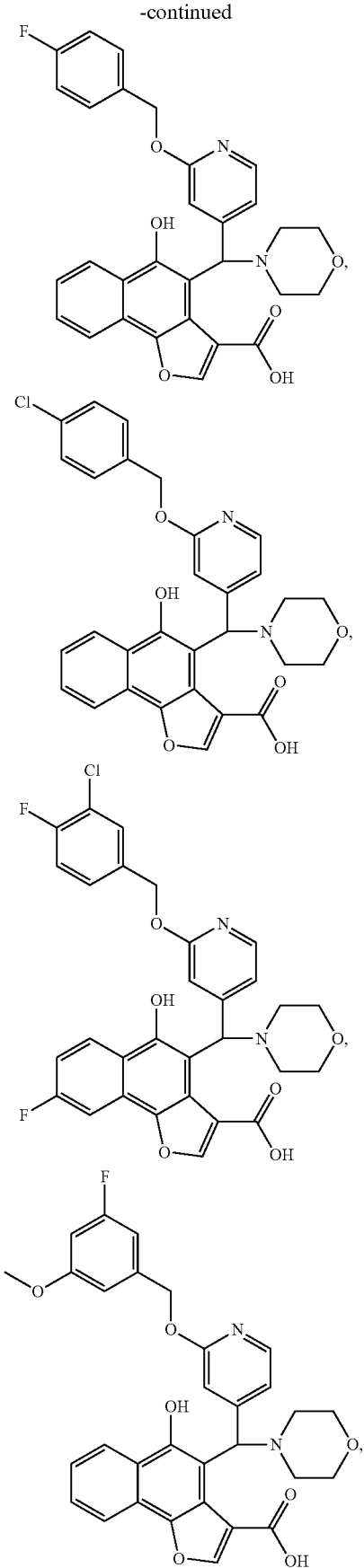
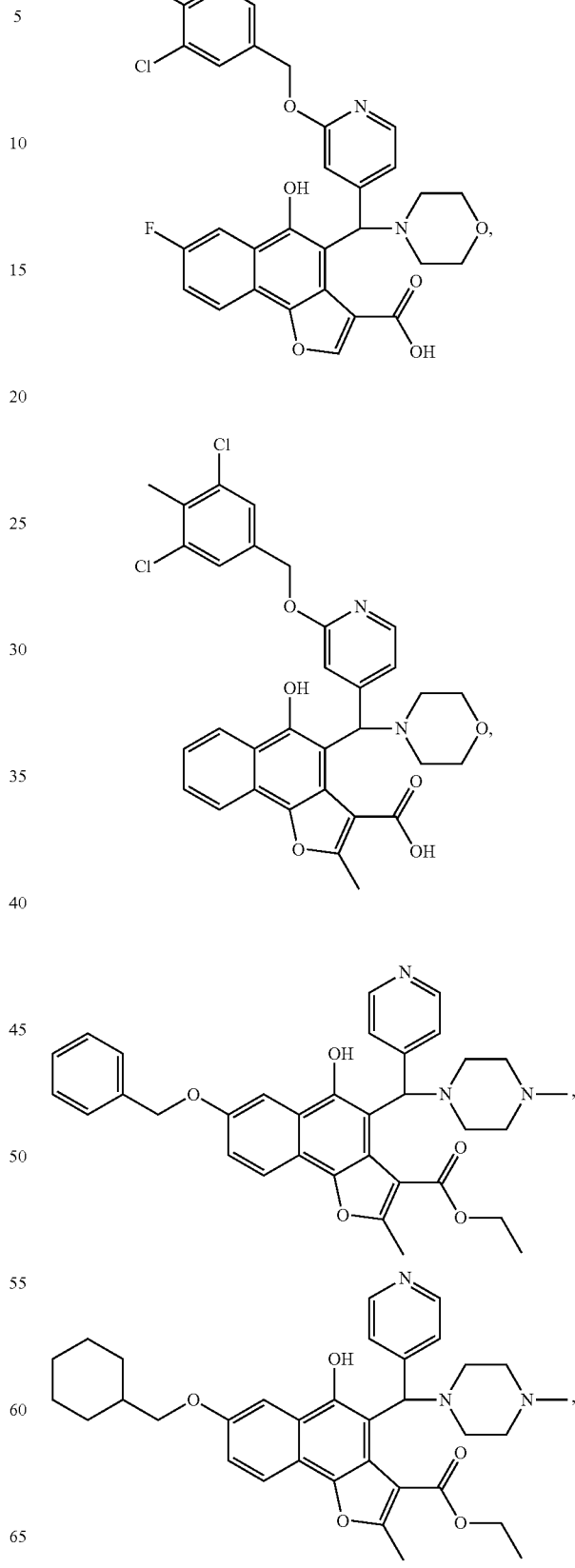

53
-continued
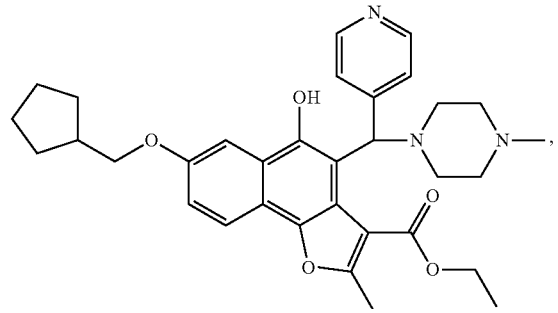
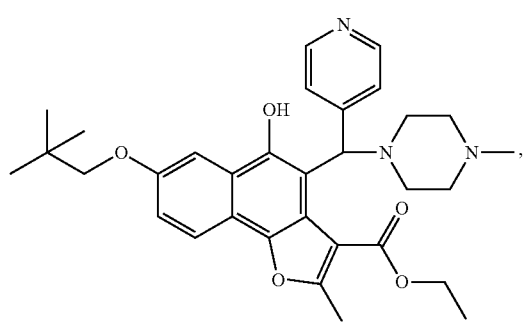
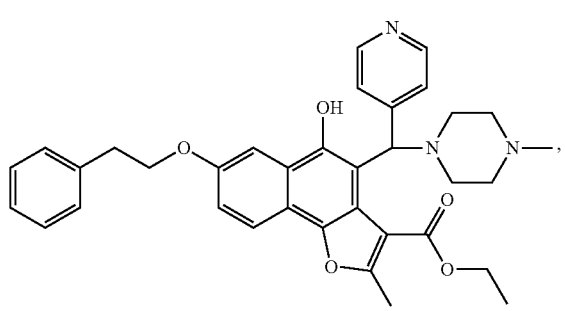
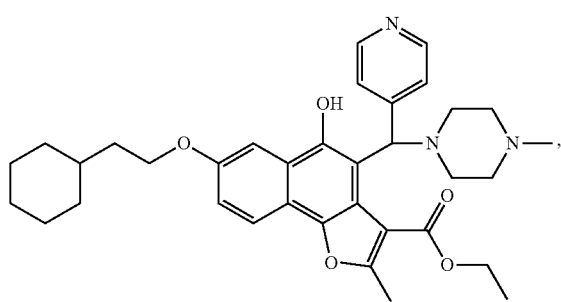
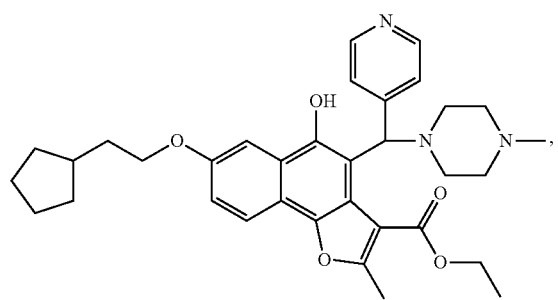
54
-continued
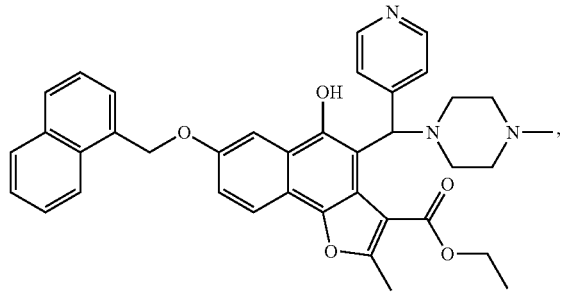
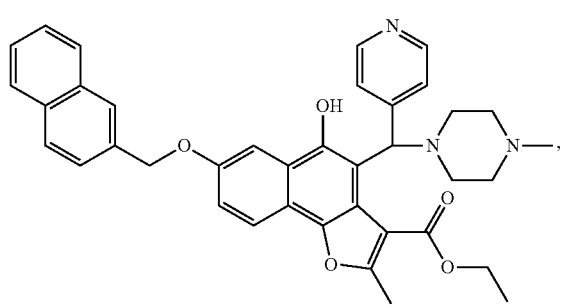
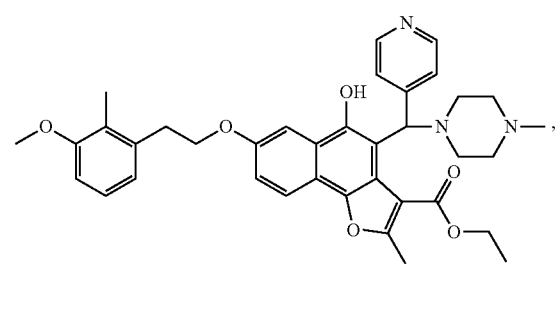
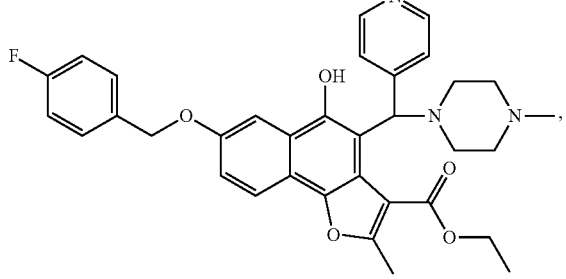
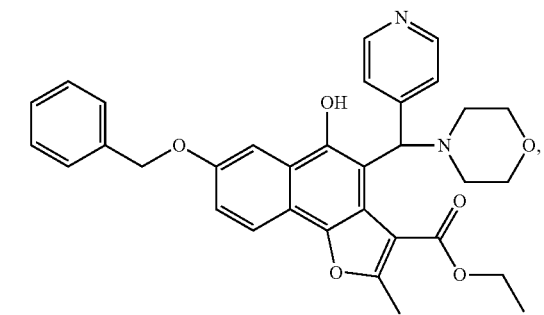

55
-continued
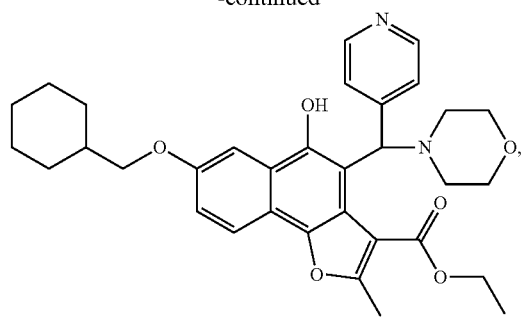
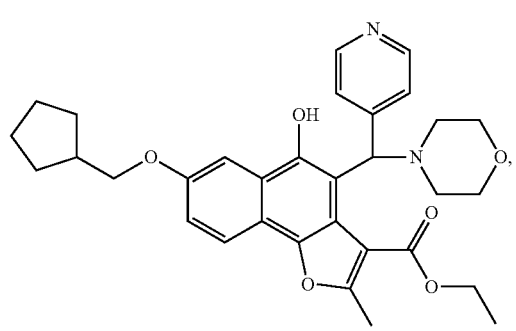
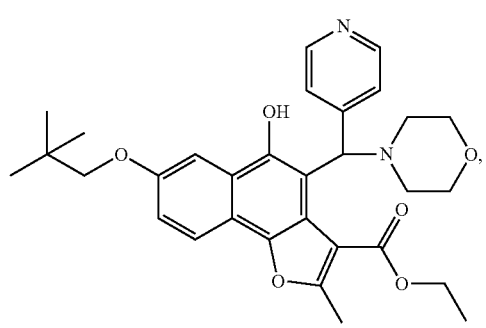
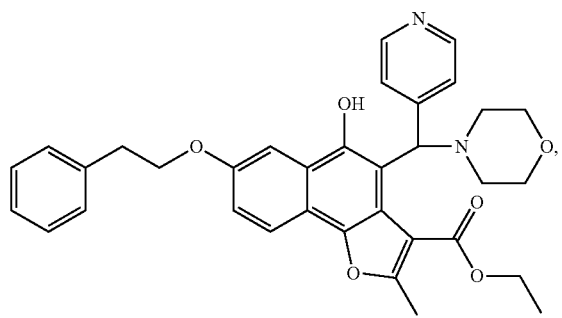
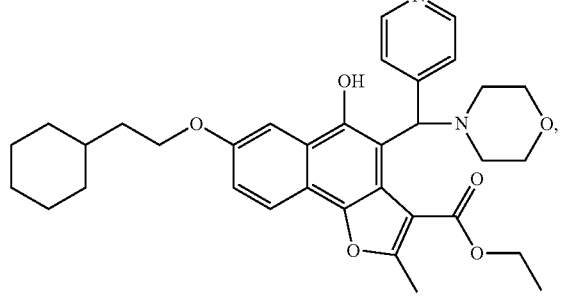
56
-continued
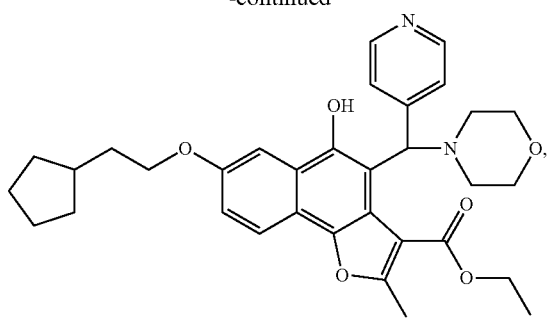
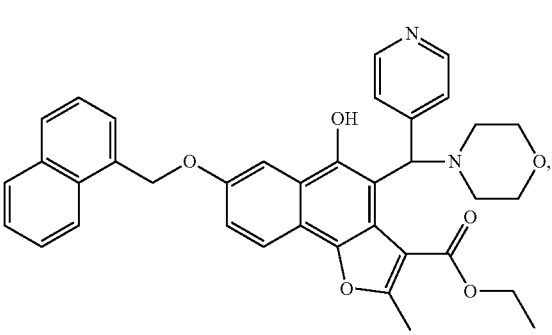
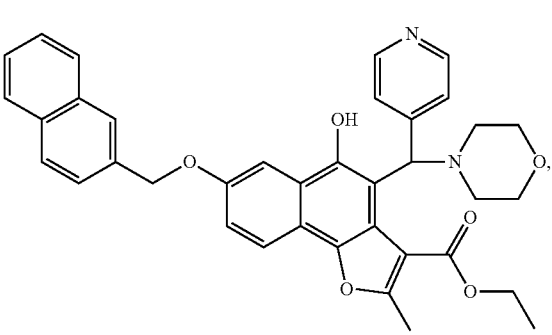
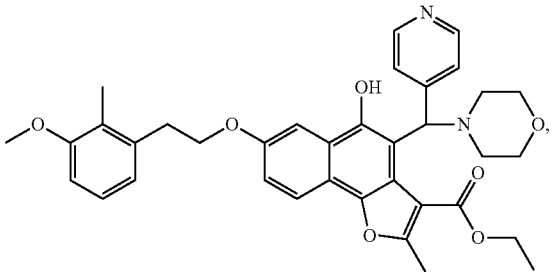
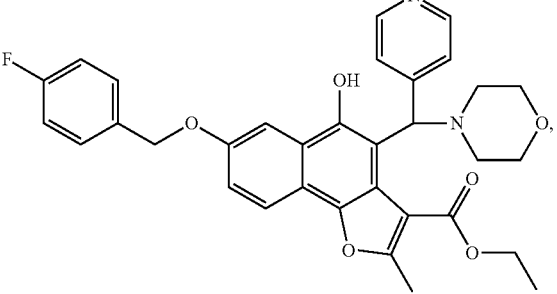

57
-continued
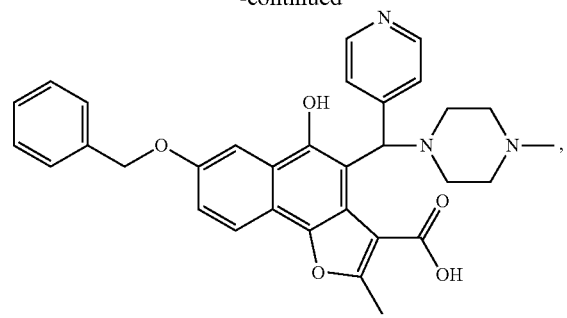
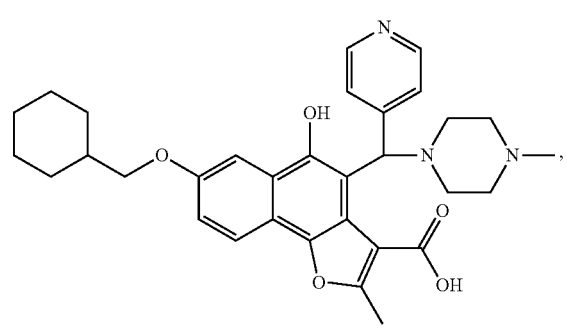
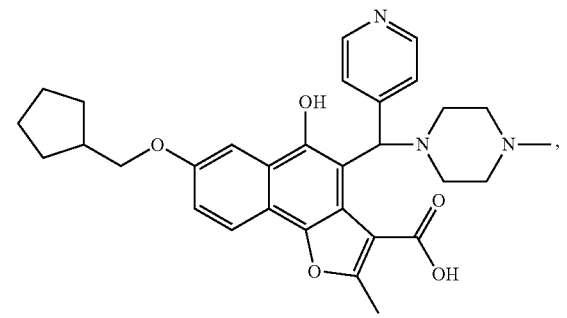
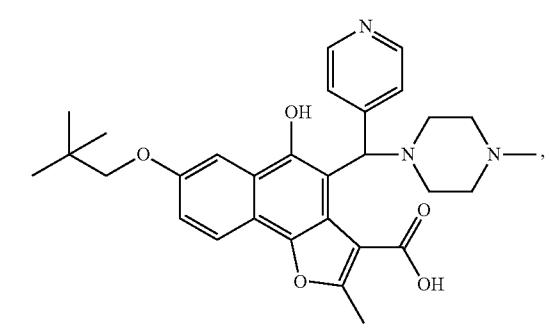
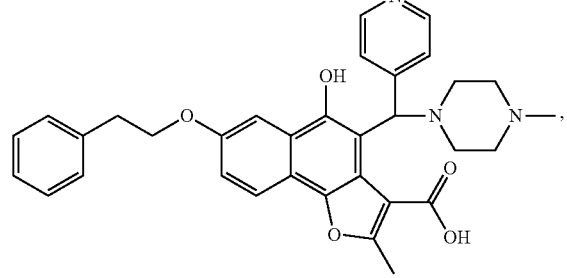
58
-continued
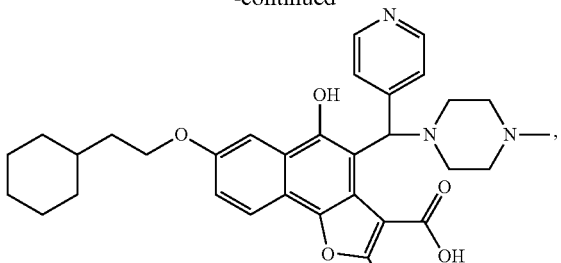
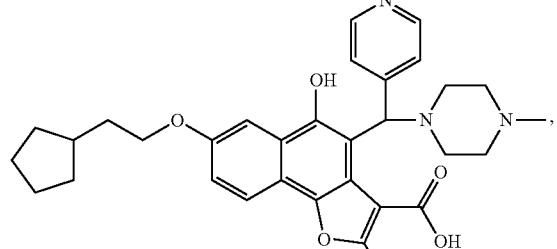
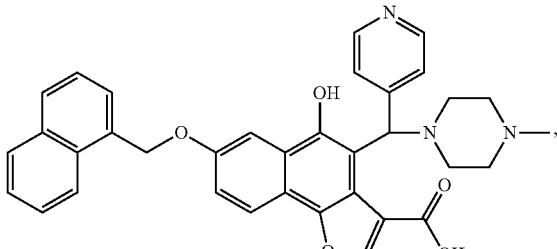
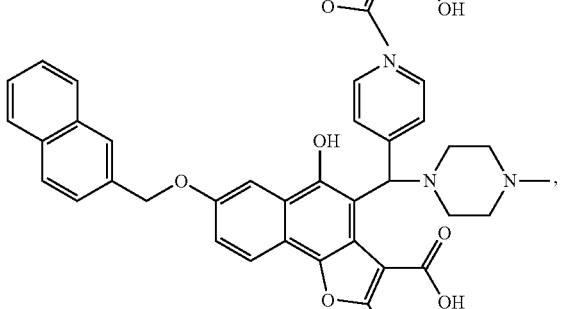
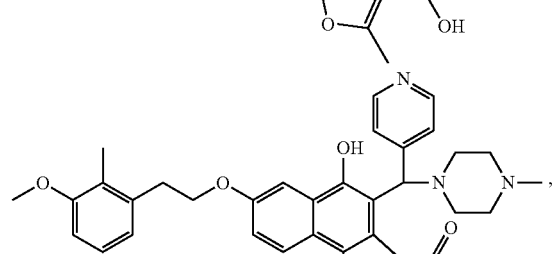
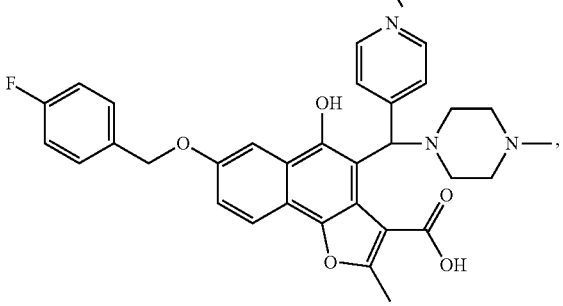

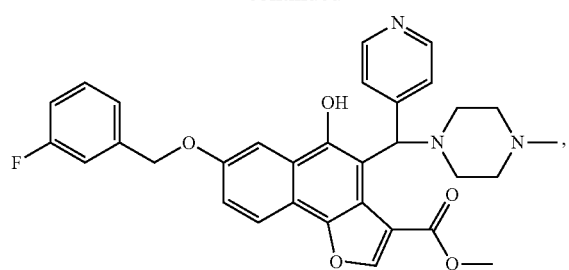
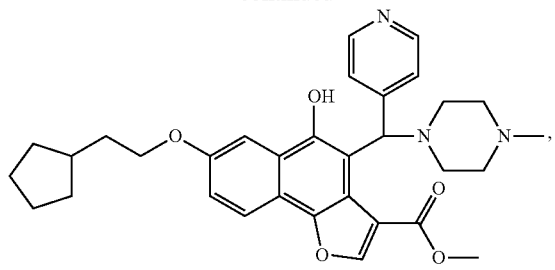
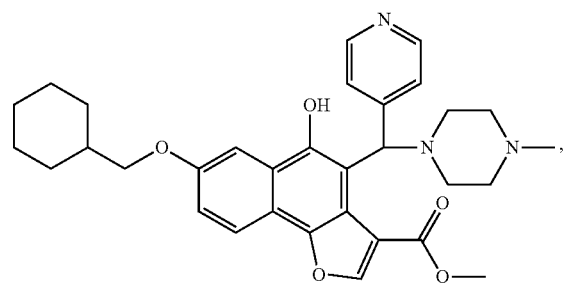
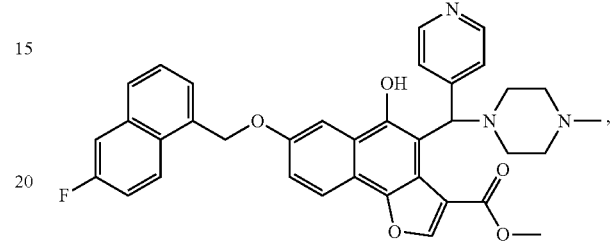
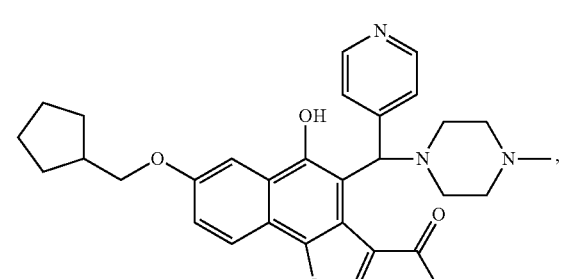
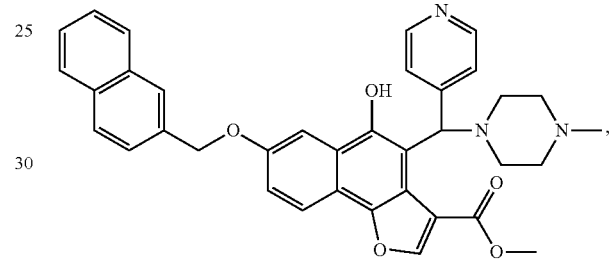
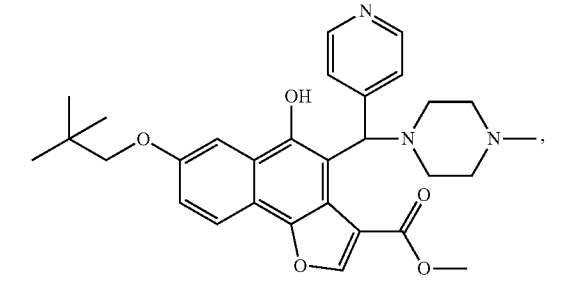
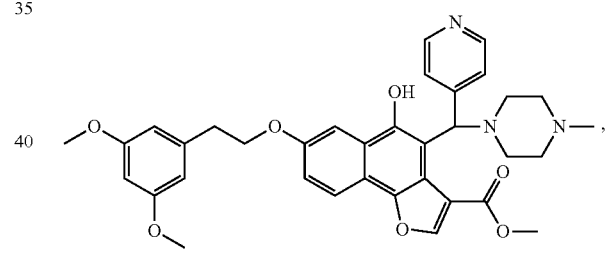
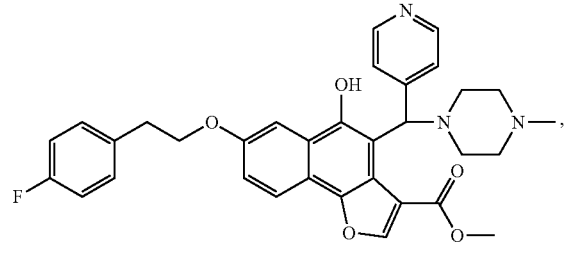
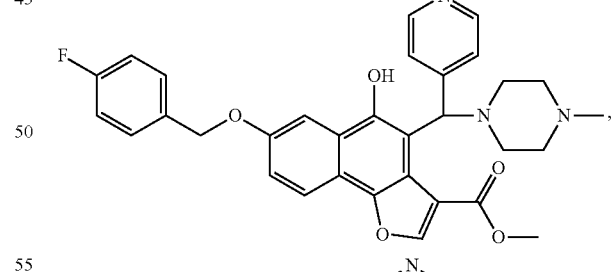
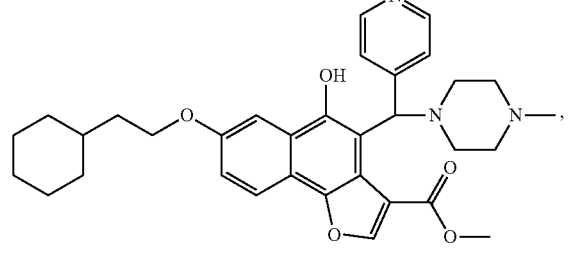
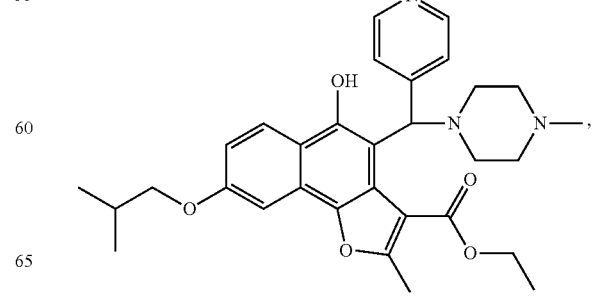

61
-continued
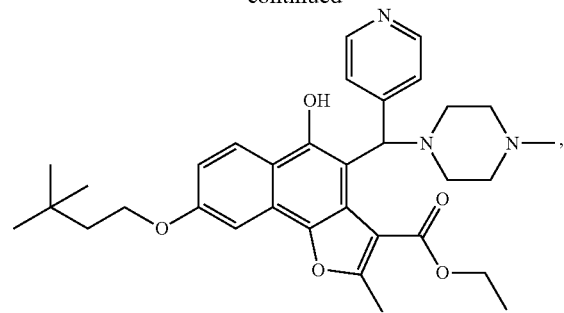
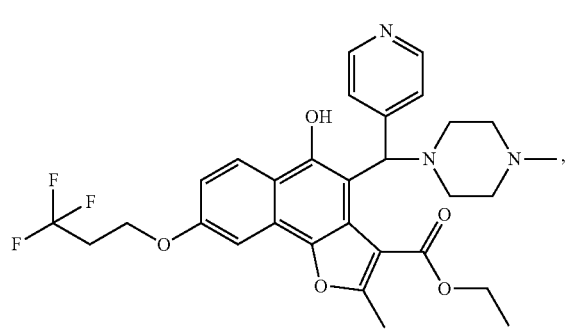
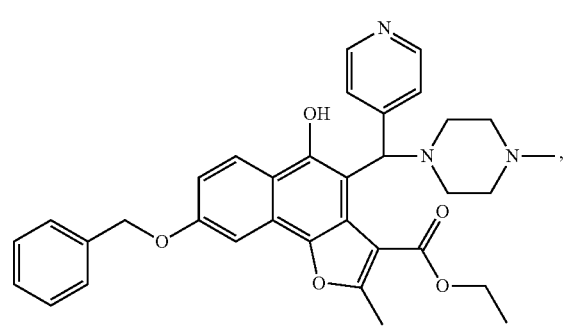
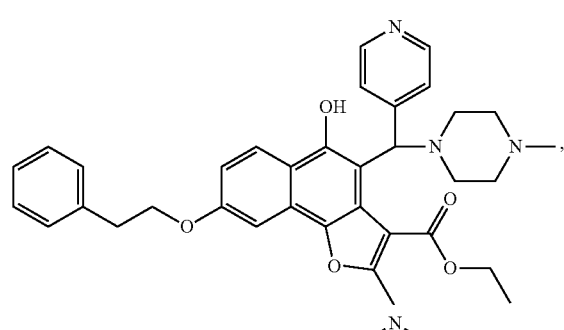
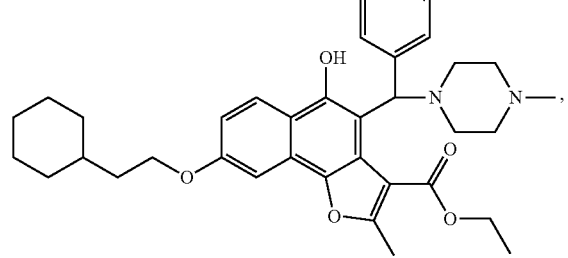
62
-continued
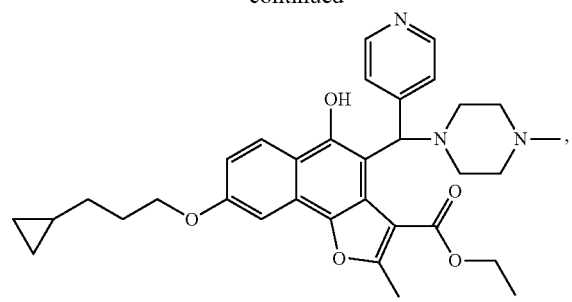
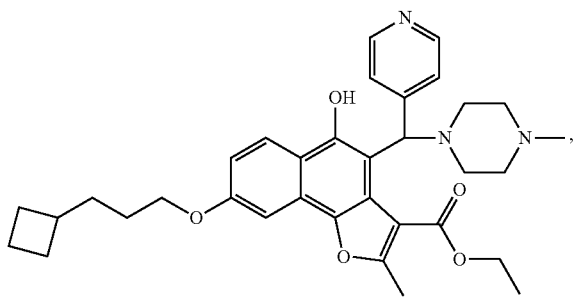
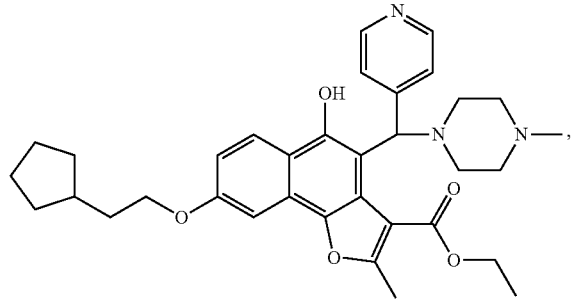
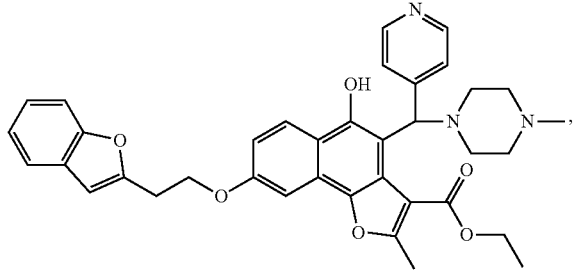
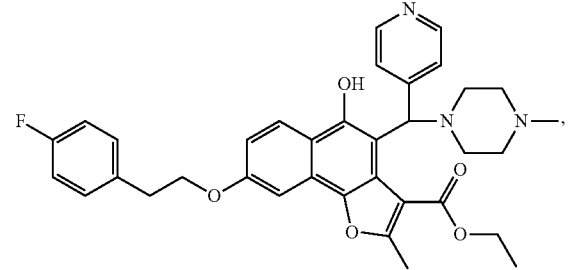

63
-continued
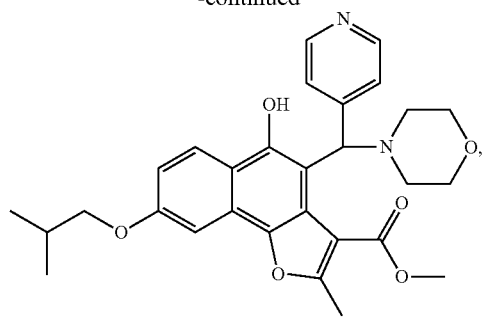
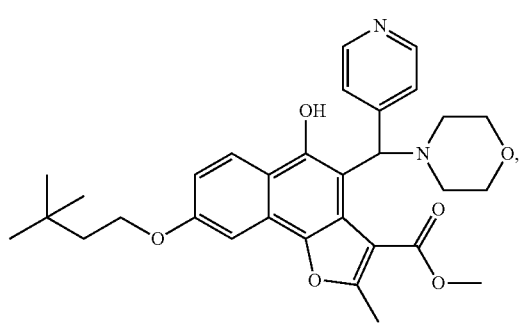
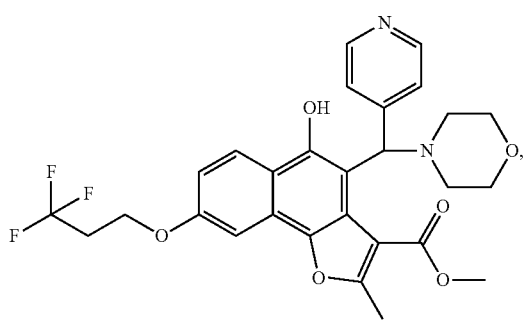
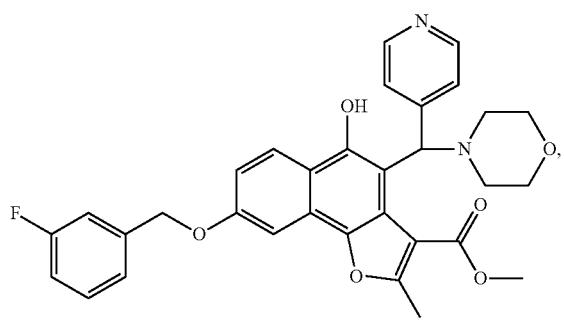
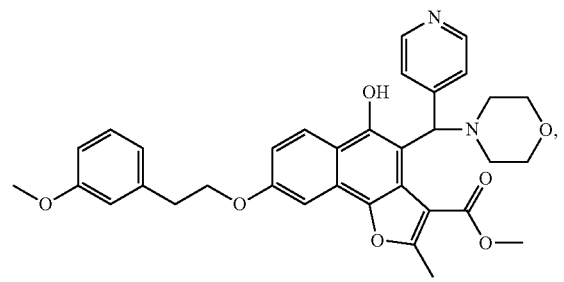
64
-continued
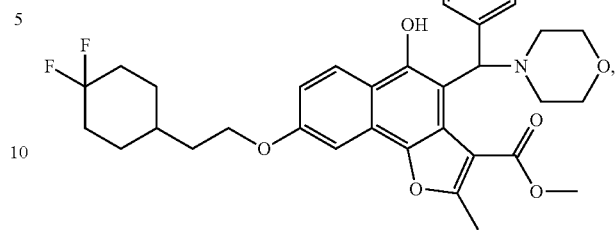
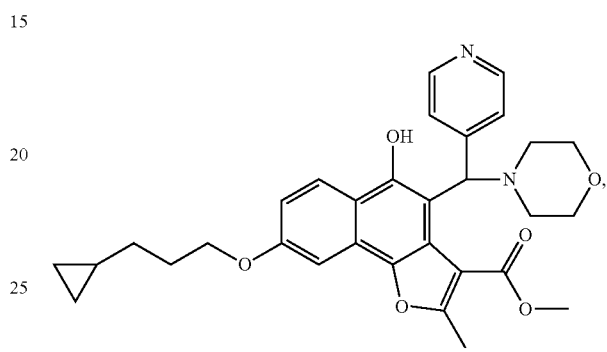
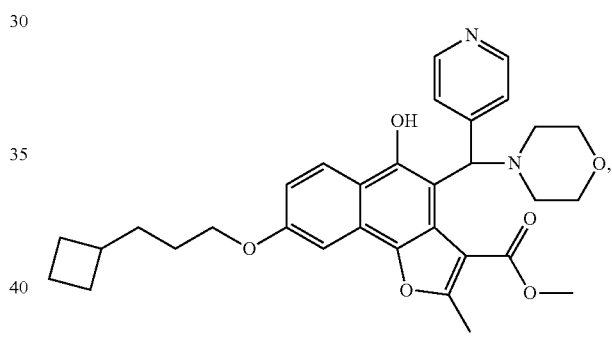
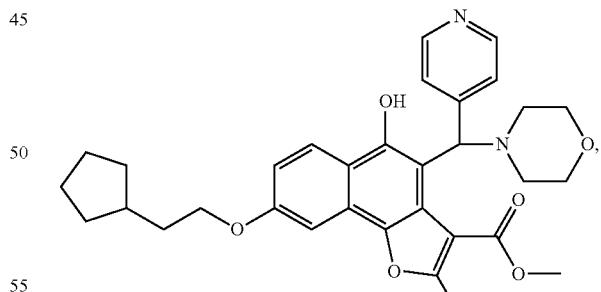
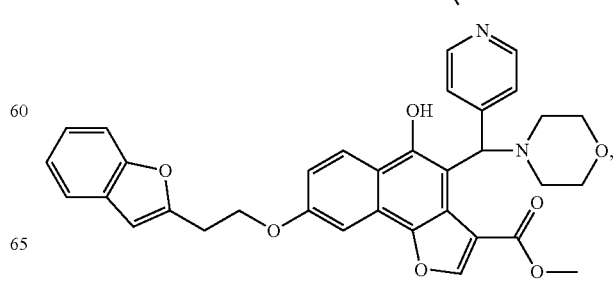

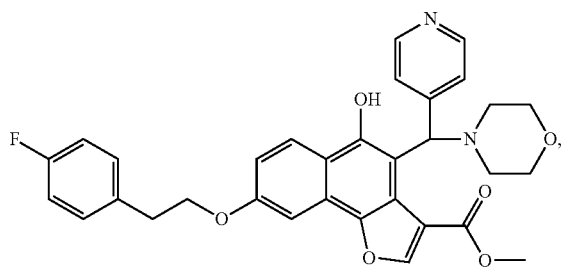
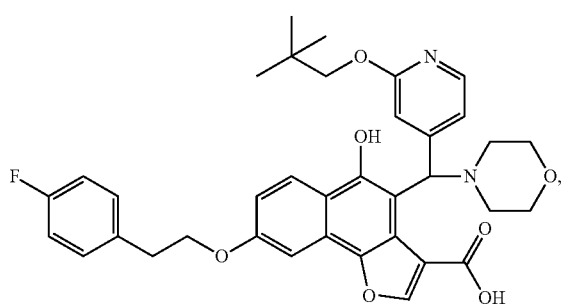
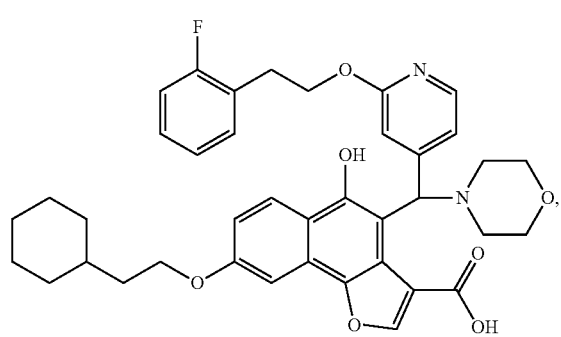
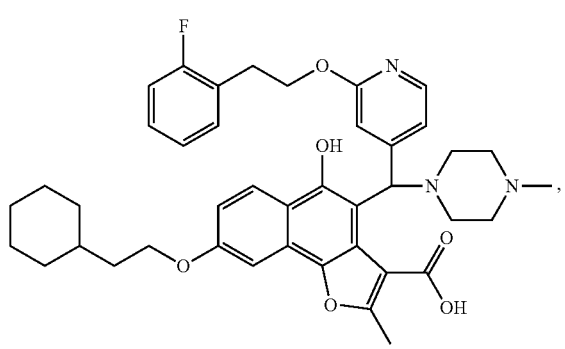
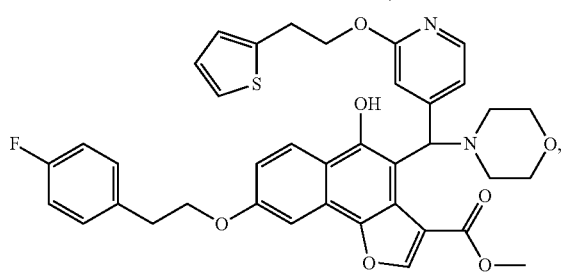
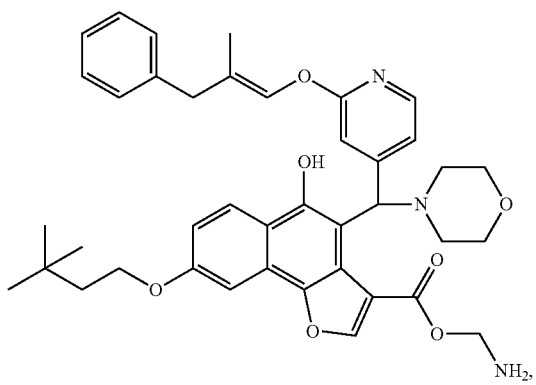 [SMILES: C/C(=C\Oc1cc(C(c2c(O)c3ccc(OCCC(C)(C)C)cc3c3occ(C(=O)OCN)c23)N2CCOCC2)ccn1)Cc1ccccc1]
or a pharmaceutically acceptable salt, solvate, or prodrug thereof.
In some embodiments, the present invention provides the following Mcl-1 inhibitors:
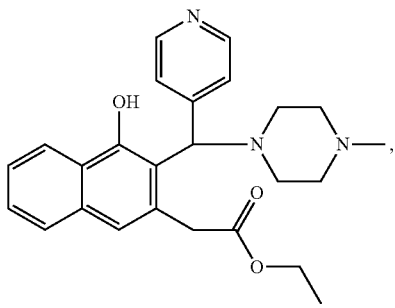
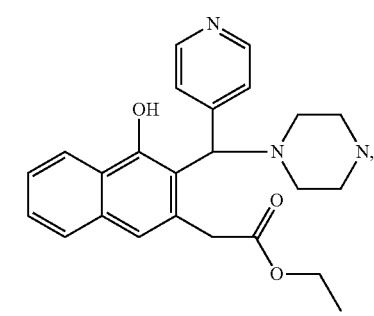
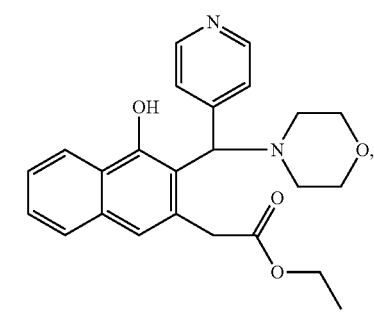

-continued

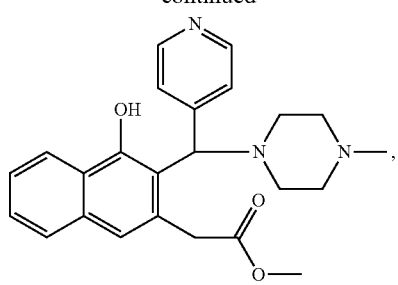

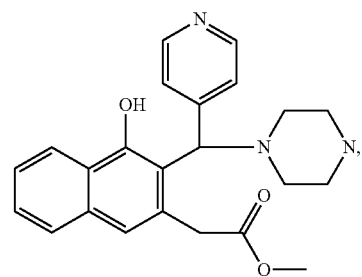

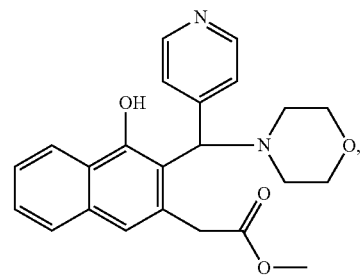

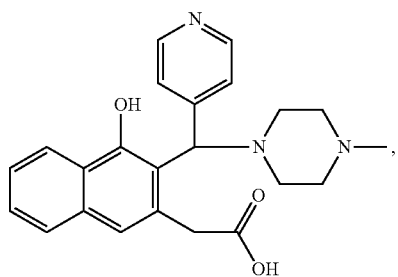

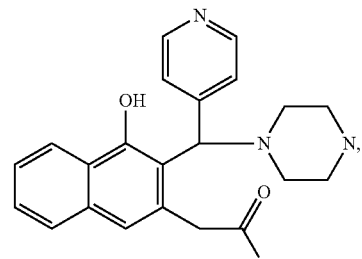

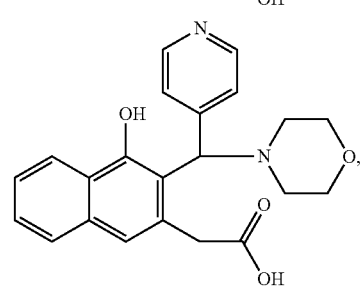

-continued

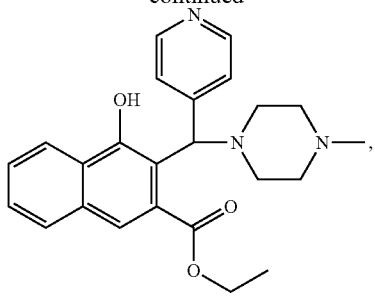

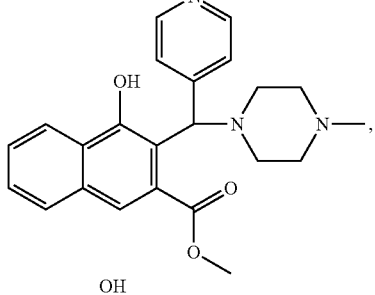

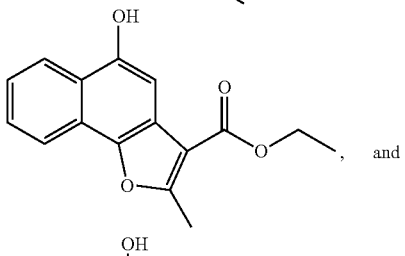

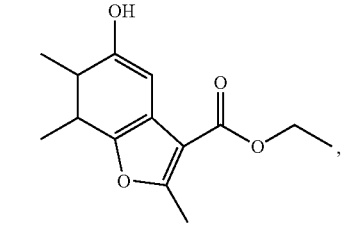 [SMILES: CCOC(=O)c1c(C)oc2c1C=C(O)C(C)C2C]

or a pharmaceutically acceptable salt, solvate, or prodrug thereof.

The invention also provides the use of compounds to induce cell cycle arrest and/or apoptosis in cells containing functional Mcl-1 proteins. The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In other embodiments, the compounds can be used to treat hyperproliferative diseases characterized by expression of functional Mcl-1 and/or Mcl-1 related proteins.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents.

Experiments conducted during the course of developing embodiments for the present invention further identified

UMI-1033

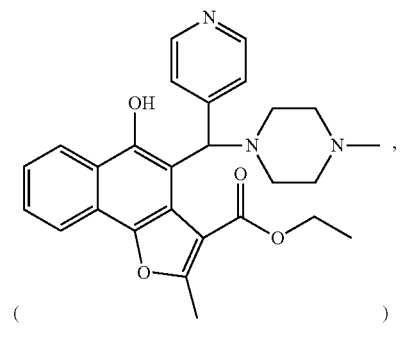

( )

UMI-1007

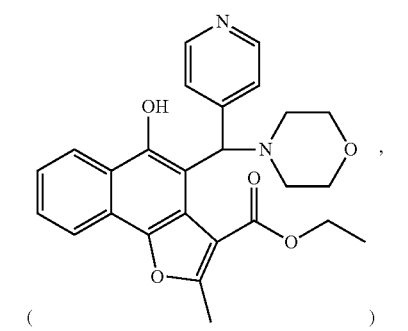

( )

UMI-1008

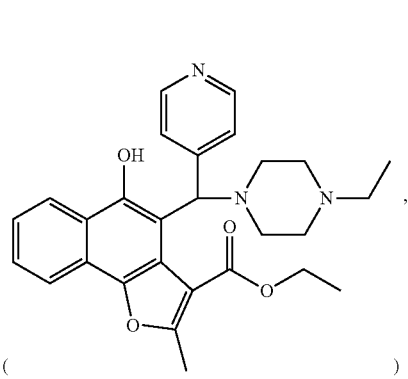

( )

UMI-1009

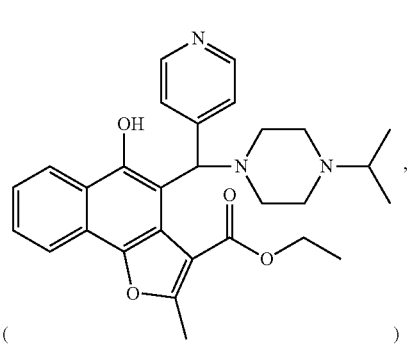

( )

UMI-1035

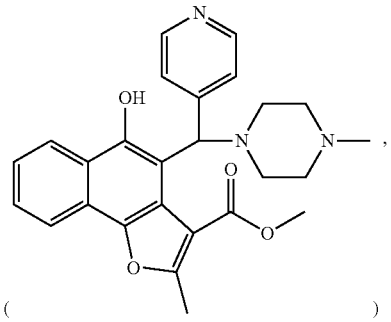

( )

UMI-1026

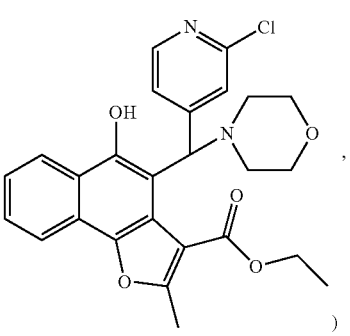

( )

UMI-1036

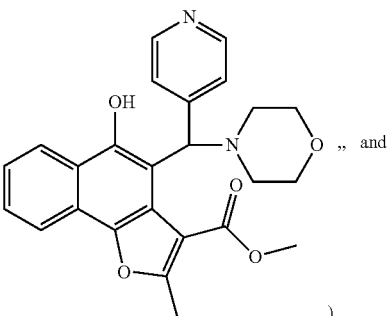

( ), and

UMI-1042

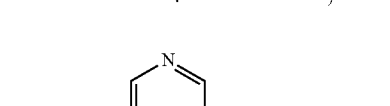
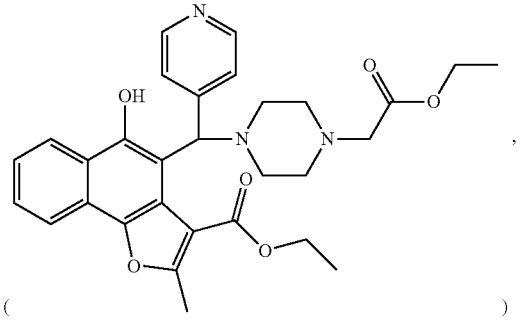

( )

as selective Mcl-1 inhibitors. Indeed, a predicted computational model showed that the interaction between UMI-1033 and Mcl-1 is mediated by highly conserved BH3 elements forming the hydrophobic pockets h2 and h3, and hydrogen bonding network including the conserved hydrogen bond interaction with Arg 263 and A260 (see, e.g., FIG. 5).

From a functional standpoint, UMI-1033 was shown to effectively target cellular Mcl-1, and its dose-dependent cytotoxic activity and induction of apoptosis depend on Bax and Bak, suggesting that this class of compounds function as BH3 mimetics (see, e.g., FIGS. 9-12).

Accordingly, the present invention further provides methods for treating cancer through administration of therapeutic amounts of any of the compounds described in Formula I (e.g., UMI-1033, UMI-1007, UMI-1008, UMI-1009, UMI-1026, UMI-1036, UMI-1042, and/or UMI-1035) to a subject suffering from cancer. The methods are not limited to a particular type of cancer. In some embodiments, the cancer is any cancer having Mcl-1 protein activity. In some embodiments, the cancer is melanoma. In some embodiments, the cancer is acute myeloid leukemia (AML). Indeed, experiments conducted during the course of developing embodiments, for the present invention further demonstrated that targeting of Mcl-1 is a useful strategy for the treatment of AML, and that UMI-1009 was able to induce apoptosis in AML human cells through activation of the intrinsic apoptotic pathway.

In some embodiments, administration of any of the compounds described in Formula I (e.g., UMI-1033, UMI-1007, UMI-1008, UMI-1009, UMI-1026, UMI-1036, UMI-1042, and/or UMI-1035) results in inhibition of Mcl-1 protein activity. In some embodiments, the administered compound of Formula I (e.g., UMI-1033) binds Mcl-1 protein within its BH3 groove. In some embodiments, the administered compound of Formula I (e.g., UMI-1033) inhibits cell growth and increases cellular apoptosis for cells having Mcl-1 activity. In some embodiments, the compound of Formula I (e.g., UMI-1033) are co-administered with one or more anticancer agents.

BRIEF DESCRIPTION OF DRAWINGS

FIG. 9 shows the growth inhibition, $IC_{50}$, of Mcl-1 inhibitors presented in this invention against a panel of melanoma cells.

DEFINITIONS

Figure 1:
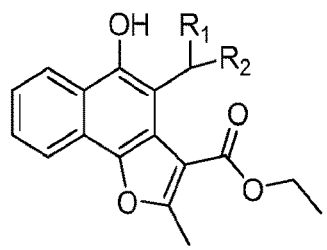
FIGS. 1, 2, 3, 4 and 6 show various [(1-piperazinyl)-4-pyridinylmethyl]-Naphtho[1,2-b]furan compounds and $IC_{50}$ values for binding to Mcl-1.
Figure 2:
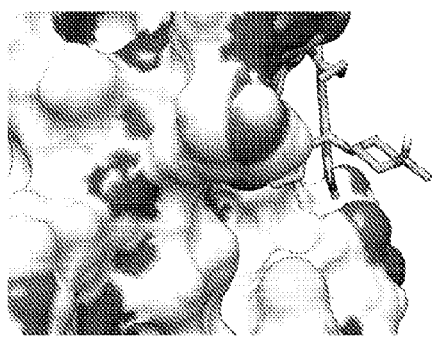
Figure 2:

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a [(1-piperazinyl)-4-pyridinylmethyl]-Naphtho[1,2-b]furan compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "functional Mcl-1," as used herein, refers to wild-type Mcl-1 expressed at normal, high, or low levels and mutant Mcl-1 that retains at least about 5% of the activity of wild-type Mcl-1, e.g., at least about 10%, about 20%, about 30%, about 40%, about 50%, or more of wild-type activity.

The term "Mcl-1-related protein," as used herein, refers to proteins that have partial sequence homology (e.g., at least 5%, 10%, 25%, 50%, 75%, 85%, 95%, 99%, 99.999%) with Mcl-1, have tumor suppressor activity, and are inhibited by interaction with a compound of the present invention (e.g., UMI-1033, UMI-1007, UMI-1008, UMI-1009, UMI-1026, UMI-1036, UMI-1042, and/or UMI-1035).

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Myeloid cell leukemia-1 (Mcl-1) is a potent anti-apoptotic protein, belonging to the prosurvival Bcl-2 subfamily and its role is emerging as a critical survival factor in a broad range of human cancers (see, e.g., Day C L, et al., J Biol. Chem. 2005; 280:4738-44; Day C L, et al., J Mol. Biol. 2008; 380:958-71; each herein incorporated by reference in its entirety). Functional studies have confirmed that Mcl-1 is capable of blocking apoptosis induced by various apoptotic stimuli, including chemotherapy and radiation (see, e.g., Zhou P, et al., Blood. 1997; 89:630-43; herein incorporated by reference in its entirety). There is growing evidence implicating the role of Mcl-1 in melanoma, a particularly aggressive tumor type that exhibits a high level of resistance to apoptosis. Antisense oligonucleotide/siRNA strategies to down-regulate Mcl-1 increases the melanoma cell sensitivity to apoptosis induced by dacarbazine treatment in vivo, (Thallinger C, et al., J Invest Dermatol. 2003; 120:1081-6), ionizing radiation in vitro (Anticancer Res. 2005; 25:2697-703), proteasome inhibitor bortezomib (Qin J Z, et al., Cancer Res. 2006; 66:9636-45), and endoplasmic reticulum stress (Jiang C C, et al., Cancer Res. 2008; 68:6708-17). Additionally, a small-molecule BH3 mimetic, obatoclax, which targets Mcl-1, renders melanoma cells sensitive to the Bcl-2/Bcl-$_{XL}$/Bcl-$_{WL}$, the selective antagonist, ABT-737, and to bortezomib (Qin J Z, et al., Cancer Res. 2006; 66:9636-45, Nguyen M, et al., Proc Natl Acad Sci USA. 2007; 104:19512-7). The role of Mcl-1 in melanoma cell resistance to anoikis was also reported (Boisvert-Adamo K, et al., Mol Cancer Res. 2009; 7:549-56). In addition, Mcl-1 has been demonstrated to be essential for development and survival of acute myeloid leukemia cells (see, e.g., Glaser S P, et al., Genes Dev 2012; 26:120-125). Thus, Mcl-1 represents a very attractive molecular target for developing a new class of cancer therapy for treatment of cancers associated with Mcl-1 activity (e.g., pancreatic cancer) (e.g., acute myeloid leukemia) by overcoming resistance to chemotherapeutic agents.

Potent small molecule inhibitors of Bcl-2 subfamily include the Bad-like BH3 mimetics (see, e.g., Oltersdorf T, et al., Nature. 200; 435-677-81; Tse C, et al., Cancer Res. 2008; 68:3421-8; each herein incorporated by reference in its entirety). ABT-737, one of these mimetics, binds with high affinity ($K_i \leq 1$ nM) to Bcl-2, Bcl-$x_L$, and Bcl-w but fails to bind to Mcl-1 (see, e.g., Oltersdorf T, et al., Nature. 2005; 435:677-81; herein incorporated by reference in its entirety). Several studies have shown that resistance to ABT-737 is linked to high expression levels of Mcl-1 and in many instances this resistance can be overcome by treatment with agents that down-regulate, destabilize, or inactivate Mcl-1 (see, e.g., van Delft M F, et al., Cancer Cell. 2006; 10:389-99; Chen S, et al., Cancer Res. 2007; 67:782-91; Huang S, et al., Cancer Res. 2008; 68:2944-51; each herein incorporated by reference in its entirety).

Applying a high throughput screening (HTS) approach, experiments conducted during the course of developing embodiments for the present invention identified and validated a new class of small-molecules having a [(1-piperazinyl)-4-pyridinylmethyl]-Naphtho[1,2-b]furan structure which function as inhibitors of Mcl-1 protein. FIGS. 1, 2, 3 and 4 show various [(1-piperazinyl)-4-pyridinylmethyl]-Naphtho[1,2-b]furan compounds and $IC_{50}$ values for binding with Mcl-1. In addition, such experiments identified novel selective small molecule Mcl-1 inhibitor (e.g., UMI-1033, UMI-1007, UMI-1008, UMI-1009, UMI-1036, UMI-1039, UMI-1042, and/or UMI-1035) and illustrates potency, specificity and ability to induce Bax/Bak dependent apoptosis through targeting Mcl-1 in PC and acute myeloid leukemia (AML) cells. These findings provide the basis and rational of combining UMI-1033, UMI-1007, UMI-1009, UMI-1035 and/or UMI-1036 with chemotherapy and radiation whose activity in pancreatic cancer and/or acute myeloid leukemia is restrained by Mcl-1.

Accordingly, the present invention relates to compounds which function as inhibitors of Mcl-1 proteins. By inhibiting the activity of Mcl-1, these compounds sensitize cells to inducers of apoptosis and/or cell cycle arrest and, in some instances, themselves induce apoptosis and/or cell cycle arrest. Therefore, the invention relates to methods of sensitizing cells to inducers of apoptosis and/or cell cycle arrest and to methods of inducing apoptosis and/or cell cycle arrest in cells, comprising contacting the cells with a compound of the invention alone or in combination with additional agent(s), e.g., an inducer of apoptosis or a cell cycle disrupter.

The invention further relates to methods of treating, ameliorating, or preventing disorders in a patient, such as those that are responsive to induction of apoptosis, comprising administering to the patient a compound of the invention and additional agent(s), e.g., an inducer of apoptosis. Such disorders include those characterized by a dysregulation of apoptosis and those characterized by the proliferation of cells expressing functional Mcl-1 proteins (e.g., pancreatic cancer and acute myeloid leukemia).

In a particular embodiment, [(1-piperazinyl)-4-pyridinylmethyl]-Naphtho[1,2-b]furan compounds having the following Formula I:

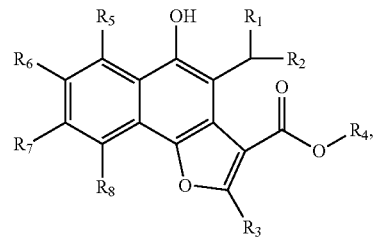

including pharmaceutically acceptable salts, solvates, and/or prodrugs thereof.

Formula I is not limited to a particular chemical moieties for R1, R2, R3 and/or R4. In some embodiments, R1, R2, R3, R4, R5, R6, R7 and/or R8 include any chemical moieties that permit the resulting compound to bind with an Mcl-1 protein. In some embodiments, R1, R2, R3, R4, R5, R6, R7 and/or R8 include any chemical moieties that permits the resulting compound to inhibit the activity of Mcl-1 protein.

In some embodiments, R1 may be, for example, hydrogen, a phenyl group (substituted or unsubstituted) or a pyridine (substituted or unsubstituted). In some embodiments, R1 may be, for example, any of the following chemical moieties: hydrogen,

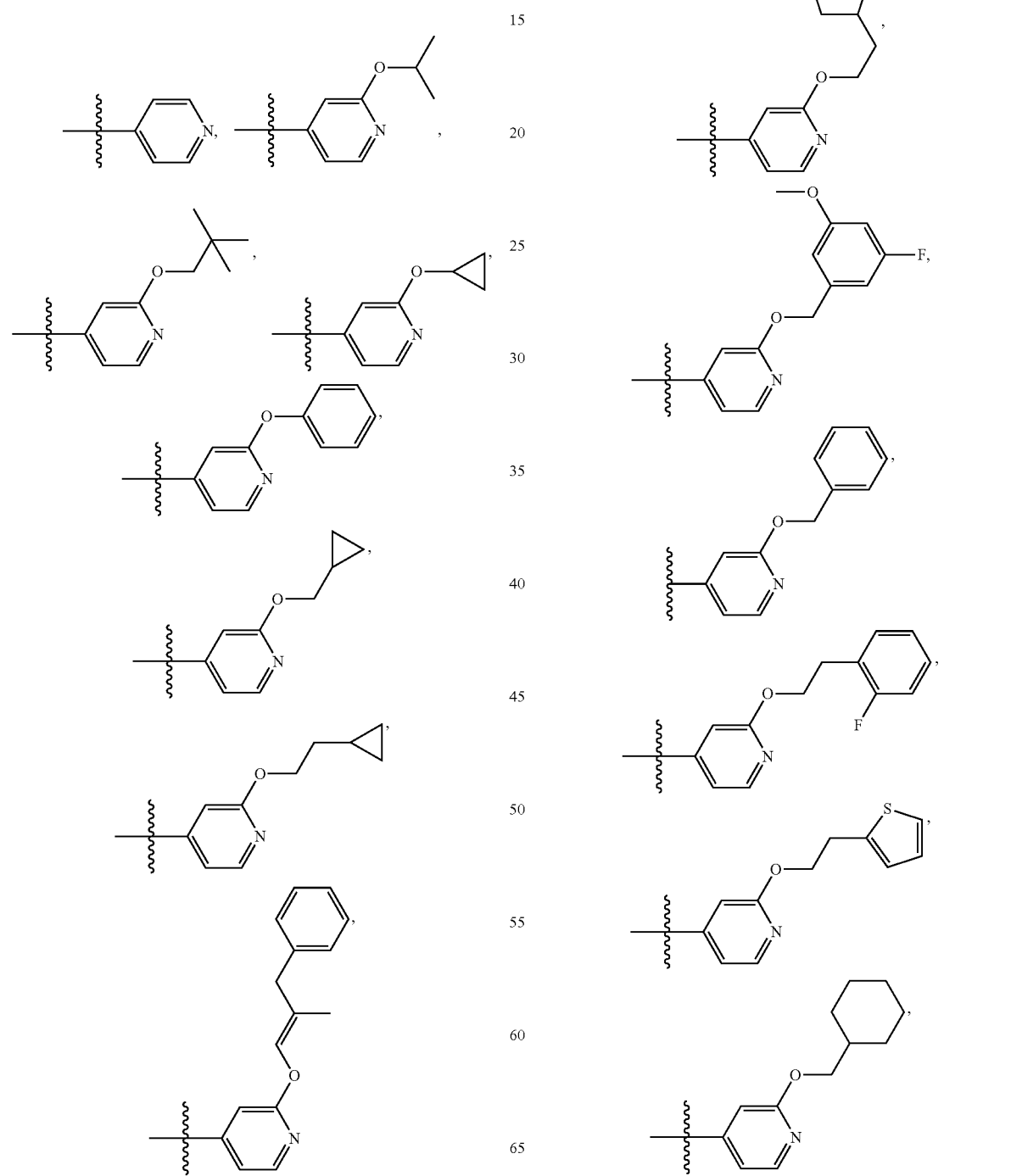

-continued

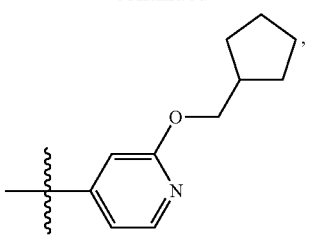
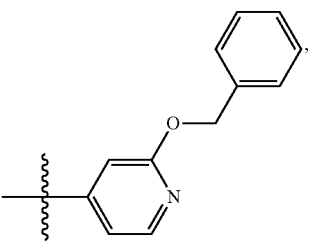
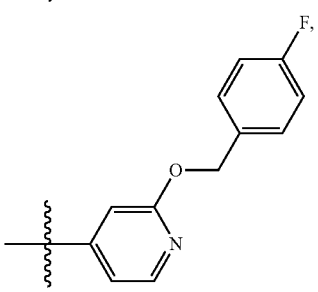
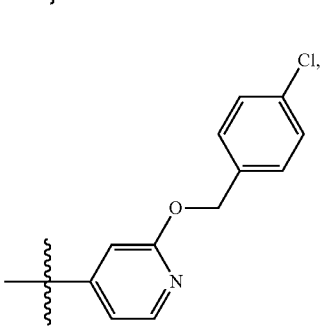
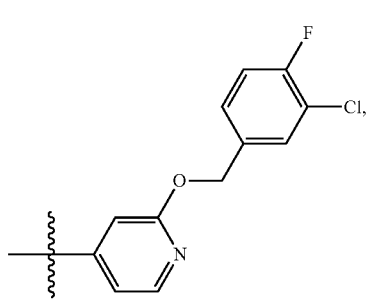
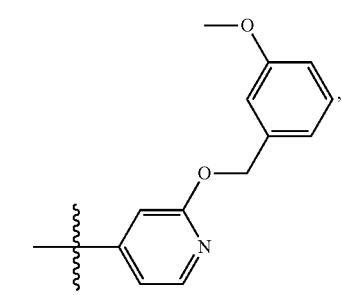

-continued

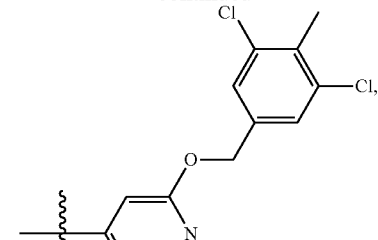
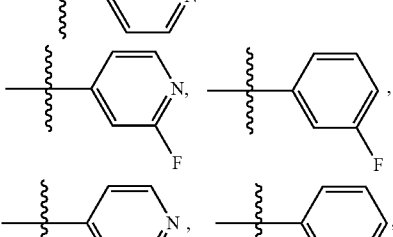
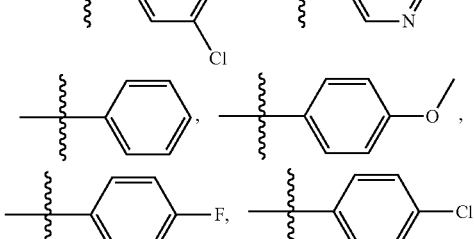
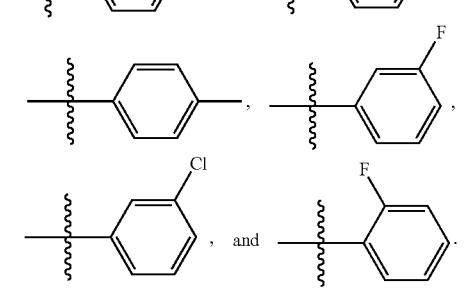

In some embodiments, R2 may be, for example, hydrogen, a piperazine group (substituted or unsubstituted), or a morpholino group (substituted or unsubstituted). In some embodiments, R2 may be, for example, any of the following chemical moieties: hydrogen,

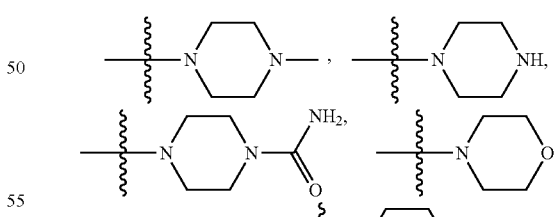
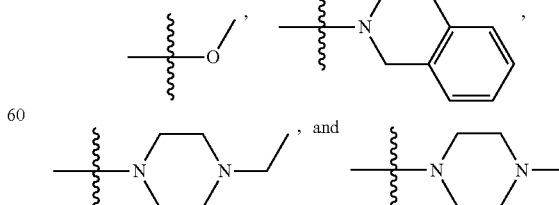

In some embodiments, R3 may be, for example, hydrogen, an alkyl moiety (substituted or unsubstituted) or aromatic (substituted or unsubstituted). In some embodiments, R3 may be, for example, hydrogen, methyl, ethyl, phenyl, or tert-butyl.

Figure 7:
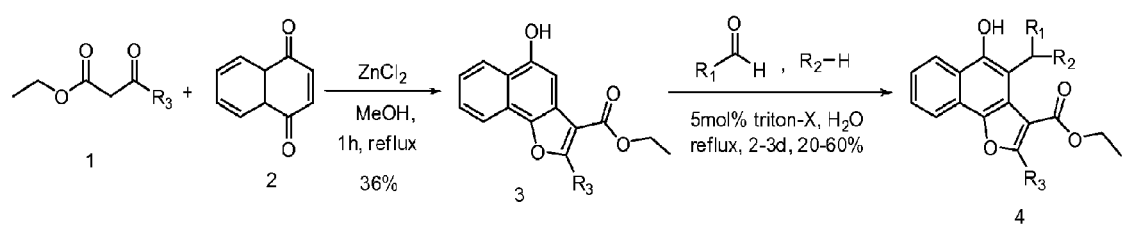
FIG. 7 shows a synthetic scheme for synthesizing compounds of Formula I where R4 is ethyl.

In some embodiments, R4 may be, for example, hydrogen or an alkyl moiety (substituted or unsubstituted). In some embodiments, R4 may be, for example,

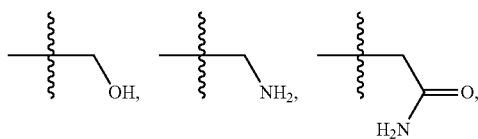

hydrogen, methyl or ethyl. FIG. 7 shows a synthetic scheme for developing compounds of Formula I where R4 is ethyl.

In some embodiments, R5, R6, R7, and R8 may independently be, for example, hydrogen,

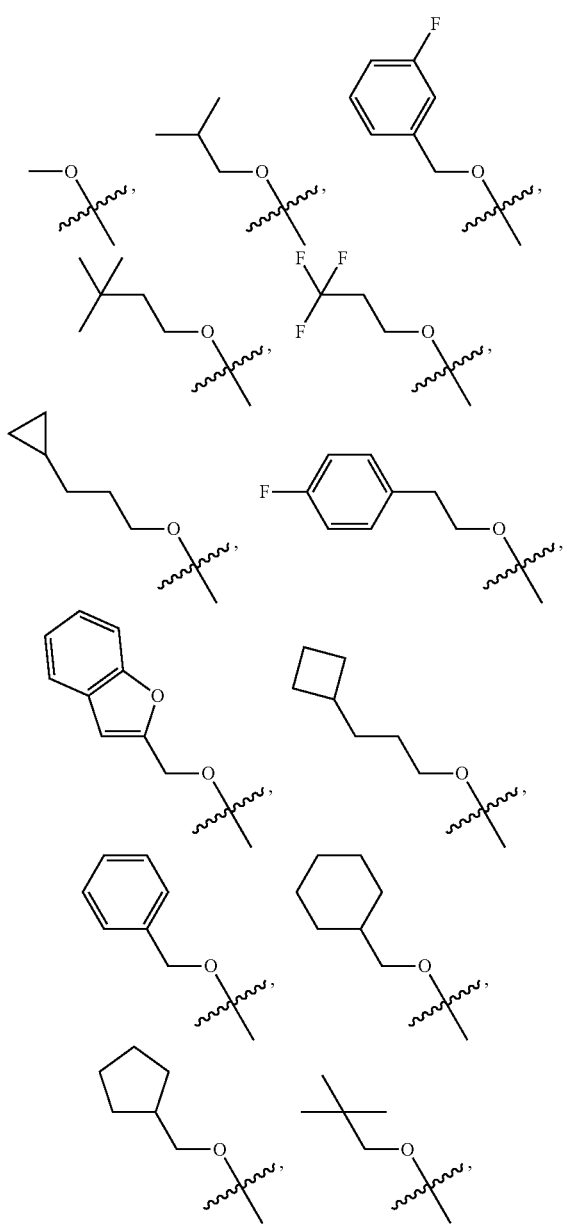

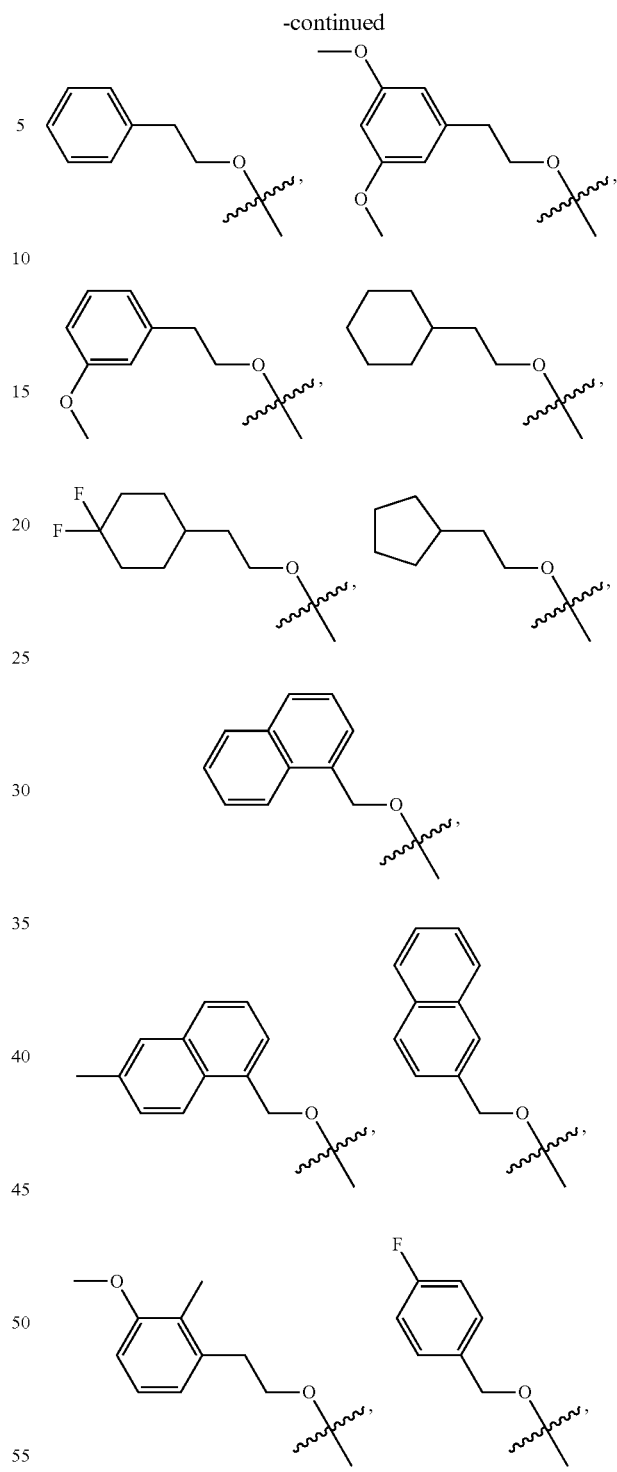

alkyl (e.g., substituted, unsubstituted) (e.g., methyl), or a halogen (e.g., chlorine, fluorine).

FIGS. 1, 2, 3, and 4 show various compounds for Formula I having various R1, R2, R3, R4, R5, R6, R7 and R8 groups, and related structure activity relationship (SAR) for each respective compound (IC$_{50}$ values were determined with fluorescence polarizing binding assay).

In some embodiments, the following compounds are encompassed within Formula I:

83
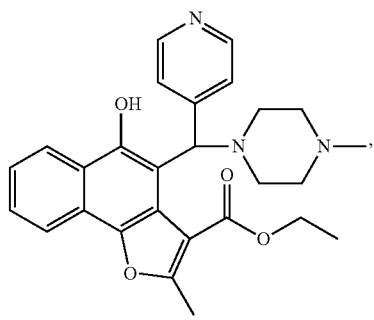
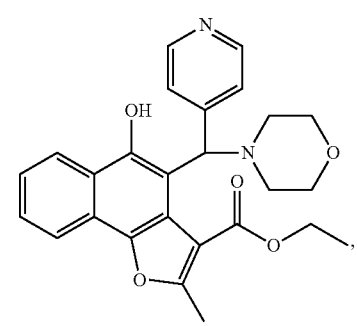
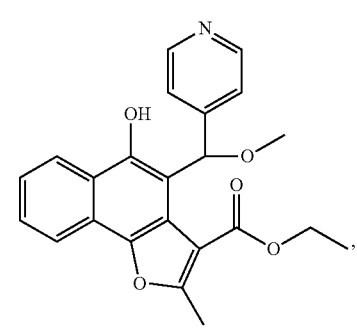
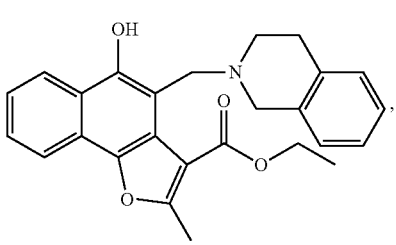
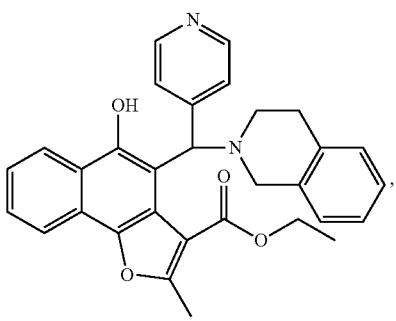
84
-continued
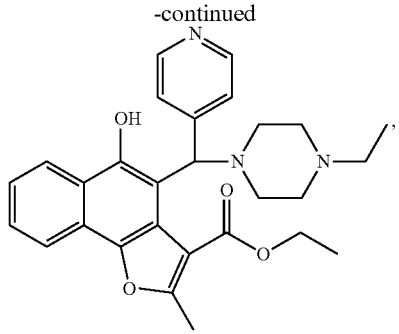
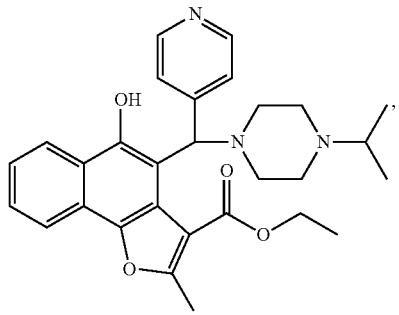
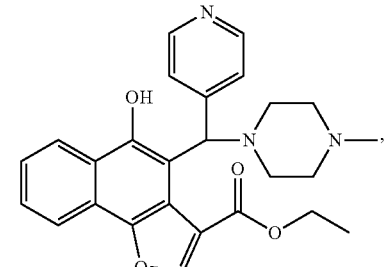
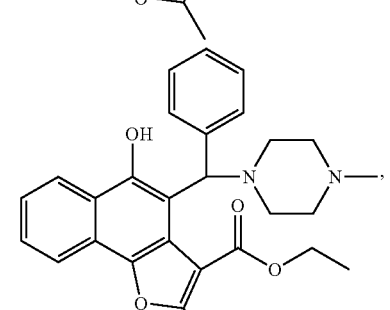
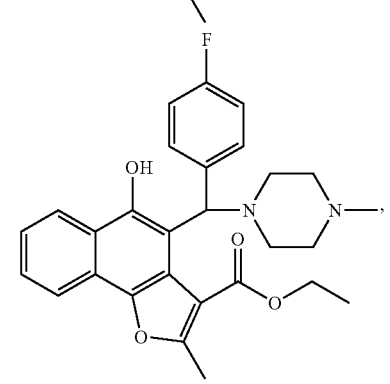

85
-continued
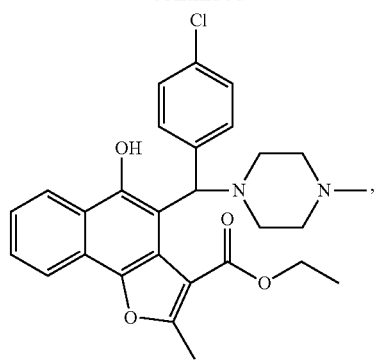
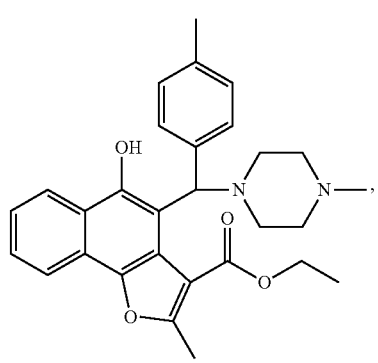
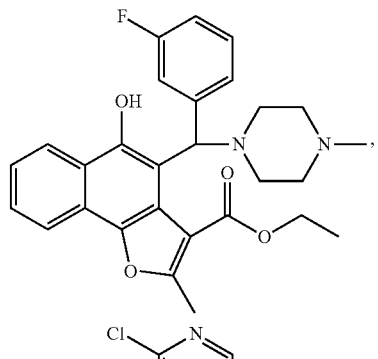
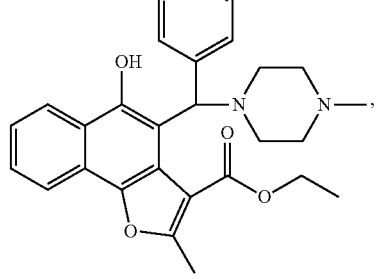
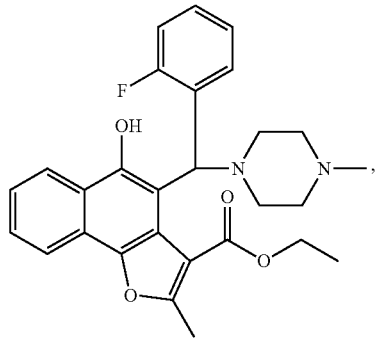
86
-continued
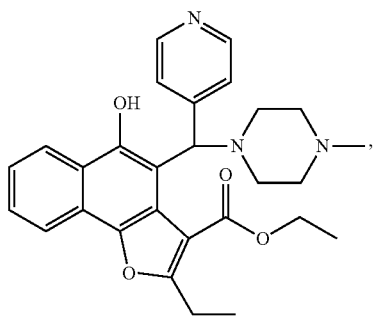
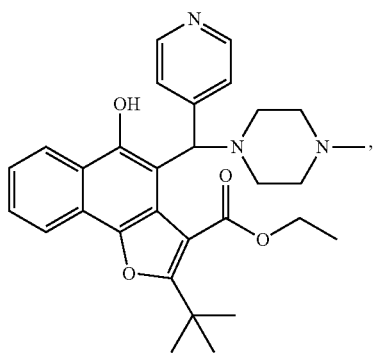
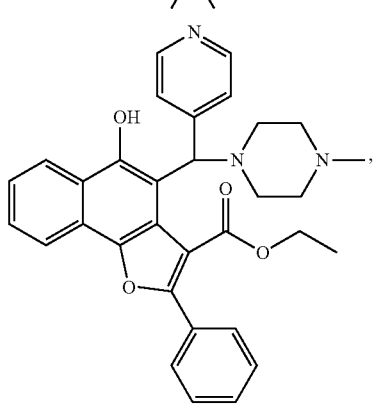
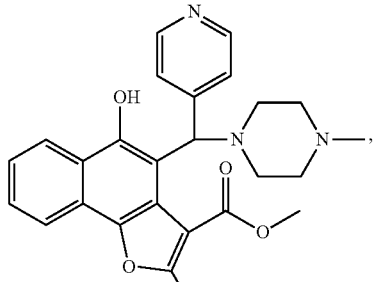
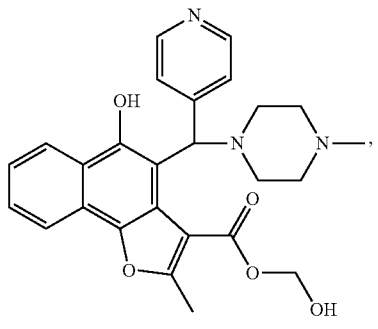

87
-continued
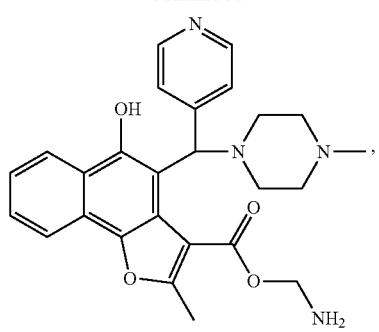
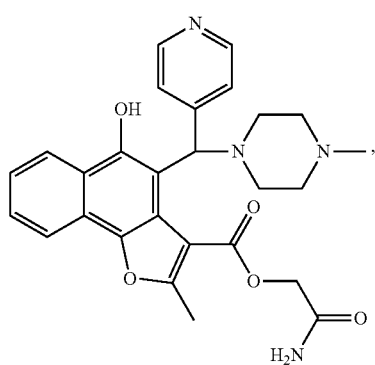
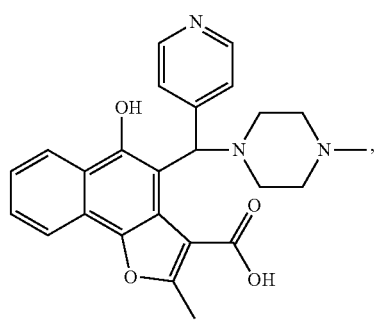
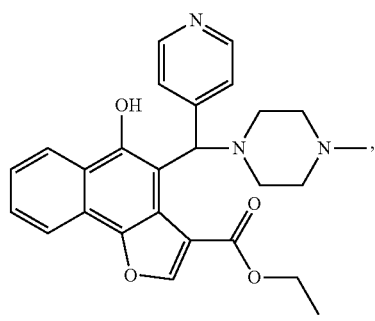
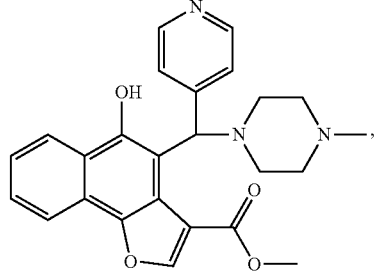
88
-continued
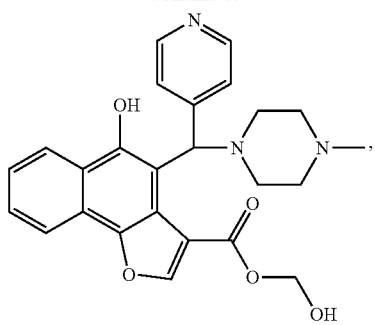
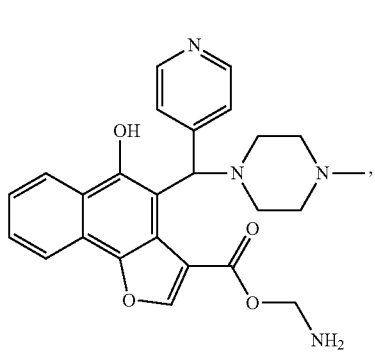
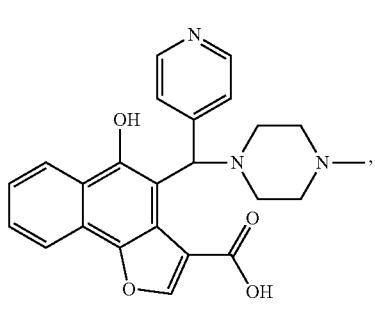
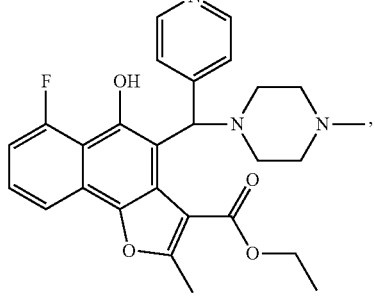
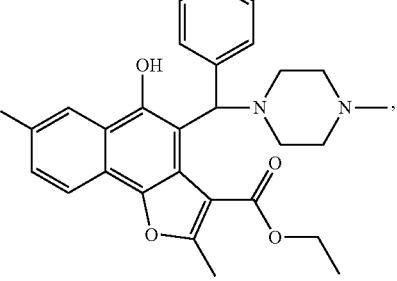

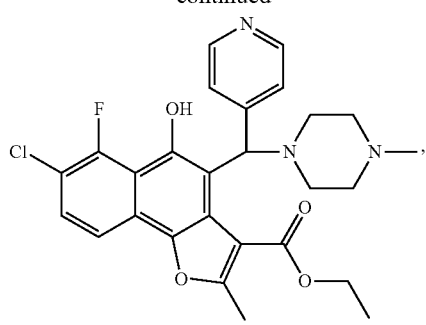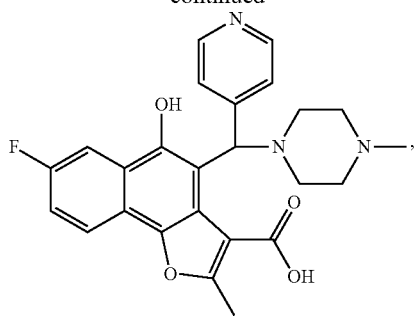

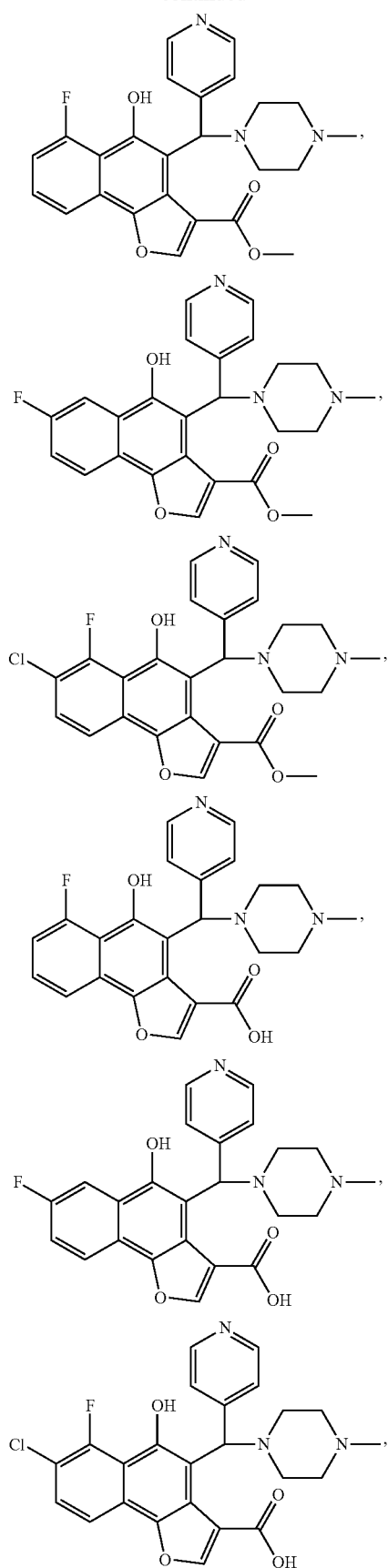
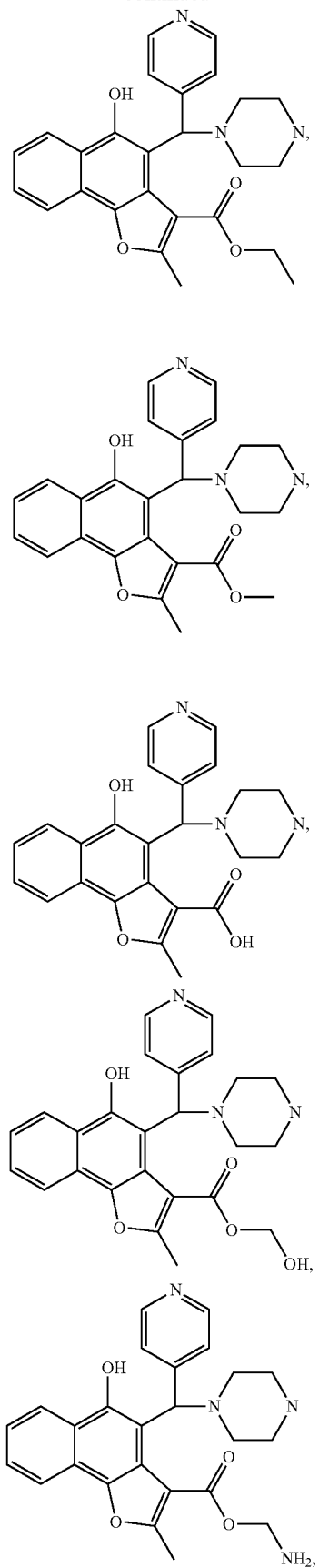

93
-continued
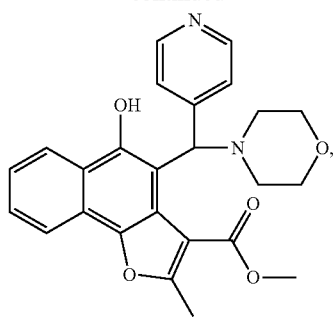
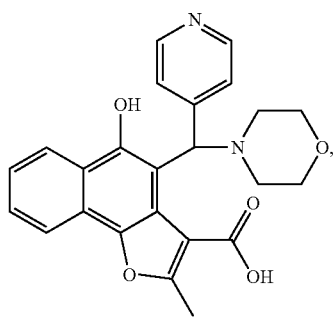
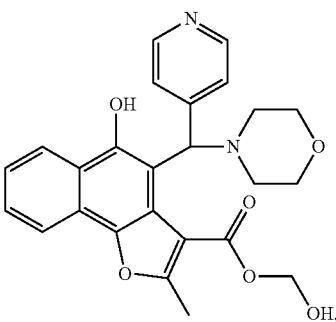
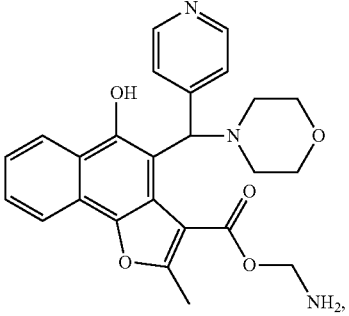
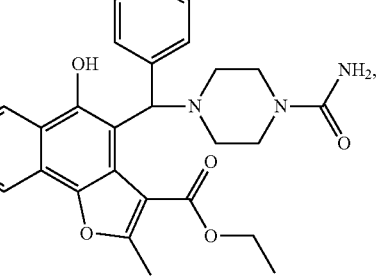
94
-continued
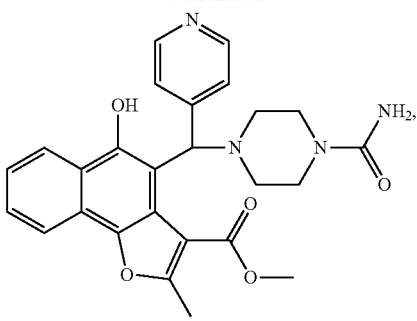
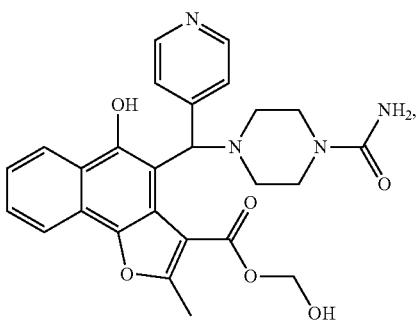
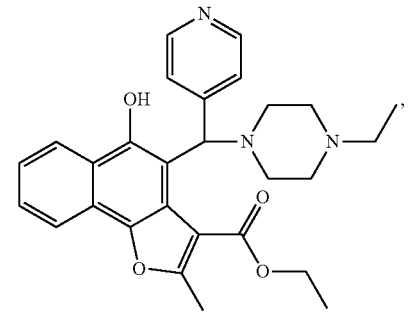
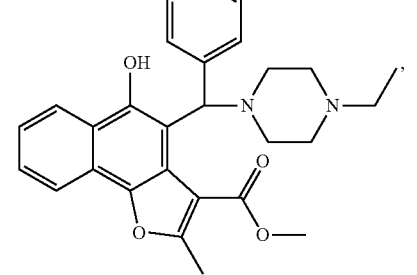

-continued
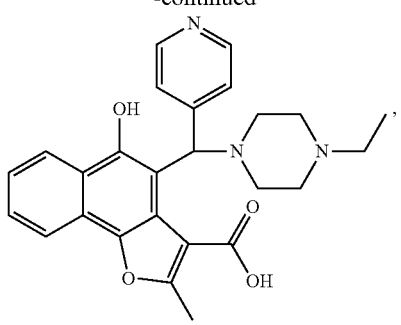
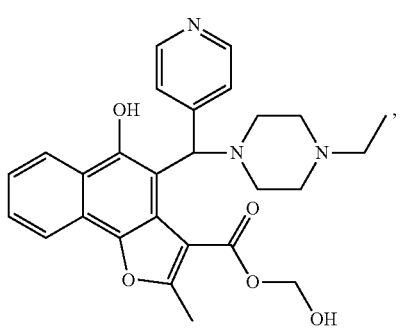
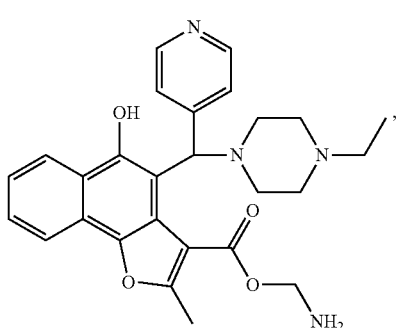
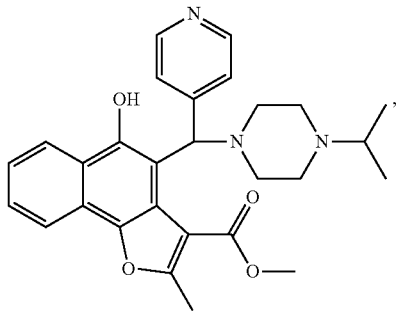
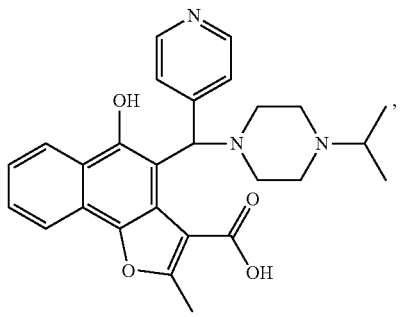
-continued
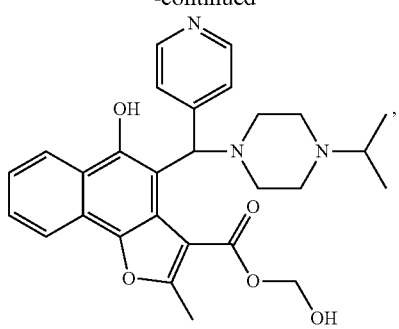
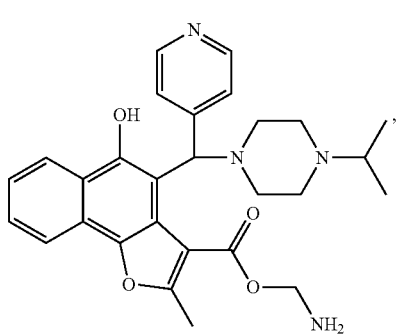
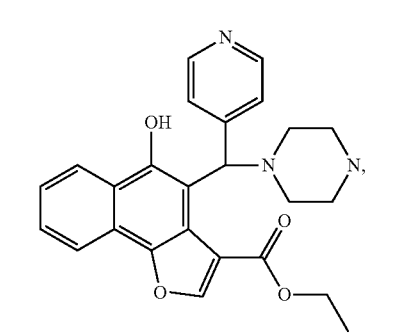
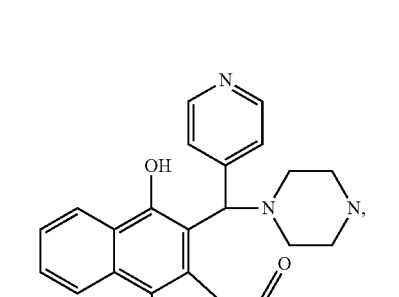
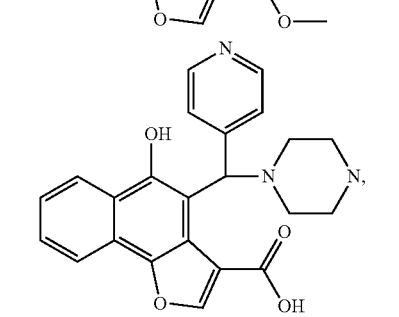

97
-continued
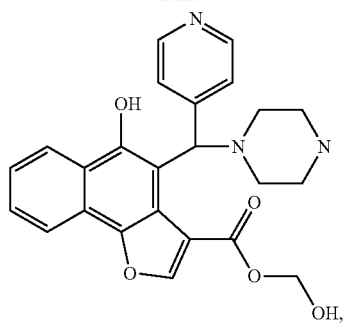
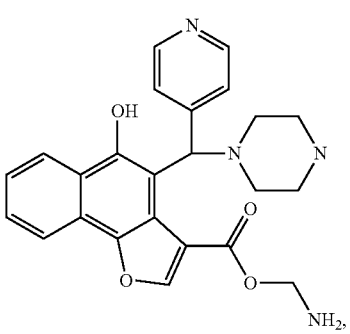
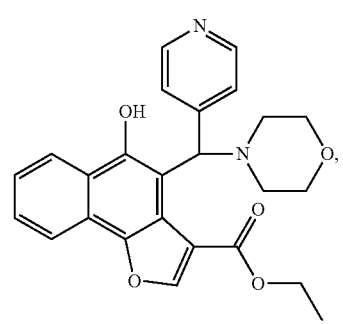
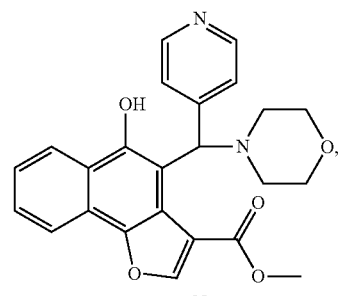
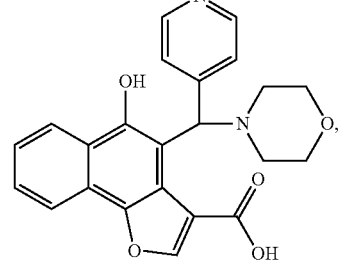
98
-continued
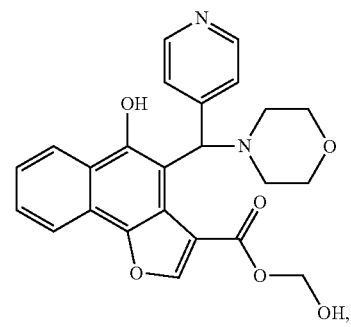
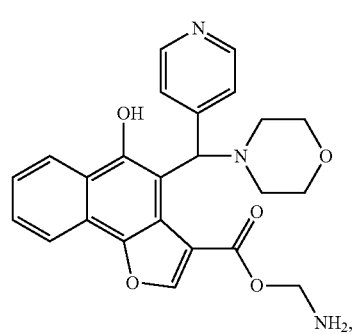
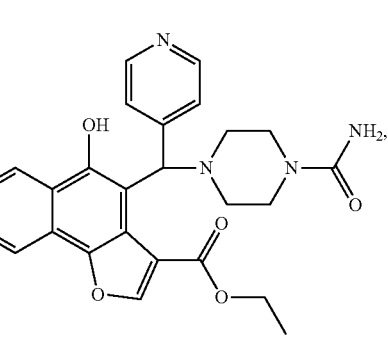
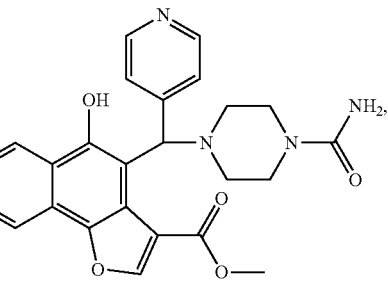
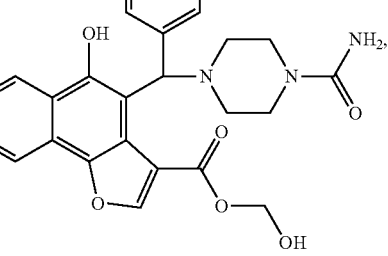

99
-continued
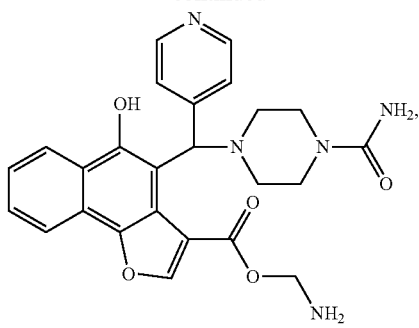
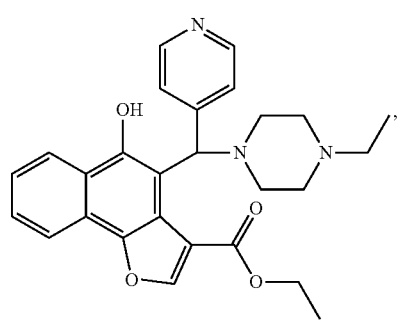
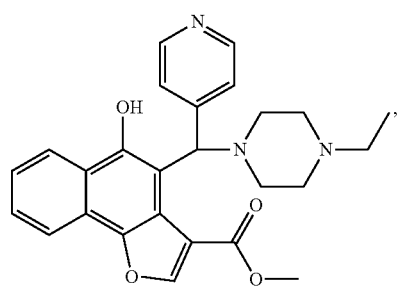
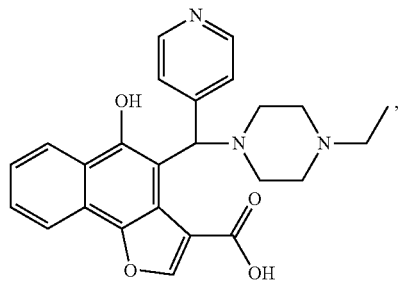
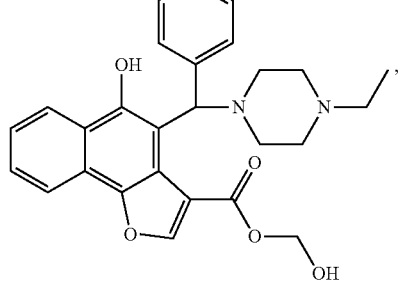
100
-continued
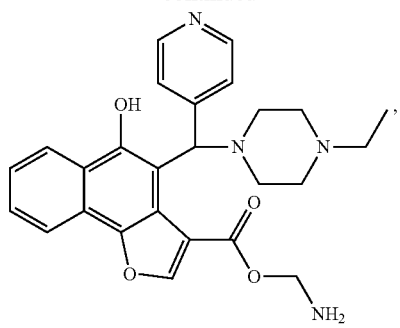
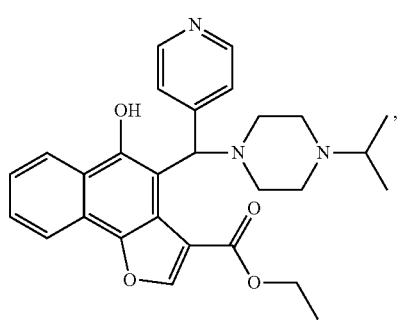
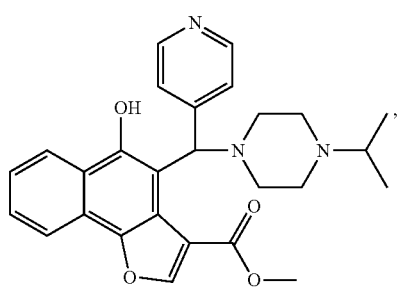
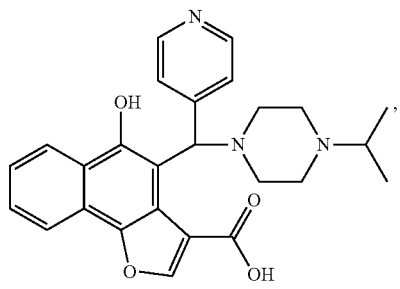
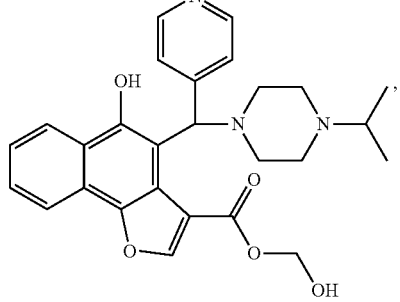

101
-continued
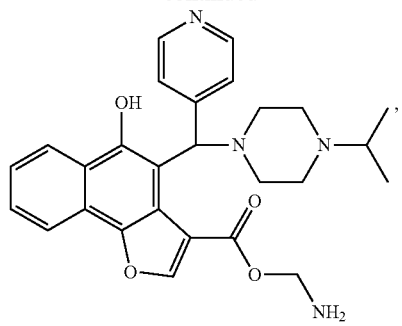
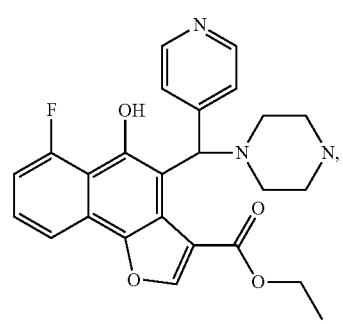
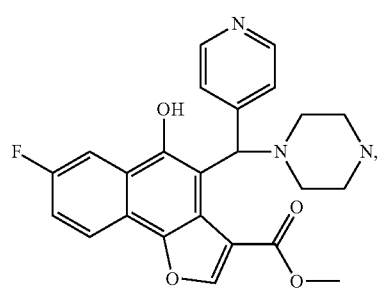
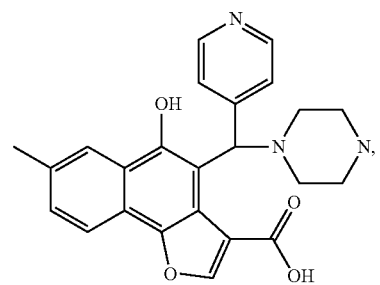
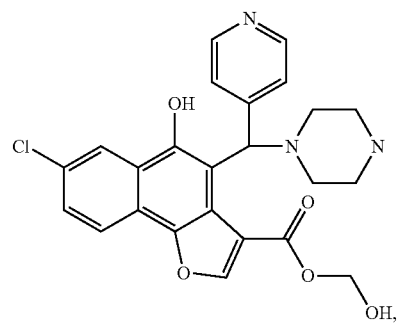
102
-continued
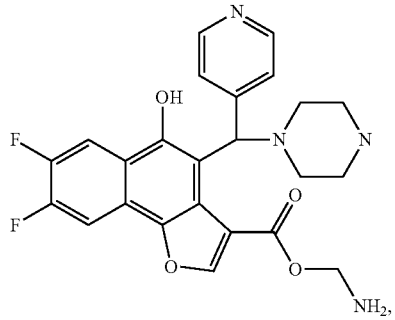
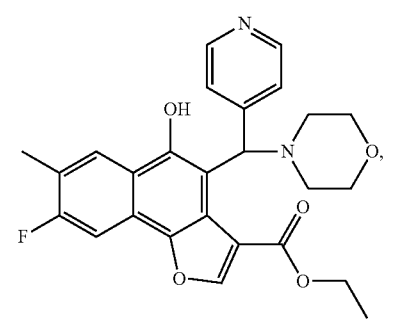
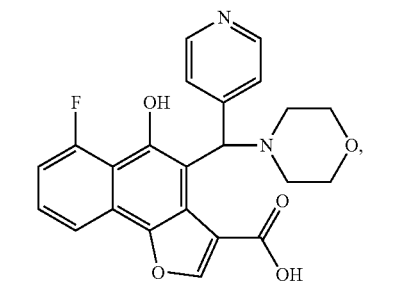
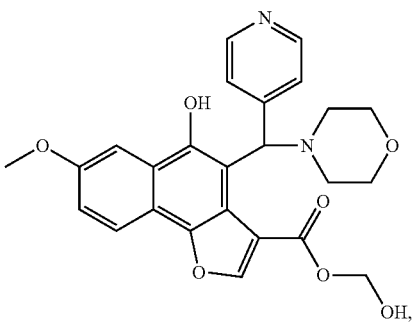
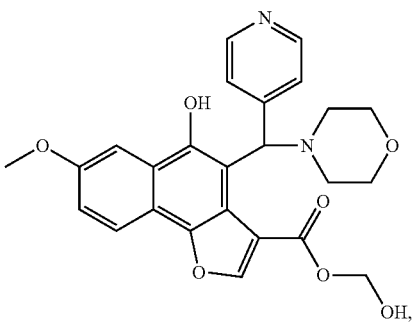

103
-continued
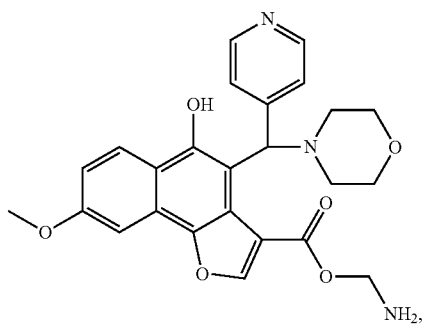
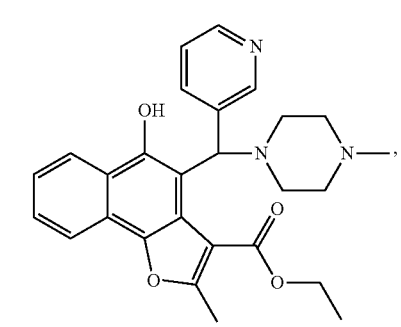
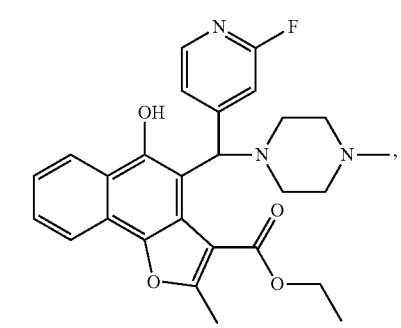
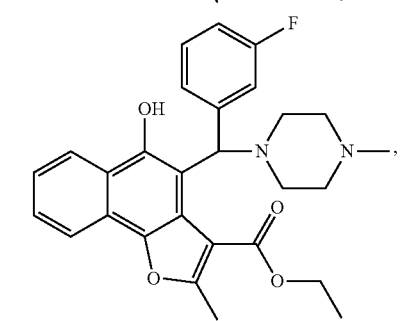
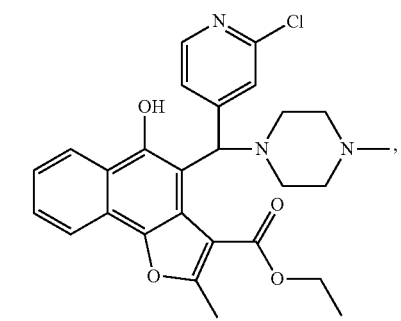
104
-continued
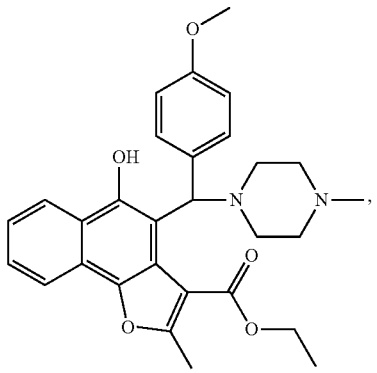
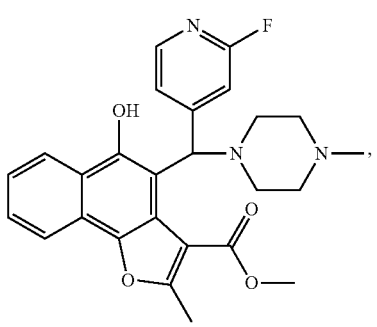
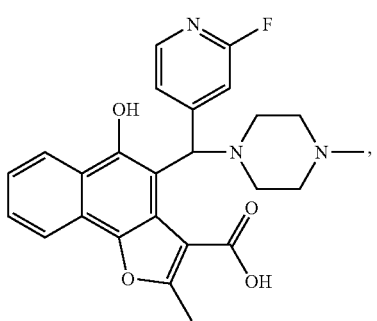
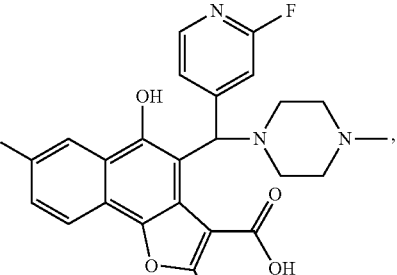
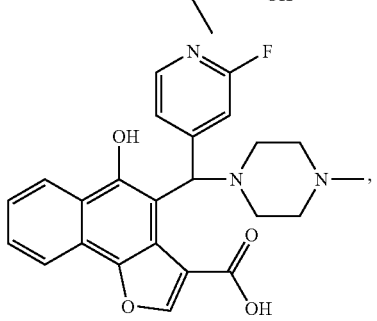

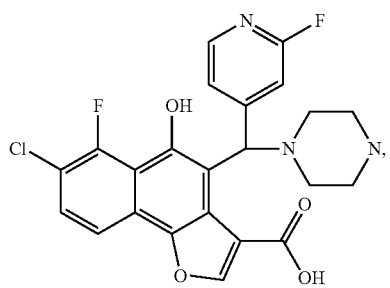
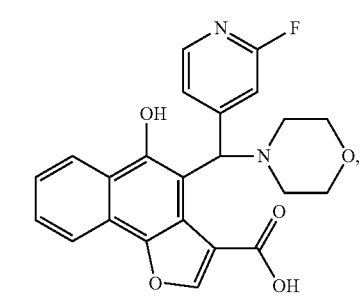
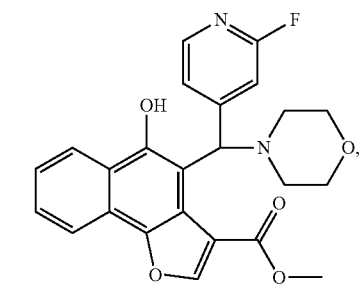
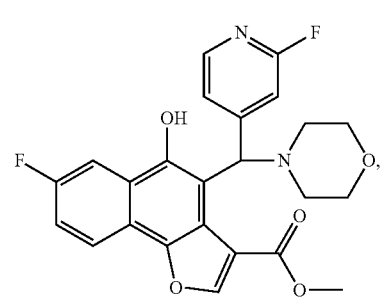
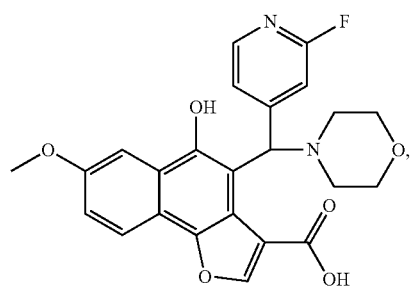
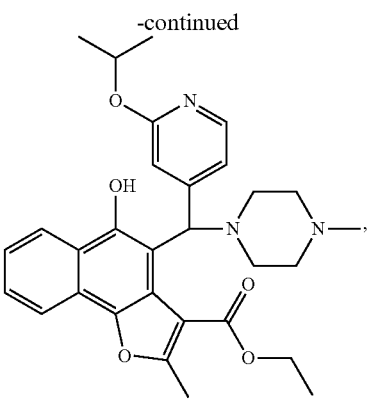
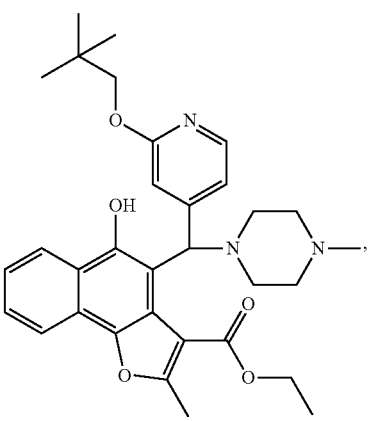
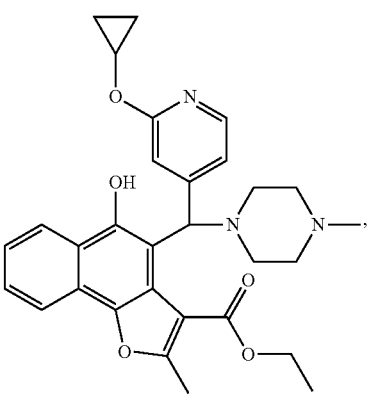
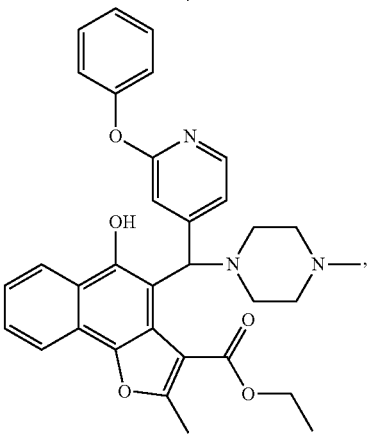

107
-continued
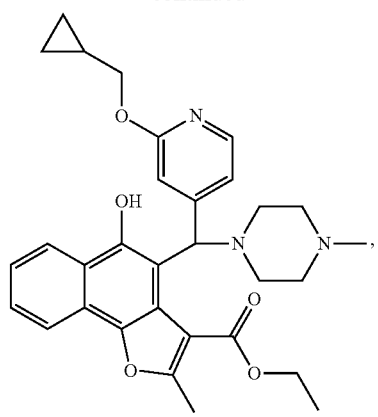
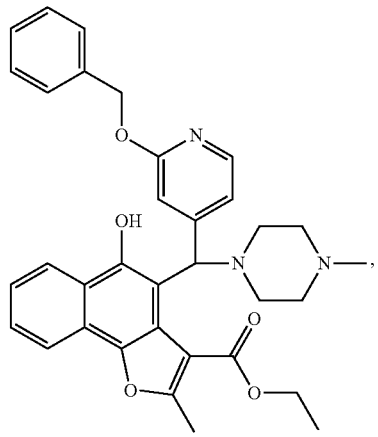
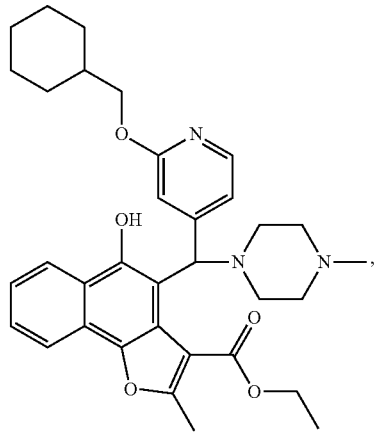
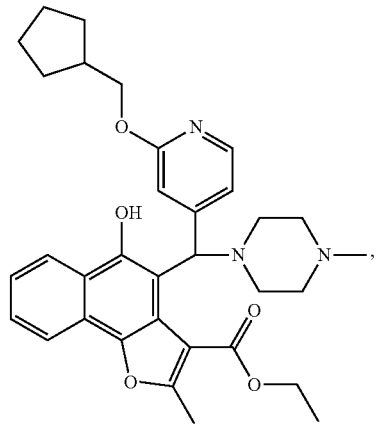
108
-continued
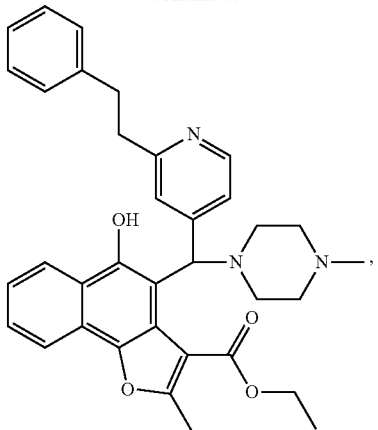
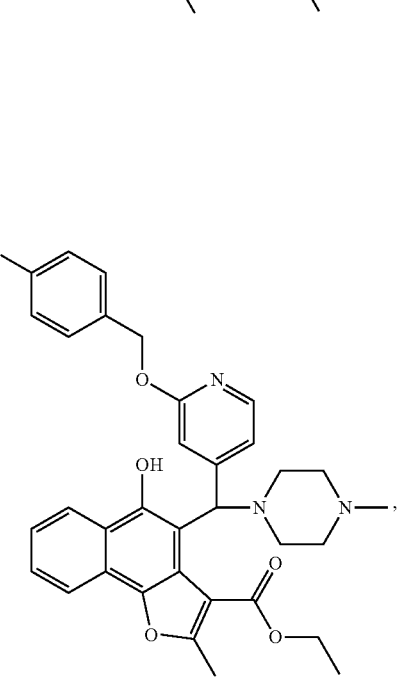
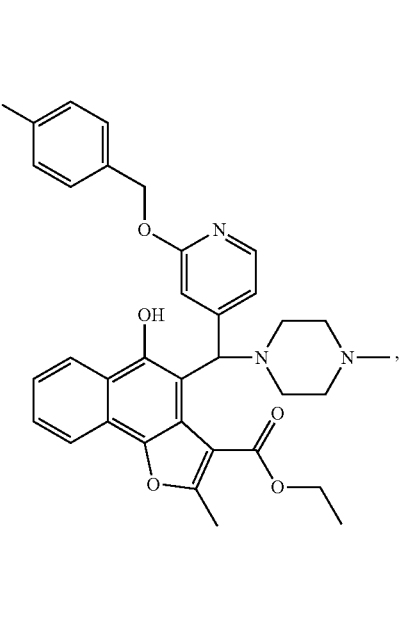

109
-continued
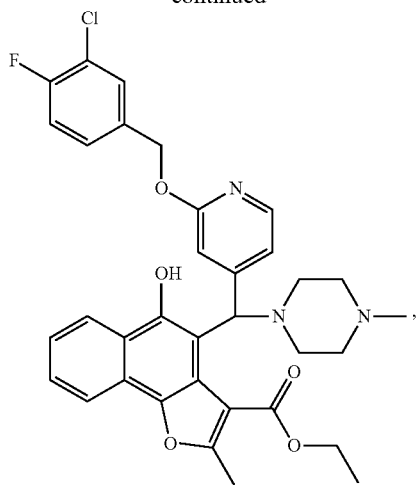
110
-continued
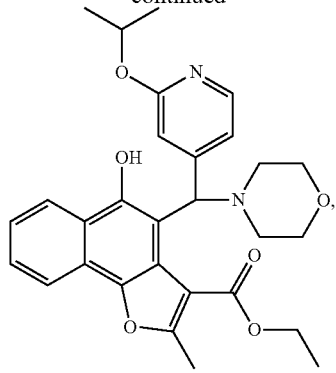
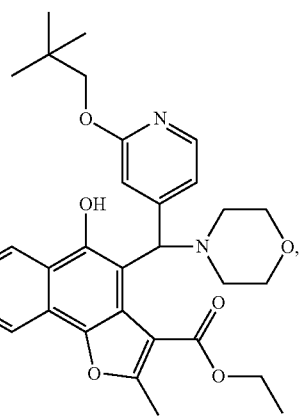
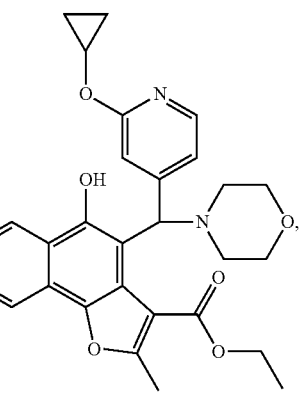
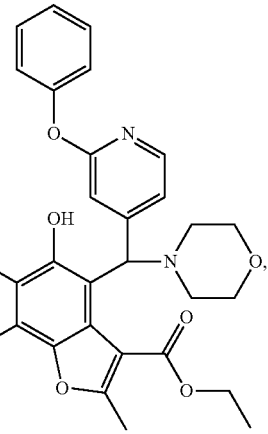

111
-continued
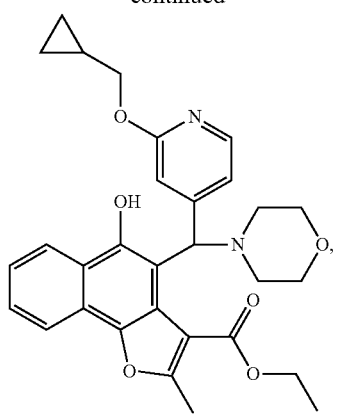
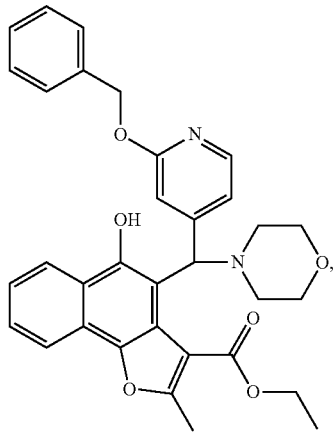
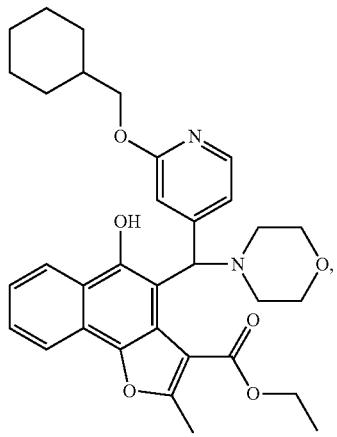
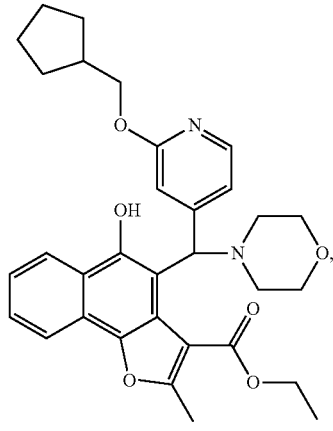
112
-continued
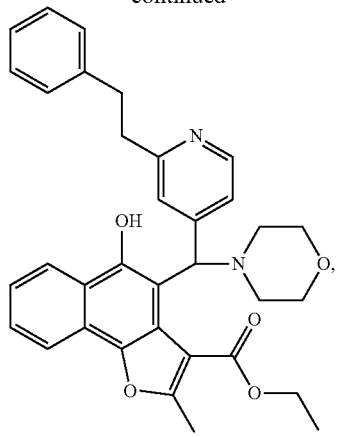
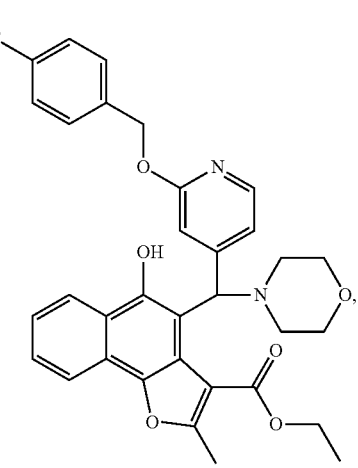
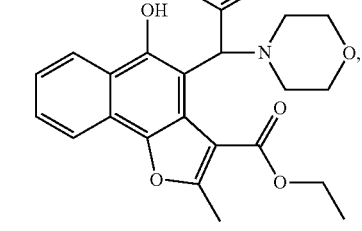

113
-continued
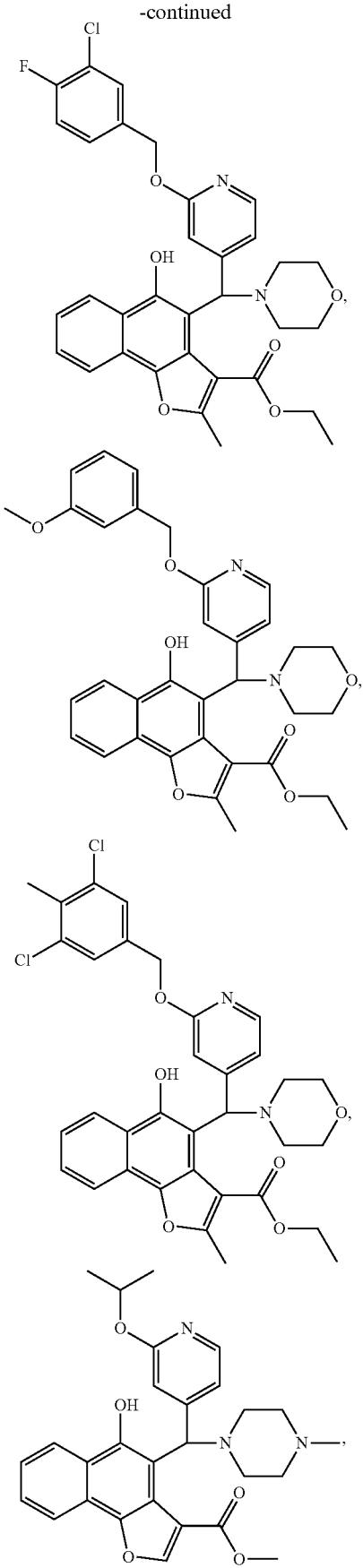
114
-continued
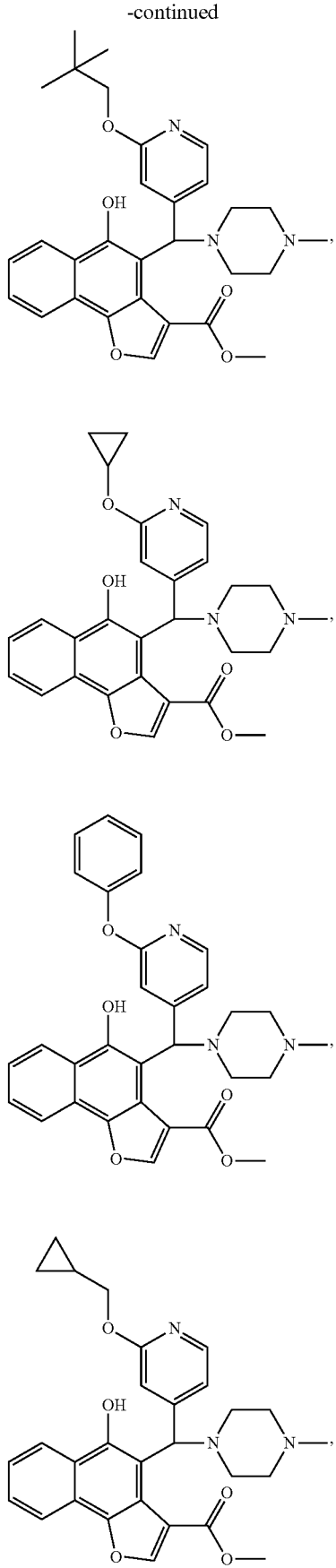

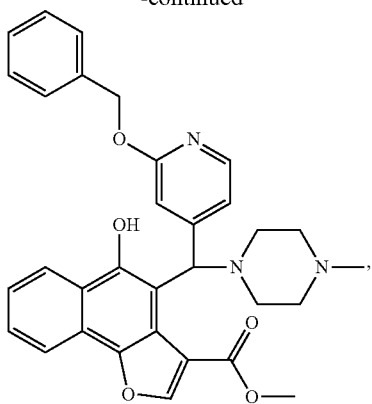
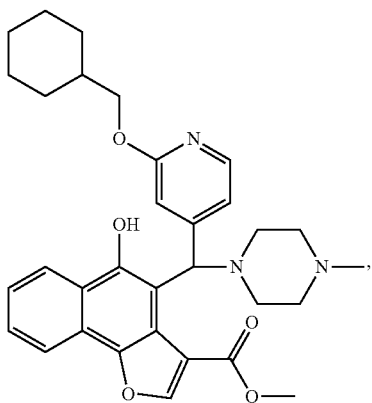
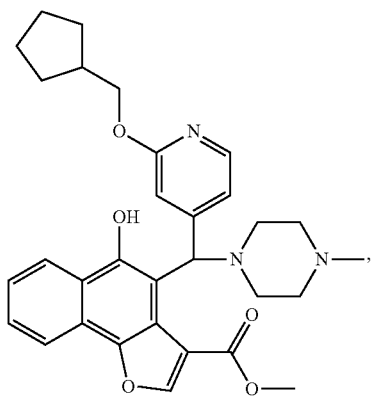
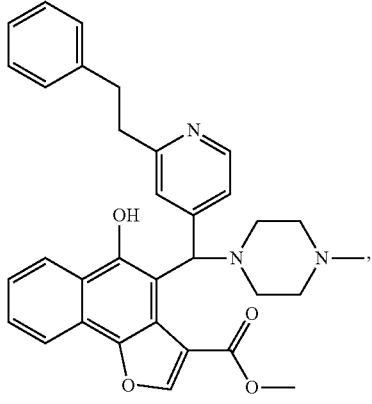
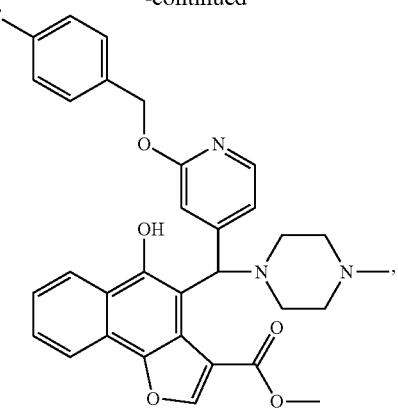
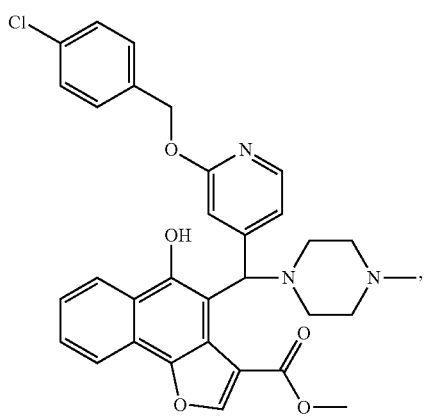
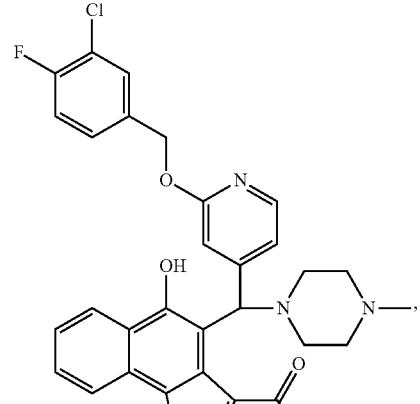
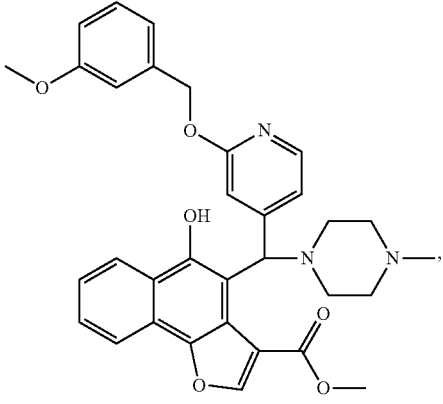

117
-continued
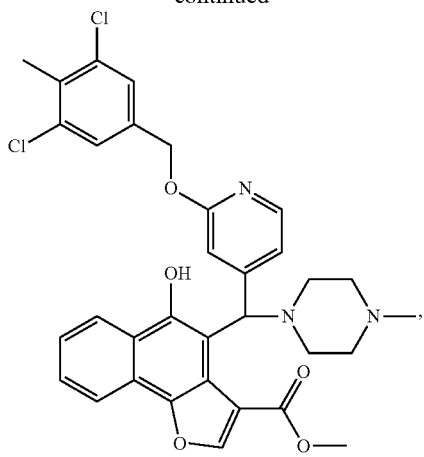
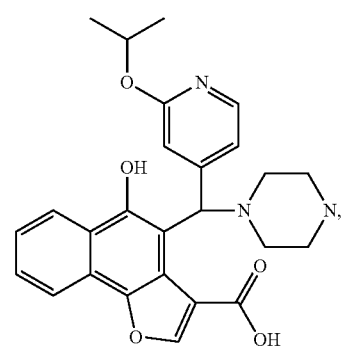
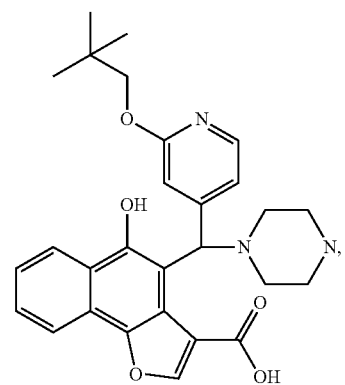
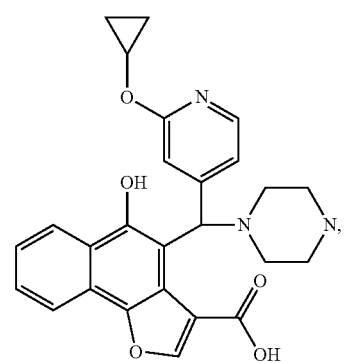
118
-continued
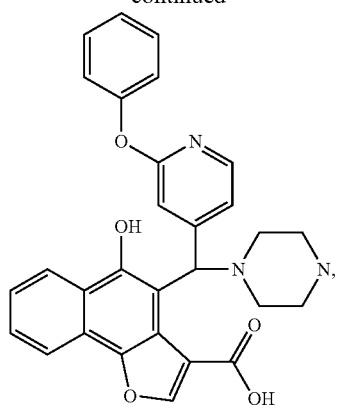
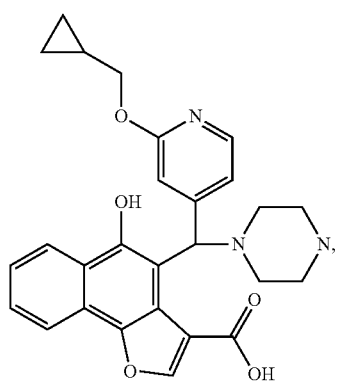
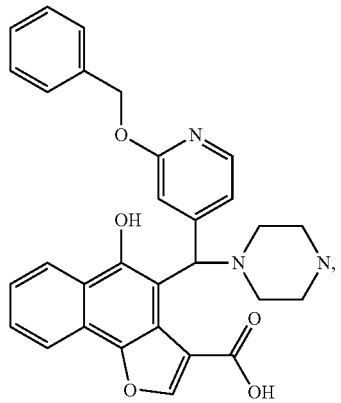
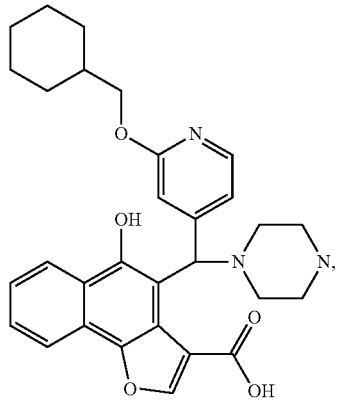

119
-continued
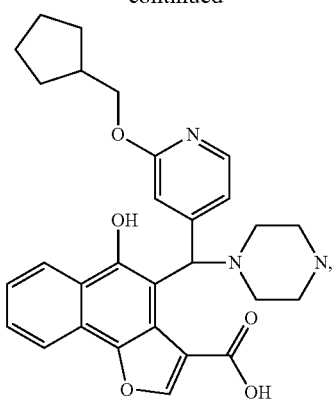
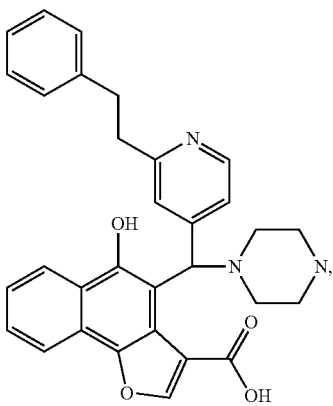
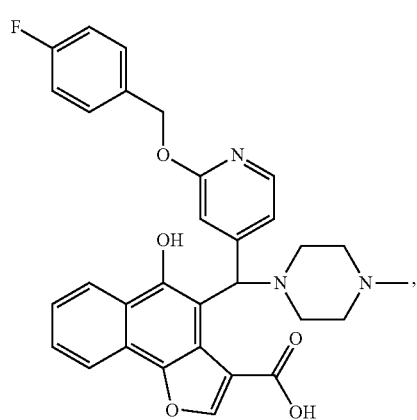
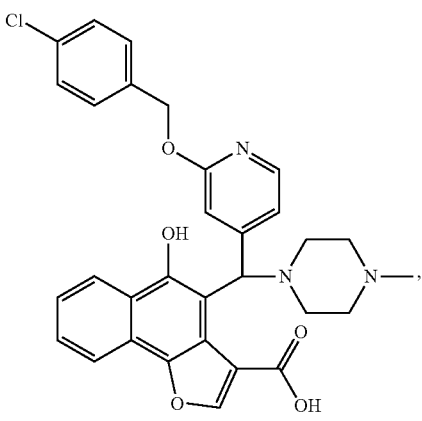
120
-continued
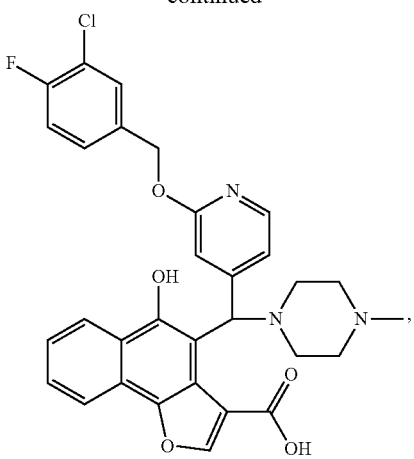
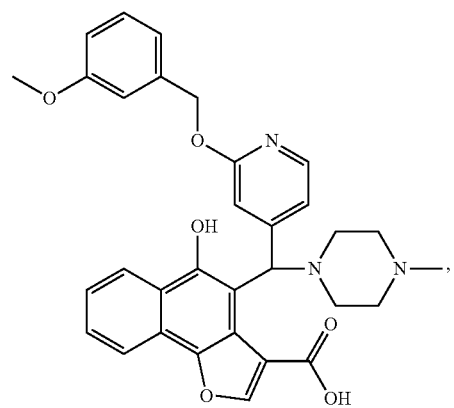
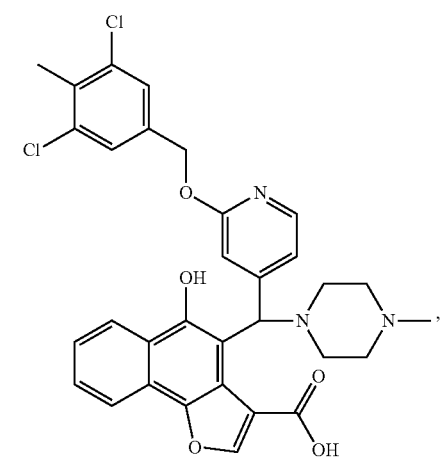
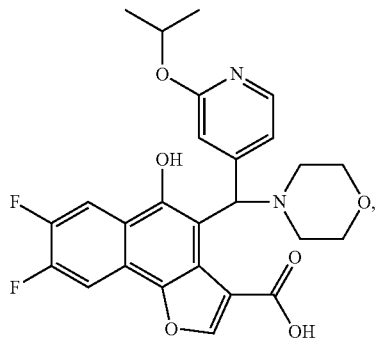

121
-continued
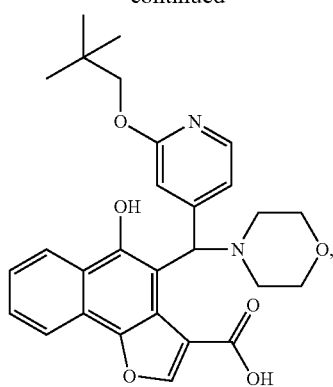
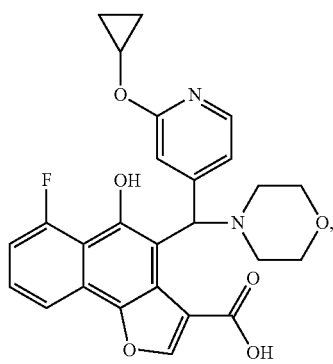
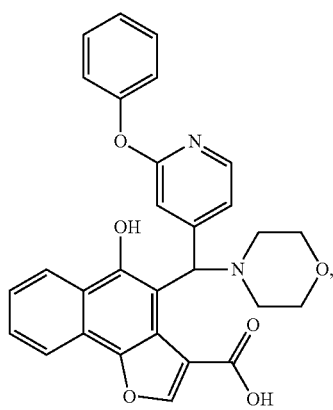
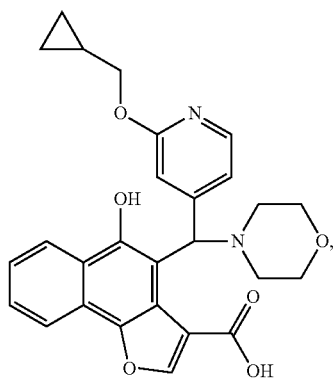
122
-continued
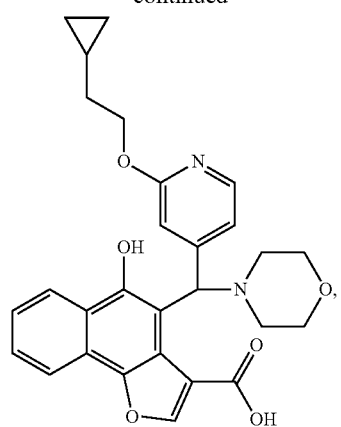
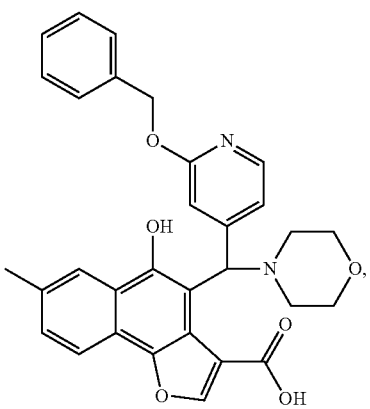
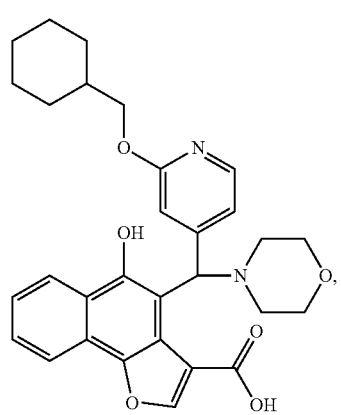
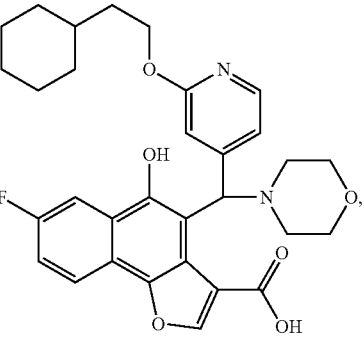

123
-continued
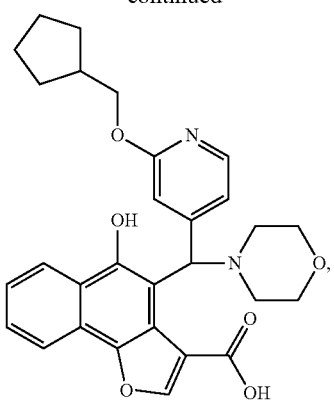
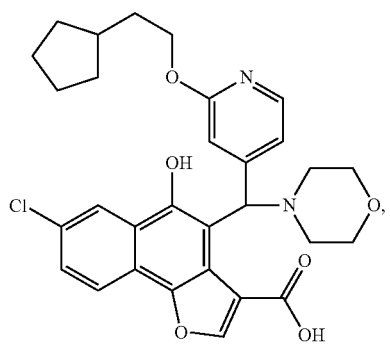
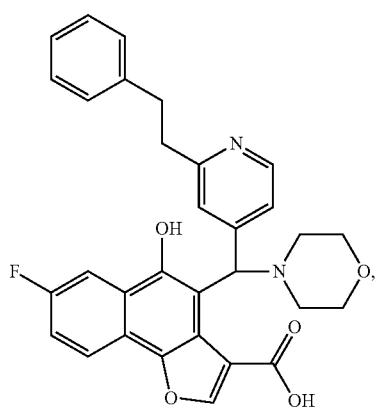
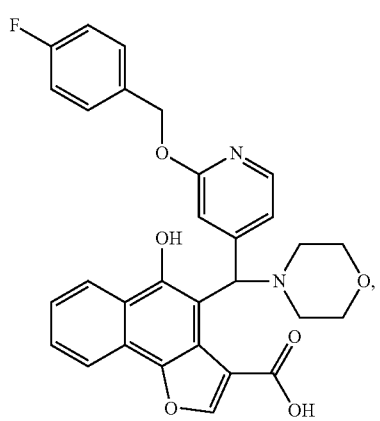
124
-continued
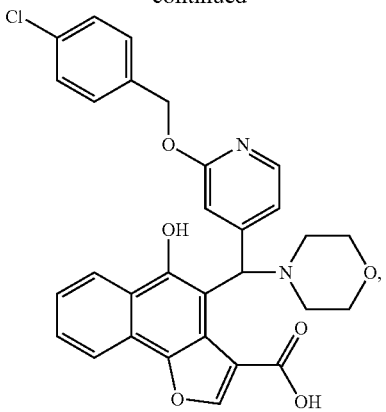
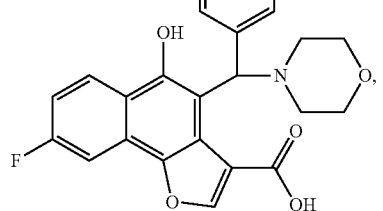
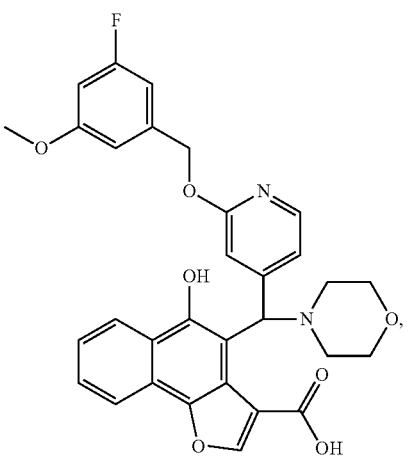

125
-continued
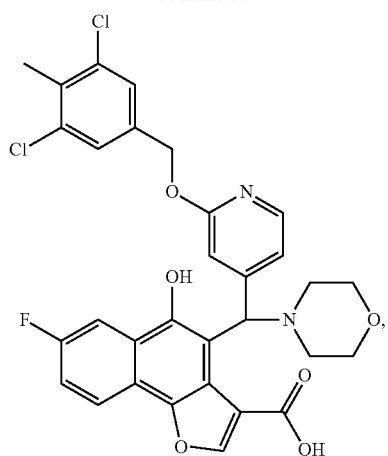
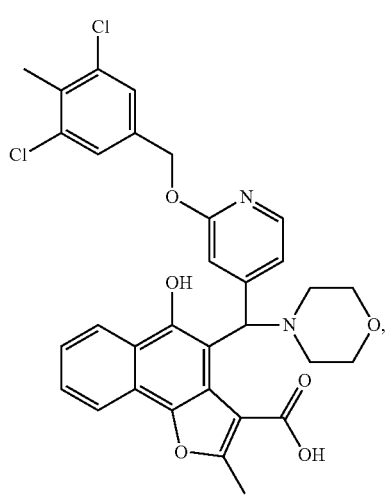
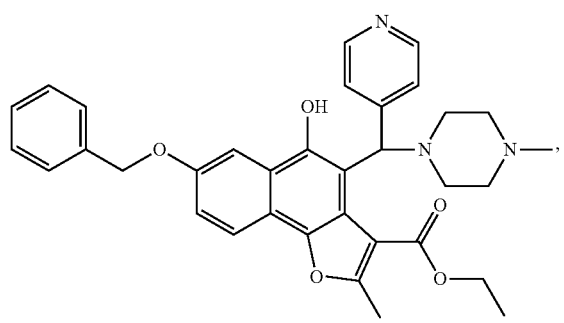
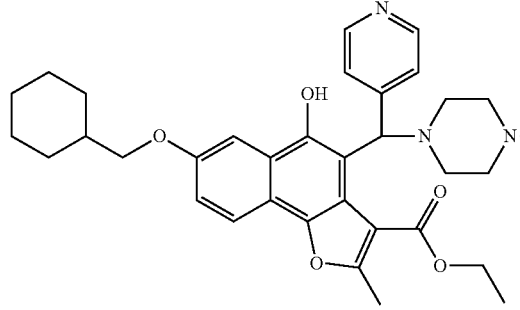
126
-continued
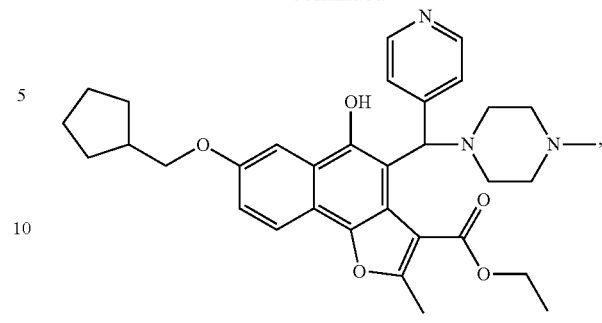
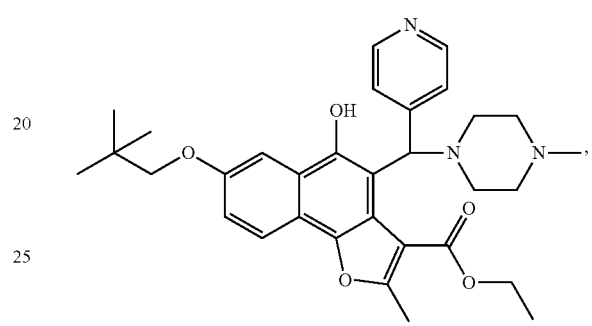
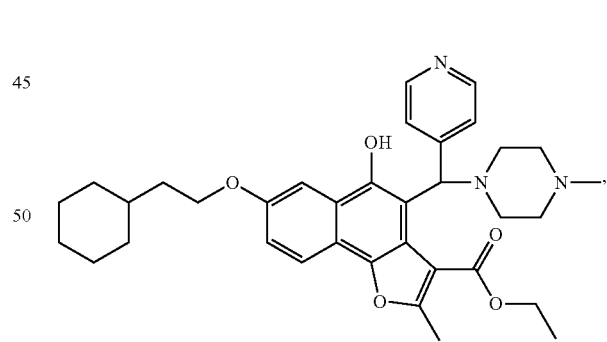
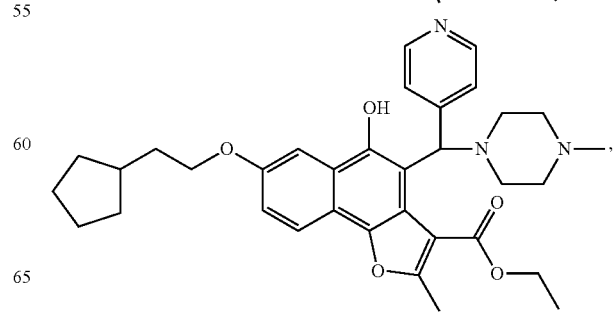

127
-continued
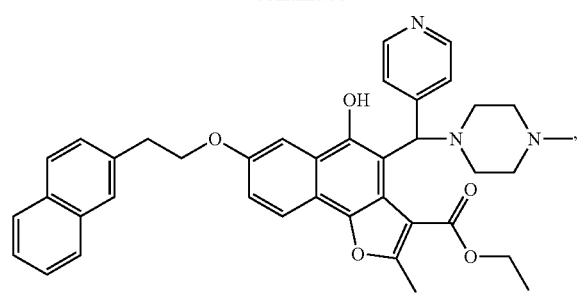
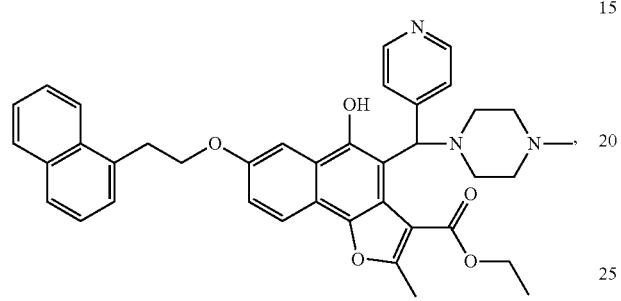
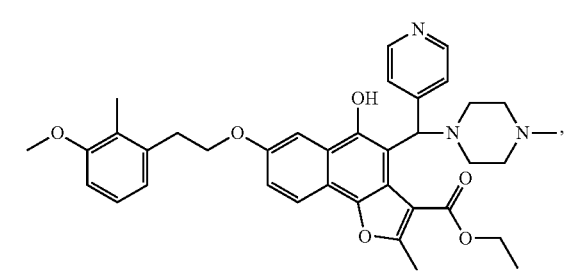
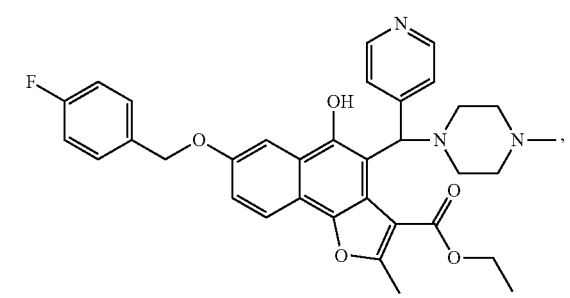
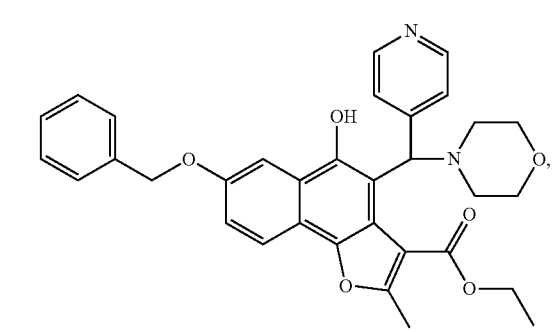
128
-continued
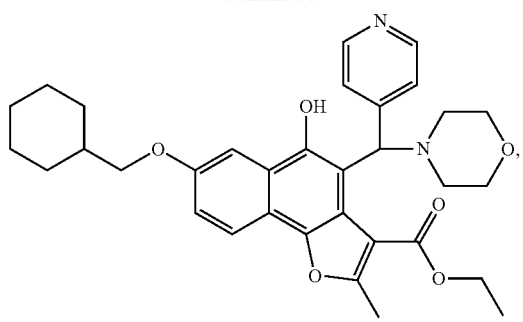
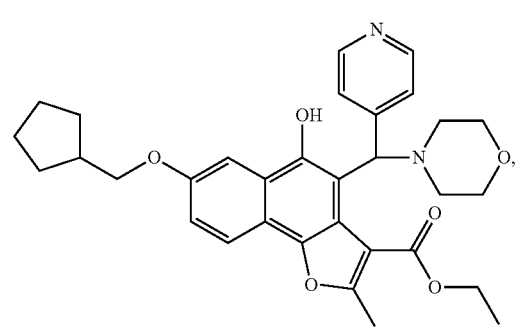
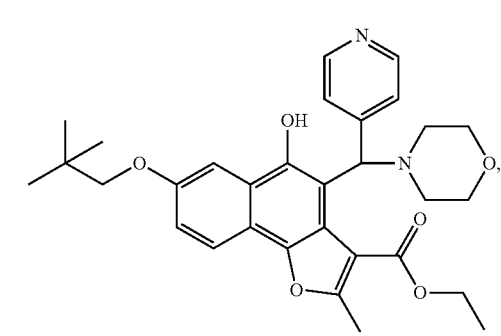
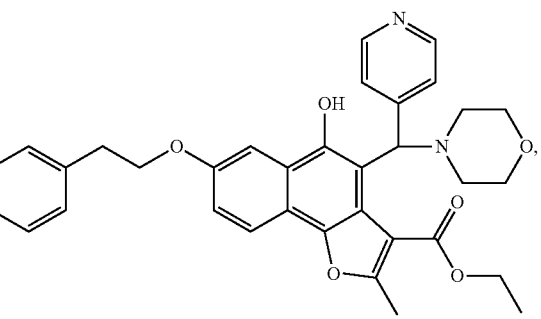
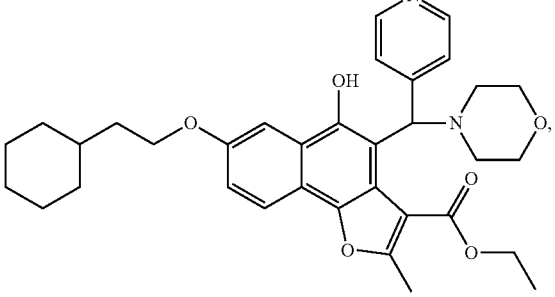

129
-continued
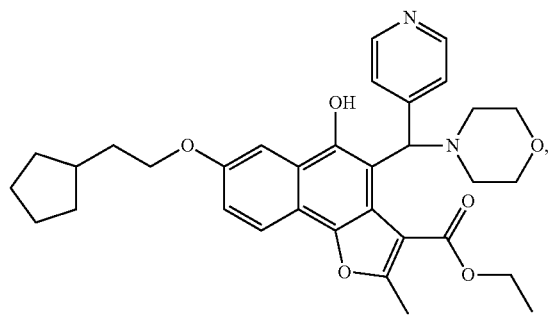
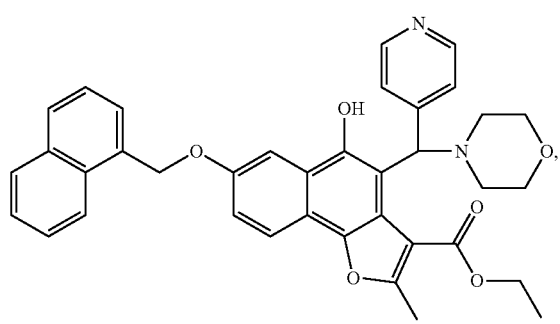
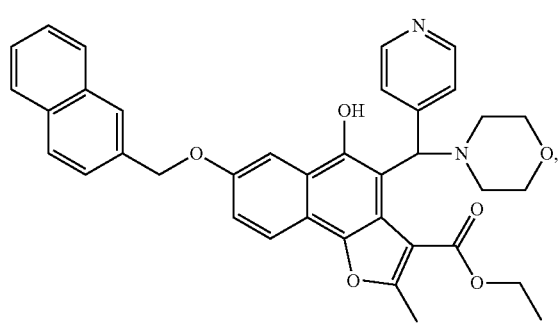
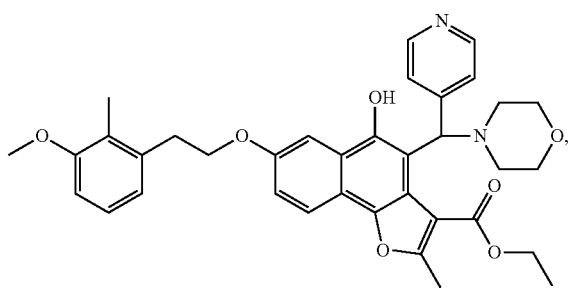
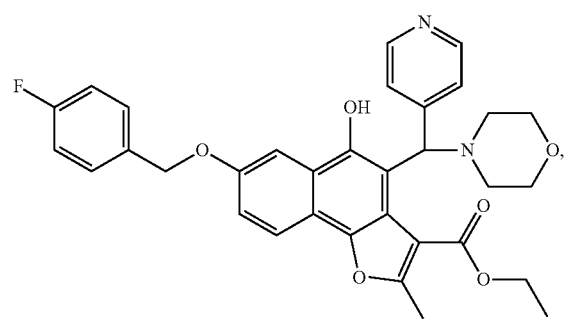
130
-continued
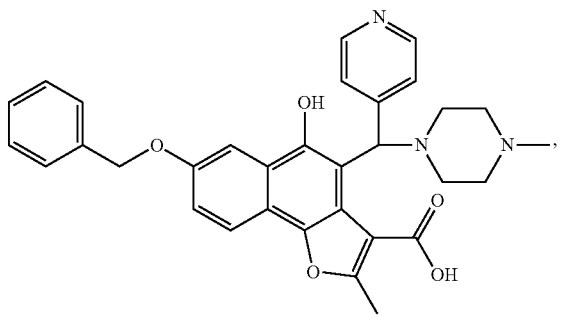
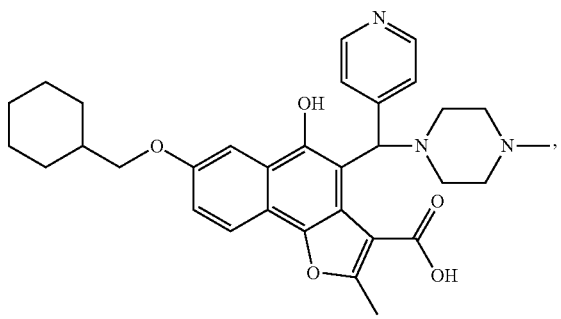
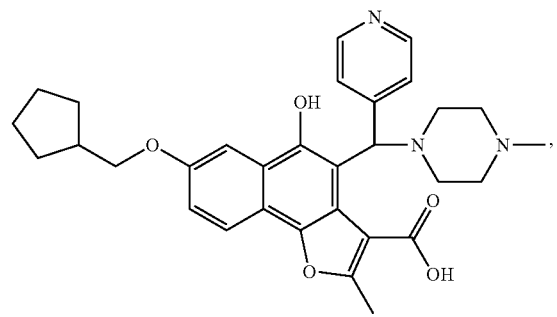
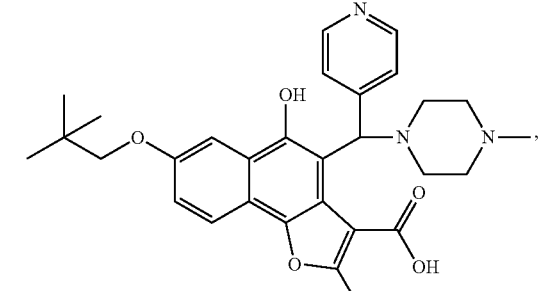
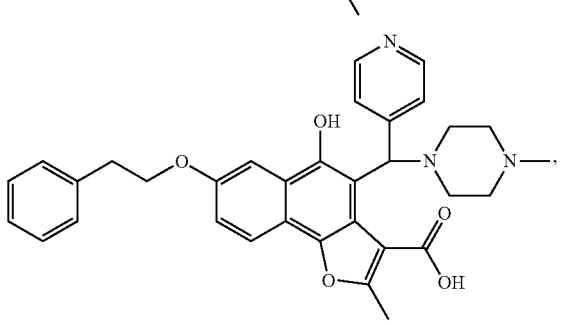

131
-continued
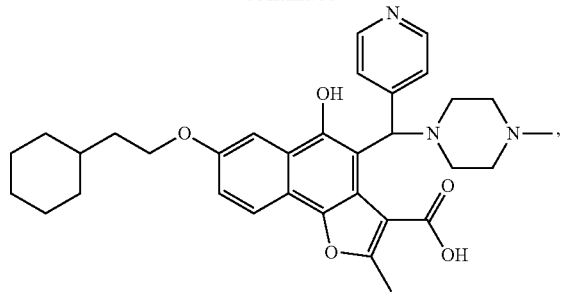
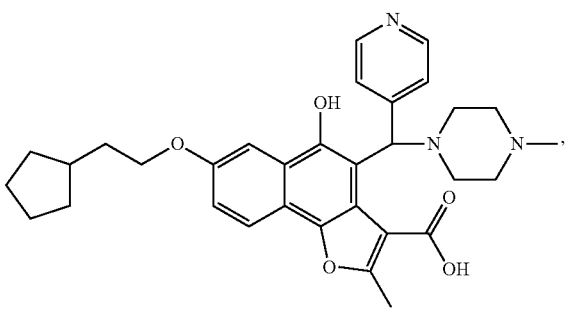
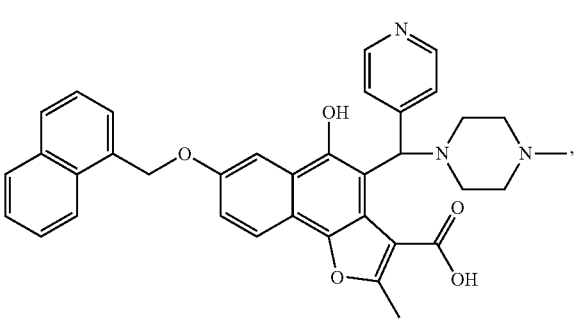
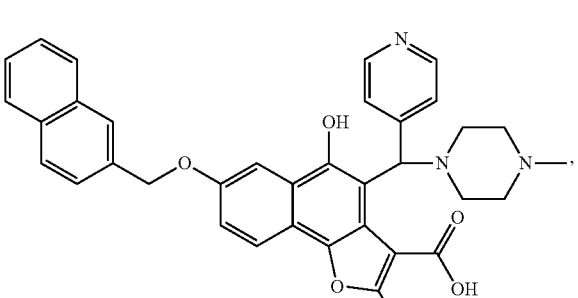
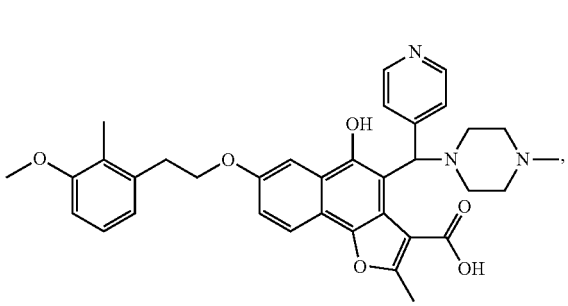
132
-continued
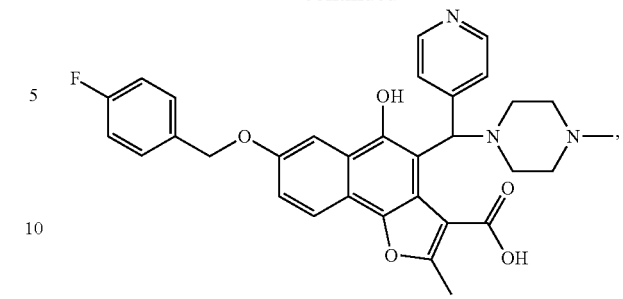
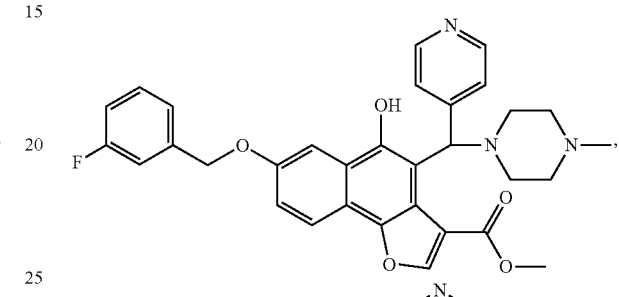
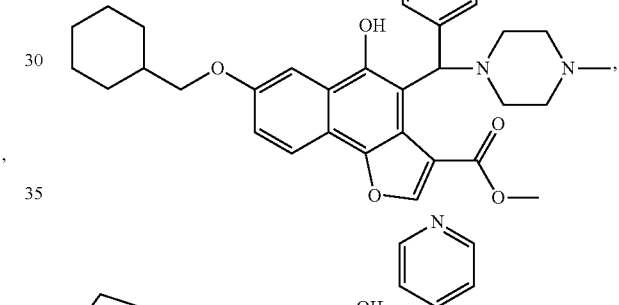
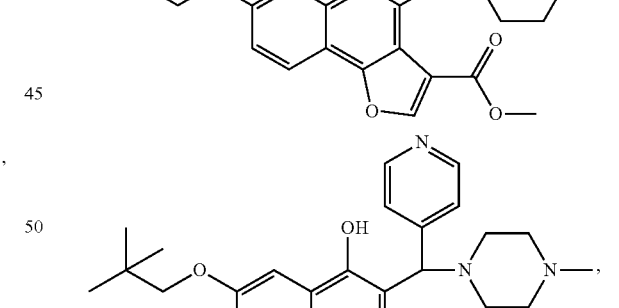
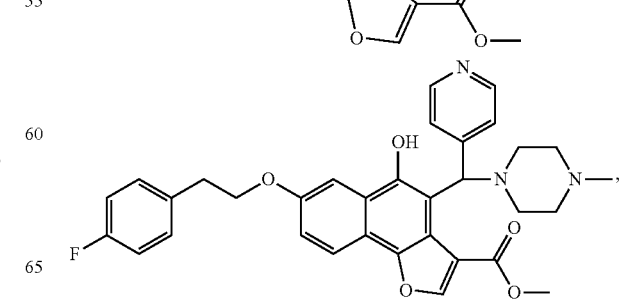

133
-continued
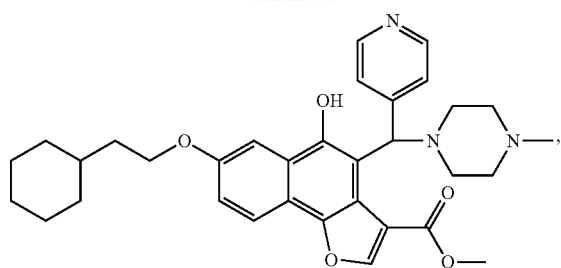
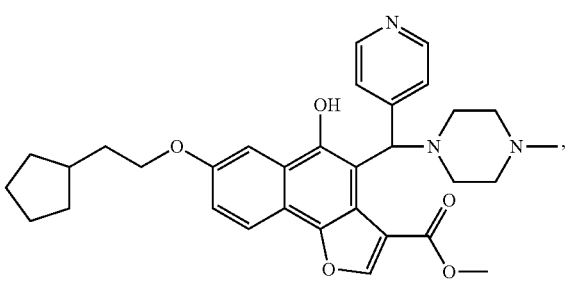
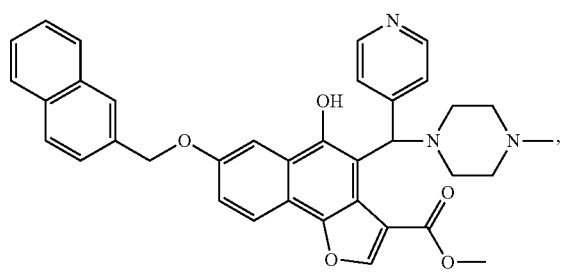
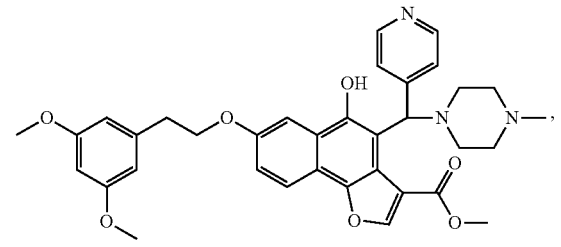
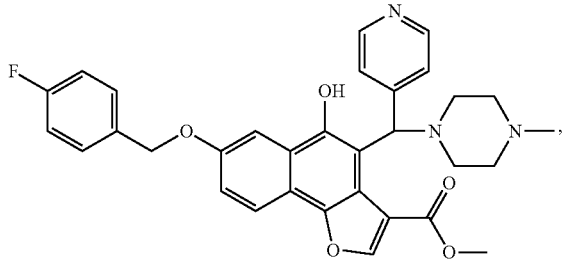
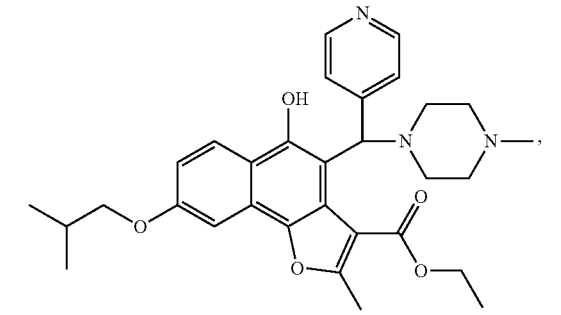
134
-continued
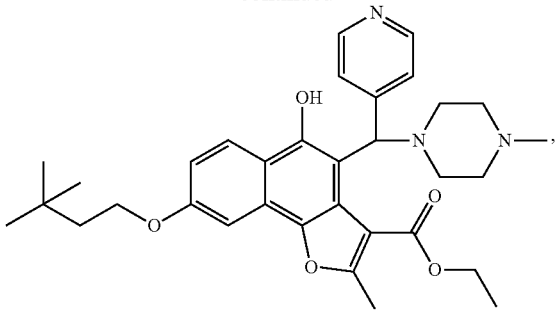
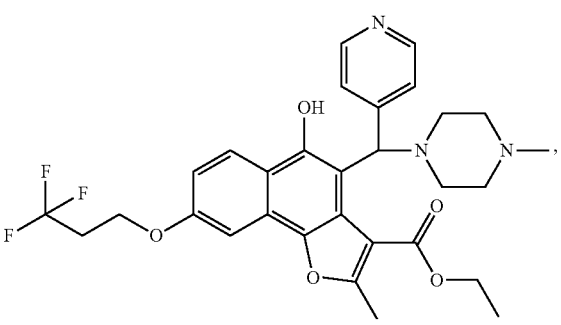
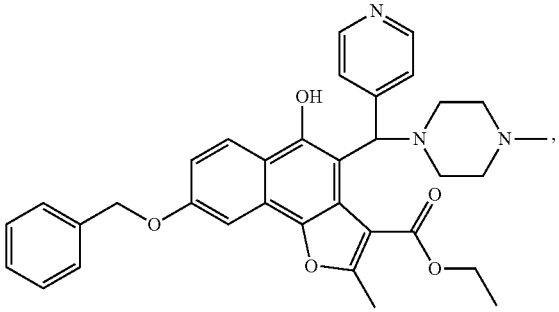
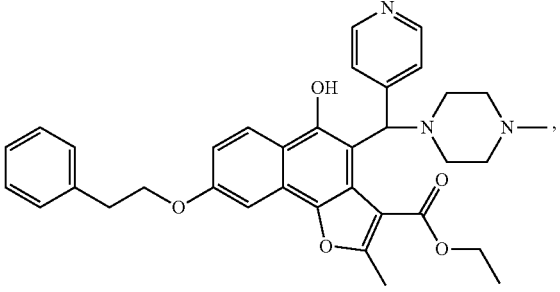
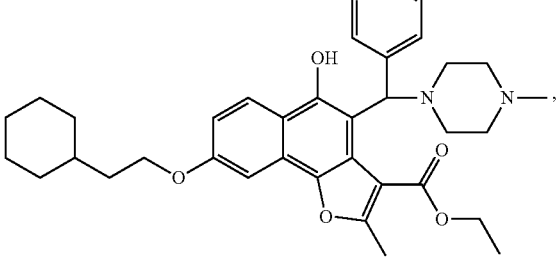

135
-continued
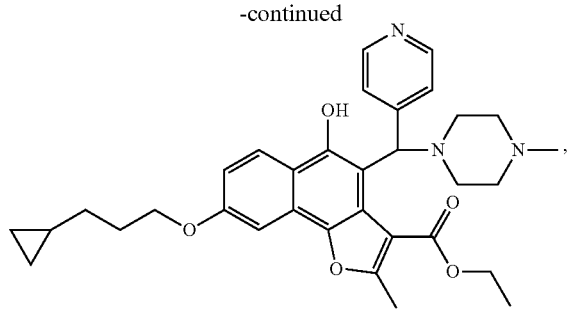
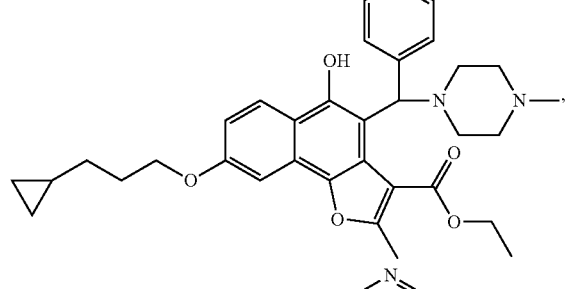
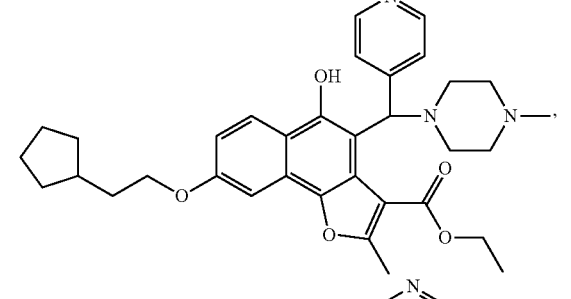
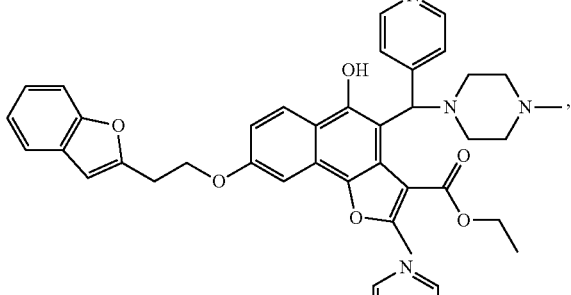
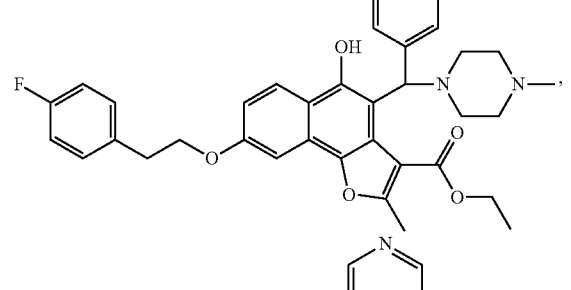
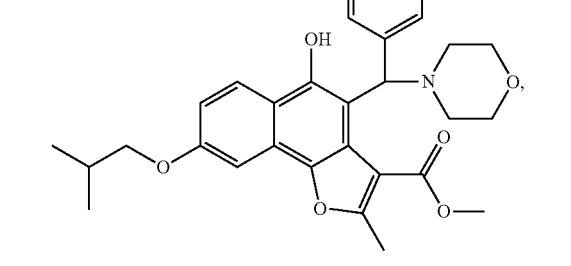
136
-continued
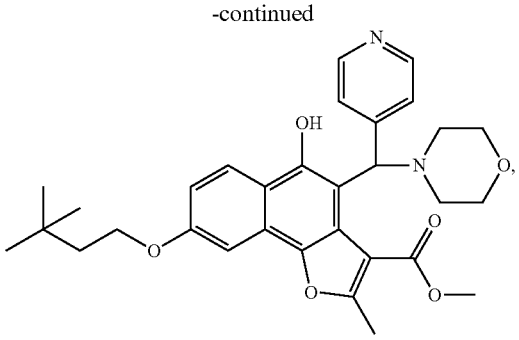
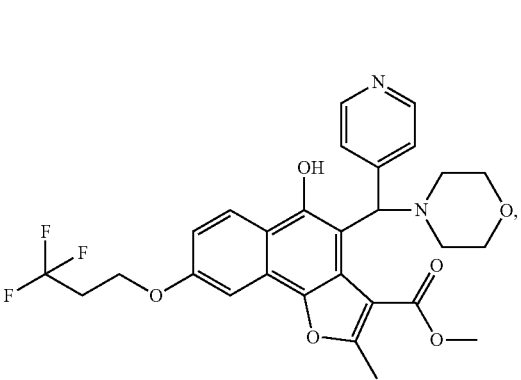
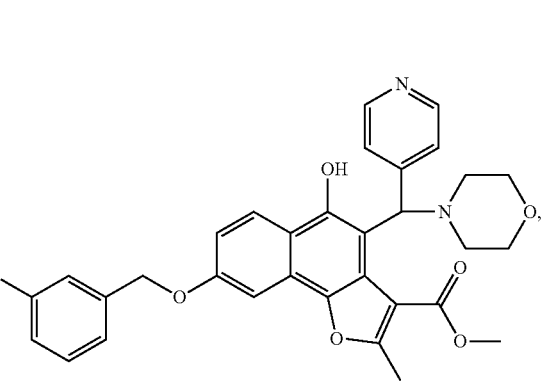
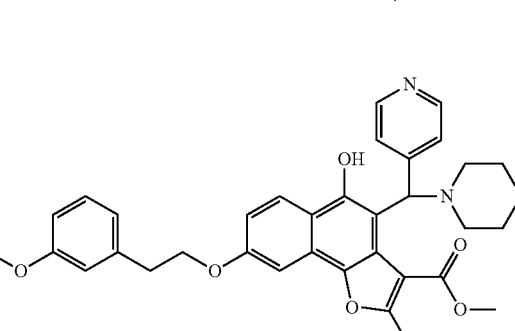
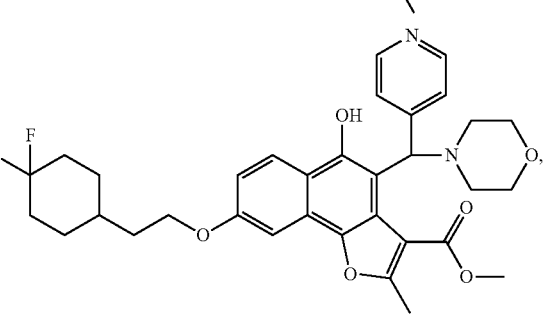

137
-continued
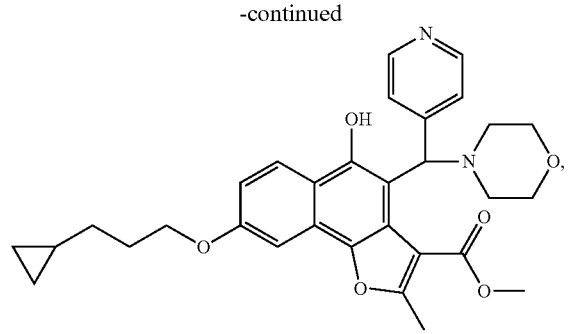
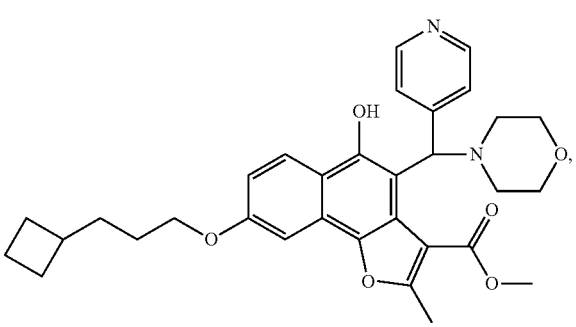
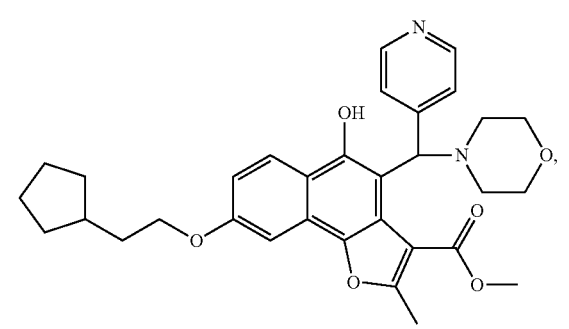
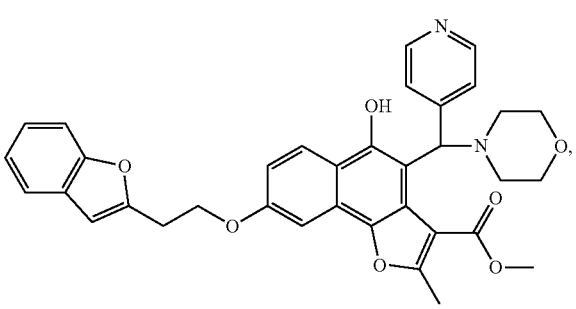
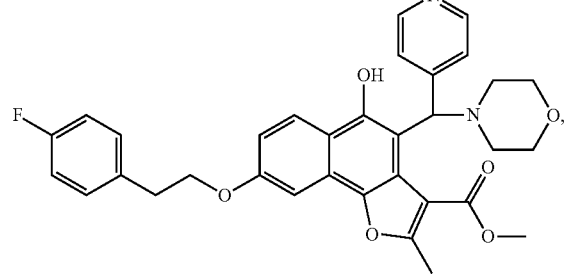
138
-continued
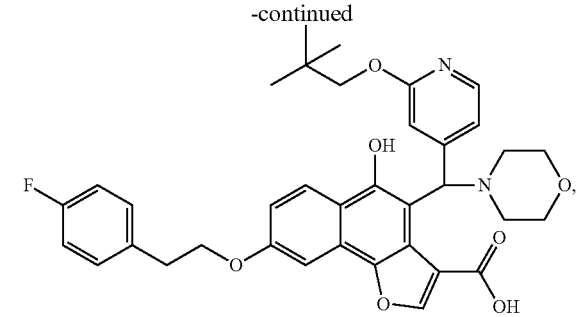
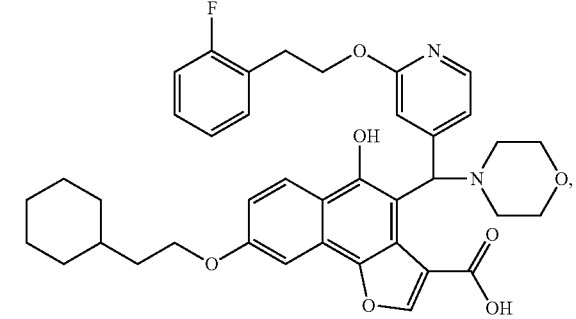
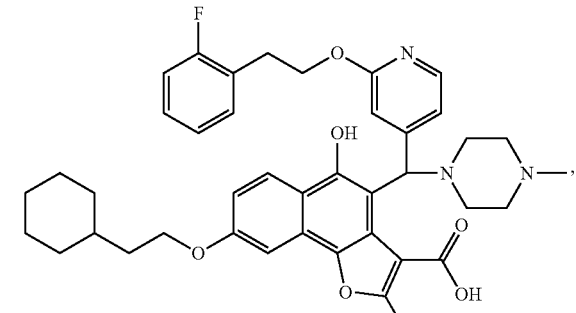
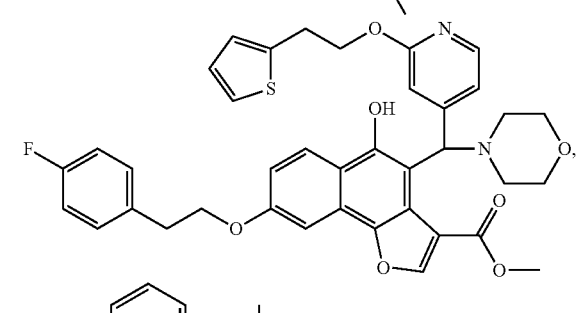
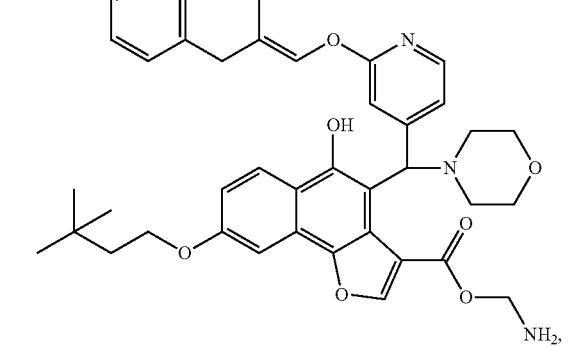
or a pharmaceutically acceptable salt, solvate, or prodrug thereof.
In some embodiments, the present invention provides the following Mcl-1 inhibitors:

139
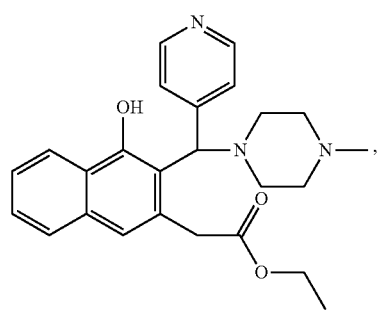
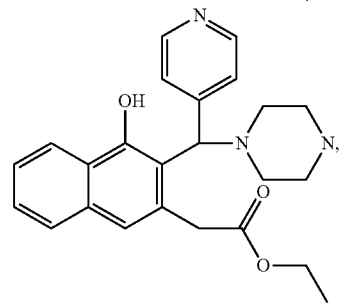
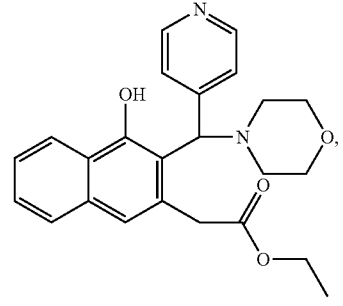
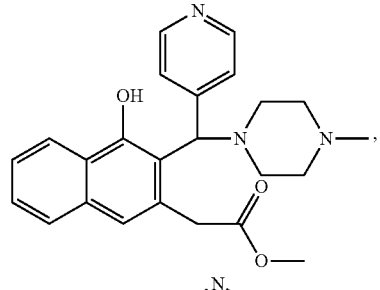
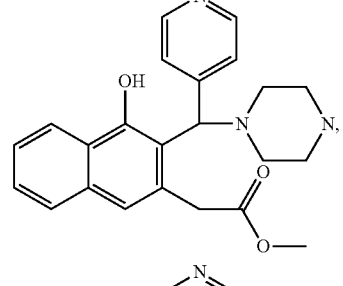
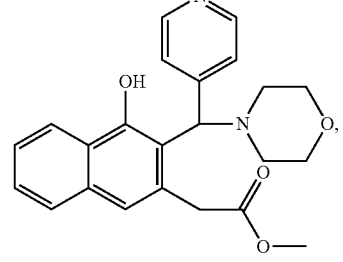
140
-continued
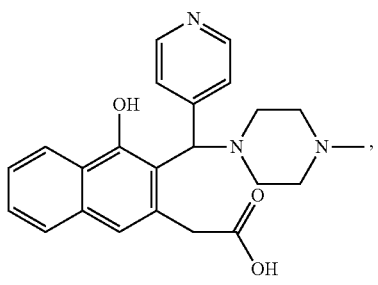
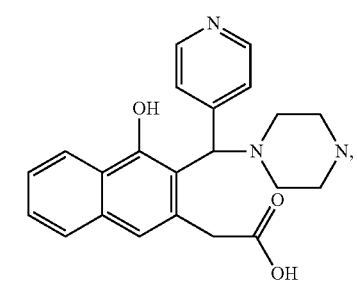
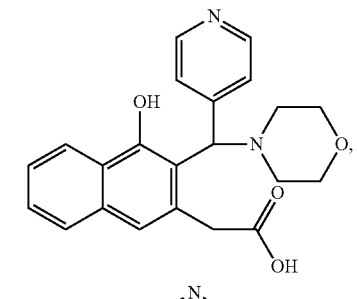
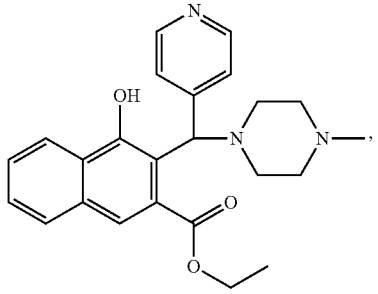
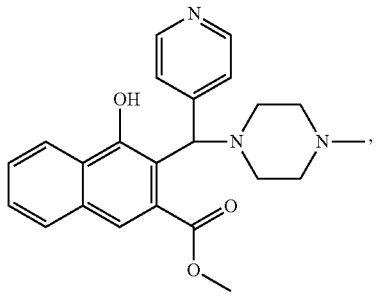
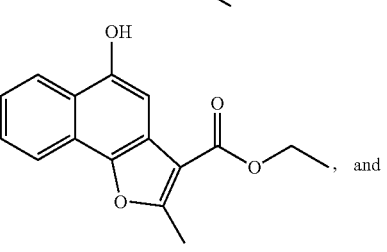
, and -continued

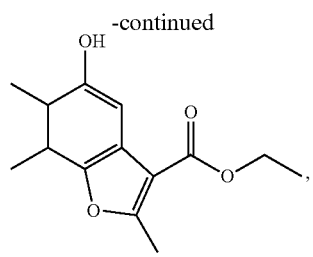

or a pharmaceutically acceptable salt, solvate, or prodrug thereof.

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The Mcl-1 inhibitors of the present invention (e.g., [(1-piperazinyl)-4-pyridinylmethyl]-Naphtho[1,2-b]furan compounds) can be used to induce apoptosis in any disorder that can be treated, ameliorated, or prevented by the induction of apoptosis. In one embodiment, the inhibitors can be used to induce apoptosis in cells comprising functional Mcl-1 and/or Mcl-1-related proteins.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, acute myeloid leukemia (AML), breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having Mcl-1 protein and/or Mcl-1-related protein expression.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is a anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-K B modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); antiandrogens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus ; bleomycin $A_2$ and bleomycin $B_2$) | Blenoxane | Bristol-Myers Squibb Co., NY, NY |

TABLE 1-continued

| | | |
|---|---|---|
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequs Pharmaceuticals, Inc., Menlo park, CA |

TABLE 1-continued

| | | |
|---|---|---|
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |

TABLE 1-continued

| | | |
|---|---|---|
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4':6,7]indolizino[1,2-b]quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R, 3S) - N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |

TABLE 1-continued

| | | |
|---|---|---|
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by Streptomyces plicatus) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |

TABLE 1-continued

| | | |
|---|---|---|
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R—(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

EXPERIMENTAL

Example I

This example shows a synthetic route for generating lead compounds of the present invention. In particular, synthesis of UMI-1033-class of compounds was accomplished in two steps starting from starting materials ethyl acetoacetate (see, e.g., Matiichuk, V. S.; et al., Farmatsevtichnii Zhurnal (Kiev) 2002, 6, 45-51; incorporated herein by reference in its entirety) (1) and naphthoquinone (see, e.g., Kumar, A.; et al., Tetrahedron Lett. 2010, 51, 1582-1584; incorporated herein by reference in its entirety) (2). Treatment of naphthoquinone with ethyl acetoacetate in the presence of a lewis acid, $ZnCl_2$ in refluxing MeOH readily underwent cyclocondensation reaction to afford the corresponding 5-hydroxy naphthofuran product (3) in 36% yield. The resulting naphthofuran was subjected to Mannich type condensation reaction by refluxing in the presence of appropriate aldehyde and substituted piperazine or morpholine in 5 mol % triton-X/water mixture to provide the desired product (4) with isolated yields of 20-60%. FIG. 7 shows this synthetic scheme for developing compounds of Formula I where R4 is ethyl.

Example II

Figure 5:
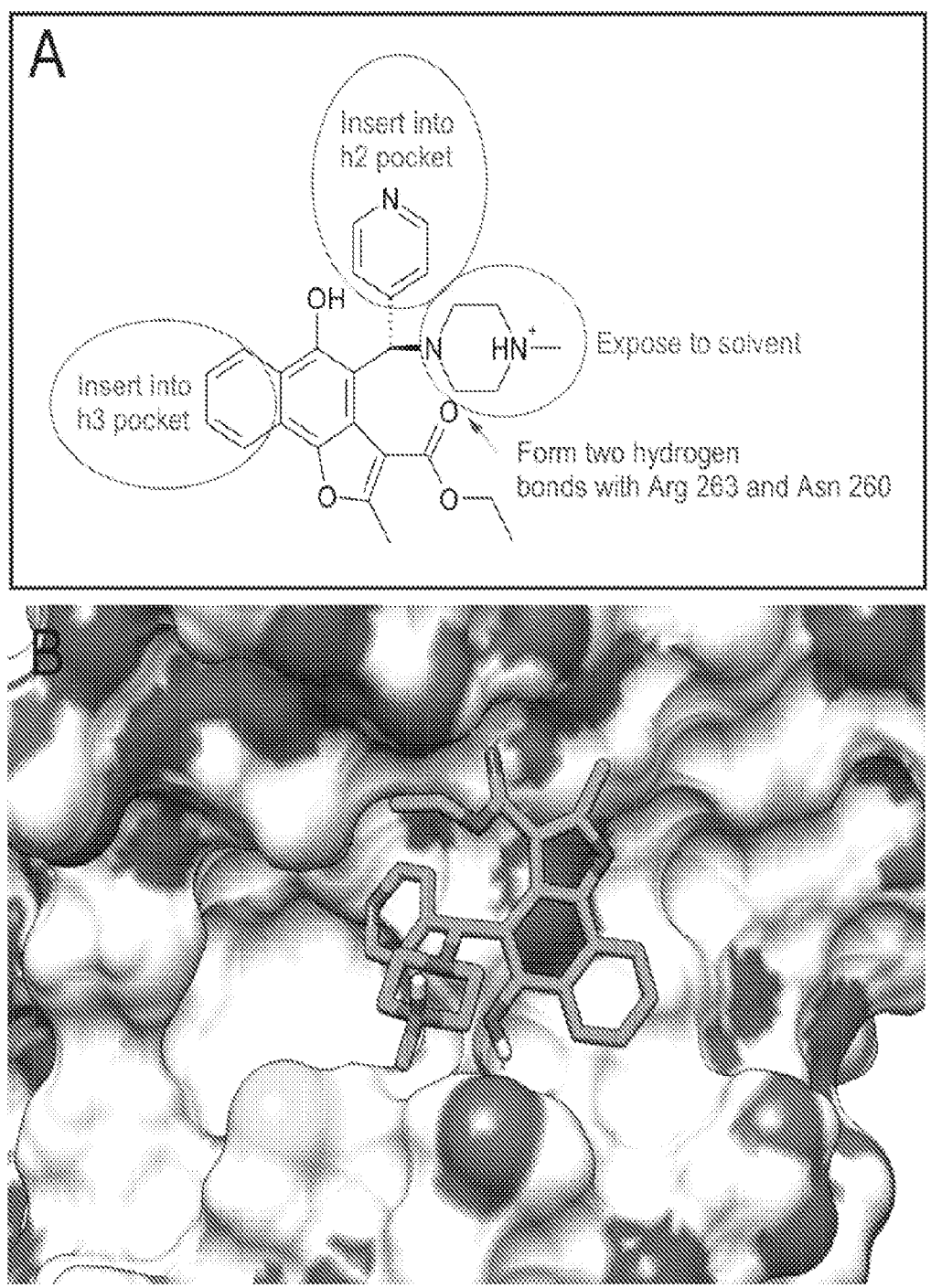
FIG. 5 describes the structure activity relationship of [(1-piperazinyl)-4-pyridinylmethyl]-Naphtho[1,2-b]furan compounds.

This example describes the binding relationship between UMI-1033 and Mcl-1. A Schrödinger's Induced Fit Docking (IFD) protocol was employed to explore the binding modes of UMI-1033 to the BH3 binding groove of Mcl-1. Both enantiomers of UMI-1033 were docked into the peptide binding groove of Mcl-1 using IFD, using the PDB structure: 2NLA. The docking poses were clustered, and the typical ones were further processed molecular dynamics (MD) simulation using Monte Carlo/Stochastic Dynamics (MC/SD) embedded in MarcroModel 9.8 by Schrödinger. The one which could clearly explain the structure-activity relationship (SAR) is shown in FIG. 5.

In this model, UMI-1033 fits and binds the BH3 binding groove very well. The pyridine ring, mimicking the residue of Leu 62 of Bim, inserts into the h2 pocket and is very close to Leu 267 and Val 253. The naphthalene ring, mimicking the residue of Ile 65 of Bim, is accommodated by the h3 pocket, forming hydrophobic interactions mainly with Val 220, which is on the rims of both the h3 and h4 pockets. The hydroxyl group attaching the naphthalene ring forms a hydrogen bond with a nitrogen atom in the imidazole ring of His 224. The ester group, mimicking the conserved Asp residue of BH3 peptides forms hydrogen bond network with Arg 263 and Asn 260. The 4-methyl-1-piperazinyl group, which is positively charged, exposes to solvent and has no direct interactions with the protein of Mcl-1, as was expected based on its hydrophilic nature.

Example III

Figure 6:
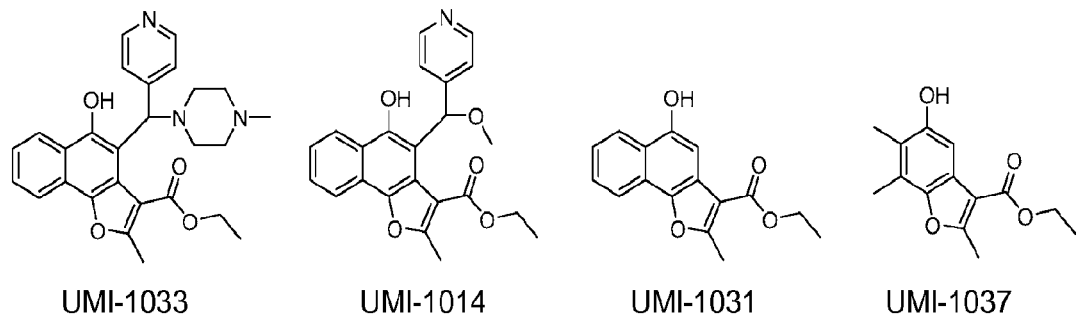
Figure 6:
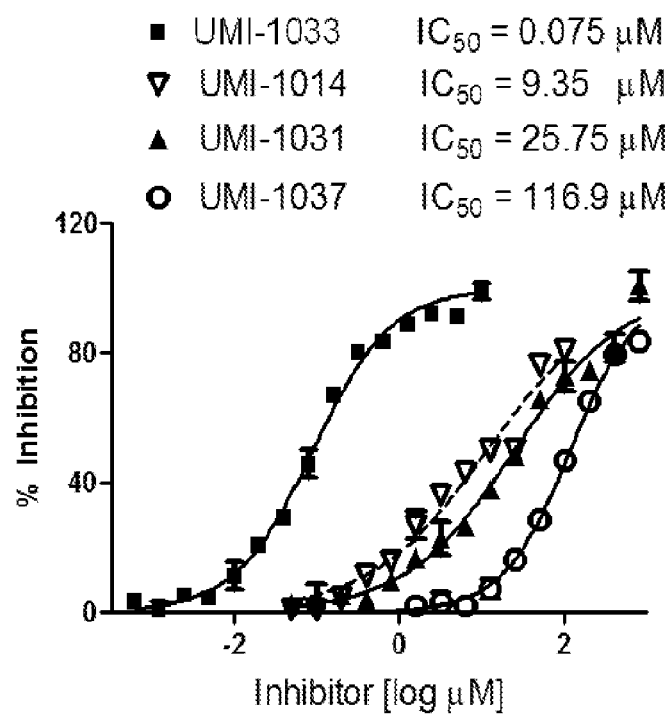

This example demonstrates that rigid 3D conformation of the ligand is critical in maintaining high affinity (see, e.g., FIGS. 1 and 6). The core structure of ([(1-piperazinyl)-4-pyridinylmethyl]-naphthofuran) of UMI-1033 is very rigid. This rigidity forces the three different rings attaching on the same carbon atom to form specific 3D conformation arrangement, which is favorite to bind to the protein of Mcl-1: one hydrophobic ring inserts into the h2 pocket; another hydrophobic fused ring inserts into the h3 pocket; the hydrophilic ring, whereas, immerses in solvent. It was predicted that disrupting of this specific 3D arrangement of the lead compound would significantly decrease the binding affinity. For this purpose several compounds were synthesized and tested (see, FIGS. 1 and 6). Compound UMI-1014, in which the 4-methyl-1-piperazinyl group is replaced by a small methoxyl group, showed 125 fold decreased binding affinity to Mcl-1 with $IC_{50}$ of 9.35 µM. If the pyridine ring in the core structure is substituted with H, compound UMI-119, is showing 28 fold reduction in binding to Mcl-1 in comparison with UMI-1033. Introducing a pyridine ring back in to the UMI-119 structure and obtaining compound UMI-1011, the binding to the protein is almost completely recovered ($IC_{50}$=190 nM) confirming that the rigidity of the molecule plays very important part for the high binding affinity of this class of compounds. Furthermore, the two fragments (compounds UMI-1031 and UMI-1037), derived from the lead compound UMI-1033, which cannot meet the specific 3D requirement, have significant decreased binding to the Mcl-1 protein, more than 350 fold. These results are furthermore suggesting that the rigid 3D conformation of this class of inhibitors is critical to keep high affinity to Mcl-1.

Example IV

This example further demonstrates binding properties of the compounds of the present invention. To further investigate and confirm the predicted binding model, whether or not the 4-Methyl-1-piperazinyl of compound UMI-1033 exposed to solvent and has not direct interactions with the protein as indicated by the mode in FIGS. 1 and 6, four different compounds in which the 4-methyl-1-piperazinyl group of compound UMI-1033 was replaced by other groups were synthesized and assayed for their abilities to inhibit Mcl-1 (see, FIG. 2). When this group was replaced by a similar but bulkier and more hydrophobic groups (compounds UMI-1008 and UMI-1009), the inhibition to Mcl-1 was kept same, demonstrating that ethyl and isopropyl groups don't have any additional contact with the protein and they are probably exposed to the solvent. When this group was replaced by a morpholinyl group, compound UMI-1007 has similar binding to Mcl-1. Both 4-methyl-1-piperazinyl group and morpholinoyl group are very common groups embedded in many drugs for improving the physico-chemical properties, in particular improving their hydrophilic properties. Indeed, when the piperazinyl group was substituted with bulkier and more hydrophobic group, as exampled by compound UMI-1011, the binding affinity to Mcl-1 decreased 3 fold with $IC_{50}$ value of 0.190 µM. One of the possible reason is that the 3,4-dihydroisoquinolin-2(1H)-yl group of compound 1011 is hydrophobic and hard to soak in solvent, which leads to decrease binding to Mcl-1 protein.

Example V

Figure 3:
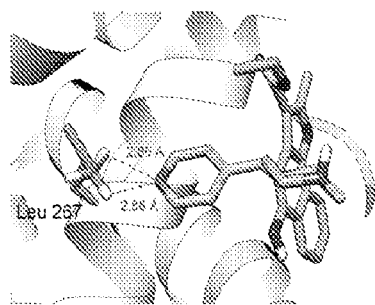
Figure 3:
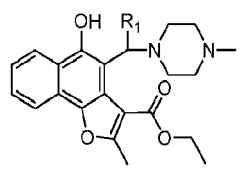

This example describes the binding properties of compounds of the present invention (see, FIG. 3). As indicated by the IFD calculations, the pyridine ring in the compound UMI-1033, inserting into the h2 pocket of Mcl-1, mimics the residue of Leu 62 of Bim and forms hydrophobic interactions mainly with Leu 267 and Val 253 of the protein. It was expected that if replacing the pyridine ring by a more hydrophobic ring, such as a benzene ring, the inhibition against Mcl-1 would be increased. However, compound UMI-1001, where the pyridine ring was replaced with a benzene ring the binding affinity to Mcl-1 protein was decreased for about 2 fold (see, FIG. 3). When the 4-pyridinyl ring was changed to a 3-pyridinyl ring, which, however, does not change the hydrophobicity properties, the activity to Mcl-1 dropped about 3 folds. After carefully examining the binding mode of compound UMI-1033 to Mcl-1, it was found that the nitrogen atom in the pyridine ring is very close to the side chain of Leu 267. Therefore, the replacement of the pyridine ring with a benzene ring will induce clash between the compound and the protein, leading to decreasing of the binding. This trend continued in compounds where hydrophobic groups were introduced at the para position of the phenyl ring (compounds UMI-118, UMI-117 and UMI-69) and the binding decreased 3, 4 and 6 fold respectively. It is noteworthy that when a fluorine atom is attached at the different three positions in the benzene ring of compound UMI-1001, the binding affinity is significantly changed. A fluorine atom at para or meta position does not affect the binding to the Mcl-1 protein (compounds UMI-118 and UMI-1003 with $IC_{50}$ values of 0.19 and 0.20 µM respectively), while attaching a fluorine atom at the ortho position leads to the significant decrease in binding affinity with $IC_{50}$ value of 2.6 µM.

Example VI

Figure 4:
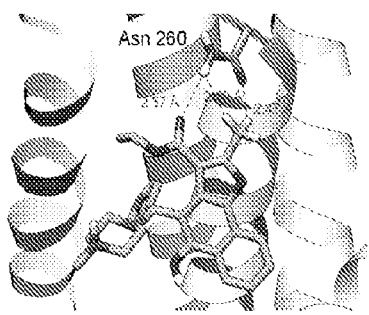
Figure 4:
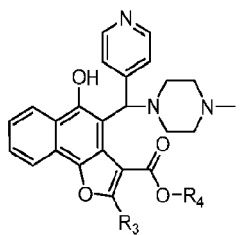

This example describes the binding properties of compounds of the present invention (see, FIG. 4). In the binding mode of compound UMI-1033, the 2-methyl-furan ring does not form direct interactions with the protein of Mcl-1. The methyl group in the furan ring is close to Asn 260, suggesting that bulker hydrophobic groups in this position will not be tolerated. Three compounds were synthesized which proved this hypothesis. The substitution of the methyl group with ethyl, tert-butyl and phenyl groups leads to decrease of the binding activity to 0.21, 0.47 and 1.21 µM, respectively.

Example VII

Figure 8:
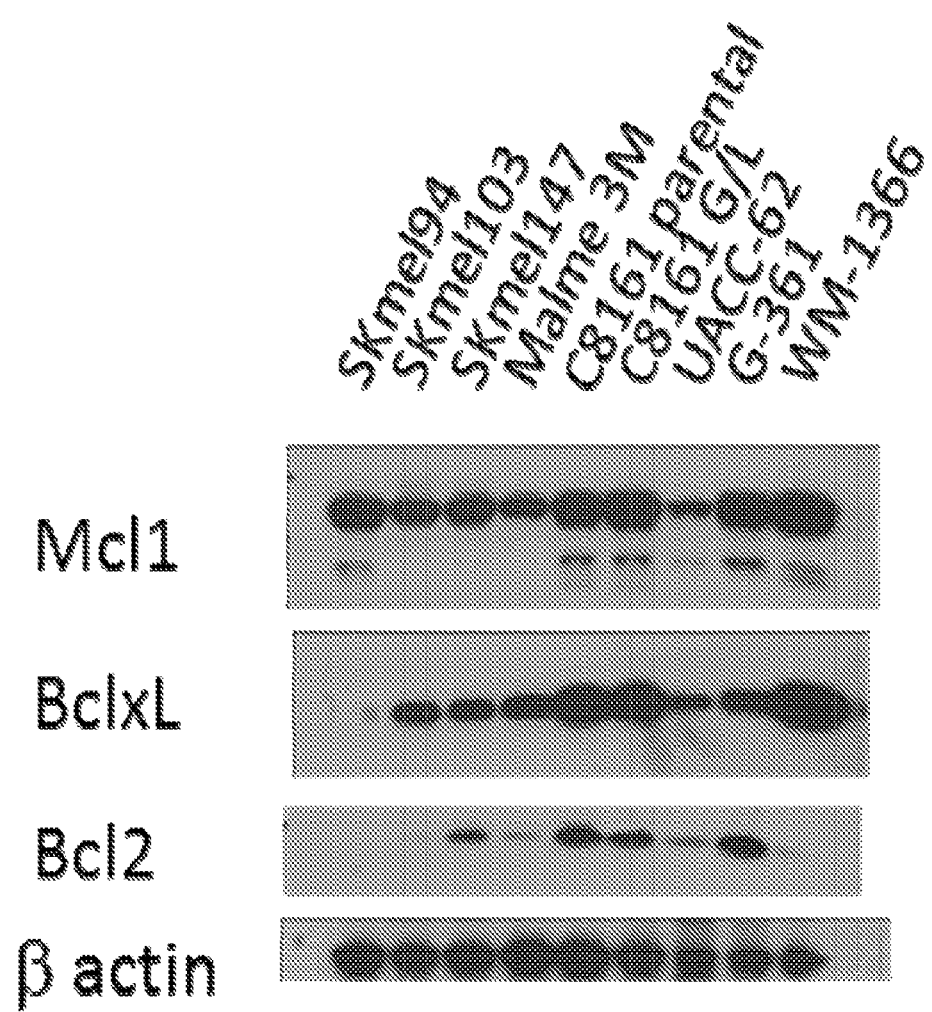
FIG. 8 shows a panel of melanoma cell lines that were tested in cell growth inhibition studies and the expression profile of three members anti-apoptotic proteins: Mcl-1, Bcl-2 and Bcl-xL.

This example demonstrates that the compounds of the present invention inhibit cell growth of a panel of melanoma cancer cell lines. FIG. 8 shows the expression profile of three members anti-apoptotic proteins: Mcl-1, Bcl-2 and Bcl-xL in a panel of melanoma cell lines that were used in cell growth inhibition studies. All of the tested cell lines have high expression level of Mcl-1 protein. FIG. 9 shows that compounds of the present invention inhibit the cell growth of all tested melanoma cell lines.

Example VIII

This example demonstrates the selective binding of Mcl-1 inhibitors against five members of Bcl-2 family anti-apoptotic proteins. As shown in Table 2, the binding profile studies showed that Mcl-1 inhibitors displayed significantly decreased binding affinities to the rest of the anti-apoptotic proteins, demonstrating high selectivity for binding to Mcl-1 protein.

TABLE 2

Binding affinity of Mcl-1 inhibitors against five members of Bcl-2 family anti-apoptotic proteins

| Compound | Mcl-1 Ki [µM] | A1 Ki [µM] | Bcl-w Ki [µM] | Bcl-2 Ki [µM] | Bcl-xL Ki [µM] |
|---|---|---|---|---|---|
| UMI-1033 | 0.020 | >25 | >30 | 16.73 | >30 |
| UMI-1007 | 0.020 | >25 | >30 | >30 | >30 |
| UMI-1009 | 0.015 | >25 | >30 | >30 | >30 |

TABLE 2-continued

Binding affinity of Mcl-1 inhibitors against five members of Bcl-2 family anti-apoptotic proteins

| Compound | Mcl-1 Ki [µM] | A1 Ki [µM] | Bcl-w Ki [µM] | Bcl-2 Ki [µM] | Bcl-xL Ki [µM] |
|---|---|---|---|---|---|
| UMI-1026 | 0.030 | >25 | >30 | >30 | >30 |
| UMI-1033-3 | 0.120 | >25 | 33 | >30 | >30 |
| UMI-1035 | 0.015 | >25 | 28 | 13.83 | >30 |
| UMI-1039 | 0.600 | >25 | >30 | >30 | >30 |

Example IX

Figure 10:
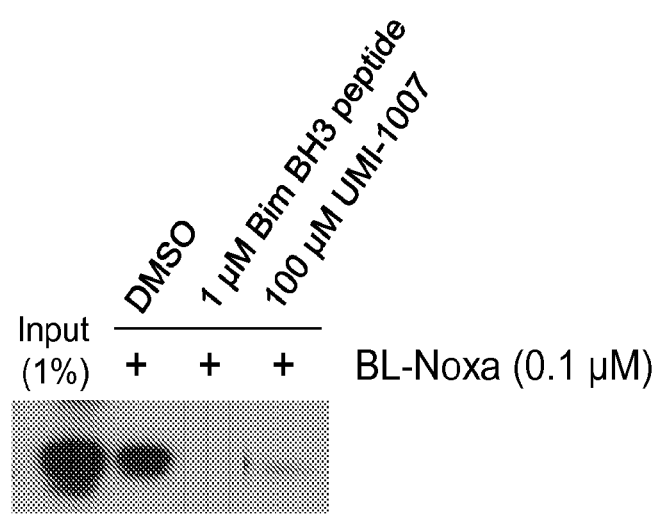
FIG. 10 shows that BL-Noxa selectively pulled down cellular Mcl-1 from 2LMP cell lysate and UMI-1007, effectively disrupts the interactions between BL-Noxa and cellular Mcl-1.

This example demonstrates that the Mcl-1 inhibitors of the present invention are able to bind cellular, endogenous Mcl-1 protein. To demonstrate that the novel class Mcl-1 inhibitors can bind cellular, endogenous Mcl-1 protein, a pull-down assay using a biotin-labeled Noxa BH3 peptide (BL-Noxa) was employed and cell lysate obtained from 2LMP cancer cell lines. As presented on FIG. 10, BL-Noxa selectively pulled down cellular Mcl-1 from 2LMP cell lysate and UMI-1007, effectively disrupted the interactions between BL-Noxa and cellular Mcl-1. Consistent with the in vitro binding results, these data demonstrate that UMI-1007 binds the endogenous, cellular Mcl-1 protein and blocks the binding of BL-Noxa to Mcl-1.

Example X

Figure 11:
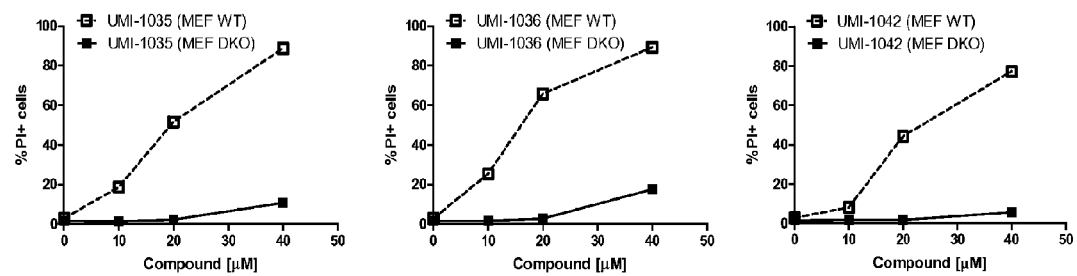
FIG. 11 shows cell viability studies using wild type (WT) murine embryonic fibroblasts (MEF) and double knockout (DKO) cells deficient in both, Bax and Bak.

This example, and FIG. 11, demonstrates that tested Mcl-1 inhibitors induce cell death mediated through Bcl-2 family in a Bax/Bak-dependent mechanisms. It is known that apoptotic effectors Bak and Bax can be suppressed by multidomain anti-apoptotic proteins such as Mcl-1. To interrogate the mechanism of action, the activity of several novel Mcl-1 inhibitors were evaluated in mouse embryonic fibroblast (MEF) cells that included wild-type (WT) as well as cells deficient in Bax/Bak (DKO). All tested compounds, UMI-1035, -1036 and -1042 induced cell death in MEF WT but not in MEF DKO cells. These results demonstrate that tested Mcl-1 inhibitors induced cell death mediated through Bcl-2 family in a Bax/Bak-dependent mechanisms.

Example XI

This example, and Table 3, demonstrates that targeting of Mcl-1 is a useful strategy for the treatment of AML. Acute myeloid leukemia (AML) frequently relapses after initial treatment. Drug resistance in AML has been attributed to high levels of the anti-apoptotic Bcl-2 family proteins. Indeed, Mcl-1 is essential for development and survival of acute myelogenous leukemia cells. Therefore the cellular activity of Mcl-1 inhibitors against AML human cancer cell lines was tested. Blockade of Mcl-1 by these inhibitors (see Table 3) killed AML-derived cell lines, HL-60 and MV4-11, but had less impact on the human CML-derived (K562) cell line. These results demonstrate that targeting of Mcl-1 may be a useful strategy for the treatment of AML.

TABLE 3

Cellular activity of Mcl-1 inhibitors. $EC_{50}$ values of tested inhibitors against leukemia human tumor cell lines.

| Compound | HL-60 $EC_{50}$ [μM] | MV4-11 $EC_{50}$ [μM] | K562 $EC_{50}$ [μM] |
|---|---|---|---|
| 1007NB | 15.98 | 12.79 | N/A |
| 1009NB | 3.98 | 7.15 | >30 |
| 1033LM | 11.30 | 7.05 | >30 |
| 1035LM | 12.30 | 6.16 | 24.64 |
| 1036LM | 16.16 | 8.22 | >30 |
| 1042LM | 14.71 | 10.10 | >30 |

Example XIII

Figure 12A:
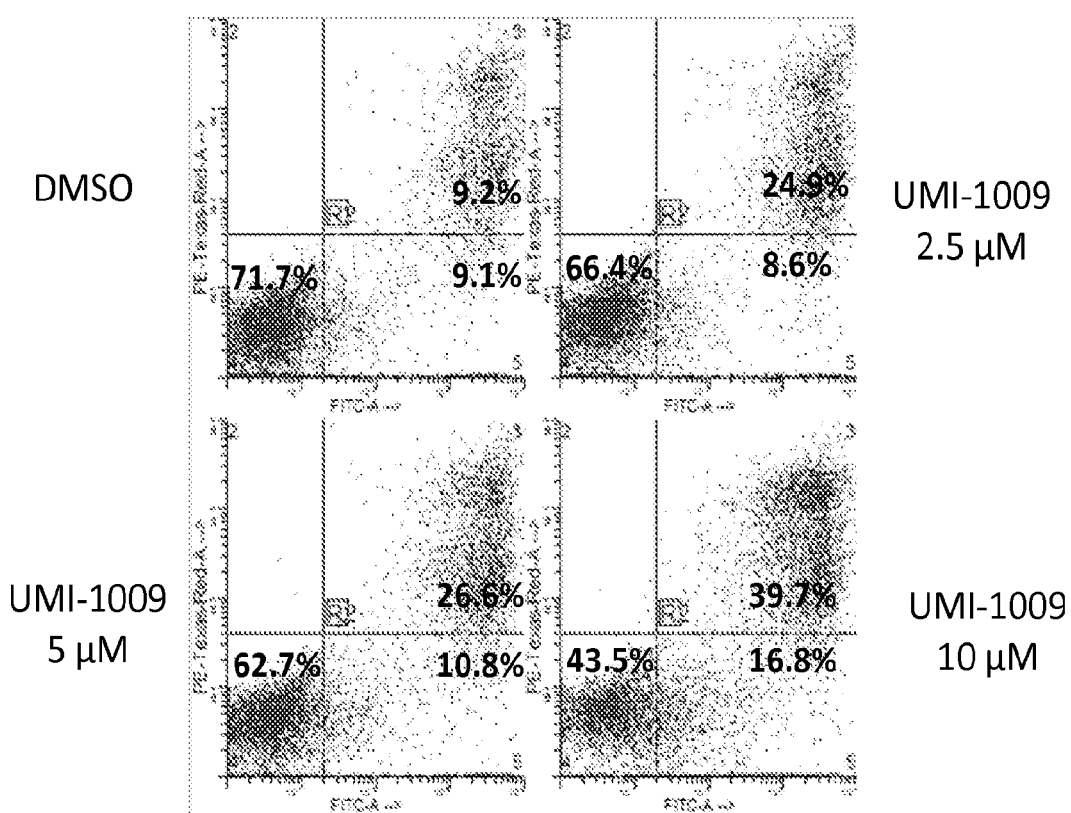
FIGS. 12A and 12B shows that UMI-1009 induces apoptosis and caspase-3 activation in HL-60 human leukemia cells.
Figure 12B:
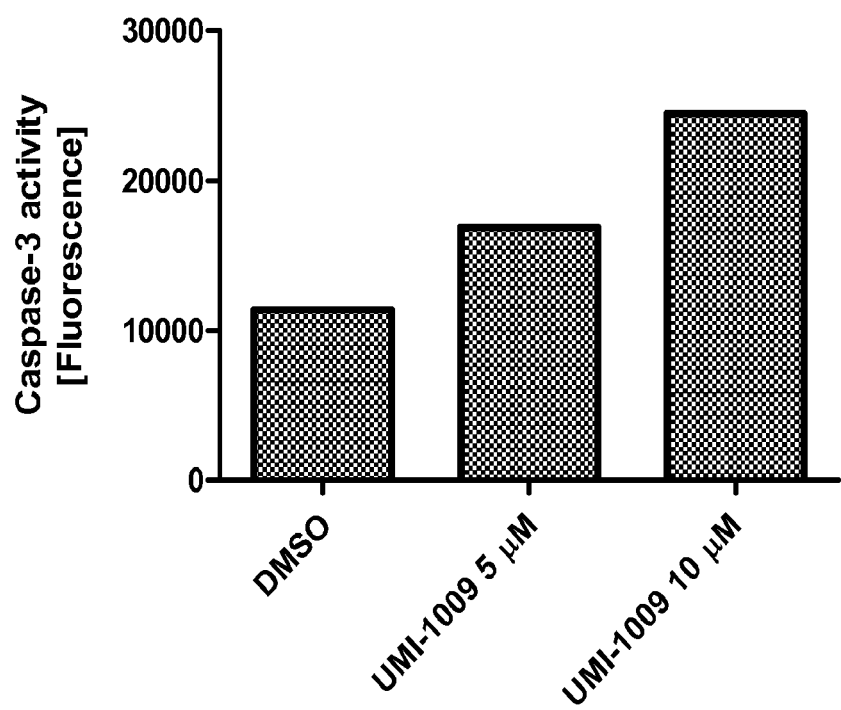

This example, and FIGS. 12A and 12B, demonstrates that that UMI-1009 induced apoptosis in AML human cells through activation of the intrinsic apoptotic pathway. To gain insights into the underlying mechanism of action for the cell growth inhibition of this class Mcl-1 inhibitors, the HL-60 cell line was selected and investigated if apoptosis contributes to the antiproliferative effect. Induction of apoptosis was monitored by flow cytometry using Annexin V and propidium iodide double staining. Consistent with the binding and functional results, UMI-1009 induced apoptosis in a dose-dependent manner and 5 and 10 μM concentrations resulted in 37% and 57%, respectively. The induction of apoptosis was accompanied by activation of caspase-3. These results demonstrated that UMI-1009 induced apoptosis in AML human cells through activation of the intrinsic apoptotic pathway.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

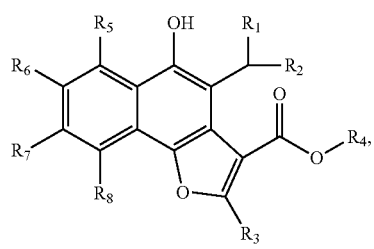

What is claimed is:

1. A compound having Formula I:
including pharmaceutically acceptable salts
wherein R1 is selected from the group consisting of:

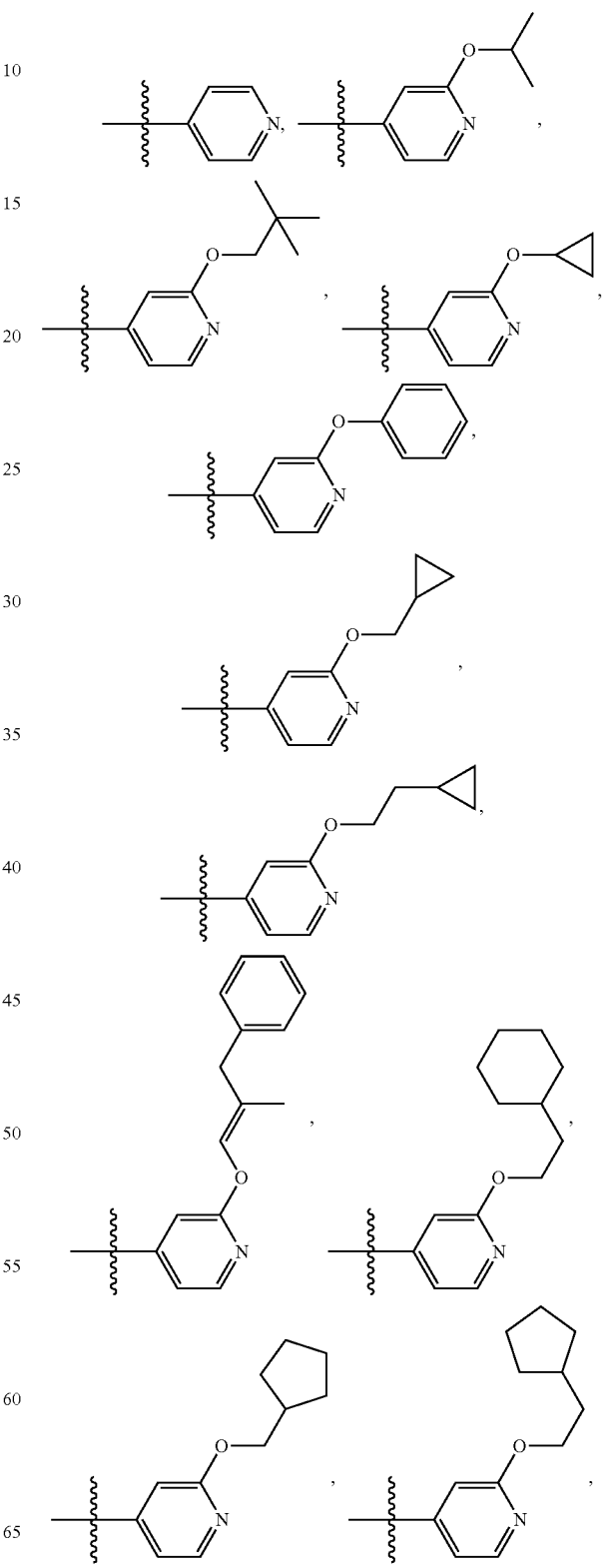

-continued
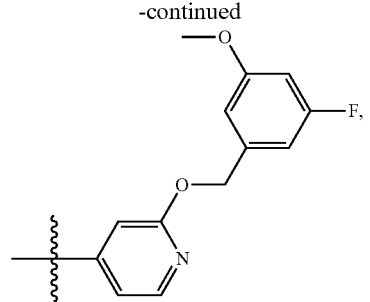
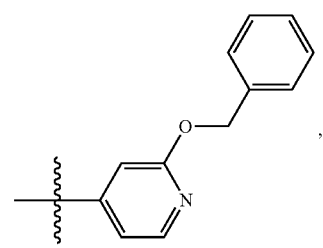
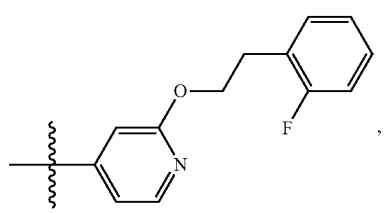
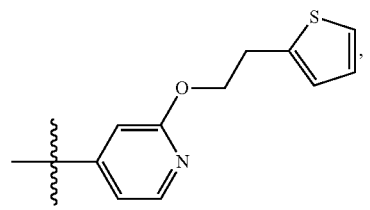
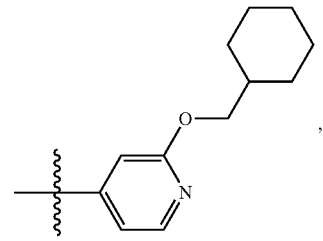
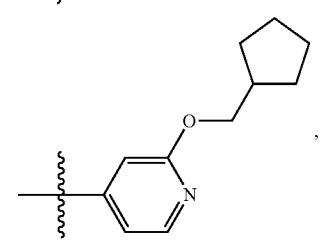
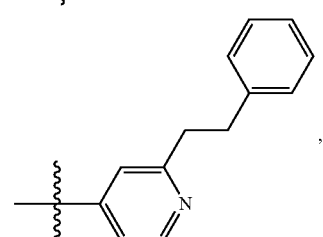
-continued
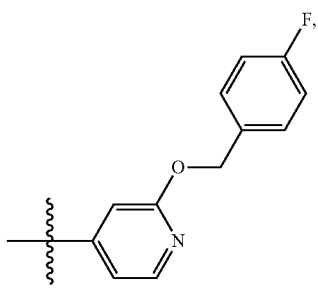
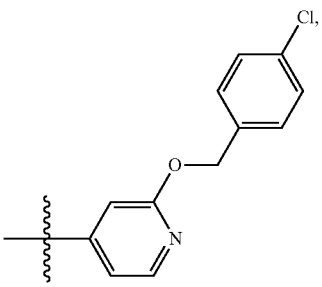
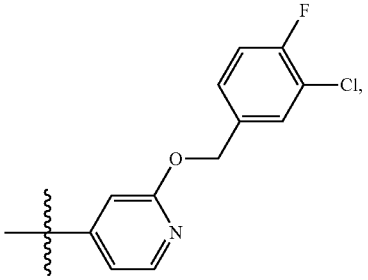
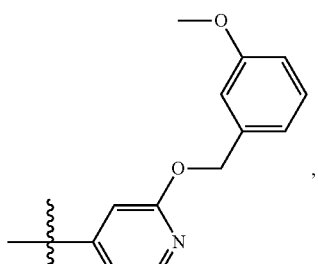
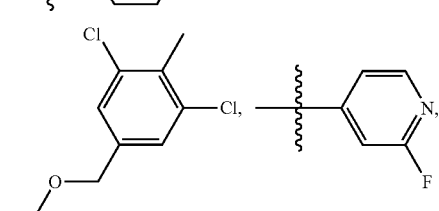
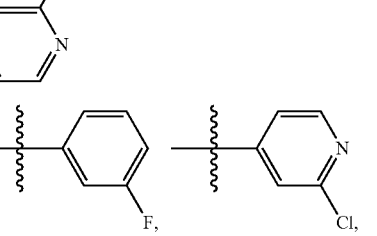
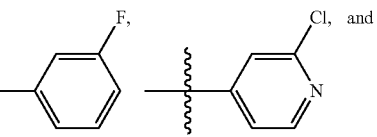

-continued
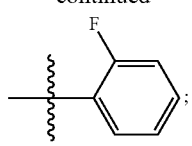
wherein R2 is selected from the group consisting of:
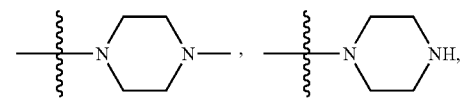
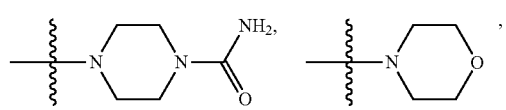
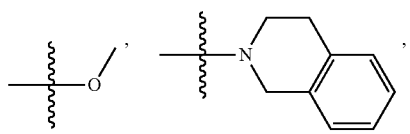
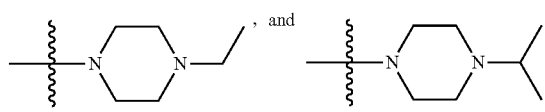
wherein R3 is selected from the group consisting of: hydrogen, methyl, ethyl, phenyl, and tert-butyl;
wherein R4 is selected from the group consisting of
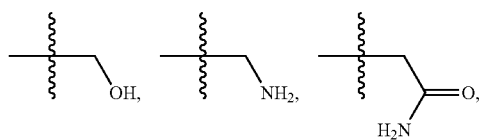
hydrogen, methyl or ethyl;
wherein R5, R6, R7 and R8 are independently selected from the group consisting of: hydrogen,
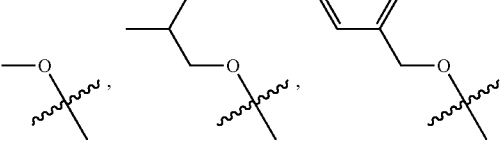
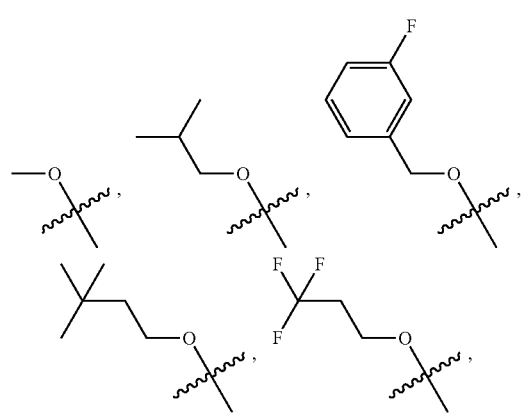
-continued
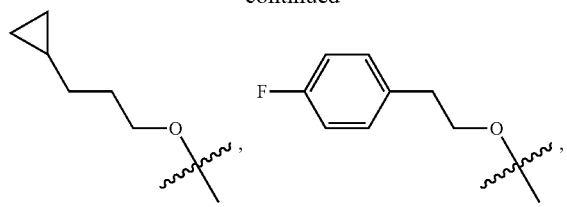
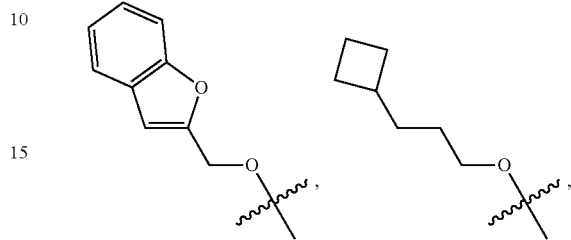
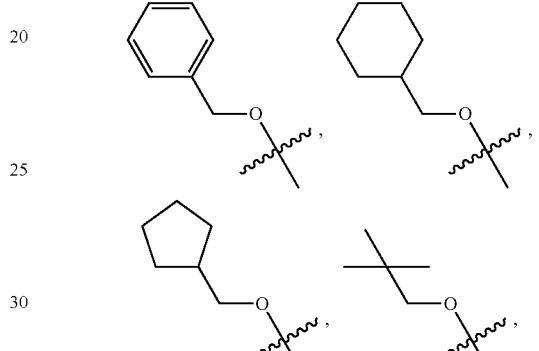
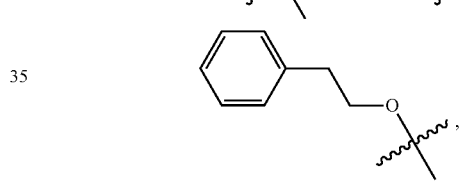
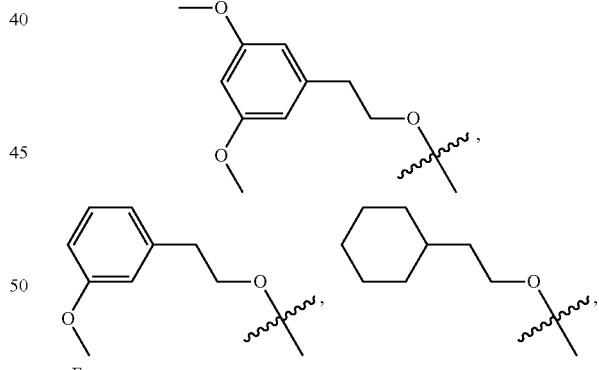
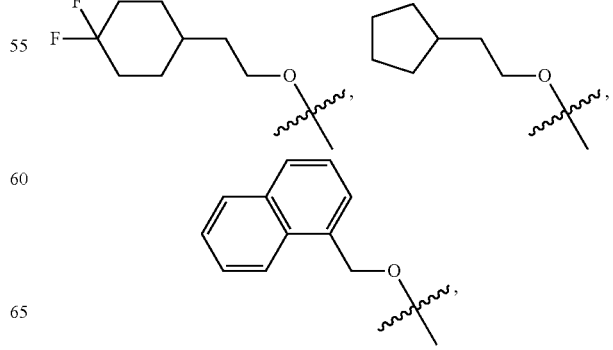

-continued
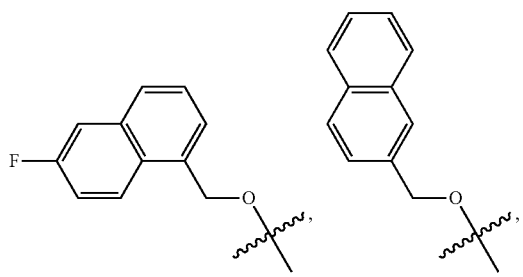
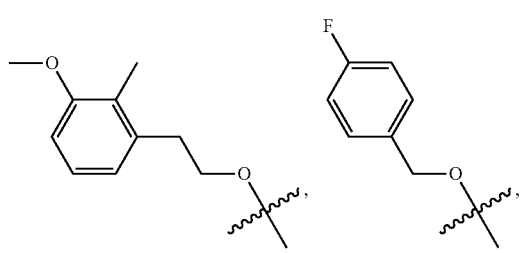
methyl, chlorine, and fluorine;
wherein the compound is not
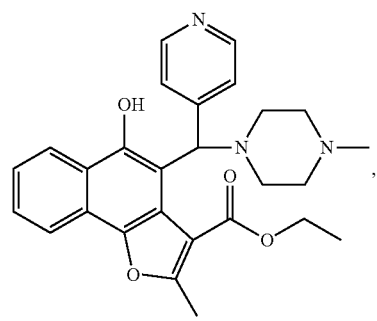 [SMILES: CCOC(=O)c1c(C)oc2c1c(C(c1ccncc1)N1CCN(C)CC1)c(O)c1ccccc12]
and provided that when R1 is
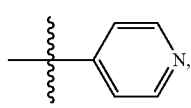 [SMILES: *c1ccncc1]
R2 is not
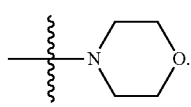
2. A compound selected from the group consisting of:
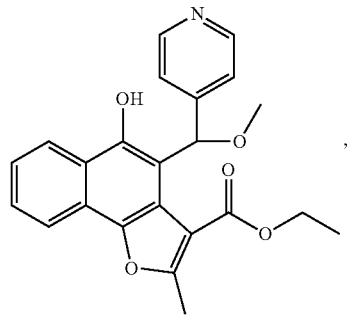
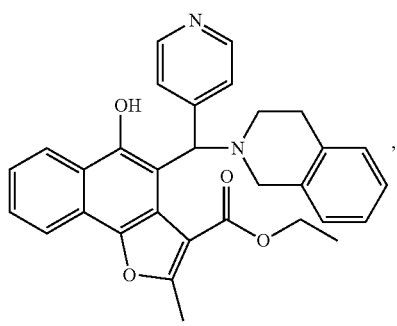 [SMILES: CCOC(=O)c1c(C)oc2c1c(C(c1ccncc1)N1CCN(C(C)C)CC1)c(O)c1ccccc12]
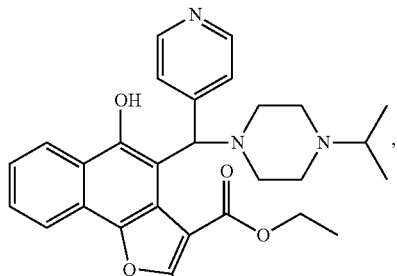
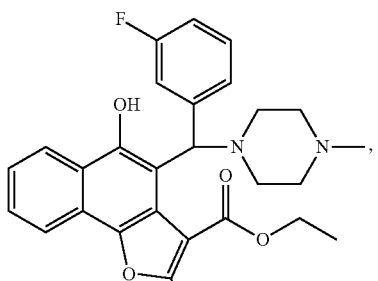
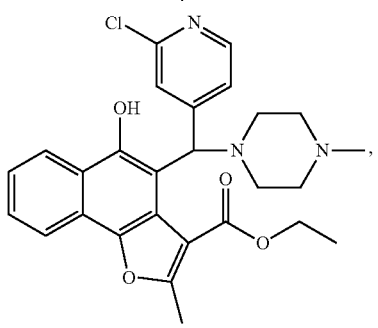

171
-continued
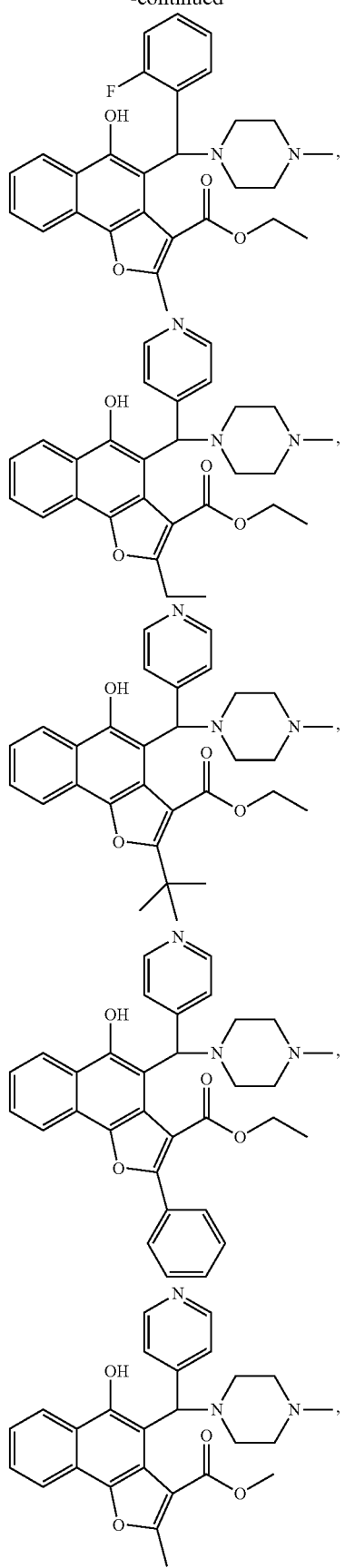
172
-continued
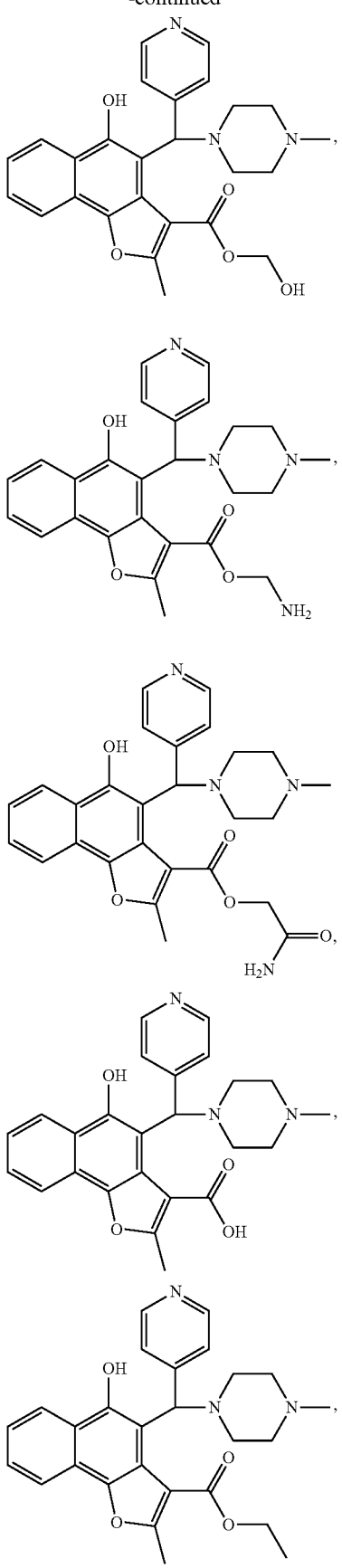

173
-continued
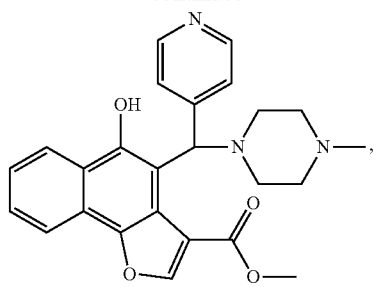
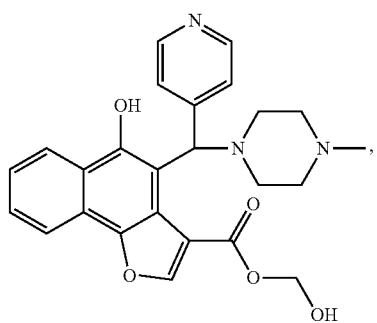
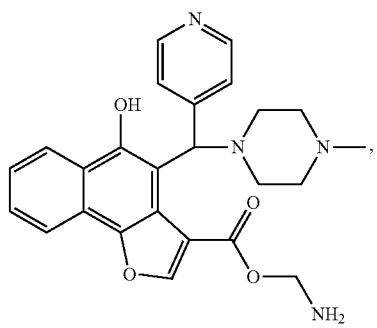
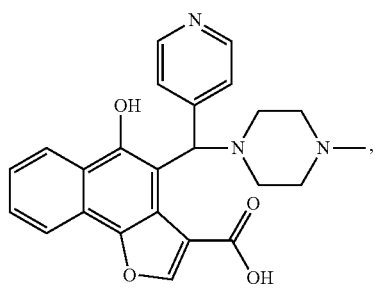
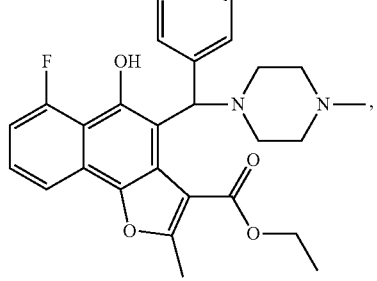
174
-continued
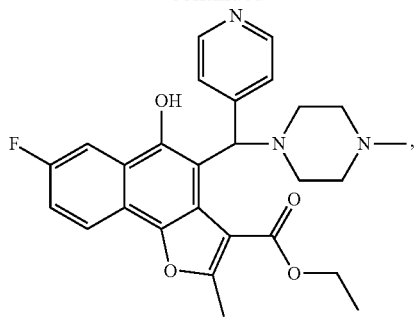
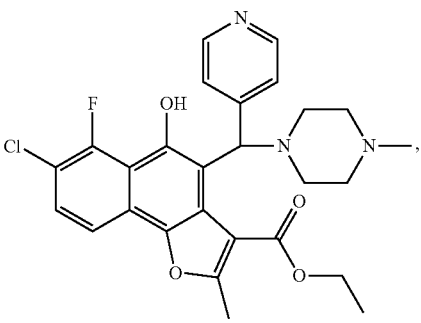
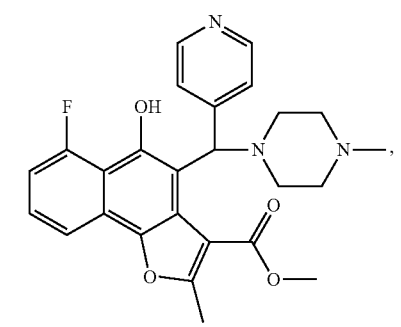
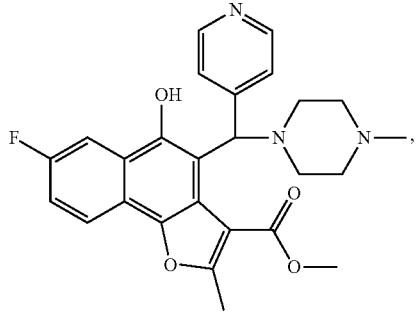
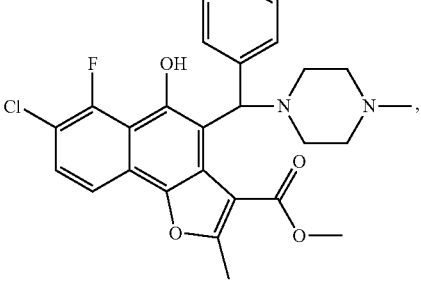

175
-continued
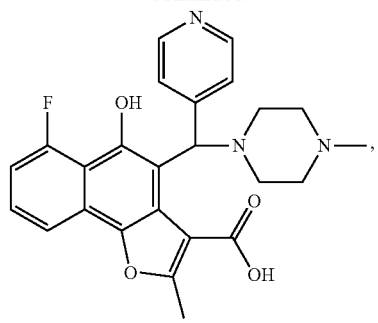
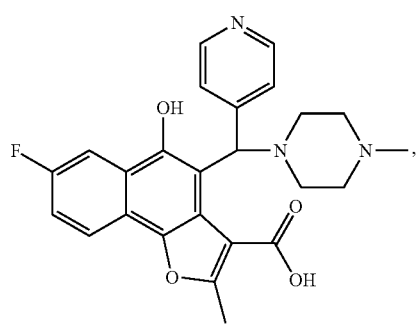
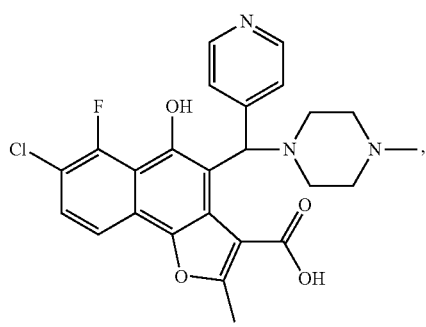
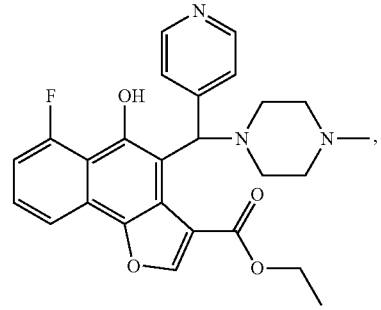
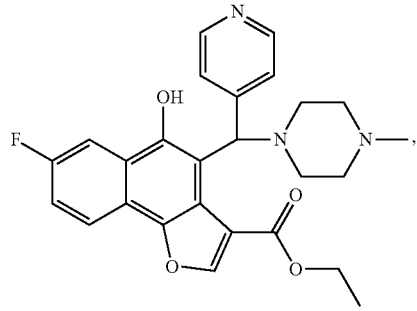
176
-continued
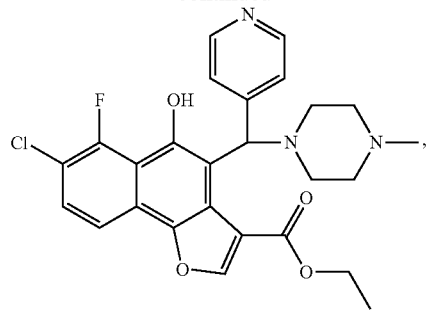
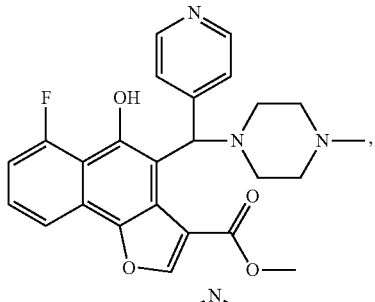
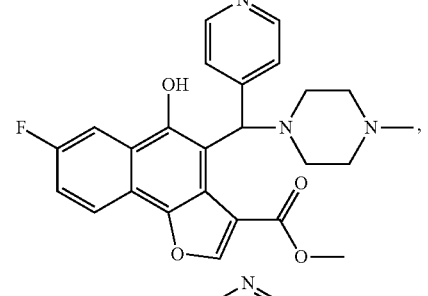
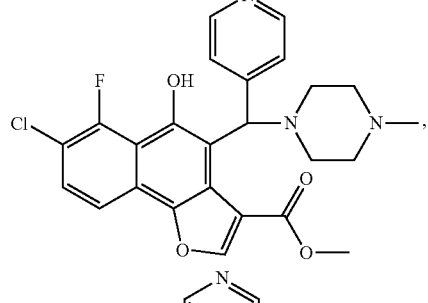
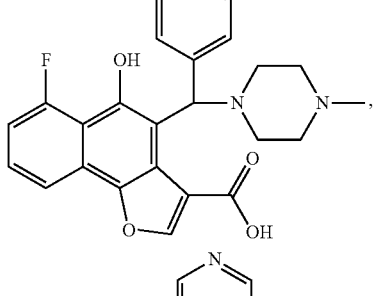
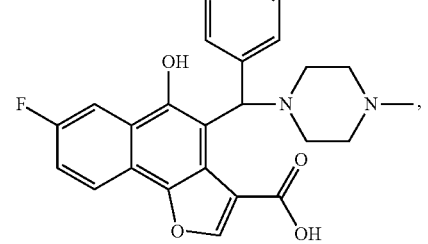

177
-continued
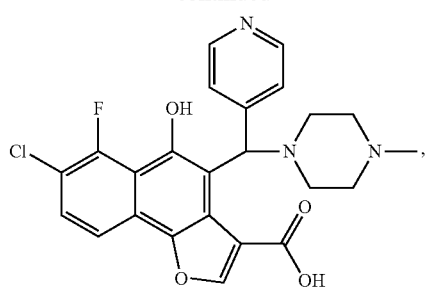
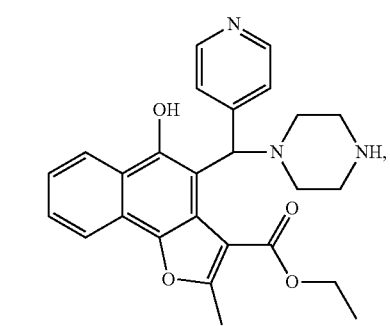
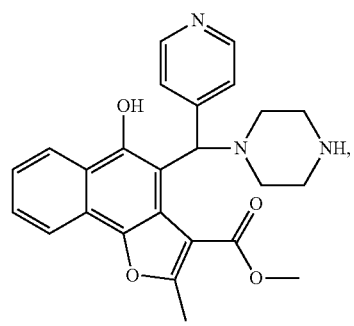
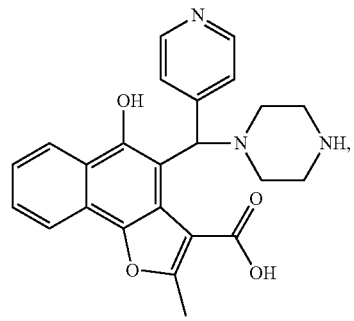
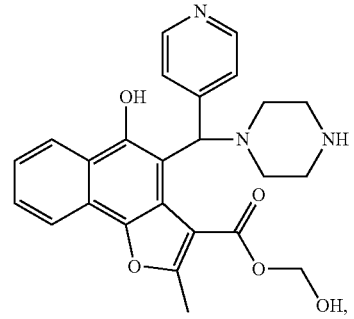
178
-continued
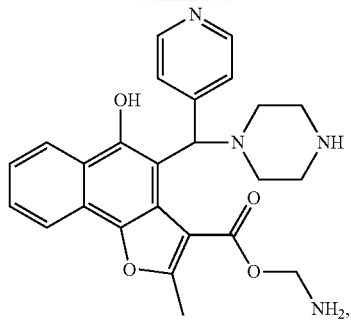
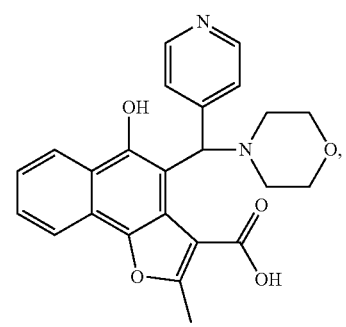
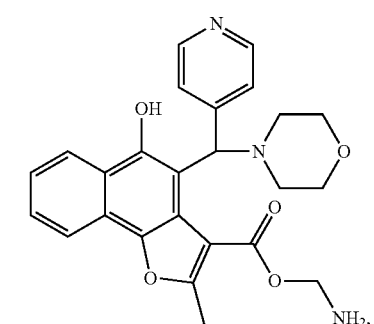
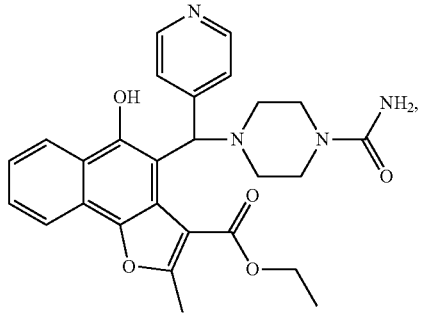
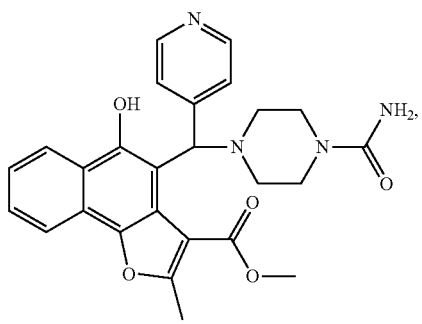

-continued
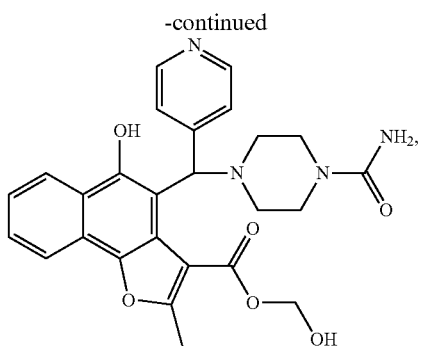
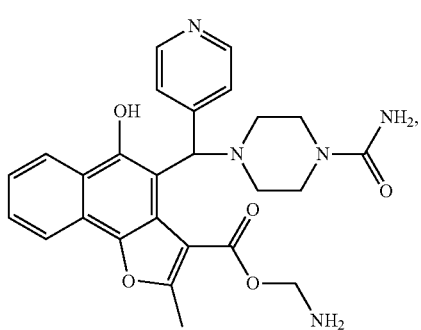
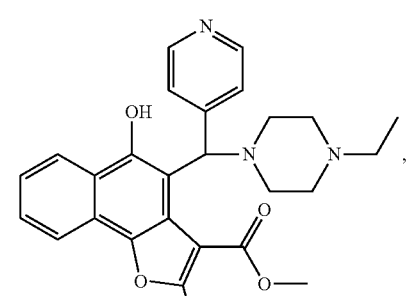
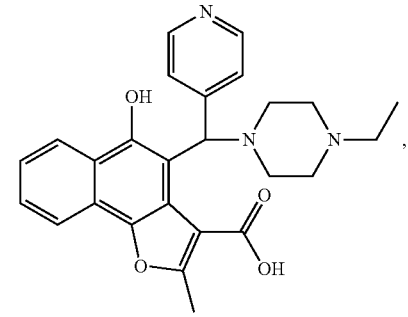
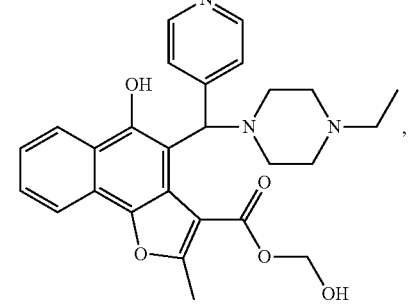
-continued
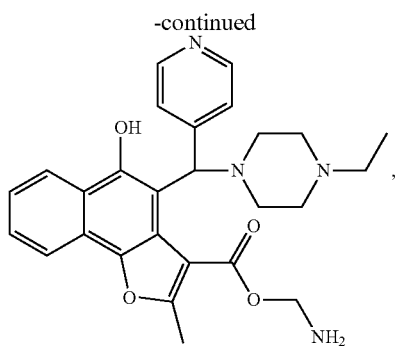
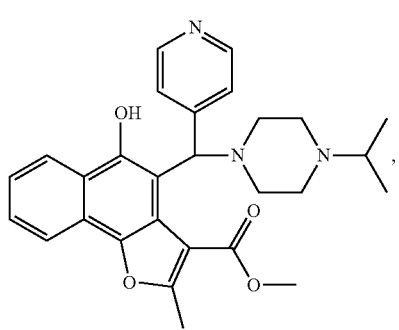
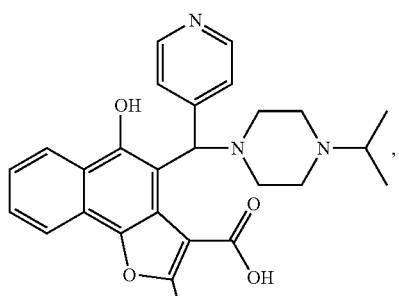
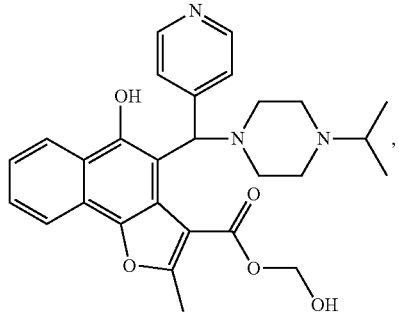
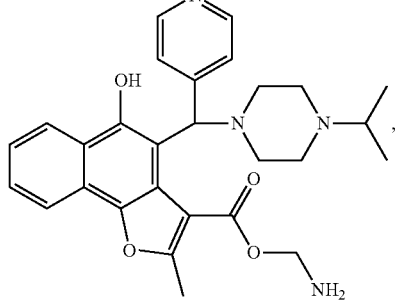

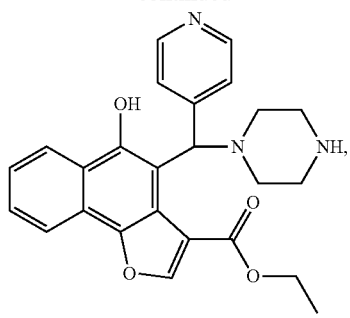
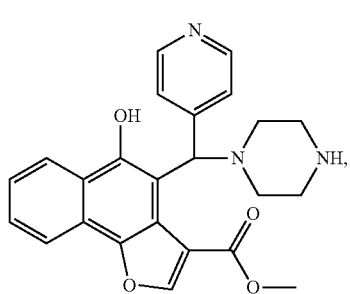
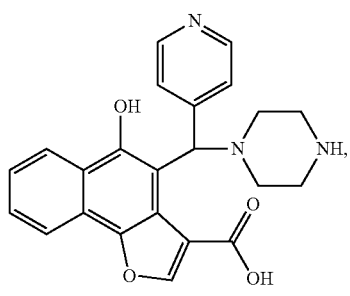
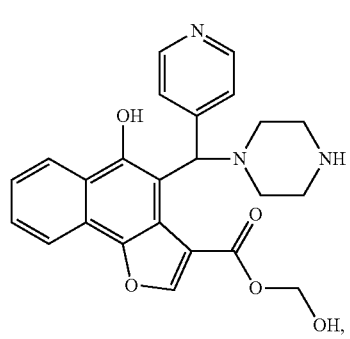
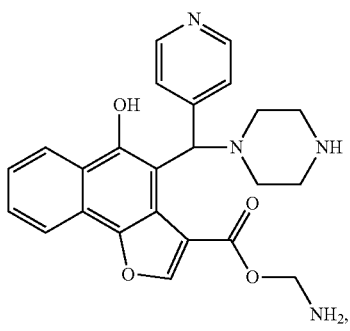
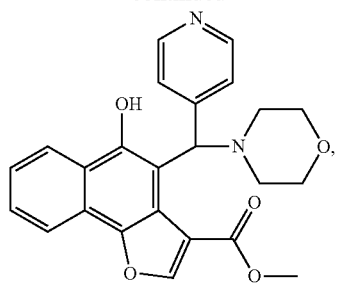
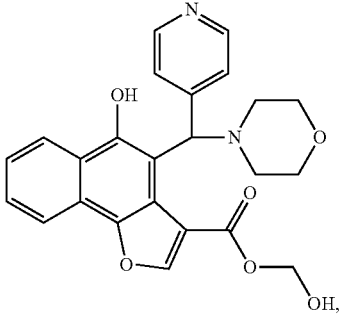
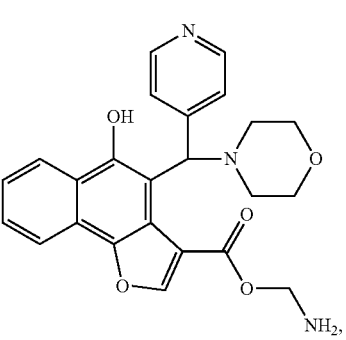
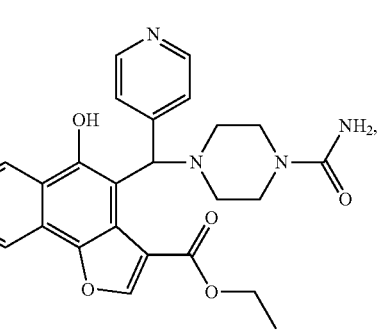
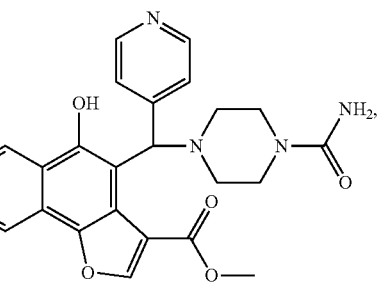

183
-continued
184
-continued
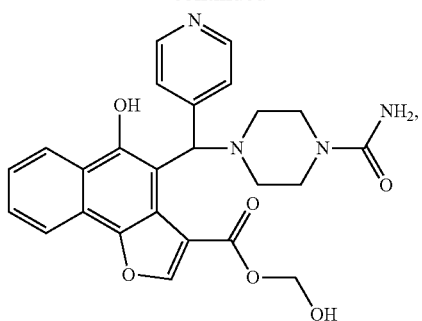
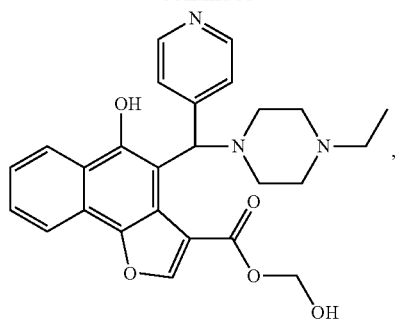

185
-continued
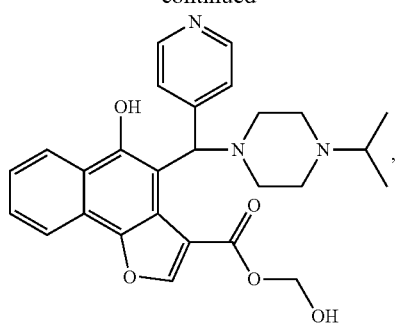
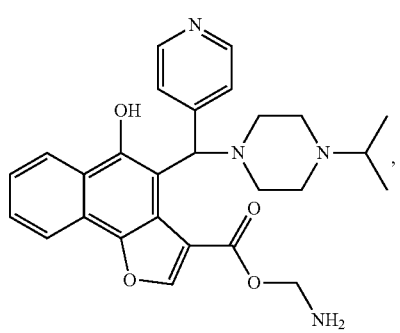
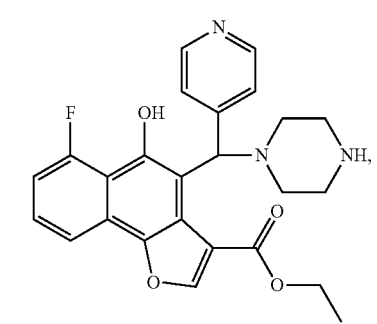
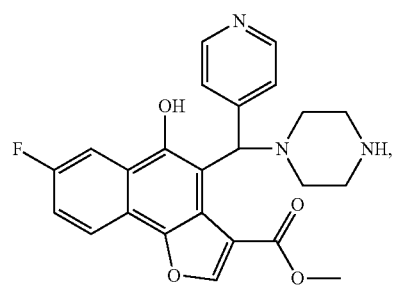
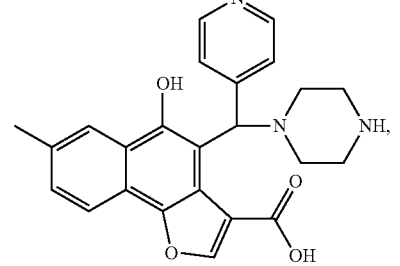
186
-continued
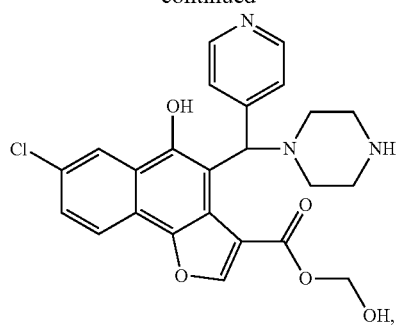
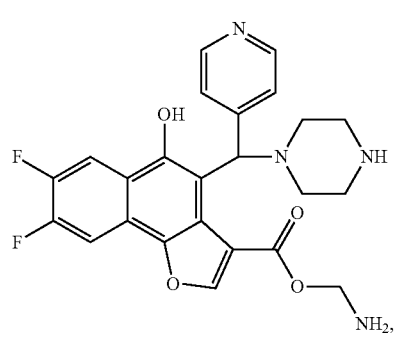
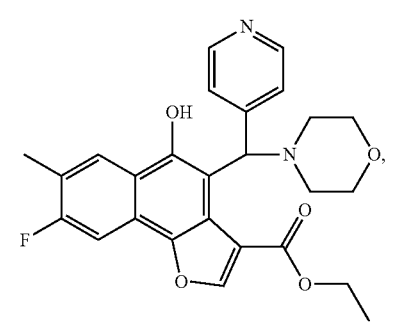
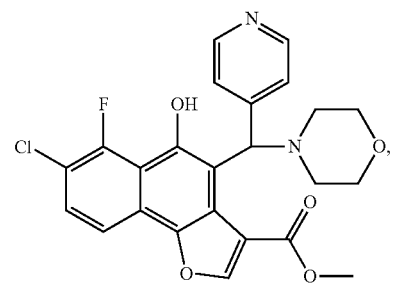
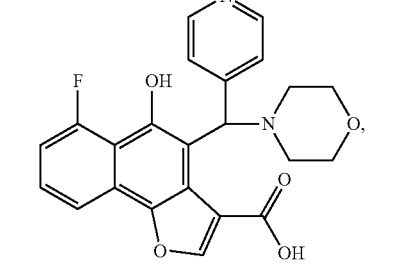

187
-continued
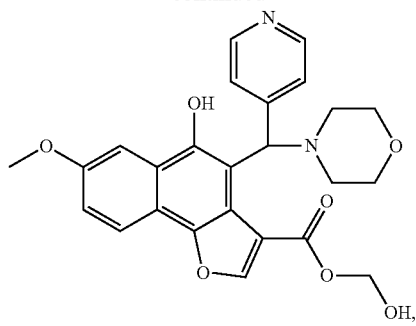
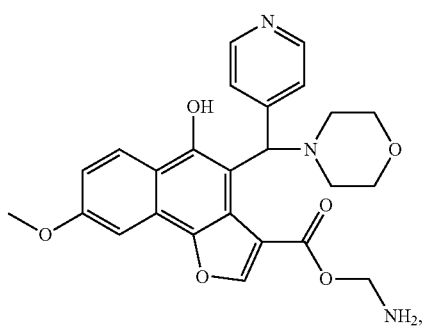
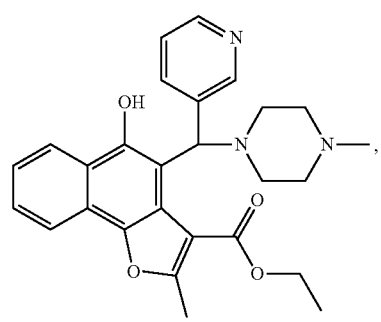
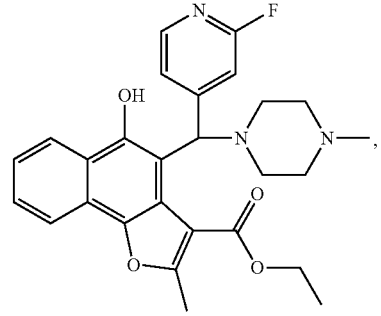
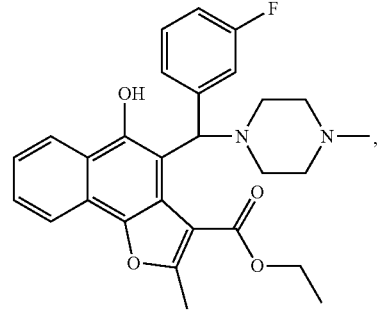
188
-continued
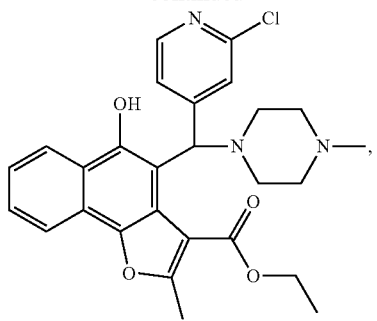
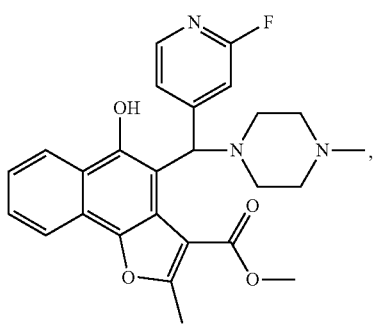
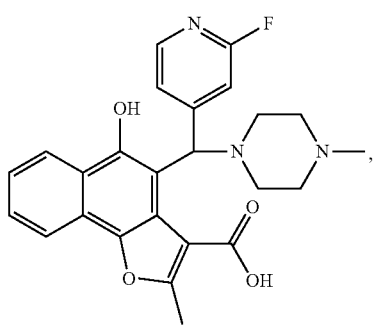
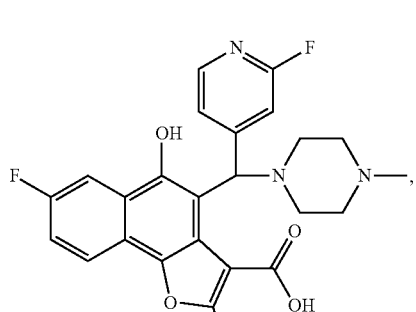
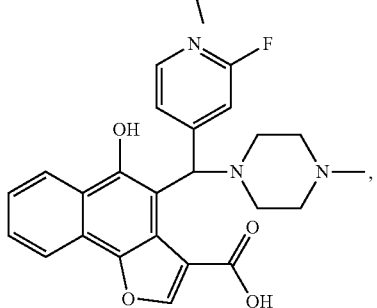

189
-continued
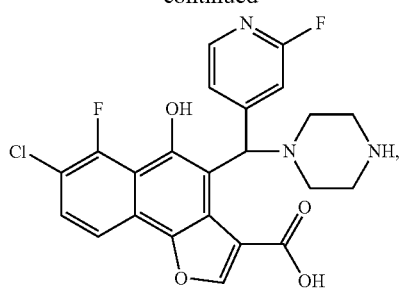
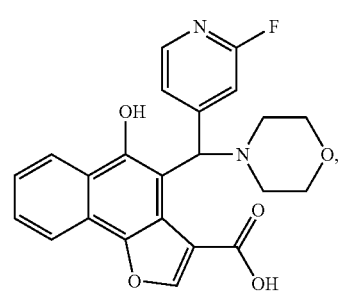
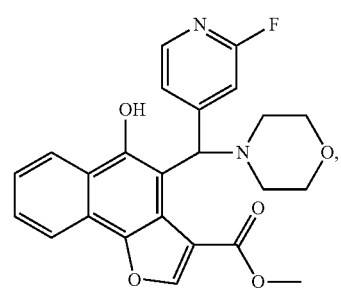
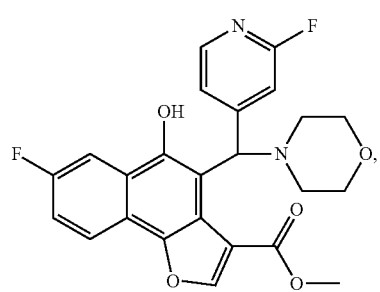
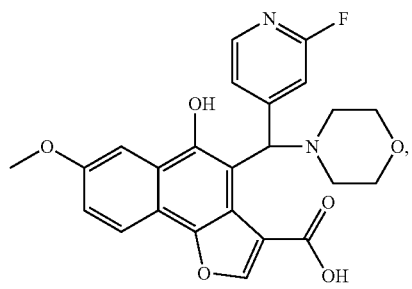
190
-continued
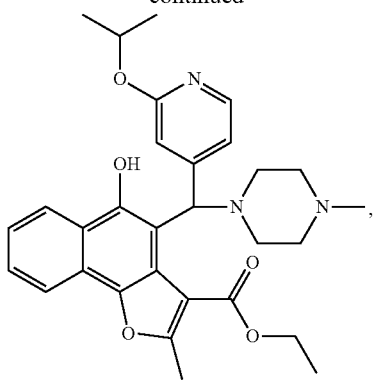
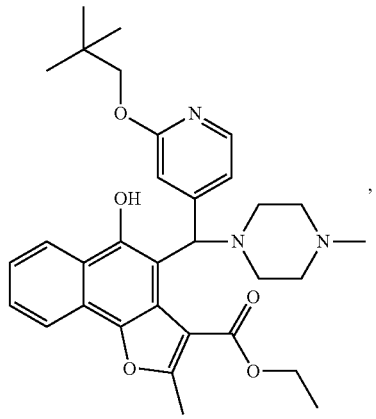
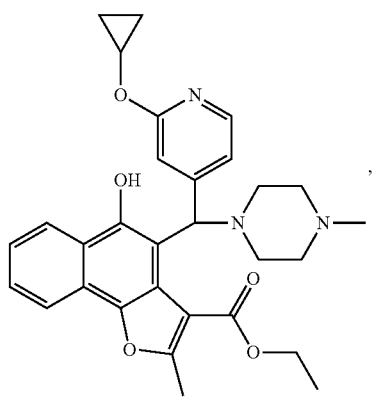
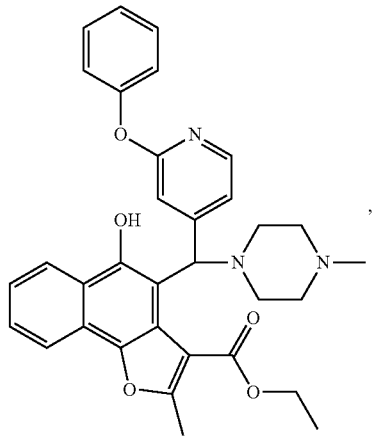

191
-continued
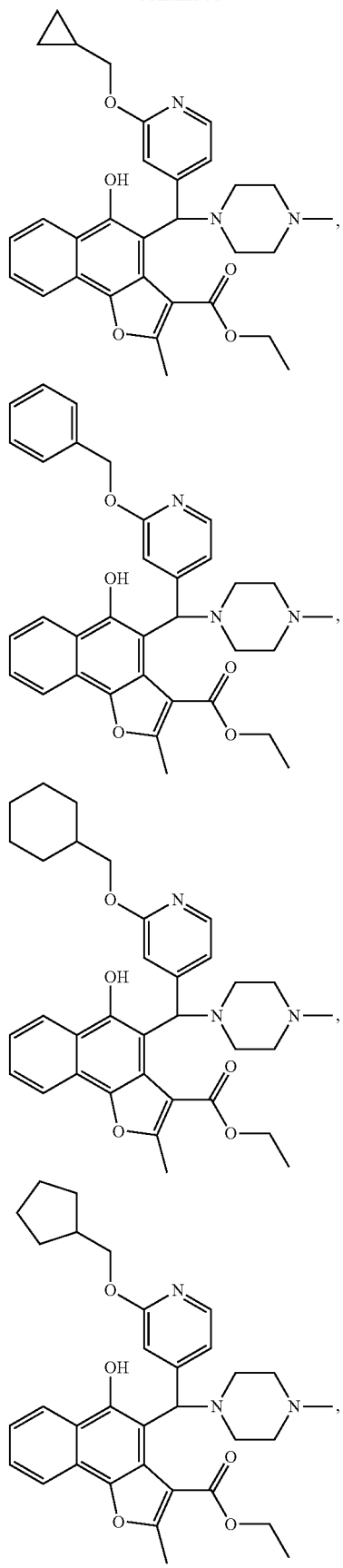
192
-continued
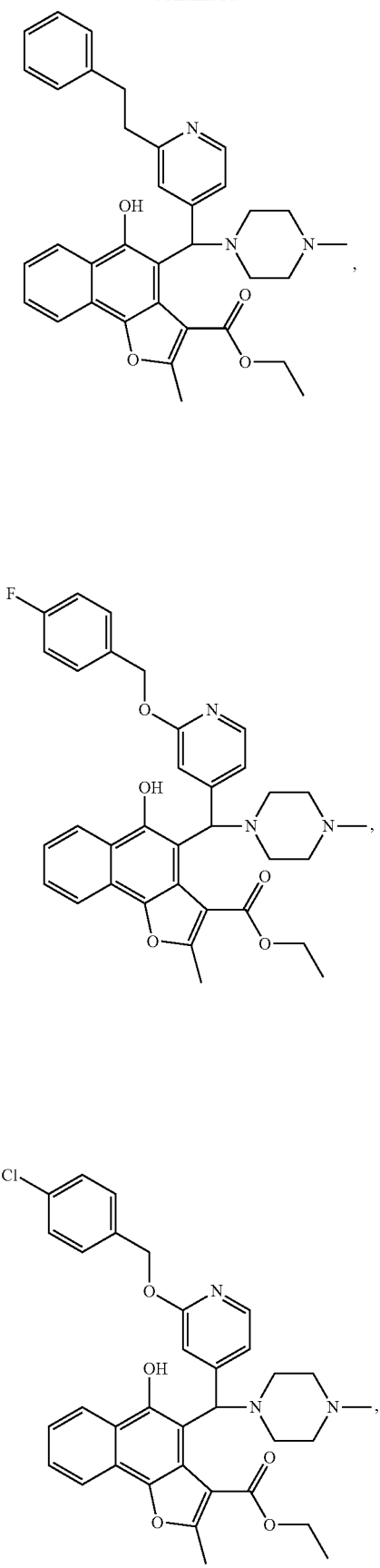

193
-continued
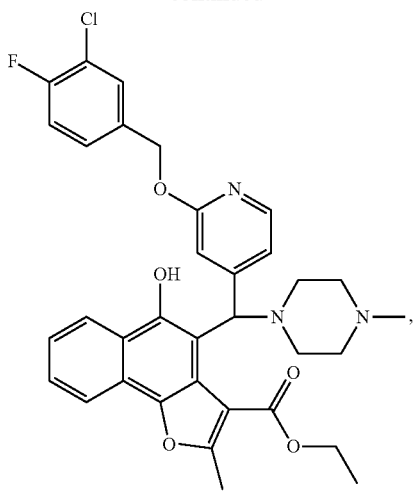
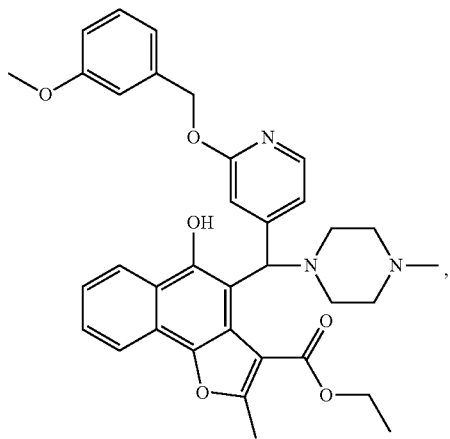
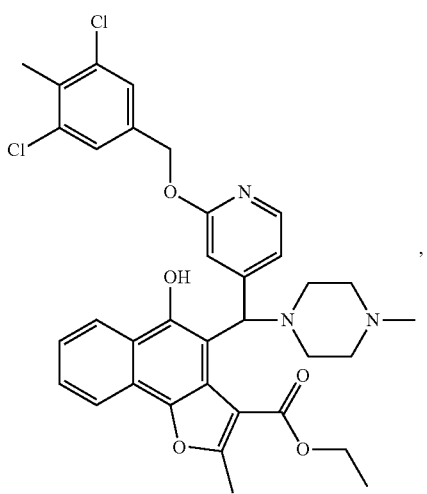
194
-continued
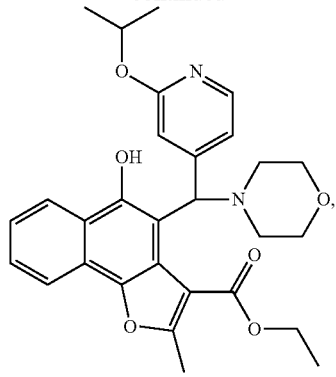
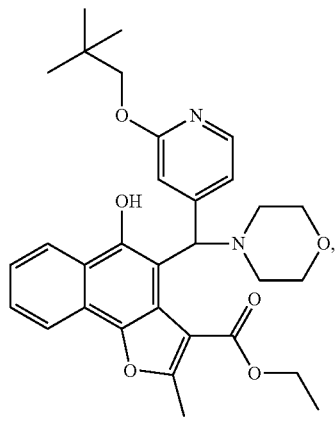
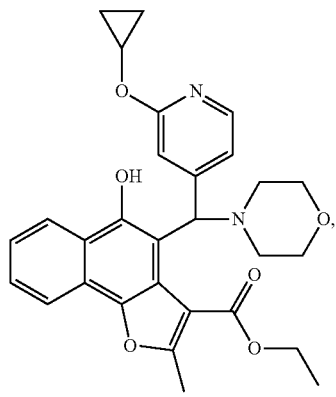
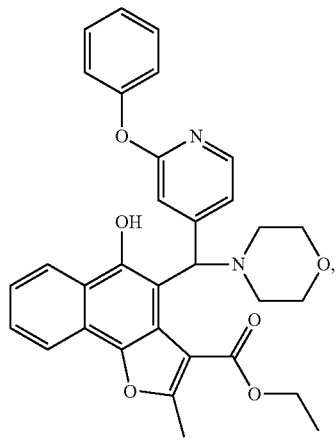

195
-continued
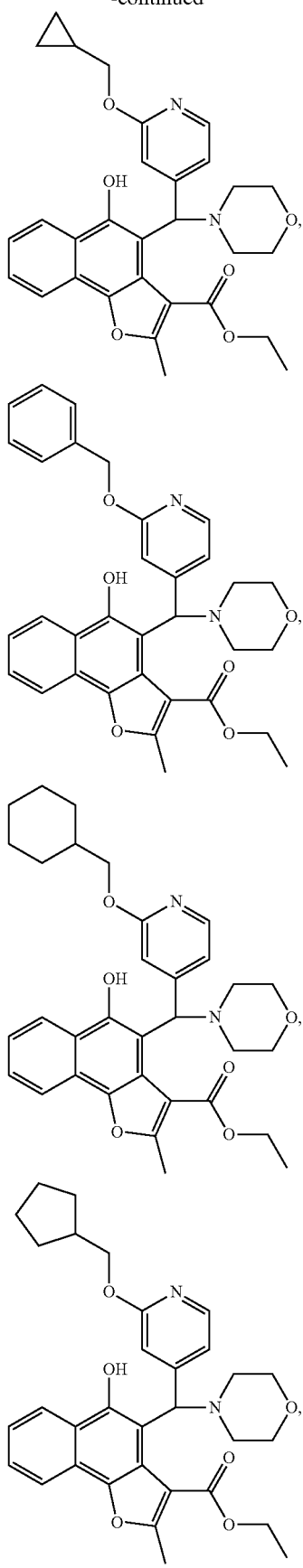
196
-continued
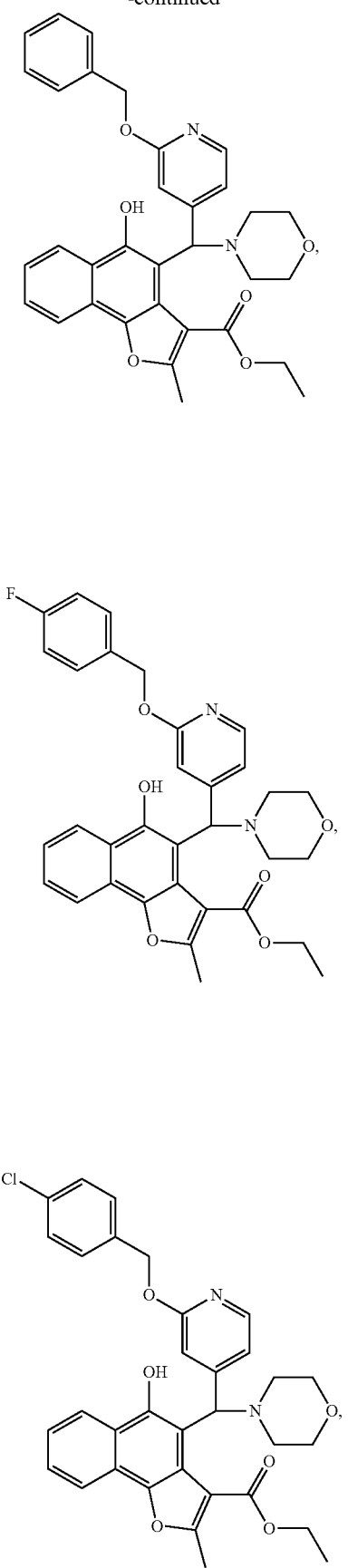

197
-continued
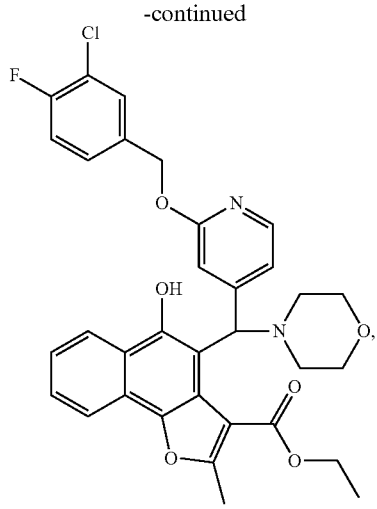
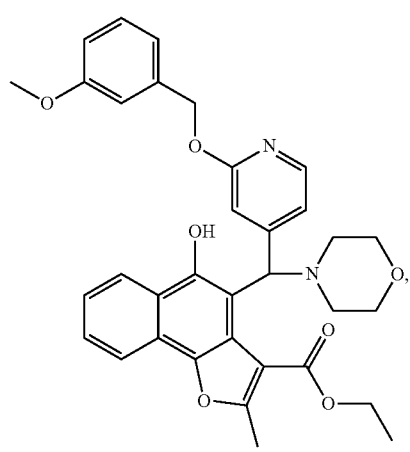
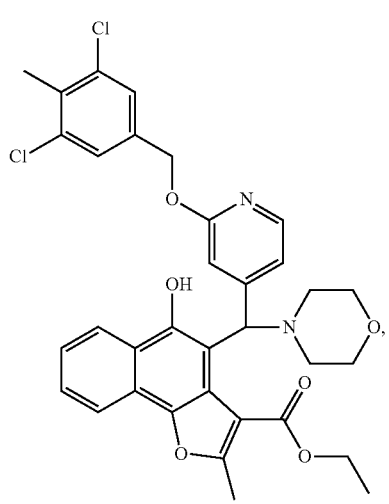
198
-continued
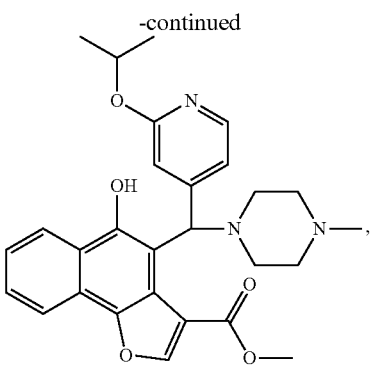
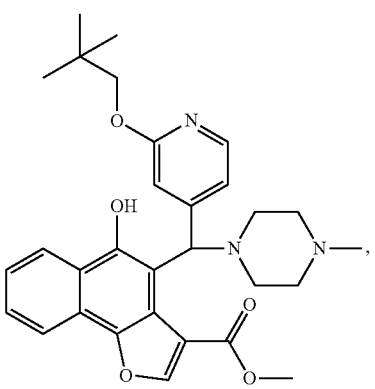
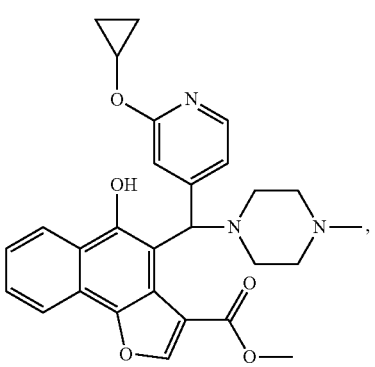
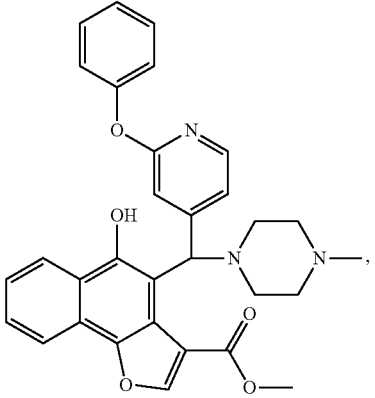

199
-continued
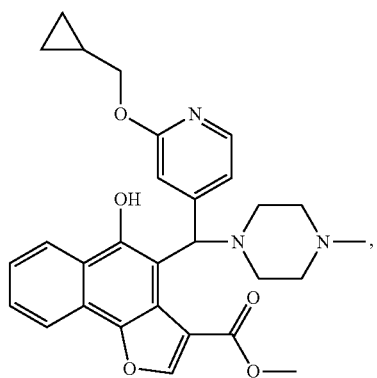
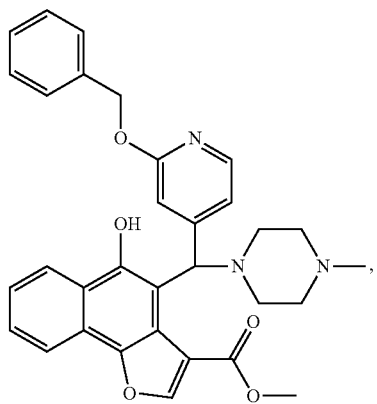
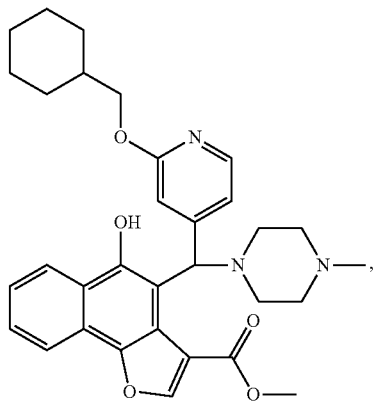
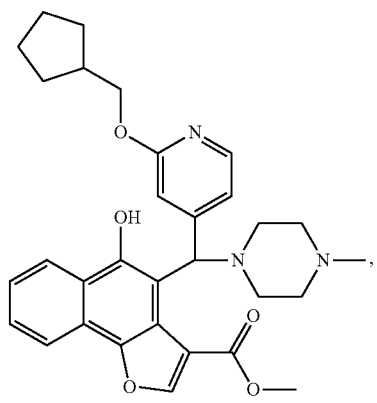
200
-continued
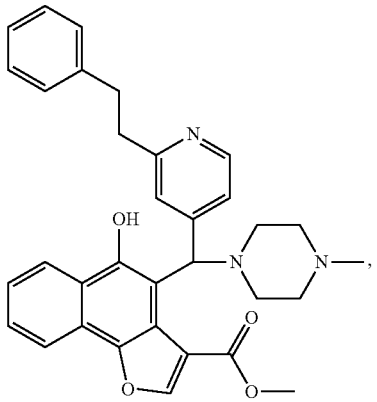
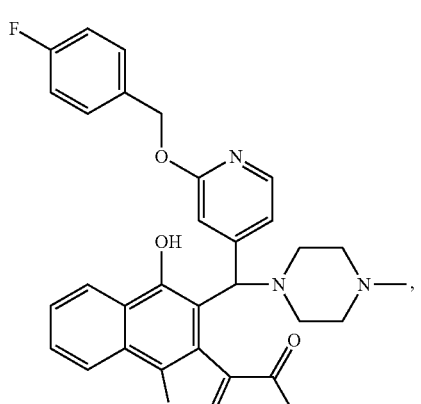
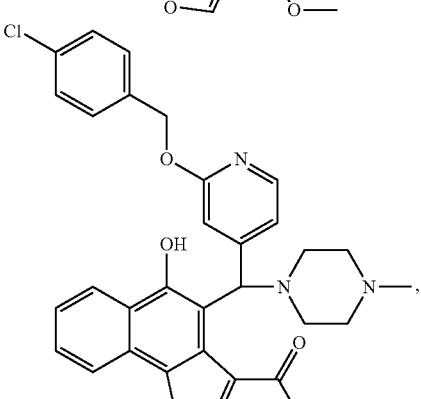
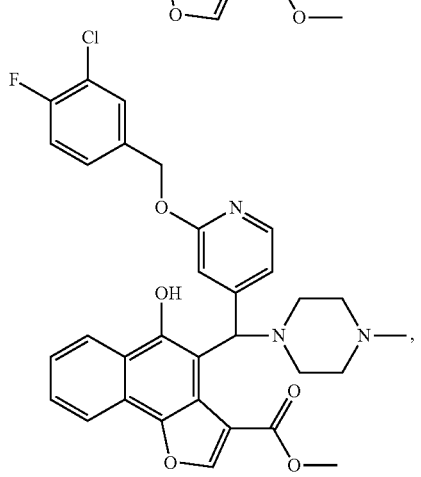

201
-continued
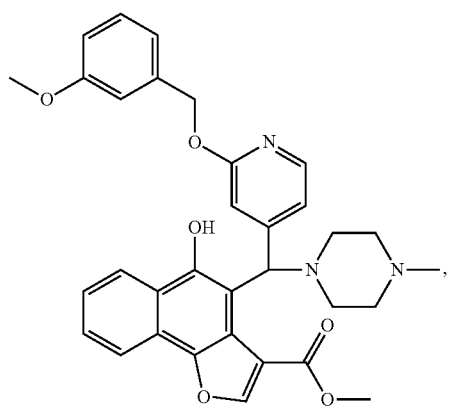
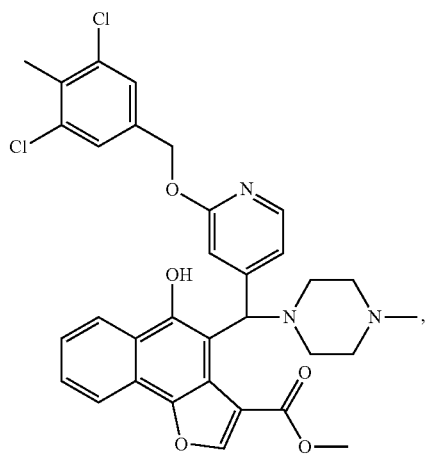
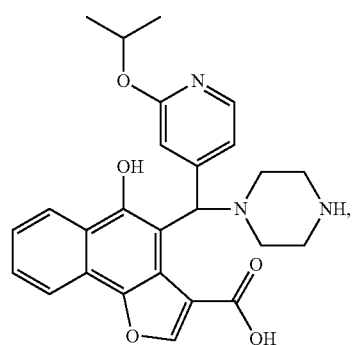
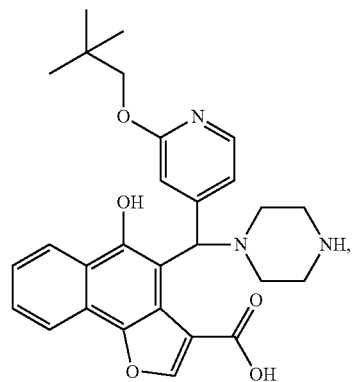
202
-continued
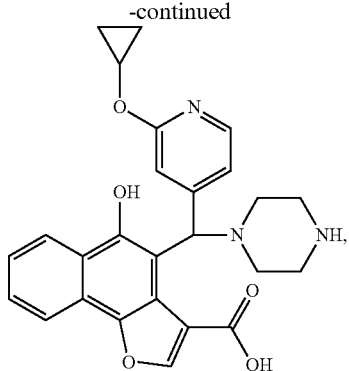
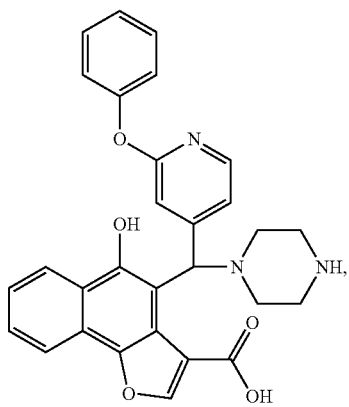
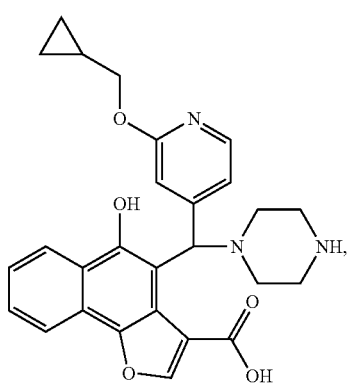
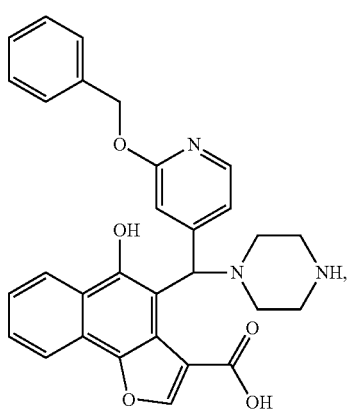

203
-continued
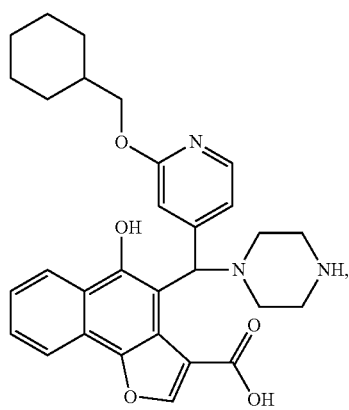
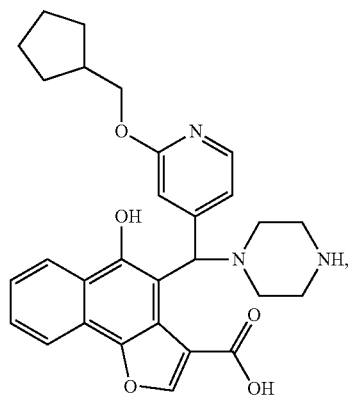
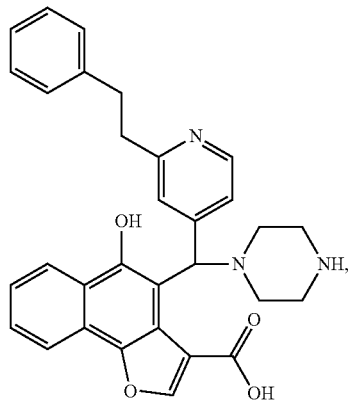
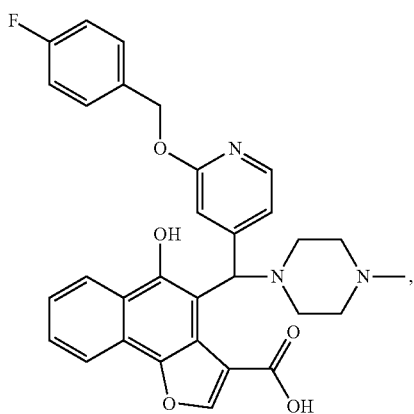
204
-continued
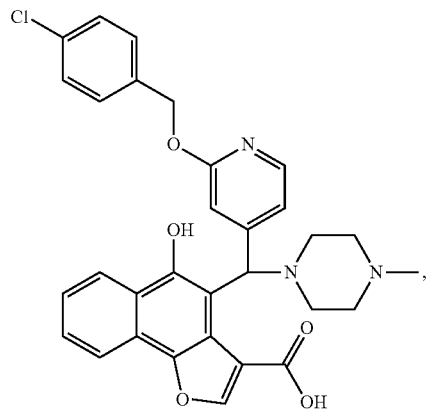
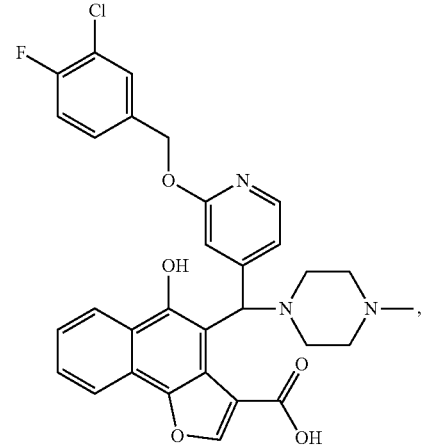
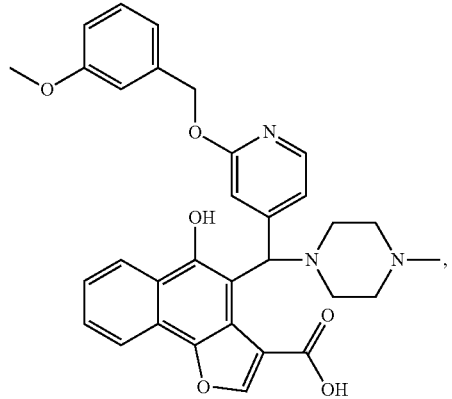
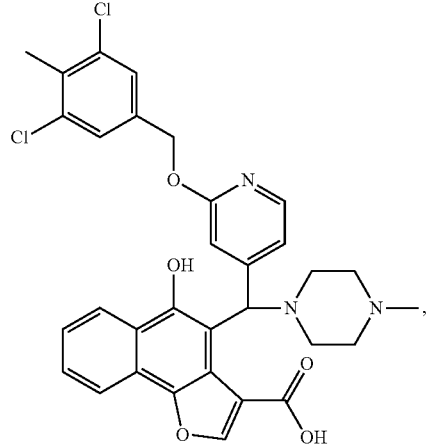

205
-continued
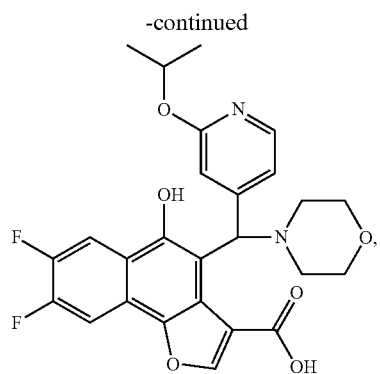
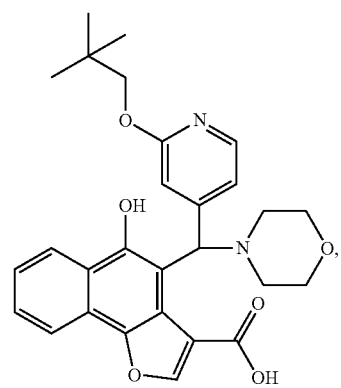
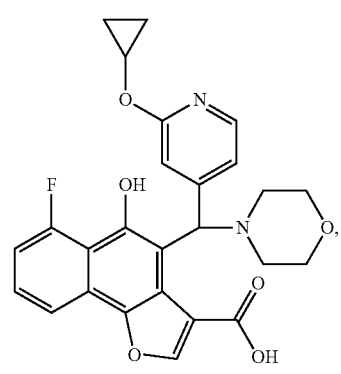
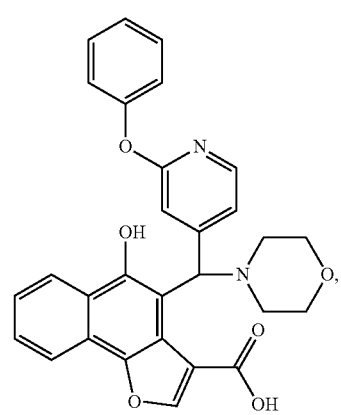
206
-continued
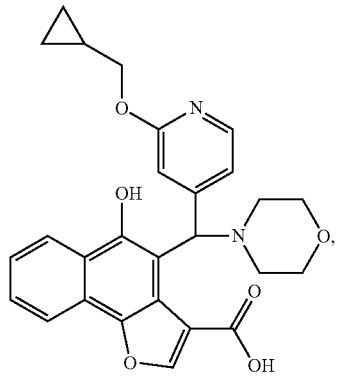
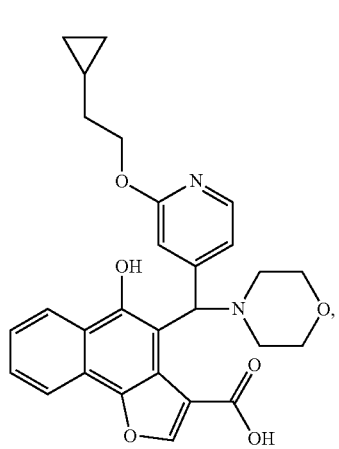
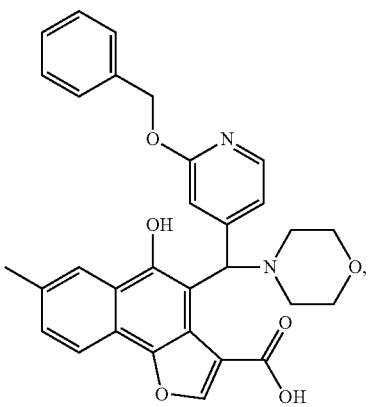
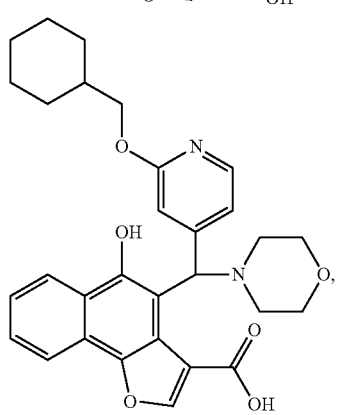

207
-continued
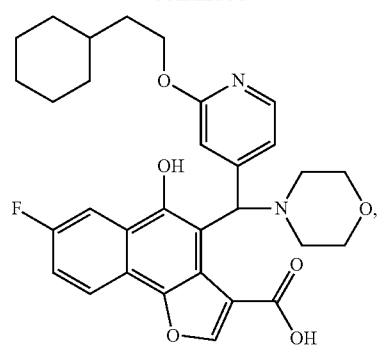
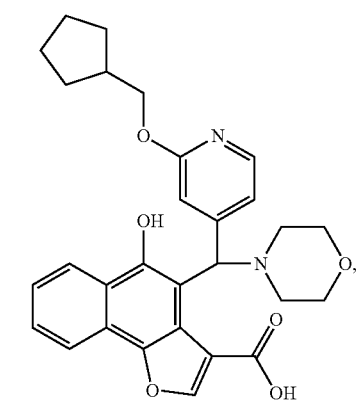
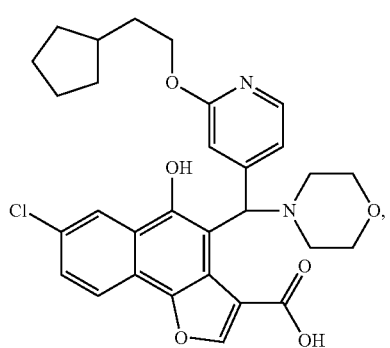
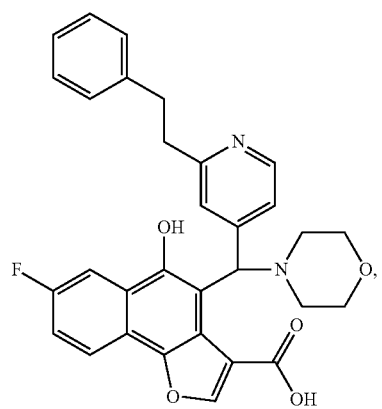
208
-continued
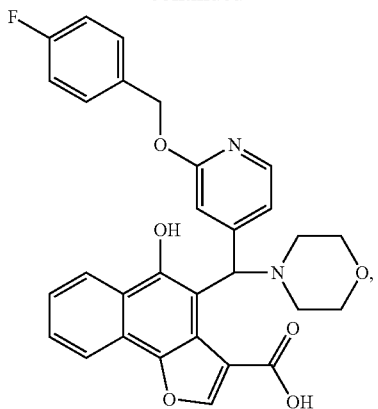
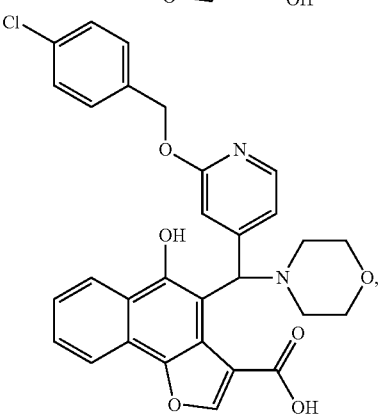
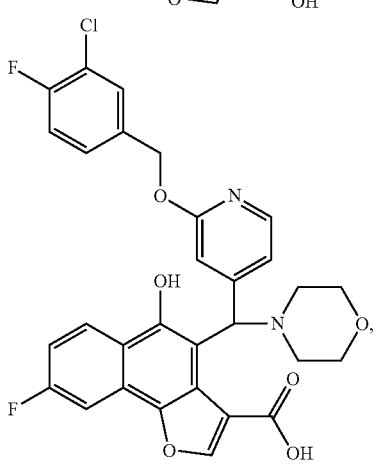
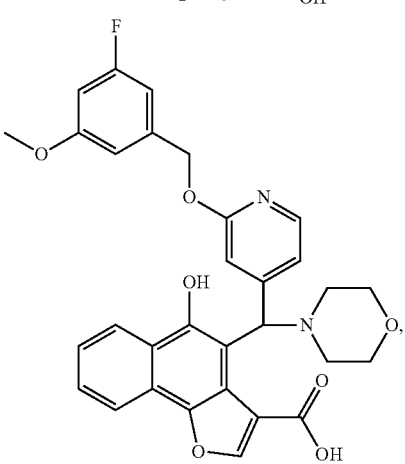

209
-continued
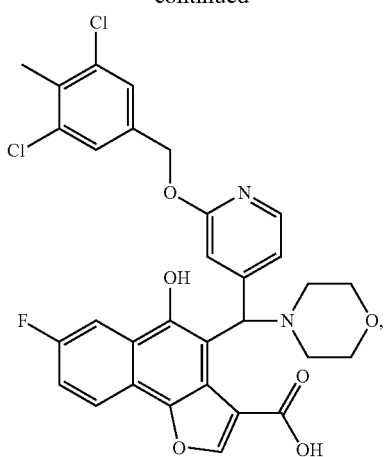
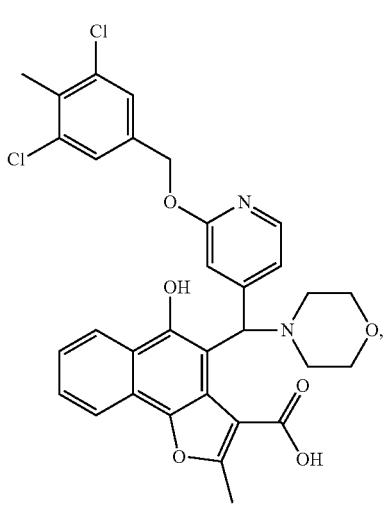
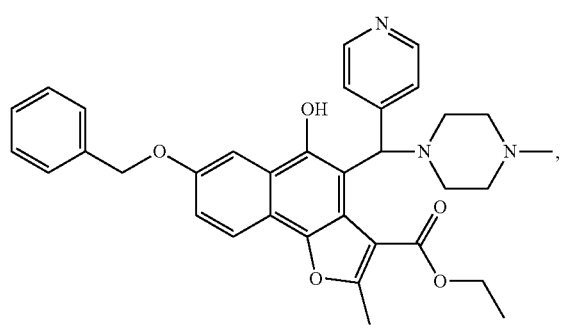
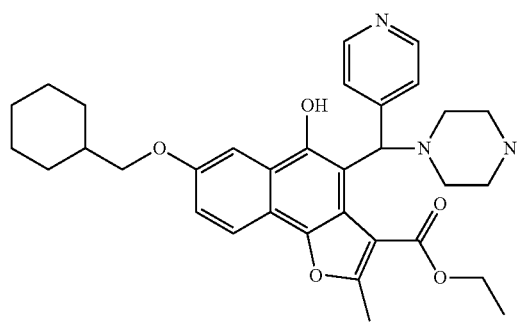
210
-continued
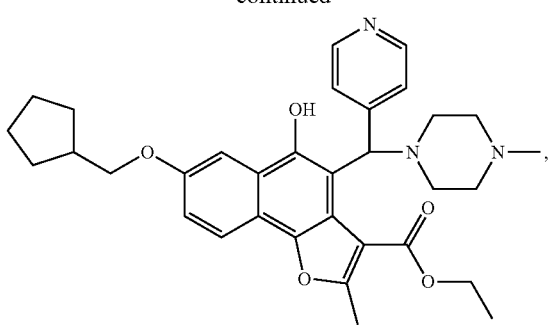
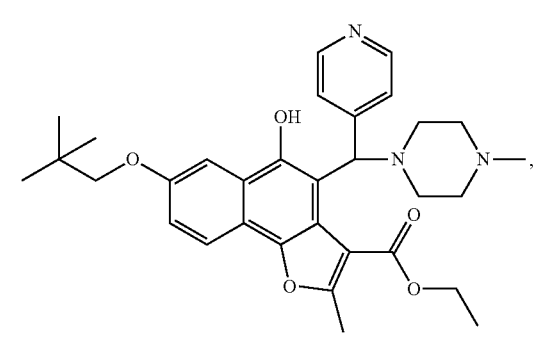
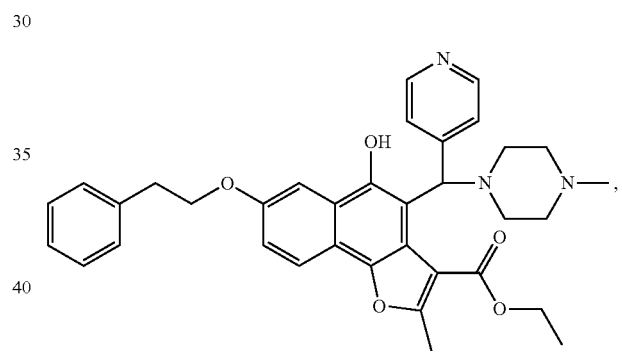
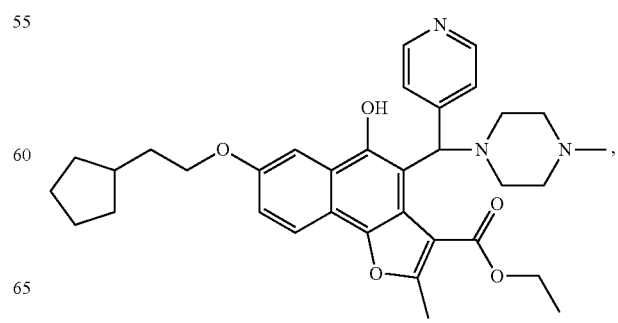

211
-continued
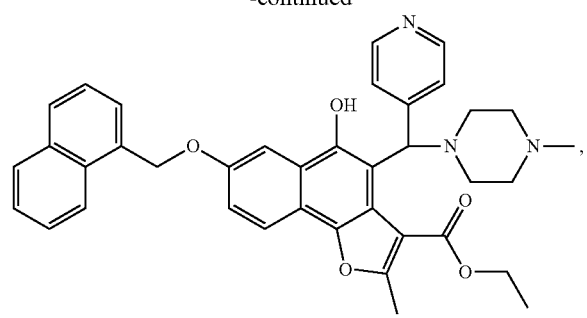
212
-continued
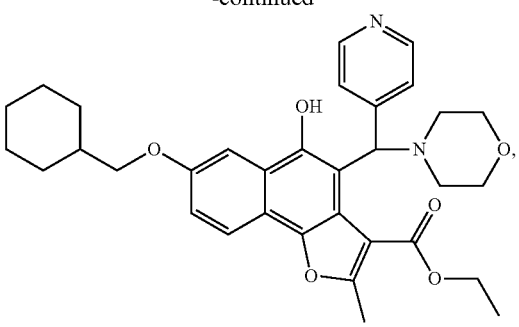
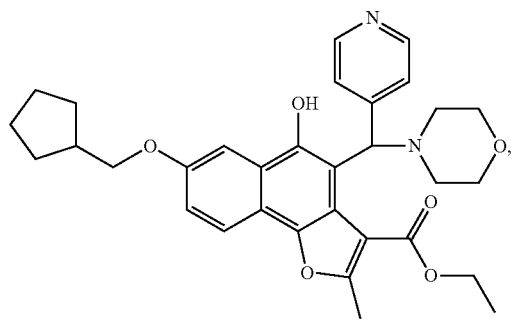
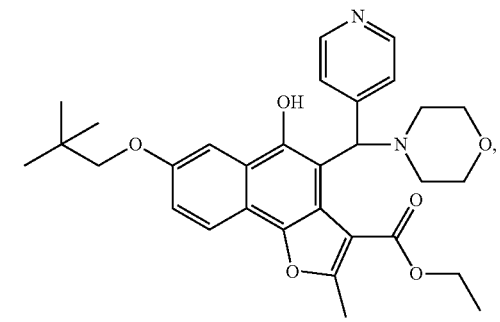
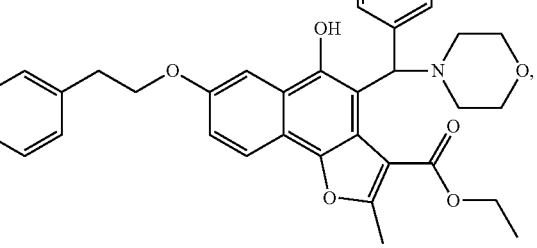
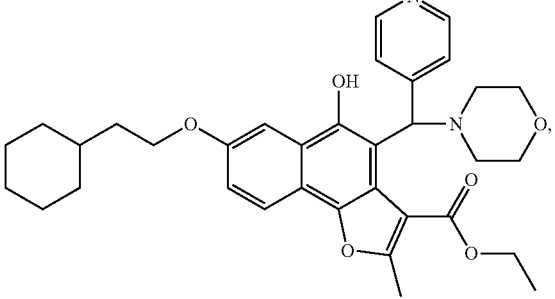

213
-continued
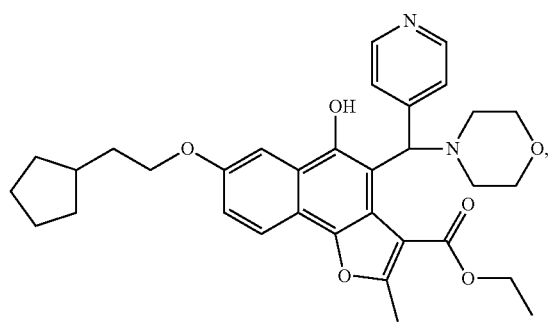
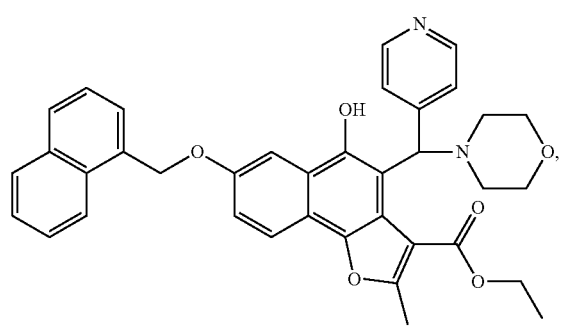
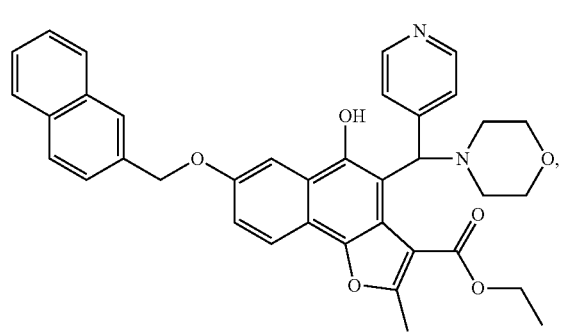
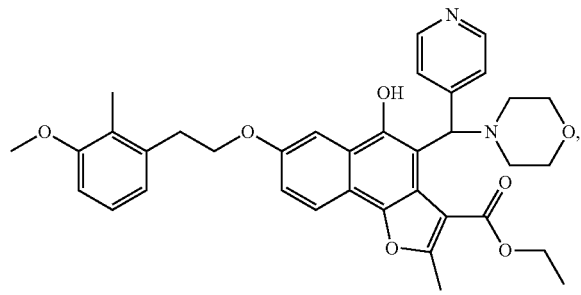
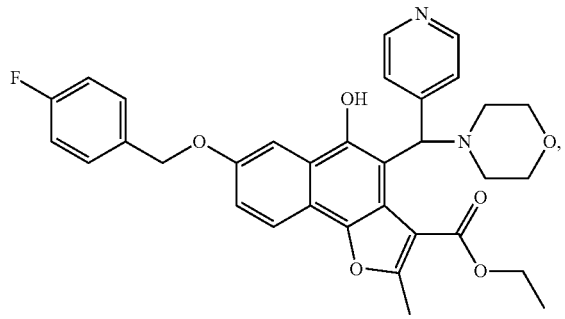
214
-continued
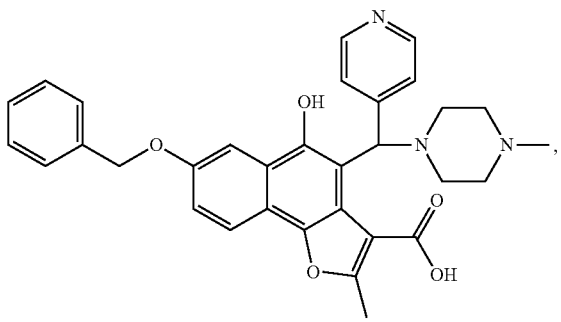
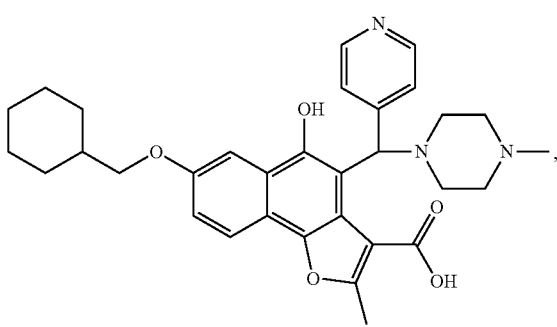
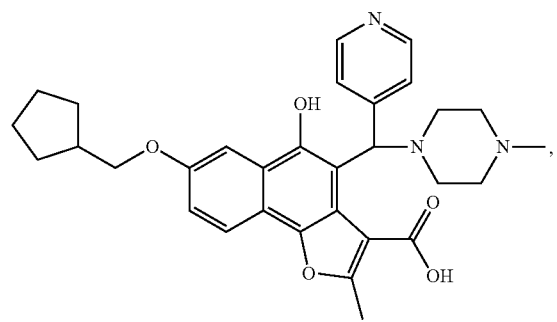
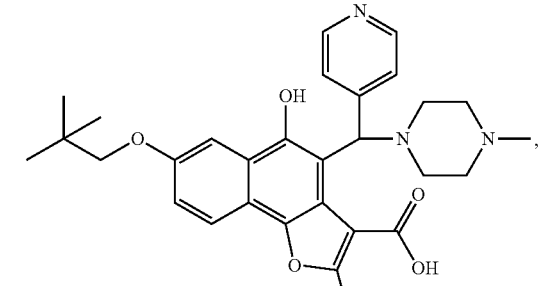
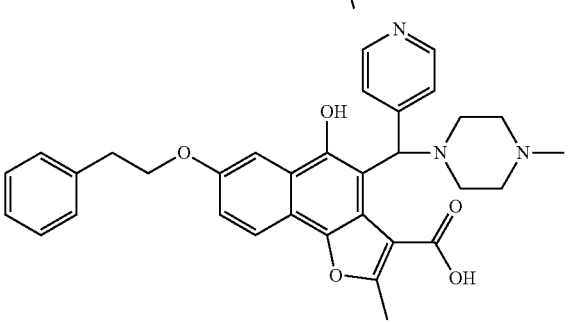

215
-continued
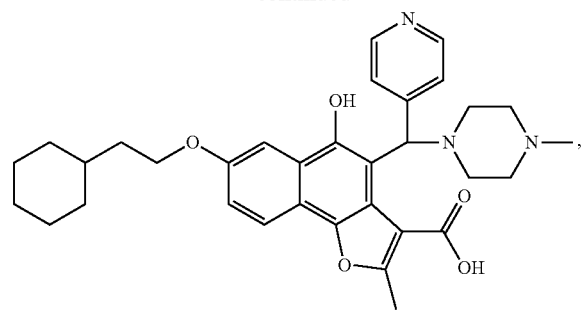
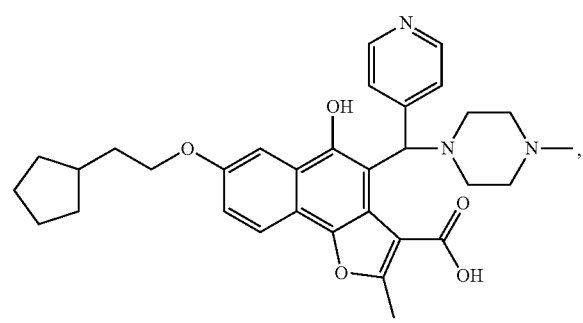
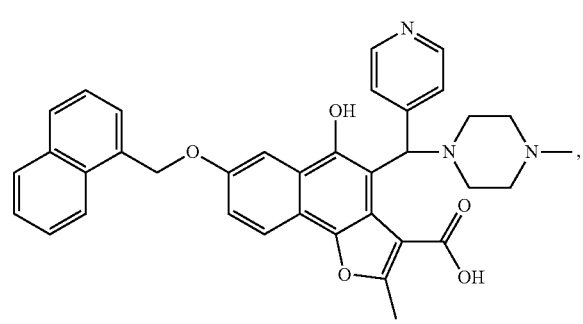
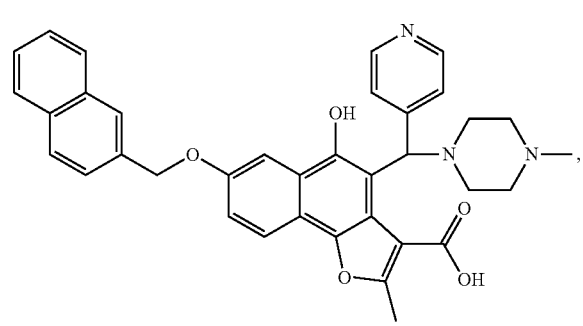
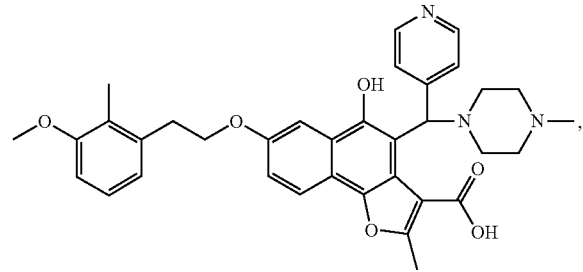
216
-continued
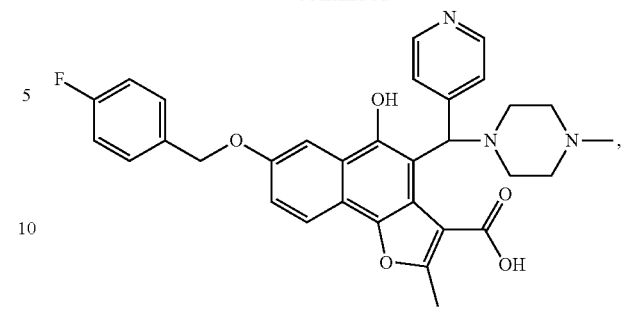
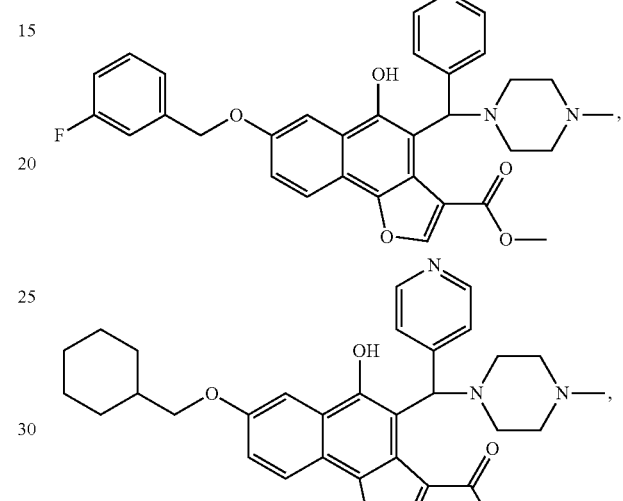
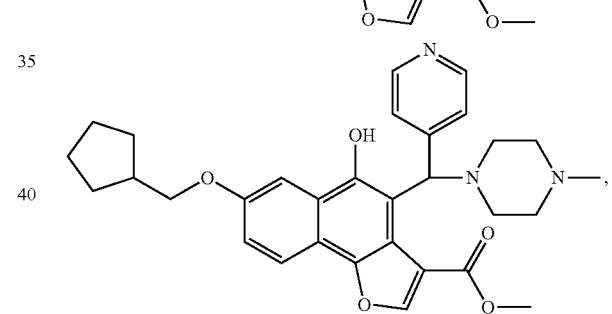
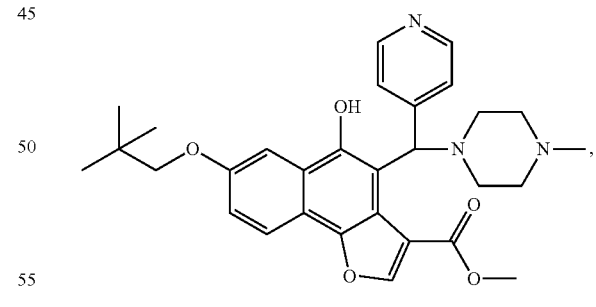
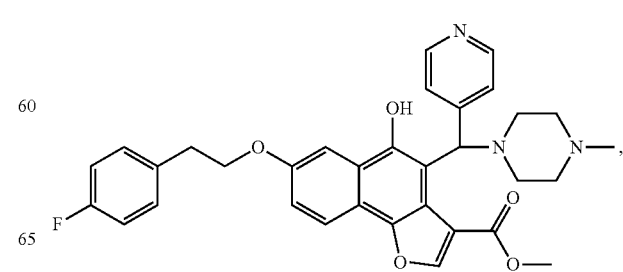

217
-continued
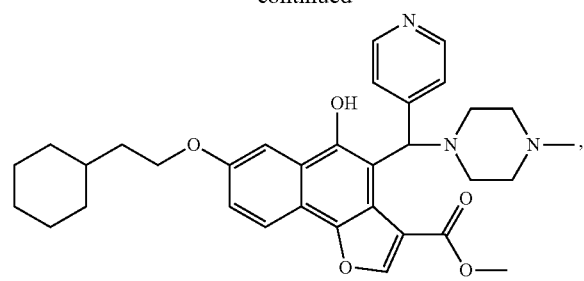
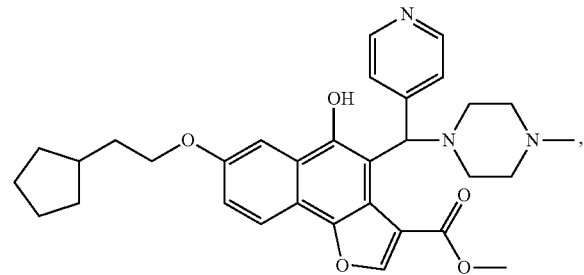
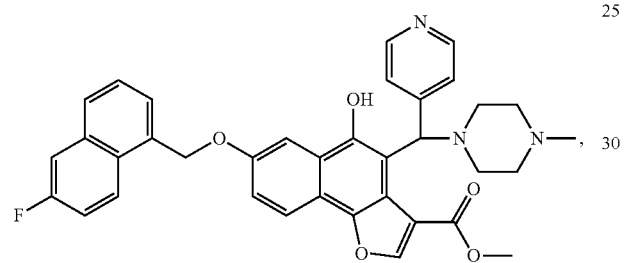
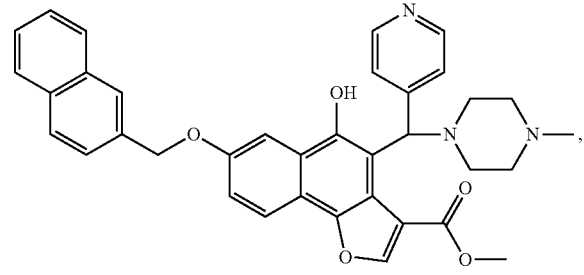
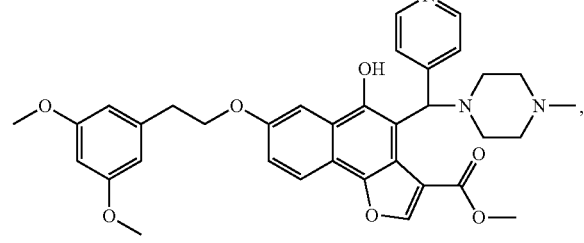
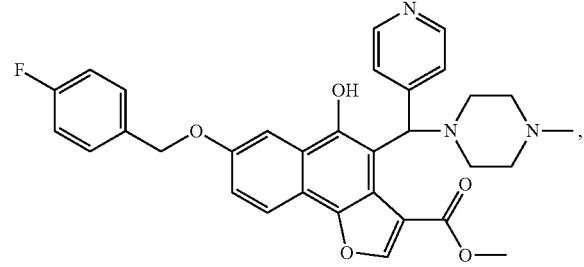
218
-continued
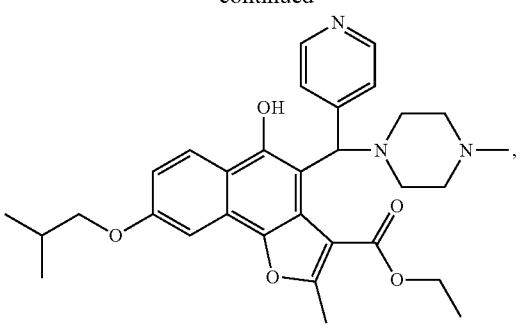
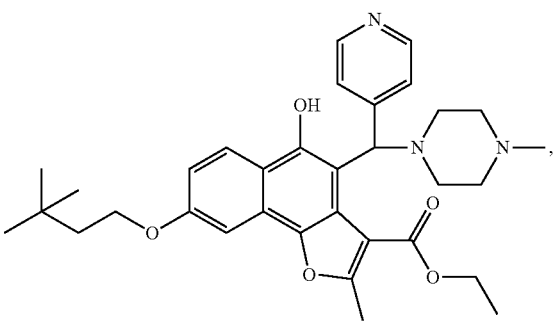
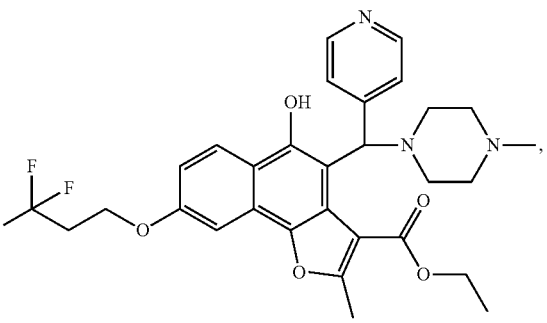
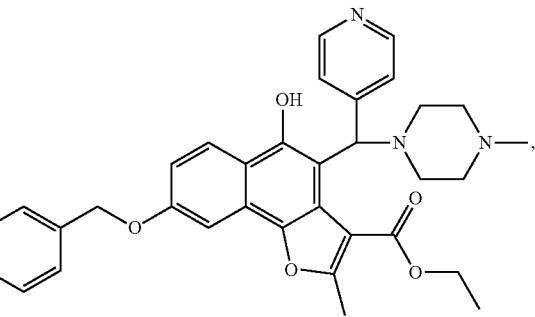
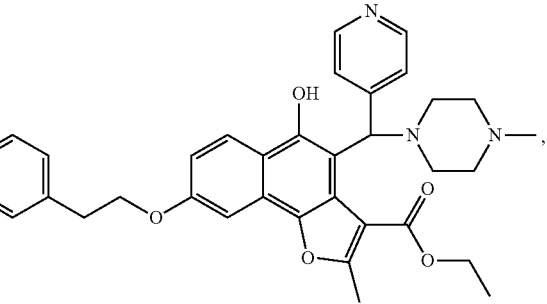

219
-continued
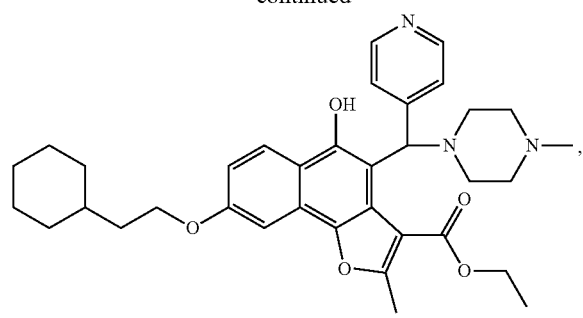
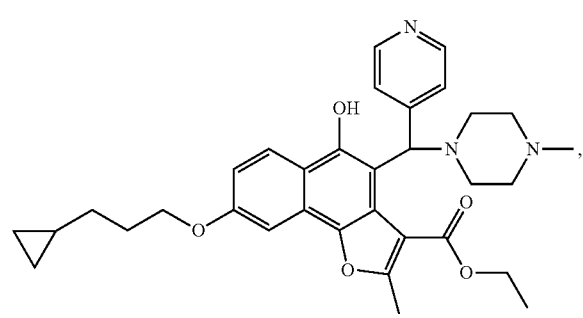
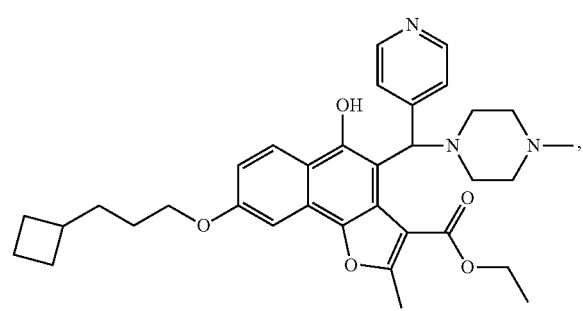
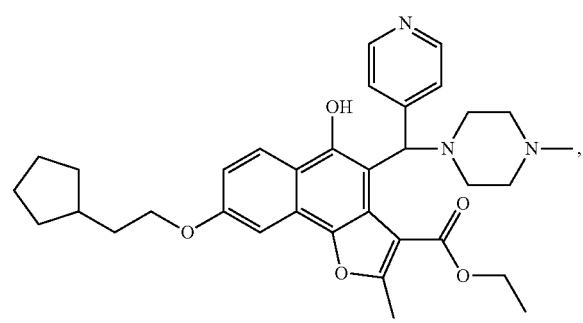
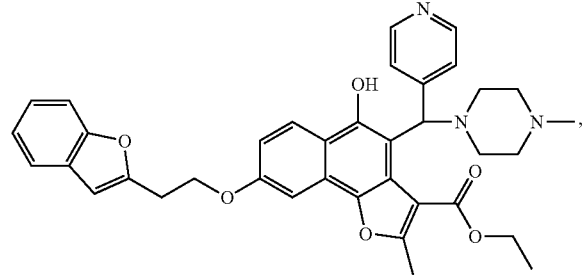
220
-continued
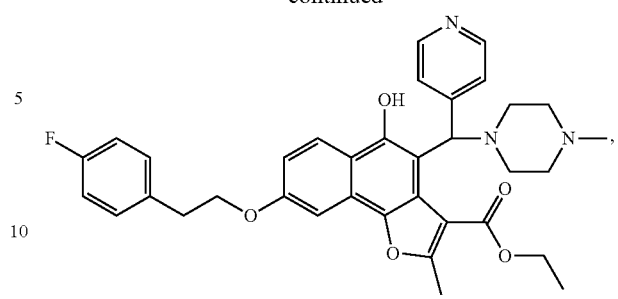
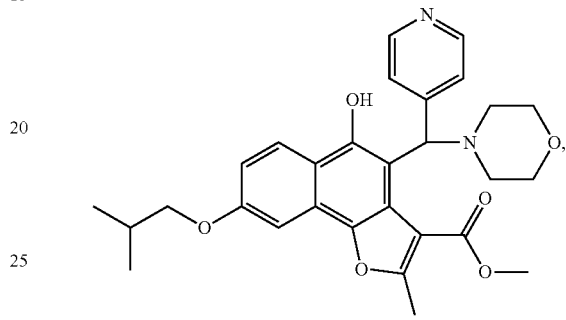
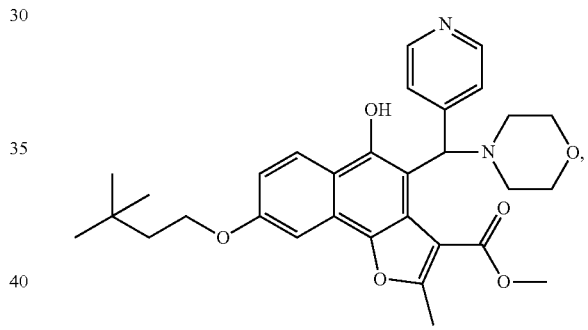
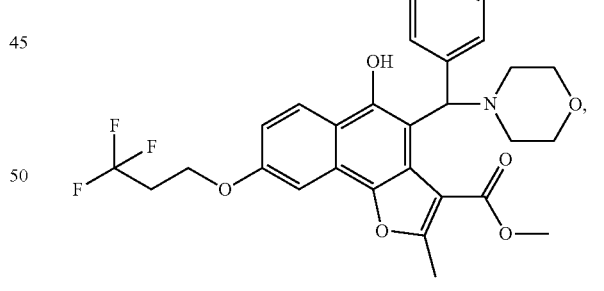
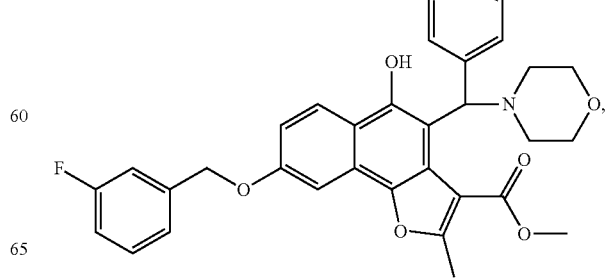

221
-continued
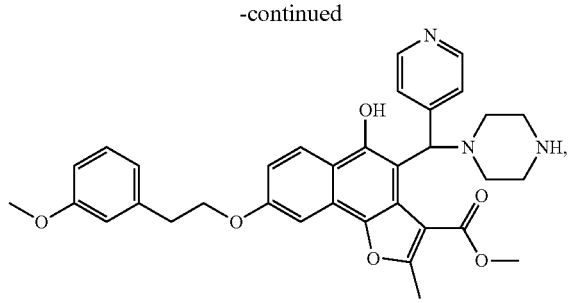
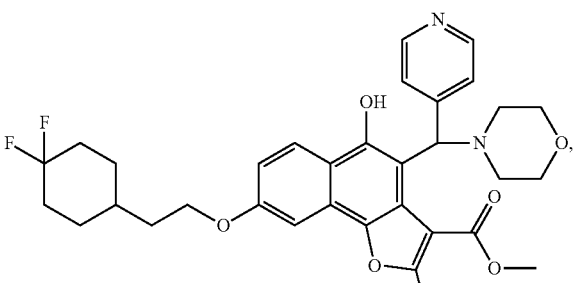
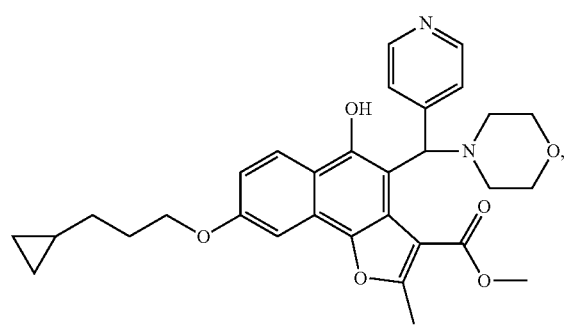
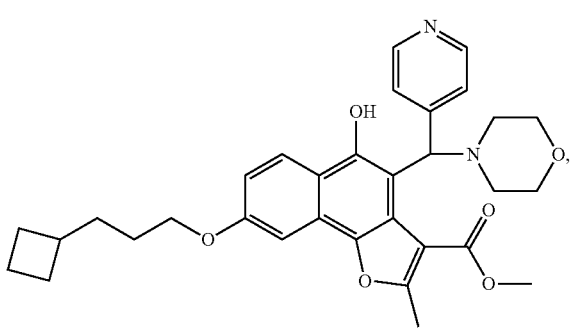
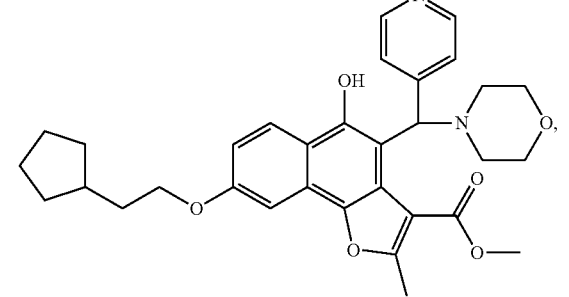
222
-continued
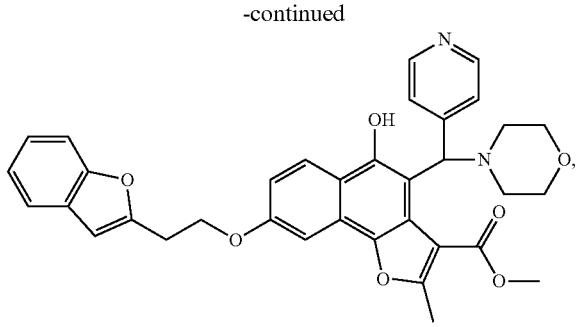
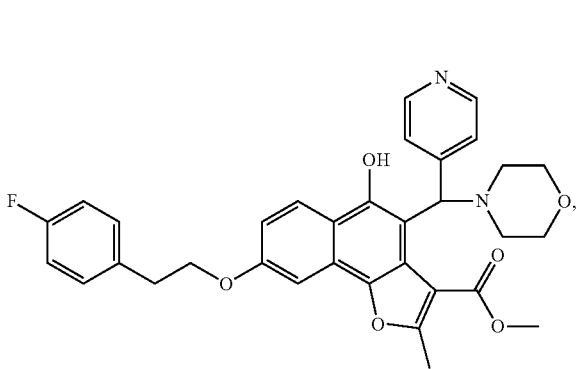
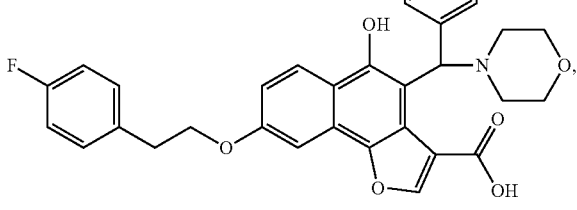
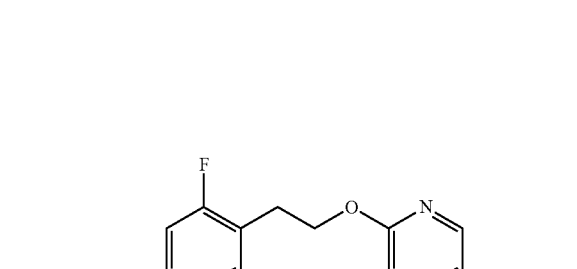
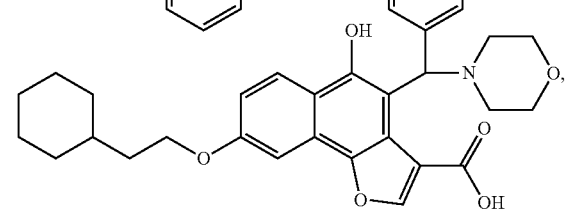

223
-continued

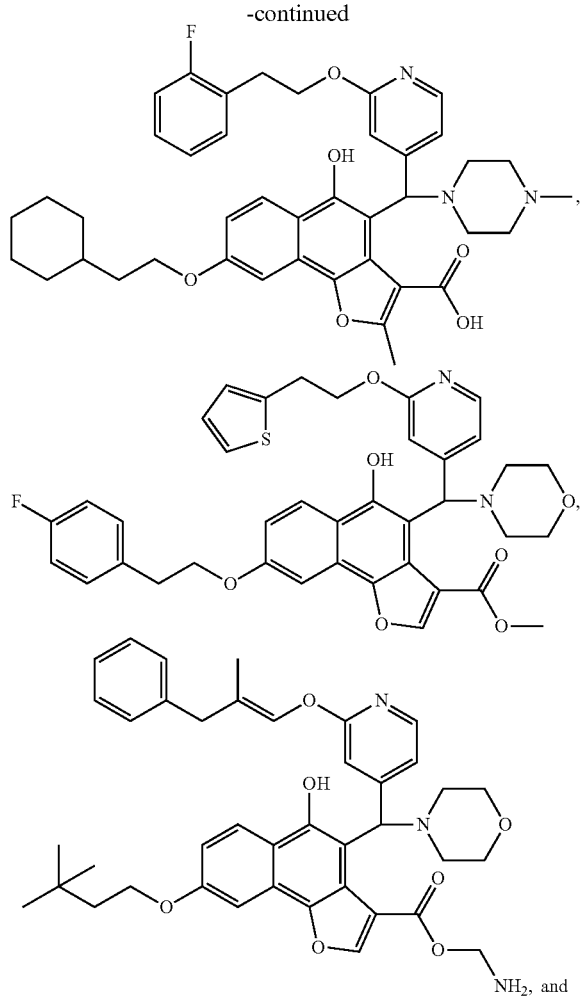

224
-continued

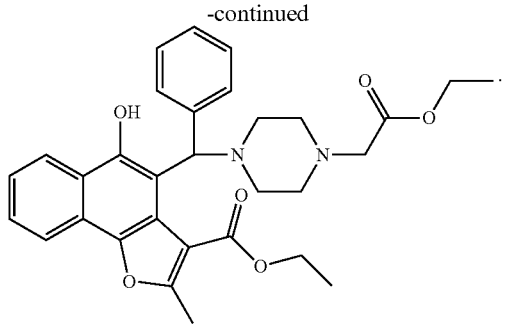

3. The compound of claim 1, wherein said compound is comprised within a pharmaceutical composition.

4. A composition comprising the compound of claim 3 and a pharmaceutically acceptable carrier.

5. A method of treating, or ameliorating melanoma or acute myeloid leukemia in a patient comprising administering to said patient a therapeutically effective amount of a compound of claim 1.

6. The method of claim 5, further comprising administering to said patient one or more anticancer agents selected from a chemotherapeutic agent and/or radiation therapy.

7. A kit comprising a compound of claim 1 and instructions for administering said compound to a patient having melanoma or acute myeloid leukemia.

8. The kit of claim 7, further comprising one or more anticancer agents selected from a chemotherapeutic agent and/or radiation therapy.

9. The kit of claim 7, wherein said compound is capable of binding to Mcl-1 protein.

10. The kit of claim 9, wherein said compound binds the BH3 groove within Mcl-1.

11. The kit of claim 10, wherein said binding results in inhibited Mcl-1 protein function.

* * * * *